US011254690B2

(12) United States Patent
Lücking et al.

(10) Patent No.: US 11,254,690 B2
(45) Date of Patent: Feb. 22, 2022

(54) PTEFB INHIBITING MACROCYCLIC COMPOUNDS

(71) Applicants: BAYER AKTIENGESELLSCHAFT, Leverkusen (DE); BAYER PHARMA AKTIENGESELLSCHAFT, Berlin (DE)

(72) Inventors: Ulrich Lücking, Berlin (DE); Daniel Hog, Düsseldorf (DE); Clara Christ, Berlin (DE); Ulrike Sack, Berlin (DE); Franziska Siegel, Berlin (DE); Philip Lienau, Berlin (DE); Nicolas Werbeck, Berlin (DE)

(73) Assignees: BAYER PHARMA AKTIENGESELLSCHAFT, Berlin (DE); BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/498,662

(22) PCT Filed: Mar. 22, 2018

(86) PCT No.: PCT/EP2018/057359
§ 371 (c)(1),
(2) Date: Sep. 27, 2019

(87) PCT Pub. No.: WO2018/177899
PCT Pub. Date: Oct. 4, 2018

(65) Prior Publication Data

US 2020/0123174 A1 Apr. 23, 2020

(30) Foreign Application Priority Data

Mar. 28, 2017 (EP) .................................... 17163377
Sep. 28, 2017 (EP) .................................... 17193837

(51) Int. Cl.
*C07D 498/18* (2006.01)
*A61P 35/00* (2006.01)
*C07D 498/08* (2006.01)

(52) U.S. Cl.
CPC ............ *C07D 498/18* (2013.01); *A61P 35/00* (2018.01); *C07D 498/08* (2013.01)

(58) Field of Classification Search
CPC .. C07D 498/08; C07D 498/18; A61K 31/529; A61K 31/439; A61P 35/00
See application file for complete search history.

(56) References Cited

U.S. PATENT DOCUMENTS 7,074,789 B2 7/2006 Armistead et al.
7,151,096 B2 12/2006 Ren et al.
7,291,616 B2 11/2007 Bhatt et al.
7,312,225 B2 12/2007 Luecking et al.
7,618,968 B2 11/2009 Bhatt et al.
9,963,464 B2 5/2018 Lucking et al.
10,214,542 B2 2/2019 Lucking et al.
10,717,749 B2 7/2020 Lucking et al.
2003/0153570 A1 8/2003 Bhatt et al.
2004/0116388 A1 6/2004 Armistead et al.
2004/0209895 A1 10/2004 Luecking et al.
2005/0176743 A1 8/2005 Luecking et al.
2007/0191393 A1 8/2007 Lucking et al.
(Continued)

FOREIGN PATENT DOCUMENTS

DE 2129678 A1 12/1971
DE 10239042 A1 3/2004
(Continued)

OTHER PUBLICATIONS

Kohoutek. Cell Division, 2009, 4:19, 1-15 (Year: 2009).*
(Continued)

*Primary Examiner* — Noble E Jarrell

(74) *Attorney, Agent, or Firm* — Wilson Sonsini Goodrich & Rosati

(57) ABSTRACT

The present invention relates to novel modified macrocyclic compounds with improved tolerability of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

(I)

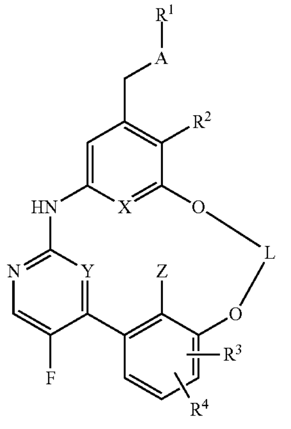

22 Claims, No Drawings

(56) References Cited

U.S. PATENT DOCUMENTS

| | | | |
|---|---|---|---|
| 2007/0232632 A1 | 10/2007 | Lucking et al. | |
| 2008/0064700 A1 | 3/2008 | Bhatt et al. | |
| 2010/0184789 A1 | 7/2010 | Wabnitz et al. | |
| 2011/0028492 A1 | 2/2011 | Barsanti et al. | |
| 2011/0306602 A1 | 12/2011 | Wabnitz et al. | |
| 2020/0347079 A1 | 11/2020 | Lucking et al. | |

FOREIGN PATENT DOCUMENTS

| | | | |
|---|---|---|---|
| EP | 1674469 | A1 | 6/2006 |
| EP | 1674470 | A1 | 6/2006 |
| EP | 1710246 | A1 | 10/2006 |
| EP | 1803723 | A1 | 7/2007 |
| EP | 1218360 | B1 | 5/2008 |
| EP | 2527332 | A1 | 11/2012 |
| WO | WO-0125220 | A1 | 4/2001 |
| WO | WO-02059110 | A1 | 8/2002 |
| WO | WO-02066481 | A1 | 8/2002 |
| WO | WO-03037346 | A1 | 5/2003 |
| WO | WO-2004009562 | A1 | 1/2004 |
| WO | 2004/026881 | A1 | 4/2004 |
| WO | WO-2004072063 | A1 | 8/2004 |
| WO | WO-2004078682 | A2 | 9/2004 |
| WO | WO-2005026129 | A1 | 3/2005 |
| WO | WO-2005037800 | A1 | 4/2005 |
| WO | WO-2006061415 | A1 | 6/2006 |
| WO | WO-2006064251 | A1 | 6/2006 |
| WO | WO-2006066956 | A2 | 6/2006 |
| WO | WO-2006066957 | A2 | 6/2006 |
| WO | WO-2006106895 | A1 | 10/2006 |
| WO | WO-2007071455 | A1 | 6/2007 |
| WO | WO-2007079982 | A1 | 7/2007 |
| WO | WO-2007147574 | A1 | 12/2007 |
| WO | WO-2007147575 | A2 | 12/2007 |
| WO | WO-2008025556 | A1 | 3/2008 |
| WO | WO-2008028590 | A1 | 3/2008 |
| WO | WO-2008060248 | A1 | 5/2008 |
| WO | WO-2008079918 | A1 | 7/2008 |
| WO | WO-2008079933 | A2 | 7/2008 |
| WO | WO-2008109943 | A1 | 9/2008 |
| WO | WO-2008129070 | A1 | 10/2008 |
| WO | WO-2008129071 | A1 | 10/2008 |
| WO | WO-2008129080 | A1 | 10/2008 |
| WO | WO-2008132138 | A1 | 11/2008 |
| WO | WO-2008140420 | A2 | 11/2008 |
| WO | WO-2009029998 | A1 | 3/2009 |
| WO | WO-2009032861 | A1 | 3/2009 |
| WO | WO-2009118567 | A2 | 10/2009 |
| WO | WO-2009132202 | A2 | 10/2009 |
| WO | WO-2010009155 | A2 | 1/2010 |
| WO | WO-2011012661 | A1 | 2/2011 |
| WO | WO-2011026917 | A1 | 3/2011 |
| WO | WO-2011029537 | A1 | 3/2011 |
| WO | WO-2011046970 | A1 | 4/2011 |
| WO | WO-2011077171 | A1 | 6/2011 |
| WO | WO-2011116951 | A1 | 9/2011 |
| WO | WO-2012009309 | A1 | 1/2012 |
| WO | WO-2012066065 | A1 | 5/2012 |
| WO | WO-2012066070 | A1 | 5/2012 |
| WO | WO-2012101062 | A1 | 8/2012 |
| WO | WO-2012101063 | A1 | 8/2012 |
| WO | WO-2012101064 | A1 | 8/2012 |
| WO | WO-2012101065 | A2 | 8/2012 |
| WO | WO-2012101066 | A1 | 8/2012 |
| WO | WO-2012117048 | A1 | 9/2012 |
| WO | WO-2012117059 | A1 | 9/2012 |
| WO | WO-2012139499 | A1 | 10/2012 |
| WO | WO-2012142329 | A1 | 10/2012 |
| WO | WO-2012143399 | A1 | 10/2012 |
| WO | WO-2013037894 | A1 | 3/2013 |
| WO | WO-2013037896 | A1 | 3/2013 |
| WO | WO-2014031937 | A1 | 2/2014 |
| WO | WO-2014060375 | A2 | 4/2014 |
| WO | WO-2014060376 | A1 | 4/2014 |
| WO | WO-2014060493 | A2 | 4/2014 |
| WO | WO-2014076028 | A1 | 5/2014 |
| WO | WO-2014076091 | A1 | 5/2014 |
| WO | WO-2014076111 | A1 | 5/2014 |
| WO | WO-2014106762 | A1 | 7/2014 |
| WO | WO-2015001021 | A1 | 1/2015 |
| WO | WO-2015136028 | A1 | 9/2015 |
| WO | 2015/155197 | A1 | 10/2015 |
| WO | WO-2015150273 | A1 | 10/2015 |
| WO | WO-2015150555 | A1 | 10/2015 |
| WO | WO-2015150557 | A1 | 10/2015 |
| WO | 2017/060167 | A1 | 4/2017 |
| WO | WO-2017055196 | A1 | 4/2017 |
| WO | WO-2017060322 | A2 | 4/2017 |
| WO | WO-2018177889 | A1 | 10/2018 |
| WO | WO-2018177899 | A1 | 10/2018 |

OTHER PUBLICATIONS

"Prevention—Prostate Cancer Foundation (PCF)", http://www.pcf.org/site/c.leJRIROrEpH/b.5802029/k.31EA/Prevention.htm, accessed Apr. 18, 2016 (Year: 2016).*

William et al., "Discovery of Kinase Spectrum Selective Macrocycle (16E)-14-Methyl-20-oxa-5,7,14,26-tetraazatetracyclo[19.3.1.1(2,6).1(8,12)]heptacosa-1(25),2(26),3,5,8(27),9,11,16,21,23-decaene (SB1317/TG02), a Potent Inhibitor of Cyclin Dependent Kinases (CDKs), Janus Kinase 2(JAK2), and Fms-like Tyrosine Kinase-3 (FLT3) for the Treatment of Cancer," Journal of Medicinal Chemistry 2012, 55, pp. 169-196.

International Search Report, PCT/EP2018/057359, European Patent Office, dated May 17, 2018.

Bark-Jones et al. EBV EBNA 2 stimulates CDK9-dependent transcription and RNA polymerase II phosphorylation on serine 5. Oncogene 25:1775-1785 (2006).

Brisard et al., Antineoplastic effects of selective CDK9 inhibition with atuveciclib on cancer stem-like cells in triple-negative breast cancer. Oncotarget 9(99): 37305-37318 (2018).

Cho et al. CYCLINg through transcription Posttranslational modification of P-TEFb regulate transcription elongation. Cell Cycle 9(9):1697-1705 (May 1, 2010).

Copeland et al. Drug-target residence time and its implications for lead optimization. Nature Reviews Drug Discovery 5:730-739 (2006).

He et al. A La-Related Protein Modulates 7SK snRNP Integrity to Suppress P-TEFb-Dependent Transcriptional Elongation and Tumorigenesis. Molecular Cell 29:588-599 (Mar. 14, 2008).

Kinoshita et al., Cyclin-dependent kinase 9 as a potential specific molecular target in NK-cell leukemia/lymphoma. Haematologica 103(12): 2059-2068 (2018).

Lücking et al. Macrocyclic aminopyrimidines as multitarget CDK and VEGF-R inhibitors with potent antiproliferative activities. ChemMedChem. 2(1):63-77 (2007).

Lu et al. Drug-target residence time: critical information for lead optimization. Curr Opin Chem Biol. 14(4):467-474 (2010).

Morales et al. Overview of CDK9 as a target in cancer research. Cell Cycle 15(4):519-527 (2016).

Qin. Is CDK9 a promising target for both primary and metastatic osteosarcoma? EBioMedicine 40:27-28 (2019).

Tummino et al.: Residence time of receptor-ligand complexes and its effect on biological function. Biochemistry. 47(20): 5481-5492 (2008) .

Wang et al. Cyclin-dependent kinase 9: a key transcriptional regulator and potential drug target in oncology, virology and cardiology. Trends in Pharmacological Sciences 29(6):302-313 (2008).

Wang et al. Discovery and Characterization of 2-Anilino-4-(Thiazol-5-yl)Pyrimidine Transcriptional CDK Inhibitors as Anticancer Agents. Chemistry & Biology 17:1111-1121 (2010).

Yang et al. Recruitment of P-TEFb for stimulation of transcriptional elongation by the bromodomain protein Brd4. Mol. Cell 19:535-545 (2005).

Zhou et al. Coordination of Transcription Factor Phosphorylation and Histone Methylation by the P-TEFb Kinase during Human Immunodeficiency Virus Type 1 Transcription.Journal of Virology 78(24):13522-13533 (Dec. 2004).

(56) References Cited

OTHER PUBLICATIONS

Zhou et al. Tax interacts with P-TEFb in a novel manner to stimulate human T-lymphotropic virus type 1 transcription. J Virol. 80(10):4781-4791 (2006).
Zhou et al. The Yin and Yang of P-TEFb Regulation: Implications for Human Immunodeficiency Virus Gene Expression and Global Control of Cell Growth and Differentiation. Microbiology and Molecular Biology Reviews 70(3):646-659 (Sep. 2006).

* cited by examiner

PTEFB INHIBITING MACROCYCLIC COMPOUNDS

CROSS REFERENCE TO RELATED APPLICATIONS

This application is the U.S. national stage entry under 35 U.S.C. 371 of PCT/EP2018/057359, filed Mar. 22, 2018, which is hereby incorporated by reference herein, which claims benefit of priority to European Patent Application Nos. 17163377.9, filed Mar. 28, 2017, and 17193837.6, filed Sep. 28, 2017.

The present invention relates to novel modified macrocyclic compounds of general formula (I) as described and defined herein, and methods for their preparation, their use for the treatment and/or prophylaxis of disorders, in particular of hyper-proliferative disorders and/or virally induced infectious diseases and/or of cardiovascular diseases. The invention further relates to intermediate compounds useful in the preparation of said compounds of general formula (I).

The family of cyclin-dependent kinase (CDK) proteins consists of members that are key regulators of the cell division cycle (cell cycle CDK's), that are involved in regulation of gene transcription (transcriptional CDK's), and of members with other functions. CDKs require for activation the association with a regulatory cyclin subunit. The cell cycle CDKs CDK1/cyclin B, CDK2/cyclin A, CDK2/cyclinE, CDK4/cyclinD, and CDK6/cyclinD get activated in a sequential order to drive a cell into and through the cell division cycle. The transcriptional CDKs CDK9/cyclin T and CDK7/cyclin H regulate the activity of RNApolymerase II via phosphorylation of the carboxy-terminal domain (CTD). Positive transcription factor b (PTEFb) is a heterodimer of CDK9 and one of the cyclin partners cyclin T1, cyclin T2a or T2b.

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). PTEFb is crucially involved in overcoming promoter-proximal pausing of RNA polymerase II and transition into a productive elongation state by phosphorylation of Ser 2 of the CTD as well as by phosphorylation and inactivation of negative elongation factors (reviewed in Jonkers and John, Nat. Rev. Mol. Cell Biol. 16, 167, 2015).

Activity of PTEFb itself is regulated by several mechanisms. About half of cellular PTEFb exists in an inactive complex with 7SK small nuclear RNA (7SK snRNA), La-related protein 7 (LARP7/PIP7S) and hexamethylene bis-acetamide inducible proteins 1/2 (HEXIM1/2, He et al., Mol Cell 29, 588, 2008). The remaining half of PTEFb exists in an active complex containing the bromodomain protein Brd4 (Yang et al., Mol Cell 19, 535, 2005). Brd4 recruits PTEFb through interaction with acetylated histones to chromatin areas primed for gene transcription. Through alternately interacting with its positive and negative regulators, PTEFb is maintained in a functional equilibrium: PTEFb bound to the 7SK snRNA complex represents a reservoir from which active PTEFb can be released on demand of cellular transcription and cell proliferation (Zhou & Yik, Microbiol Mol Biol Rev 70, 646, 2006). Furthermore, the activity of PTEFb is regulated by posttranslational modifications including phosphorylation/de-phosphorylation, ubiquitination, and acetylation (reviewed in Cho et al., Cell Cycle 9, 1697, 2010).

Deregulated activity of CDK9 kinase activity of the PTEFb heterodimer is associated with a variety of human pathological settings such as hyper-proliferative diseases (e.g. cancer), virally induced infectious diseases or cardiovascular diseases:

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of PTEFb kinase activity was shown to reduce transcriptional activity of RNA polymerase II leading to a decline of short-lived anti-apoptotic proteins, especially Mcl-1 and XIAP, reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts which are sensitive to reduced RNA polymerase II activity mediated by PTEFb inhibition (reviewed in Wang & Fischer, Trends Pharmacol Sci 29, 302, 2008).

Many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of PTEFb which in turn promotes transcriptional elongation. Furthermore, the Tat protein increases the fraction of active PTEFb by replacement of the PTEFb inhibitory proteins HEXIM1/2 within the 7SK snRNA complex. Recent data have shown that inhibition of the kinase activity of PTEFb is sufficient to block HIV-1 replication at kinase inhibitor concentrations that are not cytotoxic to the host cells (reviewed in Wang & Fischer, Trends Pharmacol Sci 29, 302, 2008). Similarly, recruitment of PTEFb by viral proteins has been reported for other viruses such as B-cell cancer-associated Epstein-Barr virus, where the nuclear antigen EBNA2 protein interacts with PTEFb (Bark-Jones et al., Oncogene, 25, 1775, 2006), and the human T-lymphotropic virus type 1 (HTLV-1), where the transcriptional activator Tax recruits PTEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. PTEFb was found to be activated by dissociation from the inactive 7SK snRNA/HEXIM1/2 complex. These findings suggest pharmacological inhibition of PTEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the PTEFb heterodimer (=CDK9 and one of the cyclin partners cyclin T1, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclinE, CDK4/cyclinD, CDK6/cyclinD) and of CDK9, is expected to impact normal proliferating tissues such as intestinal mucosa, lymphatic and hematopoietic organs, and reproductive organs. To maximize the therapeutic value of CDK9 kinase inhibitors, molecules with improved duration of action and/or high potency and efficacy and/or selectivity towards CDK9 are required.

CDK inhibitors in general as well as CDK9 inhibitors are described in a number of different publications: WO2008129070 and WO2008129071 both describe 2,4 disubstituted aminopyrimidines as CDK inhibitors in general. It is also asserted that some of these compounds may act as selective CDK9 inhibitors (WO2008129070) and as CDK5 inhibitors (WO2008129071), respectively, but no specific CDK9 $IC_{50}$ (WO2008129070) or CDK5 $IC_{50}$ (WO2008129071) data are presented. These compounds do not contain a fluorine atom in 5-position of the pyrimidine core.

WO2008129080 discloses 4,6 disubstituted aminopyrimidines and demonstrates that these compounds show an inhibitory effect on the protein kinase activity of various protein kinases, such as CDK1, CDK2, CDK4, CDK5, CDK6 and CDK9, with a preference for CDK9 inhibition (example 80).

WO2005026129 discloses 4,6 disubstituted aminopyrimidines and demonstrates that these compounds show an inhibitory effect on the protein kinase activity of various protein kinases, in particular CDK2, CDK4, and CDK9.

WO2009118567 discloses pyrimidine and [1,3,5]triazine derivatives as protein kinase inhibitors, in particular CDK2, CDK7 and CDK9.

WO2011116951 discloses substituted triazine derivatives as selective CDK9 inhibitors.

WO2012117048 discloses disubstituted triazine derivatives as selective CDK9 inhibitors.

WO2012117059 discloses disubstituted pyridine derivatives as selective CDK9 inhibitors.

WO2012143399 discloses substituted 4-aryl-N-phenyl-1,3,5-triazin-2-amines as selective CDK9 inhibitors.

EP1218360 B1, which corresponds to US2004116388A1, U.S. Pat. No. 7,074,789B2 and WO2001025220A1, describes triazine derivatives as kinase inhibitors, but does not disclose potent or selective CDK9 inhibitors.

WO2008079933 discloses aminopyridine and aminopyrimidine derivatives and their use as CDK1, CDK2, CDK3, CDK4, CDK5, CDK6, CDK7, CDK8 or CDK9 inhibitors.

WO2011012661 describes aminopyridine derivatives useful as CDK inhibitors.

WO2011026917 discloses carboxamides derived from substituted 4-phenylpyridine-2-amines as inhibitors of CDK9.

WO2012066065 discloses phenyl-heteroaryl amines as inhibitors of CDK9. A selectivity towards CDK9 over other CDK isoforms is preferred, however disclosure of CDK-inhibition data is confined to CDK 9. No bicyclic ring systems are disclosed attached to the C4 position of the pyrimidine core. Within the group attached to C4 of the pyrimidine core, alkoxy phenyls can be regarded as encompassed, but there is no suggestion for a specific substitution pattern characterised by a fluorine atom attached to C5 of the pyrimidine ring, and an aniline at C2 of the pyrimidine, featuring a substituted sulfonyl-methylene group in meta position. Compounds shown in the examples typically feature a substituted cycloalkyl group as $R^1$ but no phenyl.

WO2012066070 discloses 3-(aminoaryl)-pyridine compounds as inhibitors of CDK9. The biaryl core mandatorily consists of two heteroaromatic rings.

WO2012101062 discloses substituted bi-heteroaryl compounds featuring a 2-aminopyridine core as inhibitors of CDK9. The biaryl core mandatorily consists of two heteroaromatic rings.

WO2012101063 discloses carboxamides derived from substituted 4-(heteroaryl)-pyridine-2-amines as inhibitors of CDK9.

WO2012101064 discloses N-acyl pyrimidine biaryl compounds as inhibitors of CDK9.

WO2012101065 discloses pyrimidine biaryl compounds as inhibitors of CDK9. The biaryl core mandatorily consists of two heteroaromatic rings.

WO2012101066 discloses pyrimidine biaryl compounds as inhibitors of CDK9. Substitution $R^1$ of the amino group attached to the heteroaromatic core is confined to non-aromatic groups but does not cover substituted phenyls. Furthermore, the biaryl core mandatorily consists of two heteroaromatic rings.

WO2011077171 discloses 4,6-disubstituted aminopyrimidine derivatives as inhibitors of CDK9.

WO2014031937 discloses 4,6-disubstituted aminopyrimidine derivatives as inhibitors of CDK9.

WO2013037896 discloses disubstituted 5-fluoropyrimidines as selective inhibitors of CDK9.

WO2013037894 discloses disubstituted 5-fluoropyrimidine derivatives containing a sulfoximine group as selective inhibitors of CDK9.

Wang et al. (Chemistry & Biology 17, 1111-1121, 2010) describe 2-anilino-4-(thiazol-5-yl)pyrimidine transcriptional CDK inhibitors, which show anticancer activity in animal models.

WO2014060376 discloses substituted 4-(ortho)-fluorophenyl-5-fluoropyrimidin-2-yl amine derivatives containing a sulfone group as selective inhibitors of CDK9.

WO2014060375 discloses substituted 5-fluoro-N-(pyridin-2-yl)pyridin-2-amine derivatives containing a sulfone group as selective inhibitors of CDK9.

WO2014060493 discloses substituted N-(pyridin-2-yl)pyrimidin-4-amine derivatives containing a sulfone group as selective inhibitors of CDK9.

WO2014076028 discloses substituted 4-(ortho)-fluorophenyl-5-fluoropyrimidin-2-yl amine derivatives containing a sulfoximine group as selective inhibitors of CDK9.

WO2014076091 discloses substituted 5-fluoro-N-(pyridin-2-yl)pyridin-2-amine derivatives containing a sulfoximine group as selective inhibitors of CDK9.

WO2014076111 discloses substituted N-(pyridin-2-yl)pyrimidin-4-amine derivatives containing a sulfoximine group as selective inhibitors of CDK9.

WO2015001021 discloses 5-fluoro-N-(pyridin-2-yl)pyridin-2-amine derivatives containing a sulfoximine group as selective inhibitors of CDK9.

WO 2015136028 discloses 5-fluoro-N-(pyridin-2-yl)pyridin-2-amine derivatives containing a sulfone group as selective inhibitors of CDK9.

WO2004009562 discloses substituted triazine kinase inhibitors. For selected compounds CDK1 and CDK4 test data, but no CDK9 data is presented.

WO2004072063 describes heteroaryl (pyrimidine, triazine) substituted pyrroles as inhibitors of protein kinases such as ERK2, GSK3, PKA or CDK2.

WO2010009155 discloses triazine and pyrimidine derivatives as inhibitors of histone deacetylase and/or cyclin dependent kinases (CDKs). For selected compounds CDK2 test data is described.

WO2003037346 (corresponding to U.S. Pat. No. 7,618,968B2, U.S. Pat. No. 7,291,616B2, US2008064700A1, US2003153570A1) relates to aryl triazines and uses thereof, including to inhibit lysophosphatidic acid acyltransferase beta (LPAAT-beta) activity and/or proliferation of cells such as tumor cells.

WO2005037800 discloses sulfoximine substituted anilino-pyrimidines as inhibitors of VEGFR and CDK kinases, in particular VEGFR2, CDK1 and CDK2, having no aromatic ring directly bonded to the pyrimidine ring and having the sulfoximine group directly bonded to the aniline group. No CDK9 data are disclosed.

WO2008025556 describes carbamoyl sulfoximides having a pyrimidine core, which are useful as kinase inhibitors. No CDK9 data is presented. No molecules are exemplified, which possess a fluoropyrimidine core.

WO2002066481 describes pyrimidine derivatives as cyclin dependent kinase inhibitors. CDK9 is not mentioned and no CDK9 data is presented.

WO2008109943 concerns phenyl aminopyri(mi)dine compounds and their use as kinase inhibitors, in particular as JAK2 kinase inhibitors. The specific examples mainly focus on compounds having a pyrimidine core.

WO2009032861 describes substituted pyrimidinyl amines as JNK kinase inhibitors. The specific examples mainly focus on compounds having a pyrimidine core.

WO2011046970 concerns amino-pyrimidine compounds as inhibitors of TBK1 and/or IKK epsilon. The specific examples mainly focus on compounds having a pyrimidine core.

WO2012142329 concerns amino-pyrimidine compounds as inhibitors of TBK1 and/or IKK epsilon.

WO2012139499 discloses urea substituted anilino-pyrimidines as inhibitors of various protein kinases.

WO2014106762 discloses 4-pyrimidinylamino-benzenesulfonamide derivatives as inhibitors of polo-like kinase-1.

Macrocyclic compounds have been described as therapeutically useful substances, in particular of various protein kinases including cyclin dependent kinases. However, the documents listed below do not disclose specific compounds as inhibitors of CDK9.

WO2007147574 discloses sulfonamido-macrocycles as inhibitors of Tie2 showing selectivity over CDK2 and Aurora kinase C, inter alia for the treatment of diseases accompanied with dysregulated vascular growth.

WO2007147575 discloses further sulfonamido-macrocycles as inhibitors of Tie2 and KDR showing selectivity over CDK2 and Plk1, inter alia for the treatment of diseases accompanied with dysregulated vascular growth.

WO2006066957/EP1674470 discloses further sulfonamido-macrocycles as inhibitors of Tie2 showing low cytotoxicity, inter alia for the treatment of diseases accompanied with dysregulated vascular growth.

WO2006066956/EP1674469 discloses further sulfonamido-macrocycles as inhibitors of Tie2 showing low cytotoxicity, inter alia for the treatment of diseases accompanied with dysregulated vascular growth.

WO2004026881/DE10239042 discloses macrocyclic pyrimidine derivatives as inhibitors of cyclin dependent kinases, in particular CDK1 and CDK2, as well as VEGF-R, inter alia for the treatment of cancer. The compounds of the present invention differ from those disclosed in WO2004026881 in featuring a mandatory biaromatic portion within the macrocyclic ring system. Furthermore, none of the example compounds disclosed in WO2004026881 features a group —$CH_2$-A-$R^1$, in which A and $R^1$ are as defined for the compounds of the formula (I) of the present invention, attached to one of the two aromatic portions of the macrocyclic ring system.

WO2007079982/EP1803723 discloses macrocyclic benzenacyclononaphanes as inhibitors of multiple protein kinases, e.g. Aurora kinases A and C, CDK1, CDK2 and c-Kit, inter alia for the treatment of cancer. The compounds of the present invention differ from those disclosed in WO 2007079982 in featuring a mandatory biaromatic portion within the macrocyclic ring system. Furthermore, the compounds of the present invention do not feature a group —S(═O)(N═$R^2$)$R^1$ directly attached to the phenylene portion of the macrocyclic ring system as disclosed in WO 2007079982.

WO2006106895/EP1710246 discloses sulfoximine-macrocycle compounds as inhibitors of Tie2 showing low cytotoxicity, inter alia for the treatment of diseases accompanied with dysregulated vascular growth.

WO2012009309 discloses macrocyclic compounds fused to benzene and pyridine rings for the reduction of beta-amyloid production.

WO2009132202 discloses macrocyclic compounds as inhibitors of JAK 1, 2 and 3, TYK2 and ALK and their use in the treatment of JAK/ALK-associated diseases, including inflammatory and autoimmune disease as well as cancer.

WO2004078682/U.S. Pat. No. 7,151,096 discloses a class of cyclic compounds for treating or preventing diseases and disorders associated with cyclin-dependent kinases (CDKs) activity, particularly diseases associated with the activity of CDK2 and CDK5.

WO2015155197 discloses macrocyclic compounds as selective inhibitors of CDK9 for the treatment and/or prophylaxis of disorders, in particular of hyper-proliferative disorders and/or virally induced infectious diseases and/or of cardiovascular diseases. The compounds of the present invention differ from those in WO2015155197 by the point of attachment of bridging alkylenedioxy moiety.

WO2015150555 and WO2015150557 disclose substituted macrocylic compounds having EF2K inhibitory activity and optionally also Vps34 inhibitory activity. The compounds of the present invention differ from those in WO2015150555 and WO2015150557 i.a. by the point of attachment of the bridging moiety.

WO2008140420 discloses macrocylic compounds that may be useful as agents targeting kinase related disorders. The compounds of the present invention differ from those in WO2008140420 i.a. by the structure of the bridging moiety.

ChemMedChem 2007, 2(1), 63-77 describes macrocyclic aminopyrimidines as multitarget CDK and VEGF-R inhibitors with potent antiproliferative activity. The compounds of the present invention differ from those disclosed in said journal publication in featuring a mandatory biaromatic portion within the macrocyclic ring system. Furthermore, none of the compounds disclosed in ChemMedChem 2007, 2(1), 63-77 features a group —$CH_2$-A-$R^1$ in which A and $R^1$ are as defined for the compounds of the formula (I) or the present invention, attached to one of the two aromatic portions of the macrocyclic ring system.

Despite the fact that various inhibitors of CDKs are known, there remains a need for selective CDK9 inhibitors, especially CDK9 inhibitors which are selective at high ATP concentrations, to be used for the treatment of diseases such as hyper-proliferative diseases, viral diseases, and/or diseases of the heart, which offer one or more advantages over the compounds known from prior art, such as:

- improved activity and/or efficacy, allowing e.g. a dose reduction
- improved side effect profile, such as fewer undesired side effects, lower intensity of side effects, or reduced (cyto)toxicity
- improved duration of action, e.g. by improved pharmacokinetics and/or improved target residence time
- Specifically modified PK profile to reduce unwanted side effects A particular object of the invention is to provide selective CDK9 kinase inhibitors, which show a high anti-proliferative activity in tumor cell lines, such as HeLa, HeLa-MaTu-ADR, NCI-H460, DU145, Caco-2, B16F10, A2780 or MOLM-13, compared to compounds known from prior art.

Another particular object of the invention is to provide selective CDK9 kinase inhibitors which show an increased potency to inhibit CDK9 activity at high ATP concentrations compared to compounds known from prior art.

Another particular object of the invention is to provide selective CDK9 kinase inhibitors which show an increased target residence time compared to compounds known from prior art.

Another particular object of the invention is to provide selective CDK9 kinase inhibitors which show an improved duration of action, e.g. by improved pharmacokinetics and/or improved target residence time.

Further, it is an object of the present invention to provide selective CDK9 kinase inhibitors, which, compared to the compounds known from prior art, show a high anti-proliferative activity in tumor cell lines, such as HeLa, HeLa-MaTu-ADR, NCI-H460, DU145, Caco-2, B16F10, A2780 or MOLM-13, and/or which show an increased potency to inhibit CDK9 activity (demonstrated by a lower $IC_{50}$ value for CDK9/Cyclin T1), especially an increased potency to inhibit CDK9 activity at high ATP concentrations, and/or which show an increased target residence time compared to the compounds known from prior art.

Another particular object of the invention is to provide selective CDK9 kinase inhibitors which show an improved therapeutic window.

A further object of the invention is to provide CDK9 kinase inhibitors simultaneously featuring selectivity for CDK9/Cyclin T1 over CDK2/Cyclin E, especially at high ATP concentrations.

The present invention relates to compounds of general formula (I)

(I)

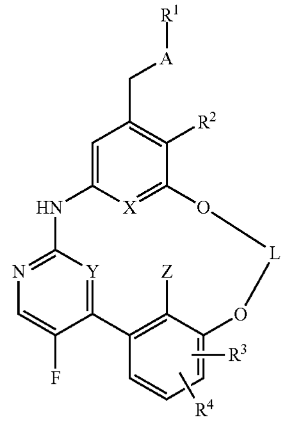

wherein

A represents a bivalent moiety selected from the group consisting of —S—, —S(═O)—, —S(═O)$_2$—, —S(═O)(═NR$^5$)—; —S(═NR$^6$)(═NR$^7$)—;

Z represents a hydrogen atom or a fluorine atom;

L represents a $C_3$-$C_8$-alkylene moiety,
 wherein said moiety is optionally substituted with
 (i) one substituent selected from hydroxy, —NR$^8$R$^9$, $C_2$-$C_3$-alkenyl-, $C_2$-$C_3$-alkynyl-, $C_3$-$C_4$-cycloalkyl-, hydroxy-$C_1$-$C_3$-alkyl, —(CH$_2$)NR$^8$R$^9$, and/or
 (ii) one or two or three or four substituents, identically or differently, selected from halogen and $C_1$-$C_3$-alkyl-,
 or wherein
 one carbon atom of said $C_3$-$C_8$-alkylene moiety forms a three- or four-membered ring together with a bivalent moiety to which it is attached, wherein said bivalent moiety is selected from —CH$_2$CH$_2$—, —CH$_2$CH$_2$CH$_2$—, —CH$_2$OCH$_2$—;

X, Y represent CH or N with the proviso that one of X and Y represents CH and one of X and Y represents N;

R$^1$ represents a group selected from $C_1$-$C_6$-alkyl-, $C_3$-$C_6$-alkenyl-, $C_3$-$C_7$-cycloalkyl-, heterocyclyl-, wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —NH$_2$, alkylamino-, dialkylamino-, acetylamino-, N-methyl-N-acetylamino-, cyclic amines, —OP(═O)(OH)$_2$, —C(═O)OH, —C(═O)NH$_2$;

R$^2$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, $C_1$-$C_3$-fluoroalkoxy-;

R$^3$, R$^4$ represent, independently from each other, a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, $C_1$-$C_3$-fluoroalkoxy-;

R$^5$ represents a group selected from a hydrogen atom, cyano, —C(═O)R$^{10}$, —C(═O)OR$^{10}$, —S(═O$_2$)R, —C(═O)NR$^8$R$^9$, $C_1$-$C_6$-alkyl-, $C_3$-$C_7$-cycloalkyl-, heterocyclyl-,
 wherein said $C_1$-$C_6$-alkyl-, $C_3$—C-cycloalkyl-, heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —NH$_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^6$, $R^7$ represents, independently from each other, a group selected from a hydrogen atom, cyano, —C(=O)$R^{10}$, —C(=O)O$R^{10}$, —S(=O)$_2$$R^{10}$, —C(=O)N$R^8$$R^9$, $C_1$-$C_6$-alkyl-, $C_3$-$C_7$-cycloalkyl-, heterocyclyl-, wherein said $C_1$-$C_6$-alkyl-, $C_3$-$C_7$-cycloalkyl-, heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-;

$R^8$, $R^9$ represent, independently from each other, a group selected from a hydrogen atom, $C_1$-$C_6$-alkyl-, $C_3$—C-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- or heteroaryl-group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^8$ and $R^9$, together with the nitrogen atom they are attached to, form a cyclic amine;

$R^{10}$ represents a group selected from $C_1$-$C_6$-alkyl-, halo-$C_1$-$C_3$-alkyl-, $C_3$-$C_7$-cycloalkyl-, heterocyclyl-, phenyl-, benzyl- and heteroaryl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or the enantiomers, diastereomers, salts, solvates or salts of solvates thereof.

Compounds according to the invention are the compounds of the formula (I) and the salts, solvates and solvates of the salts thereof, the compounds of the hereinafter recited formula which are encompassed by formula (I) and the salts, solvates and solvates of the salts thereof, and the compounds which are encompassed by formula (I) and are mentioned hereinafter as exemplary embodiments and the salts, solvates and solvates of the salts thereof, where the compounds which are encompassed by formula (I) and are mentioned hereinafter are not already salts, solvates and solvates of the salts.

The compounds according to the invention may, depending on their structure, exist in stereoisomeric forms (enantiomers, diastereomers). The invention therefore relates to the enantiomers or diastereomers and respective mixtures thereof. The stereoisomerically pure constituents can be isolated in a known manner from such mixtures of enantiomers and/or diastereomers.

If the compounds according to the invention can be in tautomeric forms, the present invention encompasses all tautomeric forms.

Further, the compounds of the present invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the present invention are physiologically acceptable salts of the compounds according to the invention. However, salts which are not suitable for pharmaceutical applications per se, but which, for example, can be used for the isolation or purification of the compounds according to the invention, are also comprised.

The term "physiologically acceptable salt" refers to a relatively non-toxic, inorganic or organic acid addition salt of a compound of the present invention, for example, see S. M. Berge, et al. "Pharmaceutical Salts," J. Pharm. Sci. 1977, 66, 1-19.

Physiologically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Physiologically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine, N-methylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol. Additionally, the compounds according to the invention may form salts with a quarternary ammonium ion obtainable e.g. by quarternisation of a basic nitrogen containing group with agents such as lower alkylhalides such as methyl-, ethyl-, propyl-, and butylchlorides, -bromides and -iodides; dialkylsulfates such as dimethyl-, diethyl-, dibutyl- and diamylsulfates, long chain halides such as decyl-, lauryl-, myristyl- and stearylchlorides, -bromides and -iodides, aralkylhalides such as benzyl- and phenethylbromides and others. Examples of suitable quarternary ammonium ions are tetramethylammonium, tetraethylammonium, tetra(n-propyl)ammonium, tetra (n-butyl)ammonium, or N-benzyl-N,N,N-trimethylammonium.

The present invention includes all possible salts of the compounds of the present invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the present invention.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulfur, fluorine, chlorine, bromine and iodine, such as $^{2}H$ (deuterium), $^{3}H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the present invention includes all possible crystalline forms, or polymorphs, of the compounds of the present invention, either as single polymorphs, or as a mixture of more than one polymorphs, in any ratio.

Accordingly, the present invention includes all possible salts, polymorphs, metabolites, hydrates, solvates, prodrugs (e.g.: esters) thereof, and diastereoisomeric forms of the the compounds of the present invention as single salt, polymorph, metabolite, hydrate, solvate, prodrug (e.g.: esters) thereof, or diastereoisomeric form, or as mixture of more than one salt, polymorph, metabolite, hydrate, solvate, prodrug (e.g.: esters) thereof, or diastereoisomeric form in any ratio.

For the purposes of the present invention, the substituents have the following meaning, unless otherwise specified:

The term "halogen", "halogen atom" or "halo" represents fluorine, chlorine, bromine and iodine, particularly bromine, chlorine or fluorine, preferably chlorine or fluorine, more preferably fluorine.

The term "alkyl-" represents a linear or branched alkyl-group having the number of carbon atoms specifically indicated, e.g. $C_1$-$C_{10}$ one, two, three, four, five, six, seven, eight, nine or ten carbon atoms, e.g. methyl-, ethyl-, n-propyl-, isopropyl-, n-butyl-, isobutyl-, sec-butyl-, tert-butyl-, pentyl-, isopentyl-, hexyl-, heptyl-, octyl-, nonyl-, decyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, or 1,2-dimethylbutyl-. If the number of carbon atoms is not specifically indicated, the term "alkyl-" represents a linear or branched alkyl-group having, as a rule, 1 to 9, particularly 1 to 6, preferably 1 to 4 carbon atoms. Particularly, the alkyl-group has 1, 2, 3, 4, 5 or 6 carbon atoms ("$C_1$-$C_6$-alkyl-"), e.g. methyl-, ethyl-, n-propyl-, isopropyl-, n-butyl-, tert-butyl-, pentyl-, isopentyl-, hexyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-, or 1,2-dimethylbutyl-. Preferably, the alkyl-group has 1, 2 or 3 carbon atoms ("$C_1$-$C_3$-alkyl"), methyl-, ethyl-, n-propyl- or isopropyl-.

The term "$C_3$-$C_8$-alkylene" is to be understood as preferably meaning a linear, bivalent and saturated hydrocarbon moiety having 3 to 8, particularly 3, 4 or 5 carbon atoms, as in "$C_3$-$C_5$-alkylene", more particularly 4 or 5 carbon atoms, as in "$C_4$-$C_5$-alkylene" e.g. ethylene, n-propylene, n-butylene, n-pentylene, or n-hexylene, preferably n-propylene or n-butylene.

The term "$C_2$-$C_6$-alkenyl-" is to be understood as preferably meaning a linear or branched, monovalent hydrocarbon group, which contains one double bond, and which has 2, 3, 4, 5 or 6 carbon atoms ("$C_2$-$C_6$-alkenyl-"). Particularly, said alkenyl group is a $C_2$-$C_3$-alkenyl-, $C_3$-$C_6$-alkenyl- or $C_3$-$C_4$-alkenyl-group. Said alkenyl-group is, for example, a vinyl-, allyl-, (E)-2-methylvinyl-, (Z)-2-methylvinyl- or isopropenyl-group.

The term "$C_2$-$C_6$-alkynyl-" is to be understood as preferably meaning a linear or branched, monovalent hydrocarbon group which contains one triple bond, and which contains 2, 3, 4, 5 or 6 carbon atoms.

Particularly, said alkynyl-group is a $C_2$-$C_3$-alkynyl-, $C_3$-$C_6$-alkynyl- or $C_3$-$C_4$-alkynyl-group. Said $C_2$-$C_3$-alkynyl-group is, for example, an ethynyl-, prop-1-ynyl- or prop-2-ynyl-group.

The term "$C_3$-$C_7$-cycloalkyl-" is to be understood as preferably meaning a saturated or partially unsaturated, monovalent, monocyclic hydrocarbon ring which contains 3, 4, 5, 6 or 7 carbon atoms. Said $C_3$-$C_7$-cycloalkyl-group is for example, a monocyclic hydrocarbon ring, e.g. a cyclopropyl-, cyclobutyl-, cyclopentyl-, cyclohexyl- or cycloheptyl-group. Said cycloalkyl- ring is non-aromatic but can optionally contain one or more double bonds e.g. cycloalkenyl-, such as a cyclopropenyl-, cyclobutenyl-, cyclopentenyl-, cyclohexenyl- or cycloheptenyl-group, wherein the bond between said ring with the rest of the molecule may be to any carbon atom of said ring, be it saturated or unsaturated. Particularly, said cycloalkyl-group is a $C_4$-$C_6$-cycloalkyl-, a $C_5$-$C_6$-cycloalkyl- or a cyclohexyl-group.

The term "$C_3$-$C_5$-cycloalkyl-" is to be understood as preferably meaning a saturated, monovalent, monocyclic hydrocarbon ring which contains 3, 4 or 5 carbon atoms. In particular said $C_3$-$C_5$-cycloalkyl-group is a monocyclic hydrocarbon ring such as a cyclopropyl-, cyclobutyl- or cyclopentyl-group. Preferably said "$C_3$-$C_5$-cycloalkyl-" group is a cyclopropyl-group.

The term "$C_3$-$C_4$-cycloalkyl-" is to be understood as preferably meaning a saturated, monovalent, monocyclic hydrocarbon ring which contains 3 or 4 carbon atoms. In particular, said $C_3$-$C_4$-cycloalkyl-group is a monocyclic hydrocarbon ring such as a cyclopropyl- or cyclobutyl-group.

The term "heterocyclyl-" is to be understood as meaning a saturated or partially unsaturated, monovalent, mono- or bicyclic hydrocarbon ring which contains 3, 4, 5, 6, 7, 8 or 9 carbon atoms and further containing 1, 2 or 3 heteroatom-containing groups selected from oxygen, sulfur, nitrogen. Particularly, the term "heterocyclyl-" is to be understood as meaning a "4- to 10-membered heterocyclic ring".

The term "a 4- to 10-membered heterocyclic ring" is to be understood as meaning a saturated or partially unsaturated, monovalent, mono- or bicyclic hydrocarbon ring which contains 3, 4, 5, 6, 7, 8 or 9 carbon atoms, and further containing 1, 2 or 3 heteroatom-containing groups selected from oxygen, sulfur, nitrogen.

A $C_3$-$C_9$-heterocyclyl- is to be understood as meaning a heterocyclyl- which contains at least 3, 4, 5, 6, 7, 8 or 9 carbon atoms and additionally at least one heteroatom as ring atoms. Accordingly in case of one heteroatom the ring is 4- to 10-membered, in case of two heteroatoms the ring is 5- to 11-membered and in case of three heteroatoms the ring is 6- to 12-membered.

Said heterocyclic ring is for example, a monocyclic heterocyclic ring such as an oxetanyl-, azetidinyl-, tetrahydrofuranyl-, pyrrolidinyl-, 1,3-dioxolanyl-, imidazolidinyl-, pyrazolidinyl-, oxazolidinyl-, isoxazolidinyl-, 1,4-dioxanyl-, pyrrolinyl-, tetrahydropyranyl-, piperidinyl-, morpholinyl-, 1,3-dithianyl-, thiomorpholinyl-, piperazinyl-, or chinuclidinyl-group. Optionally, said heterocyclic ring can contain one or more double bonds, e.g. 4H-pyranyl-, 2H-pyranyl-, 2,5-dihydro-1H-pyrrolyl-, 1,3-dioxolyl-, 4H-1,3,4-thiadiazinyl-, 2,5-dihydrofuranyl-, 2,3-dihydrofuranyl-, 2,5-dihydrothienyl-, 2,3-dihydrothienyl-, 4,5-dihydrooxazolyl-, 4,5-dihydroisoxazolyl-, or 4H-1,4-thiazinyl-group, or, it may be benzo fused.

Particularly, a $C_3$-$C_7$-heterocyclyl- is to be understood as meaning a heterocyclyl- which contains at least 3, 4, 5, 6, or 7 carbon atoms and additionally at least one heteroatom as ring atoms. Accordingly in case of one heteroatom the ring is 4- to 8-membered, in case of two heteroatoms the ring is 5- to 9-membered and in case of three heteroatoms the ring is 6- to 10-membered.

Particularly, a $C_3$-$C_6$-heterocyclyl- is to be understood as meaning a heterocyclyl- which contains at least 3, 4, 5 or 6 carbon atoms and additionally at least one heteroatom as ring atoms. Accordingly in case of one heteroatom the ring is 4- to 7-membered, in case of two heteroatoms the ring is 5- to 8-membered and in case of three heteroatoms the ring is 6- to 9-membered.

Particularly, the term "heterocyclyl-" is to be understood as being a heterocyclic ring which contains 3, 4 or 5 carbon atoms, and 1, 2 or 3 of the above-mentioned heteroatom-containing groups (a "4- to 8-membered heterocyclic ring"), more particularly said ring can contain 4 or 5 carbon atoms, and 1, 2 or 3 of the above-mentioned heteroatom-containing groups (a "5- to 8-membered heterocyclic ring"), more particularly said heterocyclic ring is a "6-membered heterocyclic ring", which is to be understood as containing 4 carbon atoms and 2 of the above-mentioned heteroatom-containing groups or 5 carbon atoms and one of the above-mentioned heteroatom-containing groups, preferably 4 carbon atoms and 2 of the above-mentioned heteroatom-containing groups.

The term "$C_1$-$C_6$-alkoxy-" is to be understood as preferably meaning a linear or branched, saturated, monovalent, hydrocarbon group of formula —O-alkyl-, in which the term "alkyl-" is defined supra, e.g. a methoxy-, ethoxy-, n-propoxy-, iso-propoxy-, n-butoxy-, iso-butoxy-, tert-butoxy-, sec-butoxy-, pentyloxy-, iso-pentyloxy-, n-hexyloxy-group, or an isomer thereof. Particularly, the "$C_1$-$C_6$-alkoxy-" group is a "$C_1$-$C_4$-alkoxy-", a "$C_1$-$C_3$-alkoxy-", a methoxy-, ethoxy-, or propoxy-group, preferably a methoxy-, ethoxy- or propoxy-group. Further preferred is a "$C_1$-$C_2$-alkoxy-" group, particularly a methoxy- or ethoxy-group.

The term "$C_1$-$C_3$-fluoroalkoxy-" is to be understood as preferably meaning a linear or branched, saturated, monovalent, $C_1$-$C_3$-alkoxy-group, as defined supra, in which one or more of the hydrogen atoms is replaced, identically or differently, by one or more fluorine atoms. Said $C_1$-$C_3$-fluoroalkoxy-group is, for example a 1,1-difluoromethoxy-, a 1,1,1-trifluoromethoxy-, a 2-fluoroethoxy-, a 3-fluoropropoxy-, a 2,2,2-trifluoroethoxy-, a 3,3,3-trifluoropropoxy-, particularly a "$C_1$-$C_2$-fluoroalkoxy-" group.

The term "alkylamino-" is to be understood as preferably meaning an alkylamino group with one linear or branched alkyl-group as defined supra. ($C_1$-$C_3$)-alkylamino- for example means a monoalkylamino-group with 1, 2 oder 3 carbon atoms, ($C_1$-$C_6$)-alkylamino- with 1, 2, 3, 4, 5 or 6 carbon atoms. The term "alkylamino-" comprises for example methylamino-, ethylamino-, n-propylamino-, iso-propylamino-, tert-butylamino-, n-pentylamino- or n-hexylamino-.

The term "dialkylamino-" is to be understood as preferably meaning an alkylamino-group having two linear or branched alkyl-groups as defined supra, which are independent from each other. ($C_1$-$C_3$)-dialkylamino- for example represents a dialkylamino-group with two alkyl-groups each of them having 1 to 3 carbon atoms per alkyl-group. The term "dialkylamino-" comprises for example: N,N-dimethylamino-, N,N-diethylamino-, N-ethyl-N-methylamino-, N-methyl-N-n-propylamino-, N-iso-propyl-N-n-propylamino-, N-tert-butyl-N-methylamino-, N-ethyl-N-n-pentylamino- and N-n-hexyl-N-methylamino-.

The term "cyclic amine" is to be understood as preferably meaning a cyclic amine group. Preferably, a cyclic amine means a saturated, monocyclic group with 4 to 10, preferably 4 to 7 ring atoms of which at least one ring atom is a nitrogen atom. Suitable cyclic amines are especially azetidine, pyrrolidine, piperidine, piperazine, 1-methylpiperazine, morpholine, thiomorpholine, which could be optionally substituted by one or two methyl groups.

The term "halo-$C_1$-$C_3$-alkyl-", or, used synonymously, "$C_1$-$C_3$-haloalkyl-", is to be understood as preferably meaning a linear or branched, saturated, monovalent hydrocarbon group in which the term "$C_1$-$C_3$-alkyl-" is defined supra, and in which one or more hydrogen atoms is replaced by a halogen atom, identically or differently, i.e. one halogen atom being independent from another. Preferably, a halo-$C_1$-$C_3$-alkyl-group is a fluoro-$C_1$-$C_3$-alkyl- or a fluoro-$C_1$-$C_2$-alkyl-group, such as for example —$CF_3$, —$CHF_2$, —$CH_2F$, —$CF_2CF_3$, or —$CH_2CF_3$, more preferably it is —$CF_3$.

The term "hydroxy-$C_1$-$C_3$-alkyl-", is to be understood as preferably meaning a linear or branched, saturated, monovalent hydrocarbon group in which the term "$C_1$-$C_3$-alkyl-" is defined supra, and in which one or more hydrogen atoms is replaced by hydroxy group, preferably not more than one hydrogen atom per carbon atom being replaced by a hydroxy group. Particularly, a hydroxy-$C_1$-$C_3$-alkyl-group is, for example, —$CH_2OH$, —$CH_2$—$CH_2OH$, —C(H)OH—$CH_2OH$, —$CH_2$—$CH_2$—$CH_2OH$.

The term "phenyl-$C_1$-$C_3$-alkyl-" is to be understood as preferably meaning a phenyl group, in which one of the hydrogen atoms is replaced by a $C_1$-$C_3$-alkyl group, as defined supra, which links the phenyl-$C_1$-$C_3$-alkyl-group to the rest of the molecule. Particularly, the "phenyl-$C_1$-$C_3$-alkyl-" is a phenyl-$C_1$-$C_2$-alkyl-, preferably it is a benzyl-group.

The term "heteroaryl-" is to be understood as preferably meaning a monovalent, aromatic ring system having 5, 6, 7, 8, 9, 10, 11, 12, 13 or 14 ring atoms (a "5- to 14-membered heteroaryl-" group), particularly 5 (a "5-membered heteroaryl-") or 6 (a "6-membered heteroaryl-") or 9 (a "9-membered heteroaryl-") or 10 ring atoms (a "10-membered heteroaryl-"), and which contains at least one heteroatom which may be identical or different, said heteroatom being such as oxygen, nitrogen or sulfur, and can be monocyclic, bicyclic, or tricyclic, and in addition in each case can be benzo-condensed. Particularly, heteroaryl- is selected from thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl- etc., and benzo derivatives thereof, such as, for example, benzofuranyl-, benzothienyl-, benzoxazolyl-, benzisoxazolyl-, benzimidazolyl-, benzotriazolyl-, indazolyl-, indolyl-, isoindolyl-, etc.; or pyridyl-, pyridazinyl-, pyrimidinyl-, pyrazinyl-, triazinyl-, etc., and benzo derivatives thereof, such as, for example, quinolinyl-, quinazolinyl-, isoquinolinyl-, etc.; or azocinyl-, indolizinyl-, purinyl-, etc., and benzo derivatives thereof; or cinnolinyl-, phthalazinyl-, quinazolinyl-, quinoxalinyl-, naphthyridinyl-, pteridinyl-, carbazolyl-, acridinyl-, phenazinyl-, phenothiazinyl-, phenoxazinyl-, xanthenyl-, or oxepinyl-, etc. Preferably, heteroaryl- is selected from monocyclic heteroaryl-, 5-membered heteroaryl- or 6-membered heteroaryl-.

The term "5-membered heteroaryl-" is understood as preferably meaning a monovalent, aromatic ring system having 5 ring atoms and which contains at least one heteroatom which may be identical or different, said heteroatom being such as oxygen, nitrogen or sulfur. Particularly, "5-membered heteroaryl-" is selected from thienyl-, furanyl-, pyrrolyl-, oxazolyl-, thiazolyl-, imidazolyl-, pyrazolyl-, isoxazolyl-, isothiazolyl-, oxadiazolyl-, triazolyl-, thiadiazolyl-, tetrazolyl-.

The term "6-membered heteroaryl-" is understood as preferably meaning a monovalent, aromatic ring system having 6 ring atoms and which contains at least one heteroatom which may be identical or different, said heteroatom being such as oxygen, nitrogen or sulfur. Particularly, "6-membered heteroaryl-" is selected from pyridyl-, pyridazinyl-, pyrimidinyl-, pyrazinyl-, triazinyl-.

The term "heteroaryl-$C_1$-$C_3$-alkyl-" is to be understood as preferably meaning a heteroaryl-, a 5-membered heteroaryl- or a 6-membered heteroaryl-group, each as defined supra, in which one of the hydrogen atoms is replaced by a $C_1$-$C_3$-alkyl-group, as defined supra, which links the heteroaryl-$C_1$-$C_3$-alkyl-group to the rest of the molecule. Particularly, the "heteroaryl-$C_1$-$C_3$-alkyl-" is a heteroaryl-$C_1$-$C_2$-alkyl-, a pyridinyl-$C_1$-$C_3$-alkyl-, a pyridinylmethyl-, a pyridinylethyl-, a pyridinylpropyl-, a pyrimidinyl-$C_1$-$C_3$-alkyl-, a pyrimidinylmethyl-, a pyrimidinylethyl-, a pyrimidinylpropyl-, preferably a pyridinylmethyl- or a pyridinylethyl- or a pyrimidinylethyl- or a pyrimidinylpropyl-group.

As used herein, the term "leaving group" refers to an atom or a group of atoms that is displaced in a chemical reaction as stable species taking with it the bonding electrons. Preferably, a leaving group is selected from the group comprising: halo, in particular a chlorine atom, a bromine atom or an iodine atom, methanesulfonyloxy-, p-toluenesulfonyloxy-, trifluoromethanesulfonyloxy-, nonafluorobutanesulfonyloxy-, (4-bromo-benzene)sulfonyloxy-, (4-nitro-benzene)sulfonyloxy-, (2-nitro-benzene)-sulfonyloxy-, (4-isopropyl-benzene)sulfonyloxy-, (2,4,6-tri-isopropyl-benzene)-sulfonyloxy-, (2,4,6-trimethyl-benzene)sulfonyloxy-, (4-tert-butyl-benzene)sulfonyloxy-, benzenesulfonyloxy-, and (4-methoxy-benzene)sulfonyloxy-.

As used herein, the term "$C_1$-$C_3$-alkylbenzene" refers to a partially aromatic hydrocarbon consisting of a benzene ring which is substituted by one or two $C_1$-$C_3$-alkyl-groups, as defined supra. Particularly, "$C_1$-$C_3$-alkylbenzene" is toluene, ethylbenzene, cumene, n-propylbenzene, ortho-xylene, meta-xylene or para-xylene. Preferably, "$C_1$-$C_3$-alkylbenzene" is toluene.

As used herein, the term "carboxamide based solvent" refers to lower aliphatic carboxamides of the formula $C_1$-$C_2$-alkyl-C(=O)—N($C_1$-$C_2$-alkyl)$_2$, or lower cyclic aliphatic carboxamides of the formula

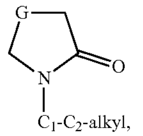

in which G represents —$CH_2$—, —$CH_2$—$CH_2$— or —$CH_2$—$CH_2$—$CH_2$—. Particularly, "carboxamide based solvent" is N,N-dimethylformamide, N,N-dimethylacetamide or N-methylpyrrolidin-2-one. Preferably, "carboxamide based solvent" is N,N-dimethylformamide or N-methylpyrrolidin-2-one.

The term "$C_1$-$C_{10}$", as used throughout this text, e.g. in the context of the definition of "$C_1$-$C_{10}$-alkyl" is to be understood as meaning an alkyl group having a finite number of carbon atoms of 1 to 10, i.e. 1, 2, 3, 4, 5, 6, 7, 8, 9 or 10 carbon atoms. It is to be understood further that said term "$C_1$-$C_{10}$" is to be interpreted as any sub-range comprised therein, e.g. $C_1$-$C_{10}$, $C_1$-$C_9$, $C_1$-$C_8$, $C_1$-$C_7$, $C_1$-$C_6$ $C_1$-$C_5$, $C_1$-$C_4$, $C_1$-$C_3$, $C_1$-$C_2$, $C_2$-$C_{10}$, $C_2$-$C_9$, $C_2$-$C_8$, $C_2$-$C_7$, $C_2$-$C_6$, $C_2$-$C_5$, $C_2$-$C_4$, $C_2$-$C_3$, $C_3$-$C_{10}$, $C_3$-$C_9$, $C_3$-$C_8$, $C_3$-$C_7$, $C_3$-$C_6$, $C_3$-$C_5$, $C_3$-$C_4$, $C_4$-$C_{10}$, $C_4$-$C_9$, $C_4$-$C_8$, $C_4$-$C_7$, $C_4$-$C_6$, $C_4$-$C_5$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$, $C_9$-$C_{10}$.

Similarly, as used herein, the term "$C_1$-$C_6$", as used throughout this text, e.g. in the context of the definition of "$C_1$-$C_6$-alkyl", "$C_1$-$C_6$-alkoxy" is to be understood as meaning an alkyl group having a finite number of carbon atoms of 1 to 6, i.e. 1, 2, 3, 4, 5 or 6 carbon atoms. It is to be understood further that said term "$C_1$-$C_6$" is to be interpreted as any sub-range comprised therein, e.g. $C_1$-$C_6$ $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, $C_5$-$C_6$.

Similarly, as used herein, the term "$C_1$-$C_4$", as used throughout this text, e.g. in the context of the definition of "$C_1$-$C_4$-alkyl", "$C_1$-$C_4$-alkoxy" is to be understood as meaning an alkyl group having a finite number of carbon atoms of 1 to 4, i.e. 1, 2, 3 or 4 carbon atoms. It is to be understood further that said term "$C_1$-$C_4$" is to be interpreted as any sub-range comprised therein, e.g. $C_1$-$C_4$, $C_1$-$C_3$, $C_1$-$C_2$, $C_2$-$C_4$, $C_2$-$C_3$, $C_3$-$C_4$.

Similarly, as used herein, the term "$C_1$-$C_3$", as used throughout this text, e.g. in the context of the definition of "$C_1$-$C_3$-alkyl", "$C_1$-$C_3$-alkoxy" or "$C_1$-$C_3$-fluoroalkoxy" is to be understood as meaning an alkyl group having a finite number of carbon atoms of 1 to 3, i.e. 1, 2 or 3 carbon atoms.

It is to be understood further that said term "$C_1$-$C_3$" is to be interpreted as any sub-range comprised therein, e.g. $C_1$-$C_3$, $C_1$-$C_2$, $C_2$-$C_3$.

Further, as used herein, the term "$C_3$-$C_6$", as used throughout this text, e.g. in the context of the definition of "$C_3$-$C_6$-cycloalkyl", is to be understood as meaning a cycloalkyl group having a finite number of carbon atoms of 3 to 6, i.e. 3, 4, 5 or 6 carbon atoms. It is to be understood further that said term "$C_3$-$C_6$" is to be interpreted as any sub-range comprised therein, e.g. $C_3$-$C_6$, $C_3$-$C_5$, $C_3$-$C_4$, $C_4$-$C_6$, $C_4$-$C_5$, $C_5$-$C_6$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms, particularly 3, 4, 5 or 6 carbon atoms. It is to be understood further that said term "$C_3$-$C_7$" is to be interpreted as any sub-range comprised therein, e.g. $C_3$-$C_7$, $C_3$-$C_6$, $C_3$-$C_5$, $C_3$-$C_4$, $C_4$-$C_7$, $C_4$-$C_6$, $C_4$-$C_5$, $C_5$-$C_7$, $C_5$-$C_6$, $C_6$-$C_7$.

A symbol  at a bond denotes the linkage site in the molecule.

As used herein, the term "one or more times", e.g. in the definition of the substituents of the compounds of the general formulae of the present invention, is understood as meaning one, two, three, four or five times, particularly one, two, three or four times, more particularly one, two or three times, even more particularly one or two times.

Where the plural form of the word compounds, salts, hydrates, solvates and the like, is used herein, this is taken to mean also a single compound, salt, isomer, hydrate, solvate or the like.

In another embodiment, the present invention concerns compounds of general formula (I), wherein A represents a bivalent moiety selected from the group consisting of —S—, —S(═O)—, —S(═O)$_2$—, —S(═O)(═NR$^5$)—; —S(═NR$^6$)(═NR$^7$)—;

Z represents a hydrogen atom or a fluorine atom;

L represents a $C_3$-$C_5$-alkylene moiety,
 wherein said moiety is optionally substituted with
 i) one substituent selected from hydroxy, $C_3$-$C_4$-cycloalkyl-, hydroxy-$C_1$-$C_3$-alkyl-, —(CH$_2$)NR$^8$R$^9$, and/or
 ii) one or two or three substituents, identically or differently, selected from halogen and $C_1$-$C_3$-alkyl-;

X, Y represent CH or N with the proviso that one of X and Y represents CH and one of X and Y represents N;

R$^1$ represents a group selected from $C_1$-$C_6$-alkyl-, $C_3$-$C_5$-cycloalkyl-,
 wherein said group is optionally substituted with one or two or three substituents, identically or differently, selected from the group consisting of hydroxy, cyano, halogen, $C_1$-$C_3$-alkyl-, fluoro-$C_1$-$C_2$-alkyl-, $C_1$-$C_3$-alkoxy-, $C_1$-$C_2$-fluoroalkoxy-, —NH$_2$, alkylamino-, dialkylamino-, cyclic amines, —OP(═O)(OH)$_2$, —C(═O)OH, —C(═O)NH$_2$;

R$^2$ represents a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, $C_1$-$C_2$-fluoroalkoxy-;

R$^3$, R$^4$ represent, independently from each other, a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, $C_1$-$C_2$-fluoroalkoxy-;

R$^5$ represents a group selected from a hydrogen atom, cyano, —C(═O)R$^{10}$, —C(═O)OR$^{10}$, —S(═O)$_2$R$^{10}$, —C(═O)NR$^8$R$^9$, $C_1$-$C_6$-alkyl-, $C_3$-$C_5$-cycloalkyl-,
 wherein said $C_1$-$C_6$-alkyl- or $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —NH$_2$, alkylamino-, dialkylamino-, cyclic amines, fluoro-$C_1$-$C_2$-alkyl-, $C_1$-$C_2$-fluoroalkoxy-;

R$^6$, R$^7$ represent, independently from each other, a group selected from a hydrogen atom, cyano, —C(═O)R$^{10}$, —C(═O)OR$^{10}$, —S(═O)$_2$R$^{10}$, —C(═O)NR$^8$R$^9$, $C_1$-$C_6$-alkyl-, $C_3$-$C_5$-cycloalkyl-,
 wherein said $C_1$-$C_6$-alkyl- or $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —NH$_2$, alkylamino-, dialkylamino-, cyclic amines, fluoro-$C_1$-$C_2$-alkyl-, $C_1$-$C_2$-fluoroalkoxy-;

R$^8$, R$^9$ represent, independently from each other, a group selected from a hydrogen atom, $C_1$-$C_6$-alkyl-, $C_3$-$C_5$-cycloalkyl-, phenyl- and benzyl-,
 wherein said $C_1$-$C_6$-alkyl-, $C_3$-$C_5$-cycloalkyl-, phenyl- or benzyl-group is optionally substituted with one, two or three substituents, identically or differently, selected from the group consisting of halogen, hydroxy, $C_1$-$C_3$-alkyl-, $C_1$-$C_3$-alkoxy-, —NH$_2$, alkylamino-, dialkylamino-, cyclic amines, fluoro-$C_1$-$C_2$-alkyl-, $C_1$-$C_2$-fluoroalkoxy-, or R$^8$ and R$^9$, together with the nitrogen atom they are attached to, form a cyclic amine;

R$^{10}$ represents a group selected from $C_1$-$C_6$-alkyl-, fluoro-$C_1$-$C_3$-alkyl-, $C_3$-$C_5$-cycloalkyl-, phenyl-, and benzyl-,
 wherein said group is optionally substituted with one, two or three substituents, identically or differently, selected from the group consisting of halogen, hydroxy, $C_1$-$C_3$-alkyl-, $C_1$-$C_3$-alkoxy-, —NH$_2$, alkylamino-, dialkylamino-, cyclic amines, fluoro-$C_1$-$C_2$-alkyl-, $C_1$-$C_2$-fluoroalkoxyor the enantiomers, diastereomers, salts, solvates or salts of solvates thereof.

In another embodiment, the present invention concerns compounds of general formula (I), wherein A represents a bivalent moiety selected from the group consisting of —S—, —S(═O)—, —S(═O)$_2$—, —S(═O)(═NR$^5$)—; —S(═NR$^6$)(═NR$^7$)—;

Z represents a hydrogen atom or a fluorine atom;

L represents a $C_3$-$C_5$-alkylene moiety,
 wherein said moiety is optionally substituted with
 (i) one substituent selected from $C_3$-$C_4$-cycloalkyl-, hydroxymethyl, and/or
 (ii) one or two or three $C_1$-$C_2$-alkyl-group substituents, identically or differently;

X, Y represent CH or N with the proviso that one of X and Y represents CH and one of X and Y represents N;

R$^1$ represents a group selected from $C_1$-$C_4$-alkyl-, $C_3$-$C_5$-cycloalkyl-,
 wherein said group is optionally substituted with one or two or three substituents, identically or differently, selected from the group consisting of hydroxy, cyano, halogen, $C_1$-$C_2$-alkyl-, $C_1$-$C_2$-alkoxy-, —NH$_2$, —C(═O)OH;

R$^2$ represents a group selected from a hydrogen atom, a fluorine atom, a chlorine atom, cyano, methyl-, methoxy-, trifluoromethyl-, trifluoromethoxy-;

R$^3$ represents a group selected from a hydrogen atom, a fluorine atom, a chlorine atom, cyano, methyl-, methoxy-, trifluoromethyl-, trifluoromethoxy-;

$R^4$ represents a hydrogen atom or a fluorine atom;

$R^5$ represents a group selected from a hydrogen atom, cyano, —C(=O)$R^{10}$, —C(=O)O$R^{10}$, —S(=O)$_2R^{10}$, —C(=O)N$R^8R^9$, $C_1$-$C_4$-alkyl-, wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, cyclic amines;

$R^6$, $R^7$ represent, independently from each other, a group selected from a hydrogen atom, cyano, —C(=O)$R^{10}$, —C(=O)O$R^{10}$, —S(=O)$_2R^{10}$, —C(=O)N$R^8R^9$, $C_1$-$C_4$-alkyl-, wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, cyclic amines;

$R^8$, $R^9$ represent, independently from each other, a group selected from a hydrogen atom, $C_1$-$C_4$-alkyl- and $C_3$-$C_5$-cycloalkyl-;

wherein said $C_1$-$C_4$-alkyl- or $C_3$-$C_5$-cycloalkyl-group is optionally substituted with one or two substituents, identically or differently, selected from the group consisting of hydroxy, $C_1$-$C_2$-alkyl-, $C_1$-$C_2$-alkoxy-, —$NH_2$, alkylamino-, dialkylamino-, cyclic amines, or $R^8$ and $R^9$, together with the nitrogen atom they are attached to, form a cyclic amine;

$R^{10}$ represents a group selected from $C_1$-$C_6$-alkyl-, fluoro-$C_1$-$C_3$-alkyl-, $C_3$-$C_5$-cycloalkyl- and benzyl-, wherein said group is optionally substituted with one substituent selected from the group consisting of halogen, hydroxy, $C_1$-$C_2$-alkyl-, $C_1$-$C_2$-alkoxy-, —$NH_2$, or the enantiomers, diastereomers, salts, solvates or salts of solvates thereof.

In a preferred embodiment, the present invention concerns compounds of general formula (I), wherein A represents a bivalent moiety selected from the group consisting of —S—, —S(=O)—, —S(=O)$_2$—, —S(=O)(=N$R^5$)—, —S(=N$R^6$)(=N$R^7$)—;

Z represents a hydrogen atom or a fluorine atom;

L represents a $C_3$-$C_5$-alkylene moiety;

X, Y represent CH or N with the proviso that one of X and Y represents CH and one of X and Y represents N;

$R^1$ represents a $C_1$-$C_4$-alkyl-group, wherein said group is optionally substituted with one or two substituents, identically or differently, selected from the group consisting of hydroxy, $C_1$-$C_2$-alkoxy-, —$NH_2$, —C(=O)OH;

$R^2$ represents a hydrogen atom or a fluorine atom;

$R^3$ represents a group selected from a hydrogen atom, a fluorine atom and a methoxy-group;

$R^4$ represents a hydrogen atom;

$R^5$ represents a group selected from a hydrogen atom, cyano, —C(=O)$R^{10}$, —C(=O)O$R^{10}$, —C(=O)N$R^8R^9$, $C_1$-$C_4$-alkyl-, wherein said $C_1$-$C_4$-alkyl-group is optionally substituted with one substituent selected from the group consisting of hydroxy, cyano, $C_1$-$C_3$-alkoxy-, —$NH_2$, alkylamino-, dialkylamino-;

$R^6$, $R^7$ represent, independently from each other, a group selected from a hydrogen atom, cyano, $C_1$-$C_4$-alkyl-, wherein said $C_1$-$C_4$-alkyl-group is optionally substituted with one hydroxy group;

$R^8$, $R^9$ represent, independently from each other, a group selected from a hydrogen atom, $C_1$-$C_4$-alkyl- and $C_3$-$C_5$-cycloalkyl-, or $R^8$ and $R^9$, together with the nitrogen atom they are attached to, form a cyclic amine;

$R^{10}$ represents a group selected from $C_1$-$C_6$-alkyl-, fluoro-$C_1$-$C_3$-alkyl-, $C_3$-$C_5$-cycloalkyl- and benzyl-, wherein said group is optionally substituted with one substituent selected from the group consisting of halogen, hydroxy, $C_1$-$C_2$-alkyl-, $C_1$-$C_2$-alkoxy-, —$NH_2$, or the enantiomers, diastereomers, salts, solvates or salts of solvates thereof.

In another preferred embodiment, the present invention concerns compounds of general formula (I), wherein A represents a bivalent moiety selected from the group consisting of —S(=O)$_2$—, —S(=O)(=N$R^5$)—, —S(=N$R^6$)(=N$R^7$)—;

Z represents a hydrogen atom or a fluorine atom;

L represents a $C_3$-$C_5$-alkylene moiety,

X, Y represent CH or N with the proviso that one of X and Y represents CH and one of X and Y represents N;

$R^1$ represents a methyl-group;

$R^2$ represents a hydrogen atom;

$R^3$ represents a group selected from a hydrogen atom or a fluorine atom;

$R^4$ represents a hydrogen atom;

$R^5$ represent a group selected from a hydrogen atom, cyano, —C(=O)$R^{10}$, —C(=O)O$R^{10}$, $C_1$-$C_4$-alkyl-, wherein said $C_1$-$C_4$-alkyl-group is optionally substituted with one substituent selected from the group consisting of hydroxy, cyano, $C_1$-$C_3$-alkoxy-, —$NH_2$, alkylamino-, dialkylamino-;

$R^6$, $R^7$ represents, independently from each other, a group selected from a hydrogen atom, cyano, $C_1$-$C_4$-alkyl-, wherein said $C_1$-$C_4$-alkyl-group is optionally substituted with one hydroxy group; $R^8$, $R^9$ represent, independently from each other, a group selected from a hydrogen atom, $C_1$-$C_2$-alkyl;

$R^{10}$ represents a $C_1$-$C_4$-alkyl group, or the enantiomers, diastereomers, salts, solvates or salts of solvates thereof.

In another preferred embodiment, the present invention concerns compounds of general formula (I), wherein A represents a bivalent moiety selected from the group consisting of —S—, —S(=O)—, —S(=O)$_2$—, —S(=O)(=N$R^5$)—;

Z represents a hydrogen atom or a fluorine atom;

L represents a $C_3$-$C_5$-alkylene moiety;

X, Y represent CH or N with the proviso that one of X and Y represents CH and one of X and Y represents N;

$R^1$ represents a $C_1$-$C_3$-alkyl-group;

$R^2$ represents a hydrogen atom or a fluorine atom;

$R^3$ represents a group selected from a hydrogen atom, a fluorine atom and a methoxy-group;

$R^4$ represents a hydrogen atom;

$R^5$ represents a group selected from a hydrogen atom, cyano, —C(=O)$R^{10}$, —C(=O)O$R^{10}$, $C_1$-$C_3$-alkyl-;

$R^6$, $R^7$ represent, independently from each other, a group selected from a hydrogen atom, cyano, —C(=O)$R^{10}$, —C(=O)O$R^{10}$, $C_1$-$C_3$-alkyl-;

$R^{10}$ represents a group selected from $C_1$-$C_4$-alkyl-, trifluoromethyl- and benzyl-, or the enantiomers, diastereomers, salts, solvates or salts of solvates thereof.

In another preferred embodiment, the present invention concerns compounds of general formula (I), wherein A represents a bivalent moiety selected from the group consisting of —S—, —S(=O)—, —S(=O)$_2$—, —S(=O)(=N$R^5$)—, —S(=N$R^6$)(=N$R^7$)—;

Z represents a group selected from a hydrogen atom and a fluorine atom;

L represents a $C_4$-$C_5$-alkylene moiety;

X, Y represent CH or N with the proviso that one of X and Y represents CH and one of X and Y represents N;
$R^1$ represents a methyl-group;
$R^2$ represents a hydrogen atom;
$R^3$ represents a hydrogen atom or a fluorine atom;
$R^4$ represents a hydrogen atom;
$R^5$ represents a group selected from a hydrogen atom, —C(═O)$OR^{10}$;
$R^6$, $R^7$ represent, independently from each other, a group selected from a hydrogen atom, —C(═O)$OR^{10}$;
$R^{10}$ represents a group selected from tert-butyl- and benzyl-,
the enantiomers, diastereomers, salts, solvates or salts of solvates thereof.

In another preferred embodiment, the present invention concerns compounds of general formula (I), wherein
Z represents a group selected from a hydrogen atom and a fluorine atom,
$R^3$ represents a fluorine atom, and
$R^4$ represents a hydrogen atom,
or the enantiomers, diastereomers, salts, solvates or salts of solvates thereof.

In another preferred embodiment, the present invention concerns compounds of general formula (I), wherein
A represents a bivalent moiety —S(═O)(═$NR^5$)—;
Z represents a group selected from a hydrogen atom and a fluorine atom,
L represents a $C_3$-$C_5$-alkylene moiety;
X, Y represent CH or N with the proviso that one of X and Y represents CH and one of X and Y represents N;
$R^1$ represents a methyl-group;
$R^2$ represents a hydrogen atom;
$R^3$ represents a fluorine atom;
$R^4$ represents a hydrogen atom;
$R^5$ represents a hydrogen atom or a —C(═O)$OR^{10}$— group;
$R^{10}$ represents a tertbutyl-group;
or the enantiomers, diastereomers, salts, solvates or salts of solvates thereof.

In particular, a preferred subject of the present invention is a compound selected from:
(rac)-tert-butyl [{[3,20-difluoro-13,18-dioxa-5,7,24-triazatetracyclo[17.3.1.$1^{2,6}$.$1^{8,12}$]pentacosa-1(23),2(25),3,5,8(24),9,11,19,21-nonaen-10-yl]methyl}(methyl)oxido-$\lambda^6$-sulfanylidene]carbamate
(rac)-3,20-difluoro-10-[(S-methylsulfonimidoyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
(rac)-tert-butyl [{[3,20-difluoro-13,18-dioxa-5,7,25-triazatetracyclo[17.3.1.$1^{2,6}$.$1^{8,12}$]pentacosa-1(23),2(25),3,5,8(24),9,11,19,21-nonaen-10-yl]methyl}(methyl)oxido-$\lambda^6$-sulfanylidene]carbamate
(rac)-3,20-difluoro-10-[(S-methylsulfonimidoyl)methyl]-13,18-dioxa-5,7,25-triazatetracyclo[17.3.1.$1^{2,6}$.$1^{8,12}$]pentacosa-1(23),2(25),3,5,8(24),9,11,19,21-nonaene
(rac)-tert-butyl [{[3,21-difluoro-13,19-dioxa-5,7,26-triazatetracyclo[18.3.1.$1^{2,6}$.$1^{8,12}$]hexacosa-1(24),2(26),3,5,8(25),9,11,20,22-nonaen-10-yl]methyl}(methyl)oxido-$\lambda^6$-sulfanylidene]carbamate
(rac)-3,21-difluoro-10-[(S-methylsulfonimidoyl)methyl]-13,19-dioxa-5,7,26-triazatetracyclo[18.3.1.$1^{2,6}$.$1^{8,12}$]hexacosa-1(24),2(26),3,5,8(25),9,11,20,22-nonaene
(rac)-tert-butyl [methyl(oxido){[3,20,23-trifluoro-13,18-dioxa-5,7,25-triazatetracyclo[1.7.3.1.$1^{2,6}$.$1^{8,12}$]pentacosa-1(23),2(25),3,5,8(24),9,11,19,21-nonaen-10-yl]methyl}-$1\lambda^6$-sulfanylidene]carbamate
(rac)-3,20,23-trifluoro-10-[(S-methylsulfonimidoyl)methyl]-13,18-dioxa-5,7,25-triazatetracyclo[17.3.1.$1^{2,6}$.$1^{8,12}$]pentacosa-1(23),2(25),3,5,8(24),9,11,19,21-nonaene
(rac)-tert-butyl [{[3,19-difluoro-13,17-dioxa-5,7,24-triazatetracyclo[16.3.1.$1^{2,6}$.$1^{8,12}$]tetracosa-1(22),2(24),3,5,8(23),9,11,18,20-nonaen-10-yl]methyl}(methyl)oxido-$\lambda^6$-sulfanylidene]carbamate
(rac)-3,19-difluoro-10-[(S-methylsulfonimidoyl)methyl]-13,17-dioxa-5,7,24-triazatetracyclo[16.3.1.$1^{2,6}$.$1^{8,12}$]tetracosa-1(22),2(24),3,5,8(23),9,11,18,20-nonaene
(rac)-3,20-difluoro-14-methyl-10-[(methylsulfanyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
Enantiomer 1 of (rac)-3,20-difluoro-14-methyl-10-[(methylsulfanyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
Enantiomer 2 of (rac)-3,20-difluoro-14-methyl-10-[(methylsulfanyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
Diastereoisomer 1 of 3,20-difluoro-14-methyl-10-[(S-methylsulfonimidoyl)methyl]-13,18-dioxa-5,7,24-triazatetracyclo[1.7.3.1.$1^{2,6}$.$1^{8,12}$]pentacosa-1(23),2(25),3,5,8(24),9,11,19,21-nonaene
Diastereoisomer 2 of 3,20-difluoro-14-methyl-10-[(S-methylsulfonimidoyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
Diastereoisomer 3 of 3,20-difluoro-14-methyl-10-[(S-methylsulfonimidoyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
Diastereoisomer 4 of 3,20-difluoro-14-methyl-10-[(S-methylsulfonimidoyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene
(rac)-3,21-difluoro-14-methyl-10-[(methylsulfanyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene
Enantiomer 1 of 3,21-difluoro-14-methyl-10-[(methylsulfanyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene
Enantiomer 2 of 3,21-difluoro-14-methyl-10-[(methylsulfanyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene
Mixture of diastereoisomers 1 and 2 of 3,21-difluoro-14-methyl-10-[(S-methylsulfonimidoyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene
Mixture of diastereoisomers 3 and 4 of 3,21-difluoro-14-methyl-10-[(S-methylsulfonimidoyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene
(rac)-3,22-difluoro-14-methyl-10-[(methylsulfanyl)methyl]-13,20-dioxa-5,7,26-triazatetracyclo[19.3.1.$1^{2,6}$.$1^{8,12}$]heptacosa-1(25),2(27),3,5,8(26),9,11,21,23-nonaene
Enantiomer 1 of 3,22-difluoro-14-methyl-10-[(methylsulfanyl)methyl]-13,20-dioxa-5,7,26-triazatetracyclo[19.3.1.$1^{2,6}$.$1^{8,12}$]heptacosa-1(25),2(27),3,5,8(26),9,11,21,23-nonaene Enantiomer 2 of 3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene Mixture of diastereoisomers 1 and 2 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene Mixture of diastereoisomers 3 and 4 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene Mixture of enantiomers of 3,20-difluoro-14-methyl-10-[(methylsulfonyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene Enantiomer 1 of 3,21-difluoro-14-methyl-10-[(methylsulfonyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene Enantiomer 2 of 3,21-difluoro-14-methyl-10-[(methylsulfonyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene Enantiomer 1 of 3,22-difluoro-14-methyl-10-[(methylsulfonyl)methyl]-13,20-dioxa-5,7,26-triazatetracyclo[19.3.1.1$^{2,6}$.1$^{8,12}$]hexacosa-1 (25),2(27),3,5,8(26),9,11,21,23-nonaene Enantiomer 2 of 3,22-difluoro-14-methyl-10-[(methylsulfonyl)methyl]-13,20-dioxa-5,7,26-triazatetracyclo[19.3.1.1$^{2,6}$.1$^{8,12}$]hexacosa-1 (25),2(27),3,5,8(26),9,11,21,23-nonaene and the enantiomers, diastereomers, salts, solvates or salts of solvates thereof.

The invention relates to compounds of formula (I), in which A represents a bivalent moiety selected from the group consisting of —S—, —S(═O)—, —S(═O)$_2$—, —S(═O)(═NR$^5$)—; —S(═NR$^6$)(═NR$^7$)—.

In another embodiment the invention relates to compounds of formula (I), in which A represents a bivalent moiety —S(═O)$_2$—, —S(═O)(═NR$^5$)—, —S(═NR$^6$)(═NR$^7$)—.

In another embodiment the invention relates to compounds of formula (I), in which A represents a bivalent moiety selected from the group consisting of —S—, —S(═O)—, —S(═O)$_2$—, —S(═O)(═NR$^5$)—.

In a preferred embodiment the invention relates to compounds of formula (I), in which A represents a bivalent moiety selected from the group consisting of —S—, —S(═O)—, —S(═O)(═NR$^5$)—, —S(═NR$^6$)(═NR$^7$)—.

In another preferred embodiment the invention relates to compounds of formula (I), in which A represents a bivalent moiety —S(═O)(═NR$^5$)—, —S(═NR$^6$)(═NR$^7$)—.

In another preferred embodiment the invention relates to compounds of formula (I), in which A represents a bivalent moiety —S(═NR$^6$)(═NR$^7$)—.

In another preferred embodiment the invention relates to compounds of formula (I), in which A represents a bivalent moiety —S(═NH)(═NH)—.

In another preferred embodiment the invention relates to compounds of formula (I), in which A represents a bivalent moiety —S(═O)$_2$—.

In another preferred embodiment the invention relates to compounds of formula (I), in which A represents a bivalent moiety —S(═O)(═NR$^5$)—.

In another preferred embodiment the invention relates to compounds of formula (I), in which A represents a bivalent moiety —S(═O)(═N—C(═O)O—C(CH$_3$)$_3$)—.

In another preferred embodiment the invention relates to compounds of formula (I), in which A represents a bivalent moiety —S(═O)(═NCH$_3$)—.

In another preferred embodiment the invention relates to compounds of formula (I), in which A represents a bivalent moiety —S(═O)(═NH)—.

In another embodiment the invention relates to compounds of formula (I), in which Z represents a hydrogen atom or a fluorine atom.

In a preferred embodiment the invention relates to compounds of formula (I), in which Z represents a fluorine atom.

In another preferred embodiment the invention relates to compounds of formula (I), in which Z represents a hydrogen atom.

The invention relates to compounds of formula (I), in which L represents a $C_3$-$C_5$ alkylene moiety, wherein said moiety is optionally substituted with i) one substituent selected from hydroxy, —NR$^8$R$^9$, $C_2$-$C_3$-alkenyl-, $C_2$-$C_3$-alkynyl-, $C_3$-$C_4$ cycloalkyl-, hydroxy-$C_1$-$C_3$-alkyl, —(CH$_2$)NR$^8$R$^9$, and/or ii) one or two or three or four substituents, identically or differently, selected from halogen and $C_1$-$C_3$-alkyl-, or wherein one carbon atom of said $C_3$-$C_8$-alkylene moiety forms a three- or four-membered ring together with a bivalent moiety to which it is attached, wherein said bivalent moiety is selected from —CH$_2$CH$_2$—, —CH$_2$CH$_2$CH$_2$—, —CH$_2$OCH$_2$—.

In a another embodiment the invention relates to compounds of formula (I), in which L represents a $C_3$-$C_5$-alkylene moiety, wherein said moiety is optionally substituted with i) one substituent selected from hydroxy, $C_3$-$C_4$-cycloalkyl-, hydroxy-$C_1$-$C_3$-alkyl-, —(CH$_2$)NR$^8$R$^9$, and/or ii) one or two or three substituents, identically or differently, selected from halogen and $C_1$-$C_3$-alkyl-.

In a another embodiment the invention relates to compounds of formula (I), in which L represents a $C_3$-$C_5$-alkylene moiety, wherein said moiety is optionally substituted with (i) one substituent selected from $C_3$-$C_4$-cycloalkyl-, hydroxymethyl, and/or (ii) one or two or three substituents, identically or differently, selected from $C_1$-$C_2$-alkyl-.

In a preferred embodiment the invention relates to compounds of formula (I), in which L represents a $C_3$-$C_5$-alkylene moiety.

In a particularly preferred embodiment the invention relates to compounds of formula (I), in which L represents a $C_4$-$C_5$-alkylene moiety.

In another particularly preferred embodiment the invention relates to compounds of formula (I), in which L represents a moiety —CH$_2$CH$_2$CH$_2$—, —CH$_2$CH$_2$CH$_2$CH$_2$— or —CH$_2$CH$_2$CH$_2$CH$_2$CH$_2$—.

In another particularly preferred embodiment the invention relates to compounds of formula (I), in which L represents a moiety —CH$_2$CH$_2$CH$_2$—.

In another particularly preferred embodiment the invention relates to compounds of formula (I), in which L represents a moiety —CH$_2$CH$_2$CH$_2$CH$_2$—.

In another particularly preferred embodiment the invention relates to compounds of formula (I), in which L represents a moiety —CH$_2$CH$_2$CH$_2$CH$_2$CH$_2$—.

The invention relates to compounds of formula (I, in which X, Y represent CH or N with the proviso that one of X and Y represents CH and one of X and Y represents N.

In another embodiment the invention relates to compounds of formula (I), in which X represents N, and in which Y represents CH.

In another embodiment the invention relates to compounds of formula (I), in which X represents CH, and in which Y represents N.

The invention relates to compounds of formula (I), in which $R^1$ represents a group selected from $C_1$-$C_6$-alkyl-, $C_3$-$C_6$-alkenyl-, $C_3$-$C_7$-cycloalkyl-, heterocyclyl-,
wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amines, —OP(=O)$(OH)_2$, —C(=O)OH, —C(=O)$NH_2$.

In another embodiment the invention relates to compounds of formula (I), in which $R^1$ represents a group selected from $C_1$-$C_6$-alkyl-, $C_3$-$C_5$-cycloalkyl-,
wherein said group is optionally substituted with one or two or three substituents, identically or differently, selected from the group consisting of hydroxy, cyano, halogen, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amines, —OP(=O)$(OH)_2$, —C(=O)OH, —C(=O)$NH_2$.

In a preferred embodiment the invention relates to compounds of formula (I), in which $R^1$ represents a group selected from $C_1$-$C_4$-alkyl-, $C_3$-$C_5$-cycloalkyl-,
wherein said group is optionally substituted with one or two or three substituents, identically or differently, selected from the group consisting of hydroxy, cyano, halogen, $C_1$-$C_2$-alkyl-, $C_1$-$C_2$-alkoxy-, —$NH_2$, —C(=O)OH.

In a preferred embodiment the invention relates to compounds of formula (I), in which $R^1$ represents a $C_1$-$C_4$-alkyl-group,
wherein said group is optionally substituted with one or two substituents, identically or differently, selected from the group consisting of hydroxy, $C_1$-$C_2$-alkoxy-, —$NH_2$, —C(=O)OH.

In a preferred embodiment the invention relates to compounds of formula (I), in which $R^1$ represents a $C_1$-$C_4$-alkyl-group.

In another preferred embodiment the invention relates to compounds of formula (I), in which $R^1$ represents a $C_1$-$C_3$-alkyl-group.

In another particularly preferred embodiment the invention relates to compounds of formula (I), in which $R^1$ represents a $C_1$-$C_2$-alkyl-group.

In another particularly preferred embodiment the invention relates to compounds of formula (I), in which $R^1$ represents a methyl-group.

In another particularly preferred embodiment the invention relates to compounds of formula (I), in which $R^1$ represents a $C_1$-$C_4$-alkyl-group, and $R^2$ represents a hydrogen atom or a fluoro atom.

In another particularly preferred embodiment the invention relates to compounds of formula (I), in which $R^1$ represents a $C_1$-$C_4$-alkyl-group, and $R^2$ represents a hydrogen atom.

In another particularly preferred embodiment the invention relates to compounds of formula (I), in which $R^1$ represents a methyl group, and $R^2$ represents a hydrogen atom.

$R^1$ is bound in all compounds according to the present invention to the sulfur atom of the group A.

The invention relates to compounds of formula (I), in which $R^2$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^2$ represents a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In a preferred embodiment the invention relates to compounds of formula (I), in which $R^2$ represents a group selected from a hydrogen atom, a fluorine atom, a chlorine atom, cyano, methyl-, methoxy-, trifluoromethyl-, trifluoromethoxy-.

In another preferred embodiment the invention relates to compounds of formula (I), in which $R^2$ represents a hydrogen atom or a fluorine atom.

In a particularly preferred embodiment the invention relates to compounds of formula (I), in which $R^2$ represents a fluorine atom.

In another particularly preferred embodiment the invention relates to compounds of formula (I), in which $R^2$ represents a hydrogen atom.

In another particularly preferred embodiment the invention relates to compounds of formula (I), in which $R^2$ represents a hydrogen atom, $R^3$ represents a fluorine atom, $R^4$ represents a hydrogen atom and Z represents a hydrogen atom.

In another particularly preferred embodiment the invention relates to compounds of formula (I), in which $R^1$ represents a methyl-group, $R^2$ represents a hydrogen atom, $R^3$ represents a fluorine atom, $R^4$ represents a hydrogen atom and Z represents a hydrogen atom.

The invention relates to compounds of formula (I), in which $R^3$, $R^4$ represent, independently from each other, a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, $C_1$-$C_3$-fluoroalkoxy-.

In another embodiment the invention relates to compounds of formula (I), in which $R^3$, $R^4$ represent, independently from each other, a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, $C_1$-$C_2$-fluoroalkoxy-.

In another embodiment the invention relates to compounds of formula (I), in which $R^3$, $R^4$ represent, independently from each other, a group selected from a hydrogen atom, a fluorine atom, a chlorine atom, cyano, methyl-, methoxy-, trifluoromethyl-, trifluoromethoxy-.

In another embodiment the invention relates to compounds of formula (I), in which $R^3$, $R^4$ represent, independently from each other, a group selected from a hydrogen atom or a fluorine atom.

In another embodiment the invention relates to compounds of formula (I), in which $R^3$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, $C_1$-$C_3$-fluoroalkoxy and in which $R^4$ represents a hydrogen atom or a fluorine atom.

In another embodiment the invention relates to compounds of formula (I), in which $R^3$ represents a group selected from a hydrogen atom, a fluorine atom, a chlorine atom, a bromine atom, cyano, $C_1$-$C_2$-alkyl-, $C_1$-$C_2$-alkoxy-, halo-$C_1$-$C_2$-alkyl-, $C_1$-$C_2$-fluoroalkoxy and in which $R^4$ represents a hydrogen atom.

In another embodiment the invention relates to compounds of formula (I), in which $R^3$ represents a group selected from a hydrogen atom, a fluorine atom, a chlorine atom, cyano, methyl-, methoxy-, trifluoromethyl-, trifluoromethoxy- and in which $R^4$ represents a hydrogen atom.

In another embodiment the invention relates to compounds of formula (I), in which $R^3$ represents a group selected from a hydrogen atom, a fluorine atom and a methoxy-group an in which $R^4$ represents a hydrogen atom.

In another embodiment the invention relates to compounds of formula (I), in which $R^3$ represents a group selected from a hydrogen atom or a fluorine atom and in which $R^4$ represents a hydrogen atom.

In another embodiment the invention relates to compounds of formula (I), in which $R^3$ represents a fluorine atom and in which $R^4$ represents a hydrogen atom.

In a preferred embodiment the invention relates to compounds of formula (I), in which $R^3$ represents a group selected from a hydrogen atom, a fluorine atom, a chlorine atom, cyano, methyl-, methoxy-, trifluoromethyl-, trifluoromethoxy-.

In a particularly preferred embodiment the invention relates to compounds of formula (I), in which $R^3$ represents a hydrogen atom or a fluorine atom.

In another particularly preferred embodiment the invention relates to compounds of formula (I), in which $R^3$ represents a fluorine atom.

In another particularly preferred embodiment the invention relates to compounds of formula (I), in which $R^3$ represents a hydrogen atom.

In a preferred embodiment the invention relates to compounds of formula (I), in which $R^4$ represents a group selected from a hydrogen atom, a fluorine atom, a chlorine atom, cyano, methyl-, methoxy-, trifluoromethyl-, trifluoromethoxy-.

In a particularly preferred embodiment the invention relates to compounds of formula (I), in which $R^4$ represents a hydrogen atom or a fluorine atom.

In another particularly preferred embodiment the invention relates to compounds of formula (I), in which $R^4$ represents a fluorine atom.

In another particularly preferred embodiment the invention relates to compounds of formula (I), in which $R^4$ represents a hydrogen atom.

In another embodiment the invention relates to compounds of formula (I), in which $R^3$ represents a group selected from a hydrogen atom, a fluorine atom, a chlorine atom, cyano, methyl-, methoxy-, trifluoromethyl-, trifluoromethoxy-, in which $R^4$ represents a hydrogen atom, and in which Z represents a hydrogen atom or a fluorine atom,
wherein $R^3$ is attached in para-position to the ring directly bonded to the phenyl-ring to which $R^3$ is attached, which is a pyridine ring if Y represents CH and a pyrimidine ring if Y represents N.

In a preferred embodiment the invention relates to compounds of formula (I), in which $R^3$ represents a hydrogen atom or a fluorine atom, in which $R^4$ represents a hydrogen atom, and in which Z represents a hydrogen atom or a fluorine atom,
wherein $R^3$ is attached in para-position to the ring directly bonded to the phenyl-ring to which $R^3$ is attached, which is a pyridine ring if Y represents CH and a pyrimidine ring if Y represents N.

In a particularly preferred embodiment the invention relates to compounds of formula (I), in which $R^3$ represents a fluorine atom, in which $R^4$ represents a hydrogen atom, and in which Z represents a hydrogen atom,
wherein $R^3$ is attached in para-position to the ring directly bonded to the phenyl-ring to which $R^3$ is attached, which is a pyridine ring if Y represents CH and a pyrimidine ring if Y represents N.

In a preferred embodiment the invention relates to compounds of formula (I), in which $R^3$ represents a fluorine atom, in which $R^4$ represents a hydrogen atom, and in which Z represents a hydrogen atom.

In another particularly preferred embodiment the invention relates to compounds of formula (I), in which $R^3$ represents a fluorine atom,
wherein $R^3$ is attached in para-position to the ring directly bonded to the phenyl-ring to which $R^3$ is attached, which is a pyridine ring if Y represents CH and a pyrimidine ring if Y represents N.

The invention relates to compounds of formula (I), in which $R^5$ represents a group selected from a hydrogen atom, cyano, —C(═O)$R^{10}$, —C(═O)O$R^{10}$, —S(═$O_2$)$R^{10}$, —C(═O)N$R^8R^9$, $C_1$-$C_6$-alkyl-, $C_3$-$C_7$-cycloalkyl-, heterocyclyl-,
wherein said $C_1$-$C_6$-alkyl-, $C_3$-$C_7$-cycloalkyl- and heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^5$ represents a group selected from a hydrogen atom, cyano, —C(═O)$R^{10}$, —C(═O)O$R^{10}$, —S(═O)$_2R^{10}$, —C(═O)N$R^8R^9$, $C_1$-$C_6$-alkyl-, $C_3$-$C_5$-cycloalkyl-,
wherein said $C_1$-$C_6$-alkyl- and $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In a preferred embodiment the invention relates to compounds of formula (I), in which $R^5$ represents a group selected from a hydrogen atom, cyano, —C(═O)$R^{10}$, —C(═O)O$R^{10}$, —S(═O)$_2R^{10}$, —C(═O)N$R^8R^9$, $C_1$-$C_4$-alkyl-,
wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, cyclic amines.

In another preferred embodiment the invention relates to compounds of formula (I), in which $R^5$ represents a group selected from a hydrogen atom, cyano, —C(═O)$R^{10}$, —C(═O)O$R^{10}$, —C(═O)N$R^8R^9$, $C_1$-$C_4$-alkyl-, wherein said $C_1$-$C_4$-alkyl-group is optionally substituted with one substituent selected from the group consisting of hydroxy, cyano, $C_1$-$C_3$-alkoxy-, —$NH_2$, alkylamino-, dialkylamino-.

In another preferred embodiment the invention relates to compounds of formula (I), in which $R^5$ represents a group selected from a hydrogen atom, cyano, —C(═O)$R^{10}$, —C(═O)O$R^{10}$, $C_1$-$C_4$-alkyl-,
wherein said $C_1$-$C_4$-alkyl-group is optionally substituted with one substituent selected from the group consisting of hydroxy, cyano, $C_1$-$C_3$-alkoxy-, —$NH_2$, alkylamino-, dialkylamino-.

In a preferred embodiment the invention relates to compounds of formula (I), in which $R^5$ represents a group selected from a hydrogen atom, cyano, —C(═O)$R^{10}$, —C(═O)O$R^{10}$, —S(═O)$_2R^{10}$, —C(═O)N$R^8R^9$, $C_1$-$C_4$-alkyl-.

In a preferred embodiment the invention relates to compounds of formula (I), in which $R^5$ represents a group selected from a hydrogen atom, —C(═O)$R^{10}$, —C(═O)O$R^{10}$, —S(═O)$_2R^{10}$, —C(═O)N$R^8R^9$, $C_1$-$C_4$-alkyl-.

In a particularly preferred embodiment the invention relates to compounds of formula (I), in which $R^5$ represents a group selected from a hydrogen atom, —C(═O)$R^{10}$, —C(═O)O$R^{10}$, —S(═O)$_2R^{10}$, —C(═O)N$R^8R^9$, methyl-.

In another preferred embodiment the invention relates to compounds of formula (I), in which $R^5$ represents a —C(═O)O$R^{10}$ group.

In another preferred embodiment the invention relates to compounds of formula (I), in which $R^5$ represents a —C(═O)$R^{10}$ group.

In another preferred embodiment the invention relates to compounds of formula (I), in which $R^5$ represents a —S(═O)$_2R^{10}$ group.

In another preferred embodiment the invention relates to compounds of formula (I), in which $R^5$ represents $C_1$-$C_4$-alkyl-group.

In another preferred embodiment the invention relates to compounds of formula (I), in which $R^5$ represents methyl-group.

In another preferred embodiment the invention relates to compounds of formula (I), in which $R^5$ represents a cyano group.

In another preferred embodiment the invention relates to compounds of formula (I), in which $R^5$ represents a —C(═O)N$R^8R^9$ group.

In a particularly preferred embodiment the invention relates to compounds of formula (I), in which $R^5$ represents a —C(═O)O—C$(CH_3)_3$) group.

In a particularly preferred embodiment the invention relates to compounds of formula (I), in which $R^5$ represents a hydrogen atom.

The invention relates to compounds of formula (I), in which $R^6$ and $R^7$, independently from each other represent a group selected from a hydrogen atom, cyano, —C(═O)$R^{10}$, —C(═O)O$R^{10}$, —S(═O)$_2R^{10}$, —C(═O)N$R^8R^9$, $C_1$-$C_6$-alkyl-, $C_3$-$C_7$-cycloalkyl-, heterocyclyl-, wherein said $C_1$-$C_6$-alkyl-, $C_3$-$C_7$-cycloalkyl-, heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In a preferred embodiment the invention relates to compounds of formula (I), in which $R^6$ and $R^7$, independently from each other represent a group selected from a hydrogen atom, cyano, —C(═O)$R^{10}$, —C(═O)O$R^{10}$, —S(═O)$_2R^{10}$, —C(═O)N$R^8R^9$, $C_1$-$C_6$-alkyl-, $C_3$-$C_5$-cycloalkyl-, wherein said $C_1$-$C_6$-alkyl- or $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In a preferred embodiment the invention relates to compounds of formula (I), in which $R^6$ and $R^7$, independently from each other represent a group selected from a hydrogen atom, cyano, —C(═O)$R^{10}$, —C(═O)O$R^{10}$, —S(═O)$_2R^{10}$, —C(═O)N$R^8R^9$, $C_1$-$C_4$-alkyl-, wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, cyclic amines.

In another preferred embodiment the invention relates to compounds of formula (I), in which $R^6$ and $R^7$, independently from each other represent a group selected from a hydrogen atom, cyano, $C_1$-$C_4$-alkyl-, wherein said $C_1$-$C_4$-alkyl-group is optionally substituted with one hydroxy group.

In another preferred embodiment the invention relates to compounds of formula (I), in which $R^6$ and $R^7$, independently from each other represent a group selected from a hydrogen atom, cyano, $C_1$-$C_4$-alkyl-, wherein said $C_1$-$C_4$-alkyl-group is optionally substituted with one hydroxy group.

In another preferred embodiment the invention relates to compounds of formula (I), in which $R^6$ and $R^7$, independently from each other represent a group selected from a hydrogen atom, cyano, —C(═O)$R^{10}$, —C(═O)O$R^{10}$, $C_1$-$C_3$-alkyl-.

In another preferred embodiment the invention relates to compounds of formula (I), in which $R^6$ and $R^7$, independently from each other represent a group selected from a hydrogen atom and —C(═O)OR.

In particularly preferred embodiment the invention relates to compounds of formula (I), in which $R^6$ and $R^7$, independently from each other represent a group selected from a hydrogen atom and $C_1$-$C_3$-alkyl-.

In another particularly preferred embodiment the invention relates to compounds of formula (I), in which $R^6$ and $R^7$, independently from each other represent a group selected from a hydrogen atom and a cyano group.

In another particularly preferred embodiment the invention relates to compounds of formula (I), in which $R^6$ and $R^7$, independently from each other represent a group selected from a hydrogen atom and a methyl-group.

In another particularly preferred embodiment the invention relates to compounds of formula (I), in which $R^6$ and $R^7$ represent a hydrogen atom;

In another embodiment the invention relates to compounds of formula (I), in which $R^6$ represents a hydrogen atom and $R^7$ represents a group selected from a hydrogen atom, cyano, —C(═O)$R^{10}$, —C(═O)O$R^{10}$, —S(═O)$_2R^{10}$, —C(═O)N$R^8R^9$, $C_1$-$C_6$-alkyl-, $C_3$-$C_7$-cycloalkyl-, heterocyclyl-, wherein said $C_1$-$C_6$-alkyl-, $C_3$-$C_7$-cycloalkyl-, heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^6$ represents a hydrogen atom and $R^7$ represents a group selected from a hydrogen atom, cyano, —C(═O)$R^{10}$, —C(═O)O$R^{10}$, —S(═O)$_2R^{10}$, —C(═O)N$R^8R^9$, $C_1$-$C_6$-alkyl-, $C_3$-$C_5$-cycloalkyl-, wherein said $C_1$-$C_6$-alkyl- or $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In a preferred embodiment the invention relates to compounds of formula (I), in which $R^6$ represents a hydrogen atom and $R^7$ represents a group selected from a hydrogen atom, cyano, —C(═O)$R^1$, —C(═O)O$R^1$, —S(═O)$_2R^{10}$, —C(═O)N$R^8R^9$, $C_1$-$C_4$-alkyl-, $C_3$-$C_5$-cycloalkyl-, wherein said $C_1$-$C_4$-alkyl- or $C_3$-$C_5$-cycloalkyl-group is optionally substituted with one substituent selected from the group consisting of fluorine, hydroxy, cyano, $C_1$-$C_3$-alkoxy-, —$NH_2$, alkylamino-, dialkylamino-, cyclic amines.

In another preferred embodiment the invention relates to compounds of formula (I in which $R^6$ represents a hydrogen atom and $R^7$ represents a group selected from a hydrogen atom, cyano, —C(=O)$R^1$, —C(=O)O$R^1$, —S(=O)$_2R^{10}$, —C(=O)N$R^8R^9$, $C_1$-$C_4$-alkyl-, $C_3$-$C_5$-cycloalkyl-, wherein said $C_1$-$C_4$-alkyl-group is optionally substituted with one hydroxy group.

In another preferred embodiment the invention relates to compounds of formula (I), in which $R^6$ represents a hydrogen atom and $R^7$ represents a group selected from a hydrogen atom, cyano, —C(=O)O$R^{10}$, —C(=O)N$R^8R^9$, $C_1$-$C_4$-alkyl-, $C_3$-$C_5$-cycloalkyl-, wherein said $C_1$-$C_4$-alkyl-group is optionally substituted with one hydroxy group.

In another preferred embodiment the invention relates to compounds of formula (I), in which $R^6$ represents a hydrogen atom and $R^7$ represents a group selected from a hydrogen atom, cyano, $C_1$-$C_4$-alkyl-, $C_3$-$C_5$-cycloalkyl-.

In another preferred embodiment the invention relates to compounds of formula (I) in which $R^6$ represents a hydrogen atom and $R^7$ represents a group selected from a hydrogen atom, cyano, $C_1$-$C_4$-alkyl-.

In a particularly preferred embodiment the invention relates to compounds of formula (I) in which $R^6$ represents a hydrogen atom and $R^7$ represents a group selected from a hydrogen atom, cyano, $C_1$-$C_3$-alkyl-, cyclopropyl-.

In a particularly preferred embodiment the invention relates to compounds of formula (I), in which $R^6$ represents a hydrogen atom and $R^7$ represents a group selected from a hydrogen atom, cyano, $C_1$-$C_3$-alkyl-.

In another particularly preferred embodiment the invention relates to compounds of formula (I) in which $R^6$ represents a hydrogen atom and $R^7$ represents a cyano group.

In another particularly preferred embodiment the invention relates to compounds of formula (I), in which $R^6$ represents a hydrogen atom and $R^7$ represents a methyl-group.

The invention relates to compounds of formula (I), in which $R^8$, $R^9$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- or heteroaryl-group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-, or $R^8$ and $R^9$, together with the nitrogen atom they are attached to, form a cyclic amine.

In another embodiment the invention relates to compounds of formula (I), in which $R^8$, $R^9$ represent, independently from each other, a group selected from a hydrogen atom, $C_1$-$C_4$-alkyl- and $C_3$-$C_5$-cycloalkyl-;

wherein said $C_1$-$C_4$-alkyl- or $C_3$-$C_5$-cycloalkyl-group is optionally substituted with one or two substituents, identically or differently, selected from the group consisting of hydroxy, $C_1$-$C_2$-alkyl-, $C_1$-$C_2$-alkoxy-, —$NH_2$, alkylamino-, dialkylamino-, cyclic amines, or $R^8$ and $R^9$, together with the nitrogen atom they are attached to, form a cyclic amine.

In another embodiment the invention relates to compounds of formula (I), in which $R^8$, $R^9$ represent, independently from each other, a group selected from a hydrogen atom, $C_1$-$C_4$-alkyl- and $C_3$-$C_5$-cycloalkyl-, or $R^8$ and $R^9$, together with the nitrogen atom they are attached to, form a cyclic amine.

In another embodiment the invention relates to compounds of formula (I), in which $R^8$, $R^9$ represent, independently from each other, a group selected from a hydrogen atom, $C_1$-$C_2$-alkyl.

In a particularly preferred embodiment the invention relates to compounds of formula (I), in which $R^8$ and $R^9$ represent, independently from each other, a group selected from a hydrogen atom and $C_1$-$C_2$-alkyl-.

In another particularly preferred embodiment the invention relates to compounds of formula (I), in which $R^8$ represents a group selected from a hydrogen atom and $C_1$-$C_2$-alkyl-, and in which $R^9$ represents a hydrogen atom.

In another particularly preferred embodiment the invention relates to compounds of formula (I), in which $R^8$ represents a group selected from a hydrogen atom and $C_1$-$C_2$-alkyl-.

In another particularly preferred embodiment the invention relates to compounds of formula (I), in which $R^9$ represents a hydrogen atom.

In another particularly preferred embodiment the invention relates to compounds of formula (I), in which $R^8$ represents a hydrogen atom, and in which $R^9$ represents a hydrogen atom.

The invention relates to compounds of formula (I), in which $R^{10}$ represents a group selected from $C_1$-$C_6$-alkyl-, halo-$C_1$-$C_3$-alkyl-, $C_3$-$C_7$-cycloalkyl-, heterocyclyl-, phenyl-, benzyl- and heteroaryl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amines, halo-$C_1$-$C_3$-alkyl-, $C_1$-$C_3$-fluoroalkoxy-.

In another embodiment the invention relates to compounds of formula (I), in which $R^{10}$ represents a group selected from $C_1$-$C_6$-alkyl-, fluoro-$C_1$-$C_3$-alkyl-, $C_3$-$C_5$-cycloalkyl-, phenyl- and benzyl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amines, fluoro-$C_1$-$C_2$-alkyl-, $C_1$-$C_2$-fluoroalkoxy-.

In a preferred embodiment the invention relates to compounds of formula (I), in which $R^{10}$ represents a group selected from $C_1$-$C_6$-alkyl-, fluoro-$C_1$-$C_3$-alkyl-, $C_3$-$C_5$-cycloalkyl- and benzyl-, wherein said group is optionally substituted with one substituent selected from the group consisting of halogen, hydroxy, $C_1$-$C_2$-alkyl-, $C_1$-$C_2$-alkoxy-, —$NH_2$.

In another preferred embodiment the invention relates to compounds of formula (I), in which $R^{10}$ represents a group selected from $C_1$-$C_4$-alkyl-, fluoro-$C_1$-$C_3$-alkyl-.

In another preferred embodiment the invention relates to compounds of formula (I), in which $R^{10}$ represents a $C_1$-$C_4$-alkyl-group.

In another preferred embodiment the invention relates to compounds of formula (I), in which $R^{10}$ represents a tert-butyl-group.

In another particularly preferred embodiment the invention relates to compounds of formula (I), in which $R^3$ represents a fluorine atom, $R^4$ represents a hydrogen atom and $R^5$ represents a hydrogen atom.

In another particularly preferred embodiment the invention relates to compounds of formula (I), in which $R^1$ represents a methyl-group, $R^3$ represents a fluorine atom, $R^4$ represents a hydrogen atom and $R^5$ represents a hydrogen atom.

In another particularly preferred embodiment the invention relates to compounds of formula (I), in which $R^1$ represents a methyl-group, $R^2$ represents a hydrogen atom, $R^3$ represents a fluorine atom, $R^4$ represents a hydrogen atom and $R^5$ represents a hydrogen atom.

In another particularly preferred embodiment the invention relates to compounds of formula (I), in which $R^1$ represents a methyl-group, $R^2$ represents a hydrogen atom, $R^3$ represents a fluorine atom, $R^4$ represents a hydrogen atom, $R^5$ represents a hydrogen atom and Z represents a hydrogen atom.

In another particularly preferred embodiment the invention relates to compounds of formula (I), in which $R^1$ represents a methyl-group and $R^5$ represents a hydrogen atom.

In another particularly preferred embodiment the invention relates to compounds of formula (I), in which $R^1$ represents a methyl-group, $R^5$ represents a hydrogen atom and Z represents a hydrogen atom.

It is to be understood that the present invention relates to any sub-combination within any embodiment of the present invention of compounds of formula (I), supra.

More particularly still, the present invention covers compounds of formula (I) which are disclosed in the Example section of this text, infra.

Very specially preferred are combinations of two or more of the abovementioned preferred embodiments.

The above mentioned definitions of groups and radicals which have been detailed in general terms or in preferred ranges also apply to the end products of the formula (I) and, analogously, to the starting materials or intermediates required in each case for the preparation.

The present invention further relates to intermediate compounds of general formula (7)

7

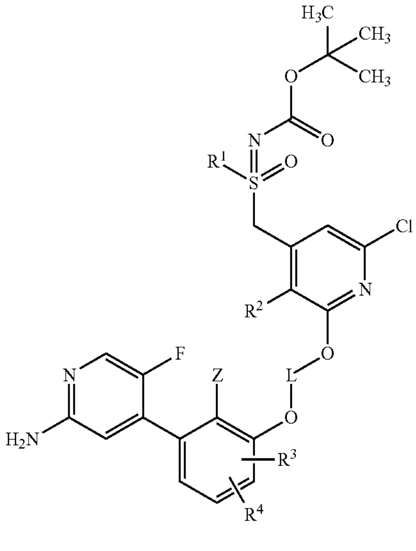

wherein Z, $R^1$, $R^2$, $R^3$, $R^4$ and L are as defined for the compound of general formula (I) according to the invention, or the enantiomers, diastereomers, salts, solvates or salts of solvates thereof.

The present invention further relates to intermediate compounds of general formula (19)

19

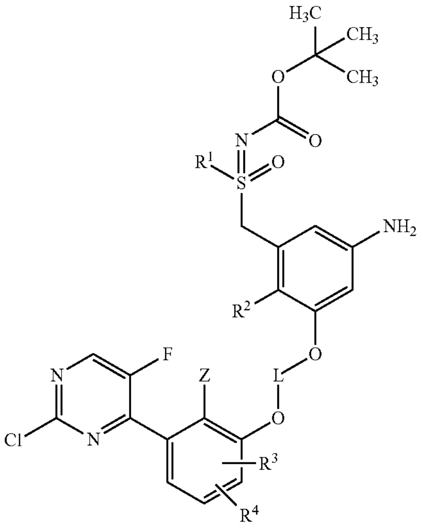

wherein Z, $R^1$, $R^2$, $R^3$, $R^4$ and L are as defined for the compound of general formula (I) according to the invention, or the enantiomers, diastereomers, salts, solvates or salts of solvates thereof.

The present invention further relates to the use of intermediate compounds of general formula (7),

19

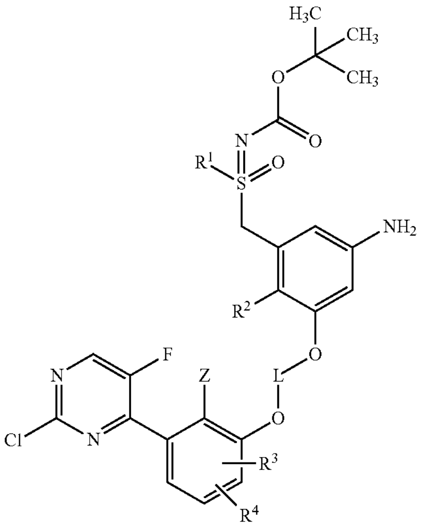

wherein Z, $R^1$, $R^2$, $R^3$, $R^4$ and L are as defined for the compound of general formula (I) according to the invention, or the enantiomers, diastereomers, salts, solvates or salts of solvates thereof, for the preparation of a compound of general formula (I) according to the invention.

The present invention further relates to the us of intermediate compounds of general formula (19),

19

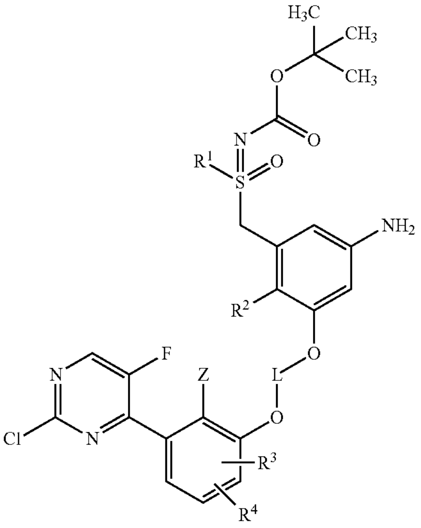

wherein Z, $R^1$, $R^2$, $R^3$, $R^4$ and L are as defined for the compound of general formula (I) according to the invention, or the enantiomers, diastereomers, salts, solvates or salts of solvates thereof, for the preparation of a compound of general formula (I) according to the invention.

The present invention further relates to a process for the preparation of a compound of formula (Ia), in which process a compound of the formula (7) wherein Z, $R^1$, $R^2$, $R^3$, $R^4$ and L are as defined for the compound of general formula (I) according to the invention,

7

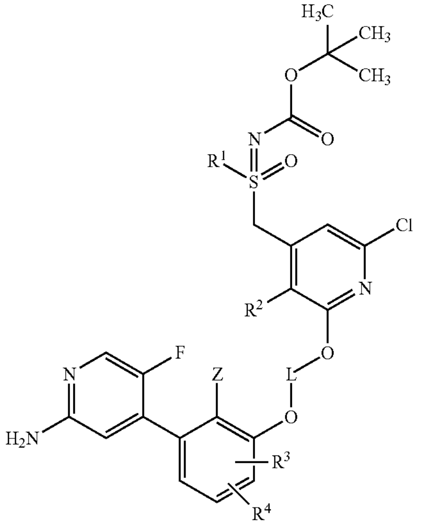

is reacted in a C—N cross-coupling reaction to give compounds of the formula (Ia), Ia

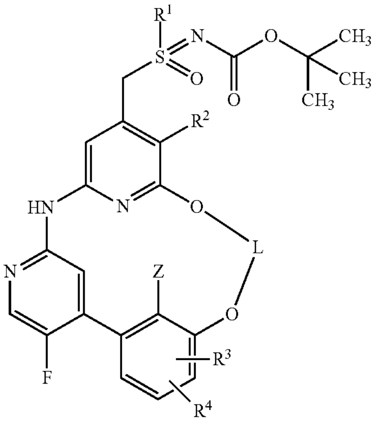

and in which process the resulting compound is optionally, if appropriate, converted with the corresponding (i) solvents and/or (ii) bases or acids to the solvates, salts and/or solvates of the salts thereof.

The present invention further relates to a process for the preparation of a compound of formula (Id), in which process a compound of the formula (19), wherein Z, $R^1$, $R^2$, $R^3$, $R^4$ and L are as defined for the compound of general formula (I) according to the invention,

19

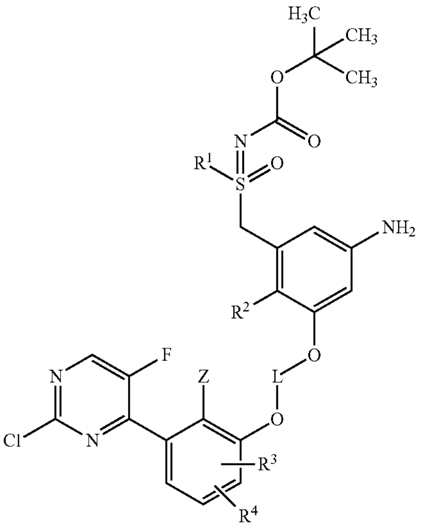

is reacted in a C—N cross-coupling reaction to give compounds of the formula (Id), Id

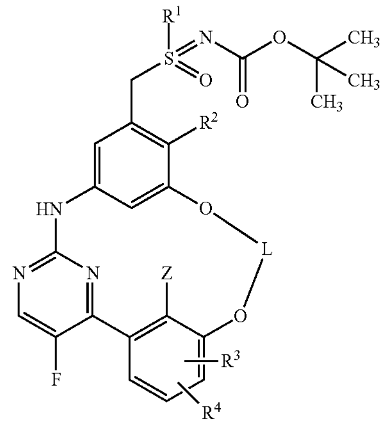

and in which process the resulting compound is optionally, if appropriate, converted with the corresponding (i) solvents and/or (ii) bases or acids to the solvates, salts and/or solvates of the salts thereof.

The present invention further relates to a process for the preparation of the compounds of formula (Ia), in which $R^1$, $R^2$, $R^3$, $R^4$, Z and L are as defined for the compound of formula (I) according to the invention, in which process compounds of formula (7),

7

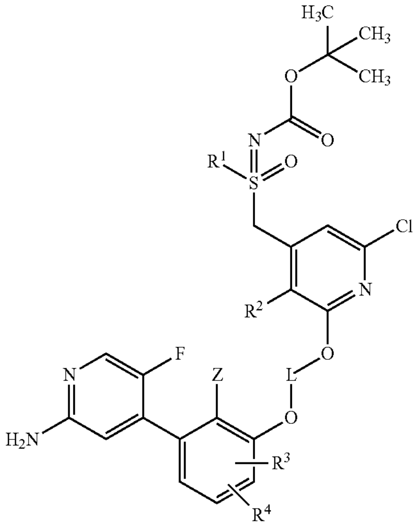

in which $R^1$, $R^2$, $R^3$, $R^4$, Z and L are as defined for the compound of formula (I) according to the invention, are reacted in an intramolecular Palladium-catalyzed C—N cross-coupling reaction, Ia

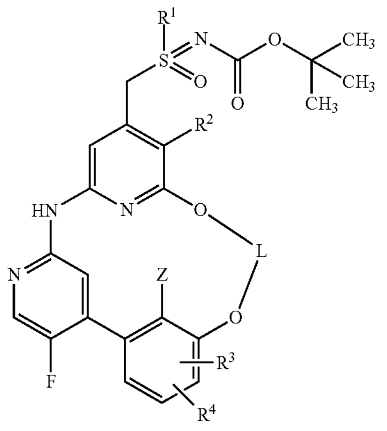

to give compounds of the formula (Ia), and in which process the resulting compounds are optionally, if appropriate, converted with the corresponding (i) solvents and/or (ii) bases or acids to the solvates, salts and/or solvates of the salts thereof.

Ib

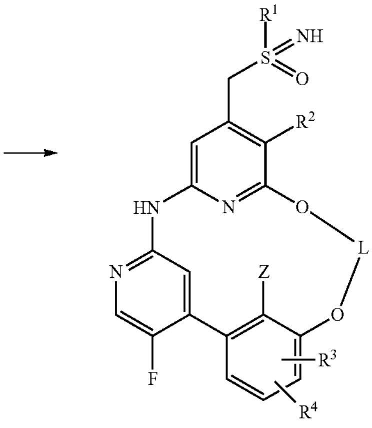

to give compounds of the formula (Ib),

The present invention further relates to a process for the preparation of the compounds of formula (Id), in which $R^1$, $R^2$, $R^3$, $R^4$, Z and L are as defined for the compound of formula (I) according to the invention, in which process compounds of formula (19)

19

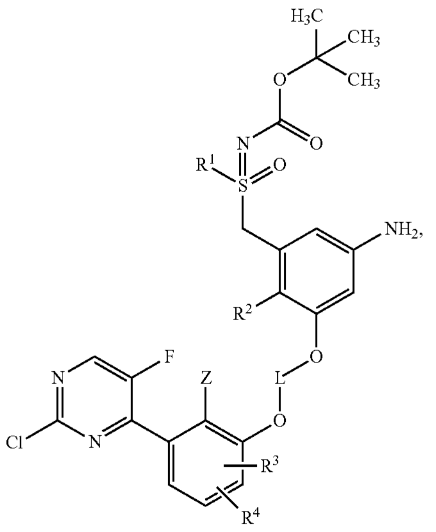

in which $R^1$, $R^2$, $R^3$, $R^4$, Z and L are as defined for the compound of formula (I) according to the invention, are reacted in an intramolecular Palladium-catalyzed C—N cross-coupling reaction, Id

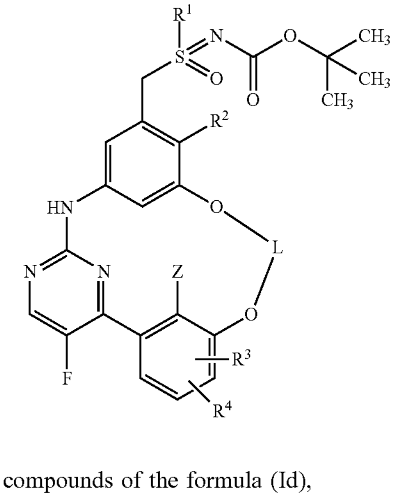

to give compounds of the formula (Id), and in which process the resulting compounds are optionally, if appropriate, converted with the corresponding (i) solvents and/or (ii) bases or acids to the solvates, salts and/or solvates of the salts thereof.

Ie

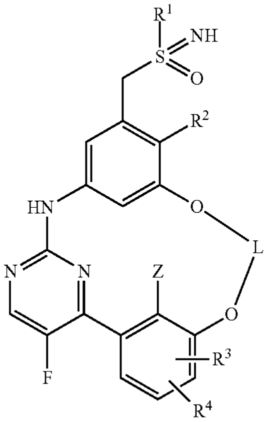

to give compounds of the formula (Ie),

The compounds according to the invention show a valuable pharmacological spectrum of action which could not have been predicted.

They are therefore suitable for use as medicaments for the treatment and/or prophylaxis of disorders in humans and animals.

The pharmaceutical activity of the compounds according to the invention can be explained by their action as selective inhibitors of CDK9, and, more significantly, as selective inhibitors of CDK9 at high ATP concentrations.

Thus, the compounds according to the general formula (I) as well as the enantiomers, diastereomers, salts, solvates and salts of solvates thereof are used as selective inhibitors for CDK9.

Furthermore, the compounds according to the invention show a particularly high potency (demonstrated by a low $IC_{50}$ value in the CDK9/CycT1 assay) for selectively inhibiting CDK9 activity, in particular at high ATP concentrations.

In context of the present invention, the $IC_{50}$ value with respect to CDK9 can be determined by the methods described in the method section below.

As compared to many CDK9 inhibitors described in the prior art, compounds of the present invention according to general formula (I) show a surprisingly high potency for inhibiting CDK9 activity, especially at high ATP concentrations, which is demonstrated by their low $IC_{50}$ value in the CDK9/CycT1 high ATP kinase assay. Thus, these compounds have a lower probability to be competed out of the ATP-binding pocket of CDK9/CycT1 kinase due to the high intracellular ATP concentration (R. Copeland et al., Nature Reviews Drug Discovery 2006, 5, 730-739). According to this property the compounds of the present invention are particularly able to inhibit CDK9/CycT1 within cells for a longer period of time as compared to classical ATP competitive kinase inhibitors. This increases the anti-tumor cell efficacy at pharmacokinetic clearance-mediated declining serum concentrations of the inhibitor after dosing of a patient or an animal.

As compared to CDK9 inhibitors in the prior art, compounds in the present invention show a surprisingly long target residence time. It has been suggested earlier that the target residence time is an appropriate predictor for drug efficacy on the basis that equilibrium-based in vitro assays inadequately reflect in vivo situations where drug concentrations fluctuate due to adsorption, distribution and elimination processes and the target protein concentration may be dynamically regulated (Tummino, P. J. and R. A. Copeland, *Residence time of receptor-ligand complexes and its effect on biological function*. Biochemistry, 2008. 47(20): p. 5481-5492; Copeland, R. A., D. L. Pompliano, and T. D. Meek, *Drug-target residence time and its implications for lead optimization*. Nature Reviews Drug Discovery, 2006. 5(9): p. 730-739).

Therefore, the equilibrium binding parameter, $K_D$, or the functional representative, $IC_{50}$, may not fully reflect requirements for in vivo efficacy. Assuming that a drug molecule can only act as long as it remains bound to its target, the "lifetime" (residence time), of the drug-target complex may serve as a more reliable predictor for drug efficacy in a non-equilibrium in vivo system. Several publications appreciated and discussed its implications for in vivo efficacy (Lu, H. and P. J. Tonge, *Drug-target residence time: critical information for lead optimization*. Curr Opin Chem Biol, 2010. 14(4): p. 467-74; Vauquelin, G. and S. J. Charlton, *Long-lasting target binding and rebinding as mechanisms to prolong in vivo drug action*. Br J Pharmacol, 2010. 161(3): p. 488-508).

One example for the impact of target residence time is given by the drug tiotropium that is used in COPD treatment. Tiotropium binds to the M1, M2 and M3 subtype of the muscarinic receptors with comparable affinities, but is kinetically selective as it has the desired long residence times only for the M3 receptor. Its drug-target residence time is sufficiently long that after washout from human trachea in vitro, tiotropium maintains inhibition of cholinergic activity with a half-life of 9 hours. This translates to protection against bronchospasms for more than 6 hours in vivo (Price, D., A. Sharma, and F. Cerasoli, *Biochemical properties, pharmacokinetics and pharmacological response of tiotropium in chronic obstructive pulmonary disease patients*. 2009; Dowling, M. (2006) Br. J. Pharmacol. 148, 927-937).

Another example is Lapatinib (Tykerb). It was found was that the long target residence time found for lapatinib in the purified intracellular domain enzyme reaction correlated with the observed, prolonged signal inhibition in tumor cells based on receptor tyrosine phosphorylation measurements. It was subsequently concluded that the slow binding kinetics may offer increased signal inhibition in the tumor, thus leading to greater potential to affect the tumor growth rates or effectiveness of co-dosing with other chemotherapeutic agents. (Wood et al (2004) *Cancer Res.* 64: 6652-6659; Lackey (2006) Current Topics in Medicinal Chemistry, 2006, Vol. 6, No. 5)

In context of the present invention, the $IC_{50}$ value with respect to CDK9 at high ATP concentrations can be determined by the methods described in the method section below. Preferably, it is determined according to Method 1b ("CDK9/CycT1 high ATP kinase assay") as described in the Materials and Method section below.

If desired, the $IC_{50}$ value with respect to CDK9 at low ATP concentration can e.g. be determined by the methods described in the method section below, according to Method 1a. ("CDK9/CycT1 kinase assay") described in the Materials and Method section below.

In context of the present invention, the target residence time of selective CDK9 inhibitors according to the present invention can be determined by the methods described in the method section below. Preferably, it is determined according to Method 8 ("Surface Plasmon Resonance PTEFb") as described in the Materials and Method section below.

Further, compounds of the present invention according to formula (I) surprisingly show a surprisingly high antiproliferative activity in tumor cell lines, such as HeLa, HeLa-MaTu-ADR, NCI-H460, DU145, Caco-2, B16F10, A2780 or MOLM-13, compared to CDK9 inhibitors described in the prior art.

In context of the present invention, the anti-proliferative activity in tumor cell lines such as HeLa, HeLa-MaTu-ADR, NCI-H460, DU145, Caco-2, B16F10, A2780 or MOLM-13 is preferably determined according to Method 3. ("Proliferation Assay") as described in the Materials and Method section below.

In context of the present invention, the aqueous solubility is preferably determined according to Method 4. ("Equilibrium Shake Flask Solubility Assay") described in the Materials and Method section below.

In context of the present invention, the metabolic stability in rat hepatocytes is preferably determined according to Method 6. ("Investigation of in vitro metabolic stability in rat hepatocytes") described in the Materials and Method section below.

In context of the present invention, the half-life in rats upon administration in vivo is preferably determined according to Method 7. ("In vivo pharmacokinetics in rats") described in the Materials and Method section below.

In context of the present invention, the apparent Caco-2 permeability values from the basal to apical compartment ($P_{app}$ A–B) or the efflux ratio (defined as the ratio (($P_{app}$ B–A)/($P_{app}$ A–B)) are preferably determined according to Method 5. ("Caco-2 Permeation Assay") described in the Materials and Method section below.

A further subject matter of the present invention is the use of the compounds of general formula (I) according to the invention for the treatment and/or prophylaxis of disorders, preferably of disorders relating to or mediated by CDK9 activity, in particular of hyper-proliferative disorders, virally induced infectious diseases and/or of cardiovascular diseases, more preferably of hyper-proliferative disorders.

The compounds of the present invention may be used to inhibit selectively the activity or expression of CDK9.

Therefore, the compounds of formula (I) are expected to be valuable as therapeutic agents. Accordingly, in another embodiment, the present invention provides a method of treating disorders relating to or mediated by CDK9 activity in a patient in need of such treatment, comprising administering to the patient an effective amount of a compound of formula (I) as defined above. In certain embodiments, the disorders relating to CDK9 activity are hyper-proliferative disorders, virally induced infectious diseases and/or of cardiovascular diseases, more preferably hyper-proliferative disorders, particularly cancer.

The term "treating" or "treatment" as stated throughout this document is used conventionally, e.g., the management or care of a subject for the purpose of combating, alleviating, reducing, relieving, improving the condition of a disease or disorder, such as a carcinoma.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals. Preferred humans include human patients suffering from or prone to suffering from a cell proliferative disorder or associated state, as described herein. The term "non-human animals" includes vertebrates, e.g., mammals, such as non-human primates, sheep, cow, dog, cat and rodents, e.g., mice, and non-mammals, such as chickens, amphibians, reptiles, etc.

The term "disorders relating to or mediated by CDK9" shall include diseases associated with or implicating CDK9 activity, for example the hyperactivity of CDK9, and conditions that accompany with these diseases. Examples of "disorders relating to or mediated by CDK9" include disorders resulting from increased CDK9 activity due to mutations in genes regulating CDK9 activity such as LARP7, HEXIM1/2 or 7sk snRNA, or disorders resulting from increased CDK9 activity due to activation of the CDK9/cyclinT/RNApolymerase II complex by viral proteins such as HIV-TAT or HTLV-TAX or disorders resulting from increased CDK9 activity due to activation of mitogenic signaling pathways.

The term "hyperactivity of CDK9" refers to increased enzymatic activity of CDK9 as compared to normal non-diseased cells, or it refers to increased CDK9 activity leading to unwanted cell proliferation, or to reduced or insufficient programmed cell death (apoptosis), or mutations leading to constitutive activation of CDK9.

The term "hyper-proliferative disorder" includes disorders involving the undesired or uncontrolled proliferation of a cell and it includes disorders involving reduced or insufficient programmed cell death (apoptosis). The compounds of the present invention can be utilized to prevent, inhibit, block, reduce, decrease, control, etc., cell proliferation and/or cell division, and/or produce apoptosis. This method comprises administering to a subject in need thereof, including a mammal, including a human, an amount of a compound of this invention, or a pharmaceutically acceptable salt, hydrate or solvate thereof which is effective to treat or prevent the disorder.

Hyper-proliferative disorders in the context of this invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia (BPH), and solid tumors, such as cancers of the breast, respiratory tract, brain, reproductive organs, digestive tract, urinary tract, eye, liver, skin, head and neck, thyroid, parathyroid, and their distant metastases. Those disorders also include lymphomas, sarcomas and leukemias.

Examples of breast cancer include, but are not limited to invasive ductal carcinoma, invasive lobular carcinoma, ductal carcinoma in situ, and lobular carcinoma in situ, and canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of the male reproductive organs include, but are not limited to prostate and testicular cancer.

Tumors of the female reproductive organs include, but are not limited to endometrial, cervical, ovarian, vaginal and vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, anal gland adenocarcinomas, and mast cell tumors.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip and oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

Fibrotic proliferative disorders, i.e. the abnormal formation of extracellular matrices, that may be treated with the compounds and methods of the present invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the present invention include tumor growth, retinopathy, including diabetic retinopathy, ischemic retinal-vein occlusion, retinopathy of prematurity and age-related macular degeneration, rheumatoid arthritis, psoriasis, and bullous disorders associated with subepidermal blister formation, including bullous pemphigoid, erythema multiforme and dermatitis herpetiformis.

The compounds of the present invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the present invention.

In a further aspect of the present invention, the compounds according to the invention are used in a method for preventing and/or treating infectious diseases, in particular virally induced infectious diseases. The virally induced infectious diseases, including opportunistic diseases, are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, preferably HIV-1 or HIV-2 and wherein the oncoretrovirus is selected from the group of: HTLV-I, HTLV-II or BLV. In a further preferred embodiment of this method, the hepadnavirus is selected from HBV, GSHV or WHV, preferably HBV, the herpesivirus is selected from the group comprising: HSV I, HSV II, EBV, VZV, HCMV or HHV 8, preferably HCMV and the flaviviridae is selected from HCV, West nile or Yellow Fever.

The compounds according to general formula (I) are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

Preferred are cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

A further subject matter of the present invention is the use of the compounds of general formula (I) according to the invention as a medicament.

A further subject matter of the present invention is the use of the compounds of general formula (I) according to the invention for the treatment and/or prophylaxis of disorders, in particular of the disorders mentioned above.

A further subject matter of the present invention is the use of the compounds of general formula (I) according to the invention for the treatment and/or prophylaxis of hyper-proliferative disorders, virally induced infectious diseases and/or of cardiovascular diseases.

A preferred subject matter of the present invention is the use of the compounds of general formula (I) according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds of general formula (I) according to the invention for the use as a medicament.

A further subject matter of the present invention are the compounds of general formula (I) according to the invention for the use of treating and/or prophylaxis of the disorders mentioned above.

A further subject matter of the present invention are the compounds of general formula (I) according to the invention for the use of treating and/or prophylaxis of hyper-proliferative disorders, virally induced infectious diseases and/or of cardiovascular diseases.

A preferred subject matter of the present invention are the compounds of general formula (I) according to the invention for the use of treating and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention are the compounds of general formula (I) according to the invention for the use in a method for the treatment and/or prophylaxis of the disorders mentioned above.

A further subject matter of the present invention are the compounds of general formula (I) according to the invention for the use in a method for the treatment and/or prophylaxis of hyper-proliferative disorders, virally induced infectious diseases and/or of cardiovascular diseases.

A preferred subject matter of the present invention are the compounds of general formula (I) according to the invention for the use in a method of treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is the use of the compounds of general formula (I) according to the invention in the manufacture of a medicament for the treatment and/or prophylaxis of disorders, in particular the disorders mentioned above.

A further subject matter of the present invention is the use of the compounds of general formula (I) according to the invention in the manufacture of a medicament for the treatment and/or prophylaxis of hyper-proliferative disorders, virally induced infectious diseases and/or of cardiovascular diseases.

A preferred subject matter of the present invention is the use of the compounds of general formula (I) according to the invention in the manufacture of a medicament for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

A further subject matter of the present invention is a method for the treatment and/or prophylaxis of disorders, in particular the disorders mentioned above, using an effective amount of the compounds of general formula (I) according to the invention.

A further subject matter of the present invention is a method for the treatment and/or prophylaxis of hyper-proliferative disorders, virally induced infectious diseases and/or of cardiovascular diseases, using an effective amount of the compounds of general formula (I) according to the invention.

A preferred subject matter of the present invention is a method for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias using an effective amount of the compounds of general formula (I) according to the invention.

Another aspect of the present invention relates to pharmaceutical combinations comprising a compound of general formula (I) according to the invention in combination with at least one or more further active ingredients.

As used herein the term "pharmaceutical combination" refers to a combination of at least one compound of general formula (I) according to the invention as active ingredient together with at least one other active ingredient with or without further ingredients, carrier, diluents and/or solvents.

Another aspect of the present invention relates to pharmaceutical compositions comprising a compound of general formula (I) according to the invention in combination with an inert, nontoxic, pharmaceutically suitable adjuvant.

As used herein the term "pharmaceutical composition" refers to a galenic formulation of at least one pharmaceutically active agent together with at least one further ingredient, carrier, diluent and/or solvent.

Another aspect of the present invention relates to the use of the pharmaceutical combinations and/or the pharmaceutical compositions according to the invention for the treatment and/or prophylaxis of disorders, in particular of the disorders mentioned above.

Another aspect of the present invention relates to the use of the pharmaceutical combinations and/or the pharmaceutical compositions according to the invention for the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Another aspect of the present invention relates to pharmaceutical combinations and/or the pharmaceutical compositions according to the invention for use of the treatment and/or prophylaxis of disorders, in particular of the disorders mentioned above.

Another aspect of the present invention relates to pharmaceutical combinations and/or the pharmaceutical compositions according to the invention for use of the treatment and/or prophylaxis of lung carcinomas, especially non-small cell lung carcinomas, prostate carcinomas, especially hormone-independent human prostate carcinomas, cervical carcinomas, including multidrug-resistant human cervical carcinomas, colorectal carcinomas, melanomas, ovarian carcinomas or leukemias, especially acute myeloid leukemias.

Compounds of formula (I) may be administered as the sole pharmaceutical agent or in combination with one or more additional therapeutic agents where the combination causes no unacceptable adverse effects.

This pharmaceutical combination includes administration of a single pharmaceutical dosage formulation which contains a compound of formula (I) and one or more additional therapeutic agents, as well as administration of the compound of formula (I) and each additional therapeutic agent in its own separate pharmaceutical dosage formulation. For example, a compound of formula (I) and a therapeutic agent may be administered to the patient together in a single oral dosage composition such as a tablet or capsule, or each agent may be administered in separate dosage formulations.

Where separate dosage formulations are used, the compound of formula (I) and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention:

Alkylating agents include, but are not limited to, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, and mitolactol; platinum-coordinated alkylating compounds include, but are not limited to, cisplatin, carboplatin, eptaplatin, lobaplatin, nedaplatin, oxaliplatin, and satraplatin;

Anti-metabolites include, but are not limited to, methotrexate, 6-mercaptopurine riboside, mercaptopurine, 5-fluorouracil alone or in combination with leucovorin, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosfite, disodium premetrexed, pentostatin, pelitrexol, raltitrexed, triapine, trimetrexate, vidarabine, vincristine, and vinorelbine;

Hormonal therapy agents include, but are not limited to, exemestane, Lupron, anastrozole, doxercalciferol, fadrozole, formestane, 11-beta hydroxysteroid dehydrogenase 1 inhibitors, 17-alpha hydroxylase/17,20 lyase inhibitors such as abiraterone acetate, 5-alpha reductase inhibitors such as finasteride and epristeride, anti-estrogens such as tamoxifen citrate and fulvestrant, Trelstar, toremifene, raloxifene, lasofoxifene, letrozole, anti-androgens such as bicalutamide, flutamide, mifepristone, nilutamide, Casodex, and anti-progesterones and combinations thereof;

Plant-derived anti-tumor substances include, e.g., those selected from mitotic inhibitors, for example epothilones such as sagopilone, ixabepilone and epothilone B, vinblastine, vinflunine, docetaxel, and paclitaxel;

Cytotoxic topoisomerase inhibiting agents include, but are not limited to, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, and combinations thereof;

Immunologicals include interferons such as interferon alpha, interferon alpha-2a, interferon alpha-2b, interferon beta, interferon gamma-1a and interferon gamma-n1, and other immune enhancing agents such as L19-IL2 and other IL2 derivatives, filgrastim, lentinan, sizofilan, TheraCys, ubenimex, aldesleukin, alemtuzumab, BAM-002, dacarbazine, daclizumab, denileukin, gemtuzumab, ozogamicin, ibritumomab, imiquimod, lenograstim, lentinan, melanoma vaccine (Corixa), molgramostim, sargramostim, tasonermin, tecleukin, thymalasin, tositumomab, Vimlizin, epratuzumab, mitumomab, oregovomab, pemtumomab, and Provenge; Merial melanoma vaccine Biological response modifiers are agents that modify defense mechanisms of living organisms or biological responses such as survival, growth or differentiation of tissue cells to direct them to have anti-tumor activity; such agents include, e.g., krestin, lentinan, sizofiran, picibanil, ProMune, and ubenimex;

Anti-angiogenic compounds include, but are not limited to, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin;

Antibodies include, but are not limited to, trastuzumab, cetuximab, bevacizumab, rituximab, ticilimumab, ipilimumab, lumiliximab, catumaxomab, atacicept, oregovomab, and alemtuzumab;

VEGF inhibitors such as, e.g., sorafenib, DAST, bevacizumab, sunitinib, recentin, axitinib, aflibercept, telatinib, brivanib alaninate, vatalanib, pazopanib, and ranibizumab; Palladia EGFR (HER1) inhibitors such as, e.g., cetuximab, panitumumab, vectibix, gefitinib, erlotinib, and Zactima;

HER2 inhibitors such as, e.g., lapatinib, trastuzumab, and pertuzumab;

mTOR inhibitors such as, e.g., temsirolimus, sirolimus/Rapamycin, and everolimus;

c-Met inhibitors;

PI3K and AKT inhibitors;

CDK inhibitors such as roscovitine and flavopiridol;

Spindle assembly checkpoints inhibitors and targeted anti-mitotic agents such as PLK inhibitors, Aurora inhibitors (e.g. Hesperadin), checkpoint kinase inhibitors, and KSP inhibitors;

HDAC inhibitors such as, e.g., panobinostat, vorinostat, MS275, belinostat, and LBH589;

HSP90 and HSP70 inhibitors;

Proteasome inhibitors such as bortezomib and carfilzomib;

Serine/threonine kinase inhibitors including MEK inhibitors (such as e.g. RDEA 119) and Raf inhibitors such as sorafenib;

Farnesyl transferase inhibitors such as, e.g., tipifarnib;

Tyrosine kinase inhibitors including, e.g., dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab, pertuzumab, and c-Kit inhibitors; Palladia, masitinib Vitamin D receptor agonists;

Bcl-2 protein inhibitors such as obatoclax, oblimersen sodium, and gossypol;

Cluster of differentiation 20 receptor antagonists such as, e.g., rituximab;

Ribonucleotide reductase inhibitors such as, e.g., gemcitabine;

Tumor necrosis apoptosis inducing ligand receptor 1 agonists such as, e.g., mapatumumab;

5-Hydroxytryptamine receptor antagonists such as, e.g., rEV598, xaliprode, palonosetron hydrochloride, granisetron, Zindol, and AB-1001;

Integrin inhibitors including alpha5-beta1 integrin inhibitors such as, e.g., E7820, JSM 6425, volociximab, and endostatin;

Androgen receptor antagonists including, e.g., nandrolone decanoate, fluoxymesterone, Android, Prost-aid, andromustine, bicalutamide, flutamide, apo-cyproterone, apo-flutamide, chlormadinone acetate, Androcur, Tabi, cyproterone acetate, and nilutamide;

Aromatase inhibitors such as, e.g., anastrozole, letrozole, testolactone, exemestane, amino-glutethimide, and formestane;

Matrix metalloproteinase inhibitors;

Other anti-cancer agents including, e.g., alitretinoin, ampligen, atrasentan bexarotene, bortezomib, bosentan, calcitriol, exisulind, fotemustine, ibandronic acid, miltefosine, mitoxantrone, I-asparaginase, procarbazine, dacarbazine, hydroxycarbamide, pegaspargase, pentostatin, tazaroten, velcade, gallium nitrate, canfosfamide, darinaparsin, and tretinoin.

The compounds of the present invention may also be employed in cancer treatment in conjunction with radiation therapy and/or surgical intervention.

Generally, the use of cytotoxic and/or cytostatic agents in combination with a compound or composition of the present invention will serve to:

(1) yield better efficacy in reducing the growth of a tumor or even eliminate the tumor as compared to administration of either agent alone, (2) provide for the administration of lesser amounts of the administered chemotherapeutic agents, (3) provide for a chemotherapeutic treatment that is well tolerated in the patient with fewer deleterious pharmacological complications than observed with single agent chemotherapies and certain other combined therapies, (4) provide for treating a broader spectrum of different cancer types in mammals, especially humans, (5) provide for a higher response rate among treated patients, (6) provide for a longer survival time among treated patients compared to standard chemotherapy treatments, (7) provide a longer time for tumor progression, and/or (8) yield efficacy and tolerability results at least as good as those of the agents used alone, compared to known instances where other cancer agent combinations produce antagonistic effects.

Furthermore, the compounds of formula (I) may be utilized, as such or in compositions, in research and diagnostics, or as analytical reference standards, and the like, which are well known in the art.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters, for example), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, for example, ascorbic acid), colorants (for example inorganic pigments, such as, for example, iron oxides) and flavour- and/or odour-masking agents.

The present invention furthermore provides medicaments comprising at least one compound according to the invention, usually together with one or more inert, nontoxic, pharmaceutically suitable adjuvants, and their use for the purposes mentioned above.

When the compounds of the present invention are administered as pharmaceuticals, to humans or animals, they can be given per se or as a pharmaceutical composition containing, for example, 0.1% to 99.5% (more preferably 0.5% to 90%) of active ingredient in combination with one or more inert, nontoxic, pharmaceutically suitable adjuvants.

Regardless of the route of administration selected, the compounds according to the invention of general formula (I) and/or the pharmaceutical composition of the present invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Materials and Methods:

The percentage data in the following tests and examples are percentages by weight unless otherwise indicated; parts are parts by weight. Solvent ratios, dilution ratios and concentration data of liquid/liquid solutions are in each case based on volume.

Examples were tested in selected biological and/or physicochemical assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological and/or physicochemical assays represent average values or median values calculated utilizing data sets obtained from testing of one or more synthetic batch.

The in vitro pharmacological, pharmacokinetic and physicochemical properties of the compounds can be determined according to the following assays and methods.

Noteworthily, in the CDK9 assays described below the resolution power is limited by the enzyme concentrations, the lower limit for $IC_{50}$s is about 1-2 nM in the CDK9 high ATP assay and 2-4 nM in the CDK low ATP assays. For compounds exhibiting $IC_{50}$s in this range the true affinity to CDK9 and thus the selectivity for CDK9 over CDK2 might be even higher, i.e. for these compounds the selectivity factors calculated in columns 4 and 7 of Table 2, infra, are minimal values, they could be also higher.

1a. CDK9/CycT1 Kinase Assay

CDK9/CycT1-inhibitory activity of compounds of the present invention was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchase from Invitrogen (Cat. No PV4131). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of CDK9/CycT1 in aqueous assay buffer [50 mM Tris/HCl pH 8.0, 10 mM MgCl2, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.25 μM=>final conc. in the 5 μl assay volume is 0.75 μM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 1 μg/ml. The reaction was stopped by the addition of 5 μl of a solution of TR-FRET detection reagents (0.2 μM streptavidine-XL665 [Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077]) in an aqueous EDTA-solution (100 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

1b. CDK9/CycT1 High ATP Kinase Assay

CDK9/CycT1-inhibitory activity of compounds of the present invention at a high ATP concentration after preincubation of enzyme and test compounds was quantified employing the CDK9/CycT1 TR-FRET assay as described in the following paragraphs.

Recombinant full-length His-tagged human CDK9 and CycT1, expressed in insect cells and purified by Ni-NTA affinity chromatography, were purchased from Life Technologies (Cat. No PV4131). As substrate for the kinase reaction biotinylated peptide biotin-Ttds-YISPLK-SPYKISEG (C-terminus in amide form) was used which can be purchased e.g. form the company JERINI peptide technologies (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 μl of a solution of CDK9/CycT1 in aqueous assay buffer [50 mM Tris/HCl pH 8.0, 10 mM MgCl2, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 3.3 mM=>final conc. in the 5 μl assay volume is 2 mM) and substrate (1.25 μM=>final conc. in the 5 μl assay volume is 0.75 μM) in assay buffer and the resulting mixture was incubated for a reaction time of 25 min at 22° C. The concentration of CDK9/CycT1 was adjusted depending of the activity of the enzyme lot and was chosen appropriate to have the assay in the linear range, typical concentrations were in the range of 0.5 μg/ml. The reaction was stopped by the addition of 3 μl of a solution of TR-FRET detection reagents (0.33 μM streptavidine-XL665 [Cisbio Bioassays, Codolet, France] and 1.67 nM anti-RB(pSer807/pSer811)-antibody from BD Pharmingen [#558389] and 2 nM LANCE EU-W1024 labeled anti-mouse IgG antibody [Perkin-Elmer, product no. AD0077]) in an aqueous EDTA-solution (167 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

2a. CDK2/CycE kinase assay

CDK2/CycE-inhibitory activity of compounds of the present invention was quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of CDK2/CycE in aqueous assay buffer [50 mM Tris/HCl pH 8.0, 10 mM MgCl2, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.25 μM=>final conc. in the 5 μl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were in the range of 130 ng/ml. The reaction was stopped by the addition of 5 μl of a solution of TR-FRET detection reagents (0.2 μM streptavidine-XL665

[Cisbio Bioassays, Codolet, France] and 1 nM anti-RB (pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

2b. CDK2/CycE High ATP Kinase Assay

CDK2/CycE-inhibitory activity of compounds of the present invention at 2 mM adenosine-tri-phosphate (ATP) was quantified employing the CDK2/CycE TR-FRET (TR-FRET=Time Resolved Fluorescence Energy Transfer) assay as described in the following paragraphs.

Recombinant fusion proteins of GST and human CDK2 and of GST and human CycE, expressed in insect cells (Sf9) and purified by Glutathion-Sepharose affinity chromatography, were purchase from ProQinase GmbH (Freiburg, Germany). As substrate for the kinase reaction biotinylated peptide biotin-Ttds-YISPLKSPYKISEG (C-terminus in amid form) was used which can be purchased e.g. form the company JERINI peptide technologies (Berlin, Germany).

For the assay 50 nl of a 100 fold concentrated solution of the test compound in DMSO was pipetted into either a black low volume 384 well microtiter plate or a black 1536 well microtiter plate (both Greiner Bio-One, Frickenhausen, Germany), 2 μl of a solution of CDK2/CycE in aqueous assay buffer [50 mM Tris/HCl pH 8.0, 10 mM MgCl2, 1.0 mM dithiothreitol, 0.1 mM sodium ortho-vanadate, 0.01% (v/v) Nonidet-P40 (Sigma)] were added and the mixture was incubated for 15 min at 22° C. to allow pre-binding of the test compounds to the enzyme before the start of the kinase reaction. Then the kinase reaction was started by the addition of 3 μl of a solution ATP (3.33 mM=>final conc. in the 5 μl assay volume is 2 mM) and substrate (1.25 μM=>final conc. in the 5 μl assay volume is 0.75 μM) in assay buffer and the resulting mixture was incubated for a reaction time of 25 min at 22° C. The concentration of CDK2/CycE was adjusted depending of the activity of the enzyme lot and was chosen appropriate to have the assay in the linear range, typical concentrations were about 10 ng/ml. The reaction was stopped by the addition of 3 μl of a solution of TR-FRET detection reagents (0.333 μM streptavidine-XL665 [Cisbio Bioassays, Codolet, France] and 1.67 nM anti-RB(pSer807/pSer811)-antibody from BD Pharmingen [#558389] and 2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (167 mM EDTA, 0.2% (w/v) bovine serum albumin in 100 mM HEPES pH 7.5).

The resulting mixture was incubated 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm was measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.07 nM (20 μM, 5.7 μM, 1.6 μM, 0.47 μM, 0.13 μM, 38 nM, 11 nM, 3.1 nM, 0.9 nM, 0.25 nM and 0.07 nM, the dilution series prepared separately before the assay on the level of the 100 fold concentrated solutions in DMSO by serial dilutions, exact concentrations may vary depending pipettors used) in duplicate values for each concentration and IC50 values were calculated using Genedata Screener™ software.

3. Proliferation Assay:

Cultivated tumour cells (HeLa, human cervical tumour cells, ATCC CCL-2; NCI-H460, human non-small cell lung carcinoma cells, ATCC HTB-177; DU 145, hormone-independent human prostate carcinoma cells, ATCC HTB-81; HeLa-MaTu-ADR, multidrug-resistant human cervical carcinoma cells, EPO-GmbH Berlin; Caco-2, human colorectal carcinoma cells, ATCC HTB-37; B16F10, mouse melanoma cells, ATCC CRL-6475) were plated at a density of 5,000 cells/well (DU145, HeLa-MaTu-ADR), 3,000 cells/well (NCI-H460, HeLa), 1,500 cells/well (Caco-2), or 1,000 cells/well (B16F10) in a 96-well multititer plate in 200 μL of their respective growth medium supplemented 10% fetal calf serum. After 24 hours, the cells of one plate (zero-point plate) were stained with crystal violet (see below), while the medium of the other plates was supplemented with the test substances in various concentrations (0 μM, as well as in the range of 0.0001-10 μM; the final concentration of the solvent dimethyl sulfoxide was adjusted to 0.1%) using a Hewlett-Packard HP D300 Digital Dispenser. The cells were incubated for 4 days in the presence of test substances. Cell proliferation was determined by staining the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were stained by adding 100 μl/measuring point of a 0.1% crystal violet solution (pH 3.0). After three washing cycles of the stained cells with water, the plates were dried at room temperature. The dye was dissolved by adding 100 μl/measuring point of a 10% acetic acid solution. The extinction was determined by photometry at a wavelength of 595 nm. The change of cell number, in percent, was calculated by normalization of the measured values to the extinction values of the zero-point plate (=0%) and the extinction of the untreated (0 m) cells (=100%). The $IC_{50}$ values (inhibitory concentration at 50% of maximal effect) were determined by means of a 4 parameter fit. A2780 human ovarian carcinoma cells (ECACC #93112519) and non-adherent MOLM-13 human acute myeloid leukemia cells (DSMZ ACC 554) were seeded at a density of 3,000 cell/well (A2780) or 5,000 cells/well (MOLM-13) in a 96-well multititer plate in 150 μL of growth medium supplemented 10% fetal calf serum. After 24 hours, cell viability of one plate (zero-point plate) was determined with the Cell Titre-Glo Luminescent Cell Viability Assay (Promega), while the medium of the other plates was supplemented with the test substances in various concentrations (0 μM, as well as in the range of 0.0001-10 μM; the final concentration of the solvent dimethyl sulfoxide was adjusted to 0.1%) using a Hewlett-Packard HP D300 Digital Dispenser. Cell viability was assessed after 72-hour exposure with the Cell Titre-Glo Luminescent Cell Viability Assay (Promega). $IC_{50}$ values (inhibitory concentration at 50% of maximal effect) were determined by means of a 4 parameter fit on measurement data which were normalized to vehicle (DMSO) treated cells (=100%) and measurement readings taken immediately before compound exposure (=0%).

4. Equilibrium Shake Flask Solubility Assay:

4a) High Throughput Determination of Aqueous Drug Solubility (100 Mmolar in DMSO)

The high throughput screening method to determine aqueous drug solubility is based on:

Thomas Onofrey and Greg Kazan, Performance and correlation of a 96-well high throughput screening method to determine aqueous drug solubility, http://www.millipore.com/publications.nsf/a73664f9f981af8c852569b9005b4eee/e565516fb76e743585256da30052db77/$FILE/AN1731EN00.pdf The assay was run in a 96-well plate format. Each well was filled with an individual compound.

All pipetting steps were performed using a robot platform.

100 μl of a 10 mmolar solution of drug in DMSO were concentrated by vacuum centrifugation and resolved in 10 μl DMSO. 990 μl phosphate buffer pH 6.5 were added. The content of DMSO amounts to 1%. The multititer plate was put on a shaker and mixed for 24 hrs at room temperature. 150 μl of the suspension were transferred to a filtration plate. After filtration using a vacuum manifold the filtrate was diluted 1:400 and 1:8000. A second microtiter plate with 20 μl of a 10 mM solution of drug in DMSO served for calibration. Two concentrations (0.005 μM and 0.0025 μM) were prepared by dilution in DMSO/water 1:1 and used for calibration. Filtrate and calibration plates were quantified by HPLC-MS/MS.

Chemicals:

Preparation of 0.1 m Phosphate Buffer pH 6.5:

61.86 g NaCl and 39.54 mg $KH_2PO_4$ were solved in water and filled up to 1 l. The mixture was diluted 1:10 with water and the pH adjusted to 6.5 by NaOH.

Materials:

Millipore MultiScreen$_{HTS}$-HV Plate 0.45 m

Chromatographic Conditions were as Follows:

HPLC column: Ascentis Express C18 2.7 μm 4.6×30 mm
Injection volume: 1 μl
Flow: 1.5 ml/min
Mobile phase: acidic gradient
A: Water/0.05% HCOOH
B: Acetonitrile/0.05% HCOOH
0 min→95% A 5% B
0.75 min→5% A 95% B
2.75 min→5% A 95% B
2.76 min→95% A 5% B
3 min→95% A 5% B The areas of sample- and calibration injections were determined by using mass spectrometry software (AB SCIEX: Discovery Quant 2.1.3. and Analyst 1.6.1). The calculation of the solubility value (in mg/l) was executed by an inhouse developed Excel macro.

4b) Thermodynamic Solubility in Water from Powder

The thermodynamic solubility of compounds in water was determined by an equilibrium shake flask method (see for example: E. H. Kerns, L. Di: Drug-like Properties: Concepts, Structure Design and Methods, 276-286, Burlington, Mass., Academic Press, 2008). A saturated solution of the drug was prepared and the solution was mixed for 24 h to ensure that equilibrium was reached. The solution was centrifuged to remove the insoluble fraction and the concentration of the compound in solution was determined using a standard calibration curve. To prepare the sample, 2 mg solid compound was weighed in a 4 mL glass vial. 1 mL phosphate buffer pH 6.5 was added. The suspension was stirred for 24 hrs at room temperature. The solution was centrifuged afterwards. To prepare the sample for the standard calibration, 2 mg solid sample was dissolved in 30 mL acetonitrile. After sonification the solution was diluted with water to 50 mL. Sample and standards were quantified by HPLC with UV-detection. For each sample two injection volumes (5 and 50 μl) in triplicates were made. Three injection volumes (5 μl, 10 μl and 20 μl) were made for the standard.

Chromatographic Conditions:

HPLC column: Xterra MS C18 2.5 μm 4.6×30 mm
Injection volume: Sample: 3×5 μl and 3×50 μl
Standard: 5 μl, 10 μl, 20 μl
Flow: 1.5 mL/min
Mobile phase: acidic gradient:
A: Water/0.01% TFA
B: Acetonitrile/0.01% TFA
0 min→95% A 5% B
0-3 min→35% A 65% B, linear gradient
3-5 min→35% A 65% B, isocratic
5-6 min→95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

4c) Thermodynamic Solubility in Citrate Buffer pH 4

Thermodynamic solubility was determined by an equilibrium shake flask method [Literature: Edward H. Kerns and Li Di (2008) Solubility Methods in: Drug-like Properties: Concepts, Structure Design and Methods, p 276-286. Burlington, Mass.: Academic Press].

A saturated solution of the drug was prepared and the solution was mixed for 24 h to ensure that equilibrium has been reached. The solution was centrifuged to remove the insoluble fraction and the concentration of the compound in solution was determined using a standard calibration curve.

To prepare the sample, 1.5 mg solid compound was weighed in a 4 ml glass vial. 1 ml Citrate buffer pH 4 was added. The suspension was put on a stirrer and mixed for 24 hrs at room temperature. The solution was centrifuged afterwards. To prepare the sample for the standard calibration, 0.6 mg solid sample was dissolved in 19 ml acetonitrile/water 1:1. After sonification the solution was filled up with acetonitrile/water 1:1 to 20 ml.

Sample and standards were quantified by HPLC with UV-detection. For each sample two injection volumes (5 and 50 μl) in triplicates were made. Three injection volumes (5 μl, 10 μl and 20 μl) were made for the standard.

Chemicals:

Citrate buffer pH 4 (MERCK Art. 109435; 1 L buffer consisting of 11,768 g citric acid, 4,480 g sodium hydroxide, 1,604 g hydrogen chloride)

Chromatographic Conditions were as Follows:

HPLC column: Xterra MS C18 2.5 μm 4.6×30 mm
Injection volume: Sample: 3×5 μl and 3×50 μl
Standard: 5 μl, 10 μl, 20 μl
Flow: 1.5 ml/min
Mobile phase: acidic gradient:
A: Water/0.01% TFA
B: Acetonitrile/0.01% TFA
0 min: 95% A 5% B
0-3 min: 35% A 65% B, linear gradient
3-5 min: 35% A 65% B, isocratic
5-6 min: 95% A 5% B, isocratic
UV detector: wavelength near the absorption maximum (between 200 and 400 nm)

The areas of sample- and standard injections as well as the calculation of the solubility value (in mg/l) were determined by using HPLC software (Waters Empower 2 FR).

The areas of sample- and standard injections as well as the calculation of the solubility value (in mg/l) were determined by using HPLC software (Waters Empower 2 FR).

5. Caco-2 Permeation Assay:

Caco-2 cells (purchased from DSMZ Braunschweig, Germany) were seeded at a density of $4.5\times10^4$ cells per well on 24 well insert plates, 0.4 m pore size, and grown for 15 days in DMEM medium supplemented with 10% fetal bovine serum, 1% GlutaMAX (100×, GIBCO), 100 U/mL penicillin, 100 μg/mL streptomycin (GIBCO) and 1% non essential amino acids (100×). Cells were maintained at 37° C. in a humified 5% $CO_2$ atmosphere. Medium was changed every 2-3 day. Before running the permeation assay, the culture medium was replaced by a FCS-free hepes-carbonate transport buffer (pH 7.2). For assessment of monolayer integrity the transepithelial electrical resistance (TEER) was measured. Test compounds were predissolved in DMSO and added either to the apical or basolateral compartment in final concentration of 2 μM in transport buffer. Before and after 2h incubation at 37° C. samples were taken from both compartments. Analysis of compound content was done after precipitation with methanol by LC/MS/MS analysis. Permeability (Papp) was calculated in the apical to basolateral (A→B) and basolateral to apical (B→A) directions.

The apparent permeability was calculated using following equation:

$$\text{Papp}=(Vr/Po)(1/S)(P2/t)$$

Where Vr is the volume of medium in the receiver chamber, Po is the measured peak area or height of the test drug in the donor chamber at t=o, S the surface area of the monolayer, P2 is the measured peak area of the test drug in the acceptor chamber after 2h of incubation, and t is the incubation time. The efflux ratio basolateral (B) to apical (A) was calculated by dividing the Papp B–A by the Papp A–B. In addition the compound recovery was calculated.

6. Investigation of In Vitro Metabolic Stability in Rat Hepatocytes

Hepatocytes from Han Wistar rats were isolated via a 2-step perfusion method. After perfusion, the liver was carefully removed from the rat: the liver capsule was opened and the hepatocytes were gently shaken out into a Petri dish with ice-cold Williams medium E (purchased from Sigma Aldrich Life Science, St Louis, Mo.). The resulting cell suspension was filtered through sterile gaze in 50 ml falcon tubes and centrifuged at 50×g for 3 min at room temperature. The cell pellet was resuspended in 30 ml WME and centrifuged through a Percoll® gradient for 2 times at 100×g. The hepatocytes were washed again with Williams' medium E (WME) and resuspended in medium containing 5% Fetal calf serum (FCS, purchased from Invitrogen, Auckland, NZ). Cell viability was determined by trypan blue exclusion.

For the metabolic stability assay liver cells were distributed in WME containing 5% FCS to glass vials at a density of $1.0\times10^6$ vital cells/ml. The test compound was added to a final concentration of 1 μM.

During incubation, the hepatocyte suspensions were continuously shaken and aliquots were taken at 2, 8, 16, 30, 45 and 90 min, to which equal volumes of cold acetonitrile were immediately added. Samples were frozen at −20° C. over night, after subsequently centrifuged for 15 minutes at 3000 rpm and the supernatant was analyzed with an Agilent 1200 HPLC-system with LCMS/MS detection.

The half-life of a test compound was determined from the concentration-time plot. From the half-life the intrinsic clearances were calculated. Together with the additional parameters liver blood flow, amount of liver cells in vivo and in vitro, the maximal oral bioavailability (Fmax) was calculated using the following scaling parameters: Liver blood flow (rat)—4.2 L/h/kg; specific liver weight—32 g/kg rat body weight; liver cells in vivo—$1.1\times10^8$ cells/g liver, liver cells in vitro—$0.5\times10^6$/ml.

7. In Vivo Pharmacokinetics in Rats

For in vivo pharmacokinetic experiments test compounds were administered to male Wistar rats intravenously at doses of 0.3 to 1 mg/kg formulated as solutions using either rat plasma or solubilizers such as PEG400 in well-tolerated amounts.

For pharmacokinetics after intravenous administration test compounds were given as i.v. bolus and blood samples were taken at 2 min, 8 min, 15 min, 30 min, 45 min, 1 h, 2 h, 4 h, 6 h, 8 h and 24 h after dosing. Depending on the expected half-life additional samples were taken at later time points (e.g. 48 h, 72 h). Blood was collected into Lithium-Heparin tubes (Monovetten®, Sarstedt) and centrifuged for 15 min at 3000 rpm. An aliquot of 100 μL from the supernatant (plasma) was taken and precipitated by addition of 400 μL ice cold acetonitrile and frozen at −20° C. over night. Samples were subsequently thawed and centrifuged at 3000 rpm, 4° C. for 20 minutes. Aliquots of the supernatants were taken for analytical testing using an Agilent 1200 HPLC-system with LCMS/MS detection. PK parameters were calculated by non-compartmental analysis using a PK calculation software.

PK parameters derived from concentration-time profiles after i.v.: CLplasma: Total plasma clearance of test compound (in L/kg/h); CLblood: Total blood clearance of test compound: CLplasma*Cp/Cb (in L/kg/h) with Cp/Cb being the ratio of concentrations in plasma and blood, AUCnorm: Area under the concentration-time curve from t=0 h to infinity (extrapolated) divided by the administered dose (in kg*h/L); $t_{1/2}$: terminal half-life (in h).

8. Surface Plasmon Resonance PTEFb

Definitions

The term "surface plasmon resonance", as used herein, refers to an optical phenomenon that allows for the analysis of the reversible associations of biological molecules in real time within a biosensor matrix, for example using the Biacore® system (GE Healthcare Biosciences, Uppsala, Sweden). Biacore® uses the optical properties of surface plasmon resonance (SPR) to detect alterations in the refractive index of a buffer, which changes as molecules in solution interact with the target immobilized on the surface. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by compound binding to the bound protein) a shift occurs in the resonance angle. This angle shift can be measured. These changes are displayed with respect to time along the y-axis of a sensorgram, which depicts the association and dissociation of any biological reaction.

The term "$K_D$", as used herein, is intended to refer to the equilibrium dissociation constant of a particular compound/target protein complex.

The term "$k_{off}$", as used herein, is intended to refer to the off-rate, i.e. the dissociation rate constant of a particular compound/target protein complex.

The term "target residence time", as used herein, is intended to refer to the inverse of the rate of dissociation rate constant ($1/k_{off}$) of a particular compound/target protein complex.

For further descriptions see:

Jönsson U et al al., 1993 Ann Biol Clin.; 51(1):19-26.
Johnsson B et al, Anal Biochem. 1991; 198(2):268-77.
Day Y et al, Protein Science, 2002; 11, 1017-1025
Myskza D G, Anal Biochem., 2004; 329, 316-323
Tummino and Copeland, Biochemistry, 2008; 47(20):5481-5492.

Biological Activity

The biological activity (e.g. as inhibitors of PTEFb) of the compounds according to the invention can be measured using the SPR assay described.

The level of activity exhibited by a given compound in the SPR assay can be defined in terms of the $K_D$ value, and preferred compounds of the present invention are compounds having a $K_D$ value of less than 1 micromolar, more preferably less than 0.1 micromolar. Furthermore, the time in residence at its target of a given compound can be defined in terms of the target residence time (TRT), and preferred compounds of the present invention are compounds having a TRT value of more than 10 minutes, more preferably more than 1 hour.

The ability of the compounds according to the invention to bind human PTEFb may be determined using surface plasmon resonance (SPR). $K_D$ values and $k_{off}$ values may be measured using a Biacore® T200 instrument (GE Healthcare, Uppsala, Sweden).

For SPR measurements, recombinant human PTEFb (CDK9/Cyclin T1 recombinant human active protein kinase purchased from ProQinase, Freiburg, Germany) is immobilized using standard amine coupling (Johnsson B et al, Anal Biochem. 1991 Nov. 1; 198(2):268-77). Briefly, carboxymethylated dextran biosensor chips (CM7, GE Healthcare) are activated with N-ethyl-N'-(3-dimethylaminopropyl)-carbodiimide hydrochloride (EDC) and N-hydroxysuccinimide (NHS) according to the supplier's instructions. Human PTEFb is diluted in 1×HBS-EP+ (GE Healthcare) and injected on the activated chip surface. Subsequently, a 1:1 solution of 1 M ethanolamine-HCl (GE Healthcare) and 1×HBS-EP is injected to block unreacted groups, resulting in approximately 4000 response units (RU) of immobilized protein. A reference surface is generated by treatment with NHS-EDC and ethanolamine-HCl. Compounds are dissolved in 100% dimethylsulfoxide (DMSO, Sigma-Aldrich, Germany) to a concentration of 10 mM and subsequently diluted in running buffer (1×HBS-EP+pH 7.4 [generated from HBS-EP+ Buffer 10× (GE Healthcare): 0.1 M HEPES, 1.5 M NaCl, 30 mM EDTA and 0.5% v/v Surfactant P20], 1% v/v DMSO). For kinetic measurements, serial dilutions of compound (0.78 nM up to 25 nM) are injected over immobilized protein. Binding kinetics is measured at 37° C. with a flow rate of 100 μl/min in running buffer. Compound concentrations are injected for 70 s followed by a dissociation time of 1100 s. The resulting sensorgrams are double-referenced against the reference surface as well as against blank injections.

The double-referenced sensorgrams are fit to a simple reversible Langmuir 1:1 reaction mechanism as implemented in the Biacore® T200 evaluation software 2.0 (GE Healthcare). In cases were full compound dissociation has not occurred at the end of the dissociation phase, the Rmax parameter (response at saturation) is fit as local variable. In all other cases, Rmax is fit as global variable. SPR measurements are summarized in Table 4

Syntheses of Compounds

The syntheses of the macrocyclic compounds of formula (I) according to the present invention are preferably carried out according to the general synthetic sequences as shown in Schemes 1a, 1b, 1c, 2a and 2b.

In addition to said routes described below, also other routes may be used to synthesise the target compounds, in accordance with common general knowledge of a person skilled in the art of organic synthesis. The order of transformations exemplified in the following Schemes is therefore not intended to be limiting, and suitable synthesis steps from various schemes can be combined to form additional synthesis sequences. In addition, modification of any of the substituents $R^1$, $R^2$, $R^3$, $R^4$, $R^5$ and/or Z can be achieved before and/or after the exemplified transformations. These modifications can be such as the introduction of protective groups, cleavage of protective groups, reduction or oxidation of functional groups, halogenation, metallation, metal catalysed coupling reactions, substitution or other reactions known to a person skilled in the art. These transformations include those which introduce a functionality allowing for further interconversion of substituents. Appropriate protective groups and their introduction and cleavage are well-known to a person skilled in the art (see for example T. W. Greene and P. G. M. Wuts in Protective Groups in Organic Synthesis, $4^{th}$ edition, Wiley 2006). Specific examples are described in the subsequent paragraphs. Further, it is possible that two or more successive steps may be performed without work-up being performed between said steps, e.g. a "one-pot" reaction, as it is well-known to a person skilled in the art.

The geometry of the sulfoximine, sulfodiimine and sulfoxide moiety renders some of the compounds of the general formula (I) chiral. Separation of racemic sulfoximines, sulfodiimines and sulfoxides into their enantiomers can be achieved by methods known to the person skilled in the art, preferably by means of preparative HPLC on chiral stationary phase.

The syntheses of the pyridine derivatives of formulae (Ia), (Ib) and (Ic), all of them constituting subsets of the general formula (I) according to the present invention, are preferably carried out according to the general synthetic sequences as shown in Schemes 1a, 1b and 1c and 1d.

Scheme 1a
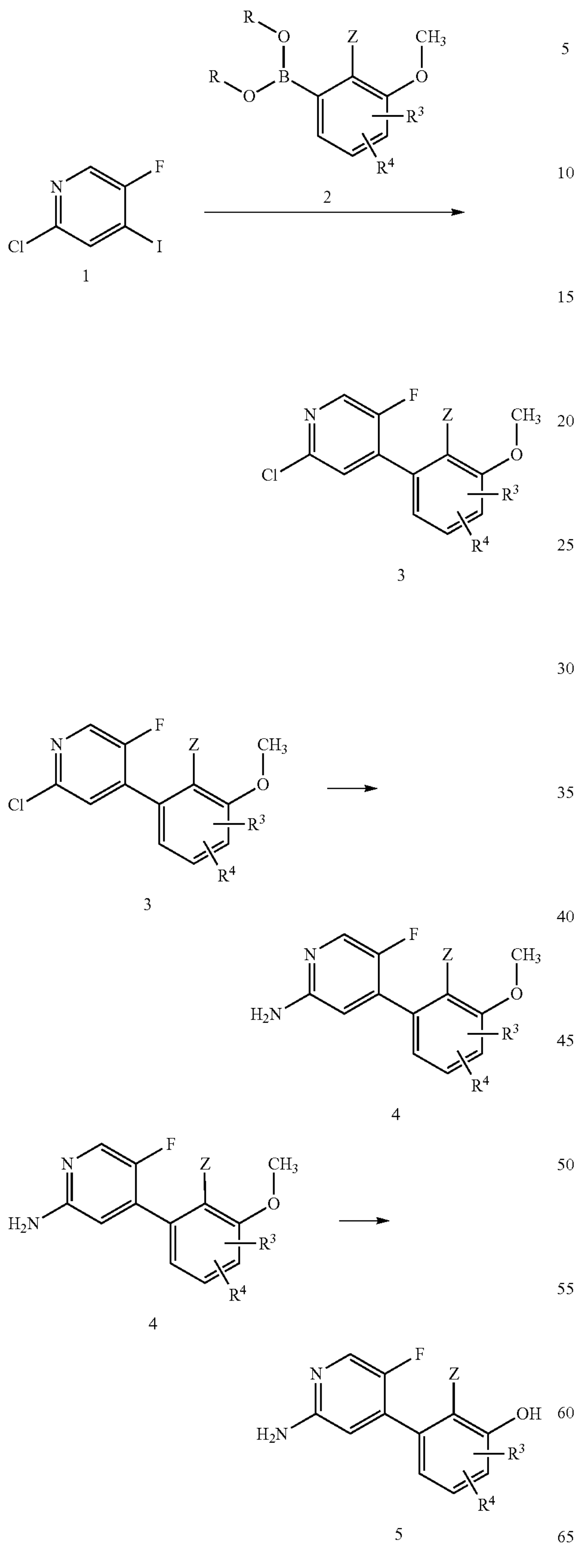
Scheme 1b
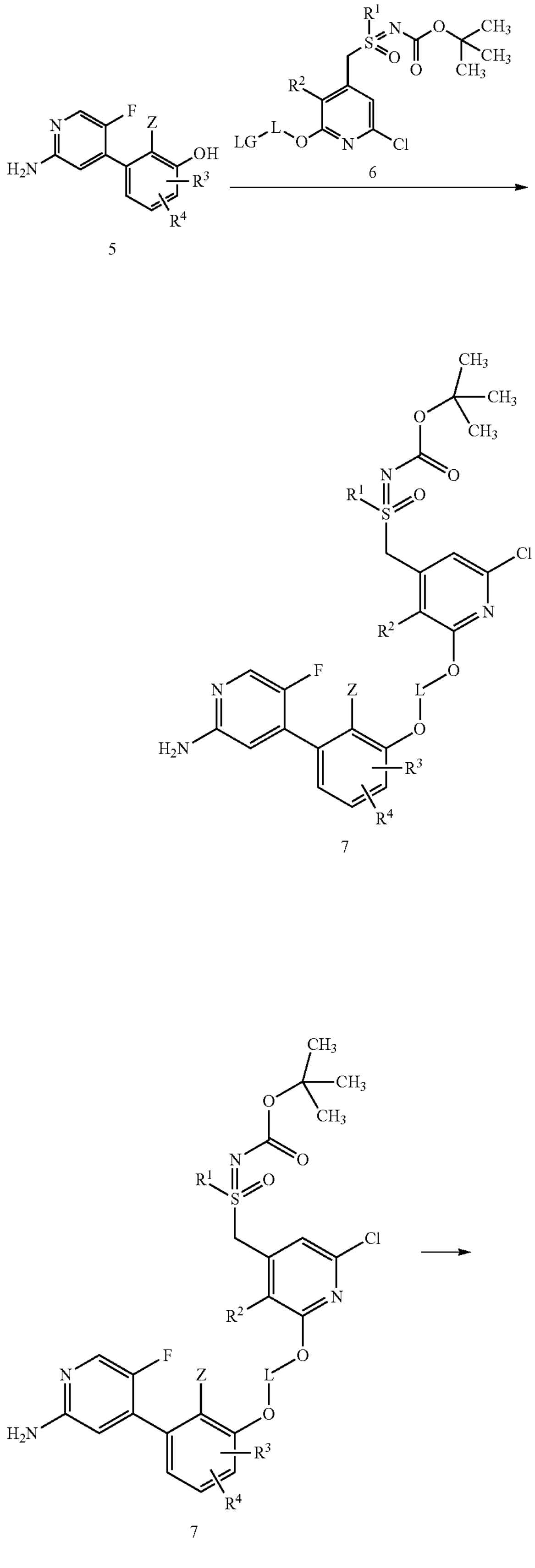

-continued

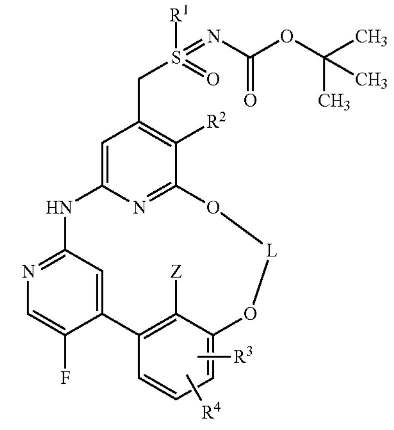

(Ia)

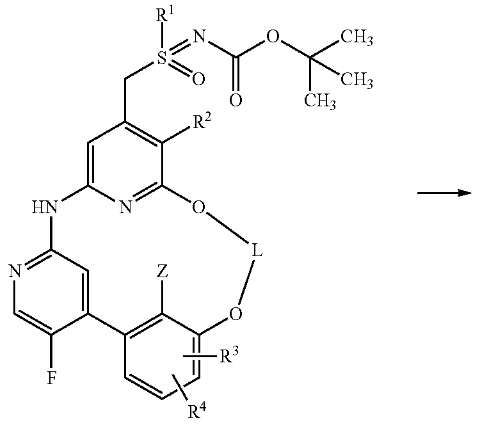

(Ia)

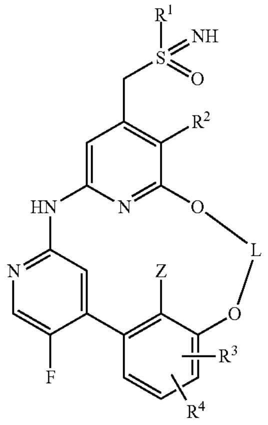

(Ib)

-continued

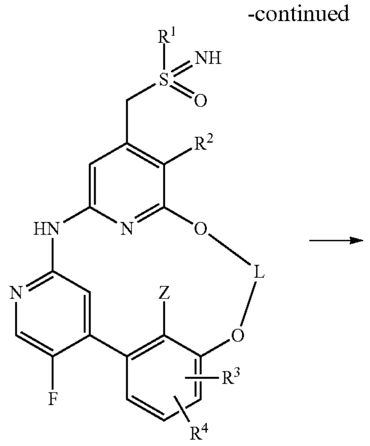

(Ib)

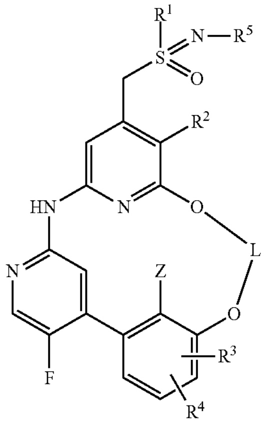

(Ic)

Schemes 1a, 1b and 1c, wherein $R^1$, $R^2$, $R^3$, $R^4$, $R^5$, Z and L are as defined for the compound of general formula (I) according to the present invention, outline the preparation of pyridine-based macrocyclic compounds of of formulae (Ia), (Ib) and (Ic), from 2-chloro-5-fluoro-4-iodopyridine (1; CAS #884494-49-9).

Said starting material (1) can be reacted with a boronic acid derivative of formula (2), in which $R^3$, $R^4$ and Z are as defined for the compound of general formula (I), to give a compound of formula (3). The boronic acid derivative (2) may be a boronic acid (R=—H) or an ester of the boronic acid, e.g. its isopropyl ester (R=—$CH(CH_3)_2$), preferably an ester derived from pinacol in which the boronic acid intermediate forms a 2-aryl-4,4,5,5-tetramethyl-1,3,2-dioxaborolane (R—R=—$C(CH_3)_2$—$C(CH_3)_2$—).

Said coupling reaction can be catalyzed by palladium catalysts, e.g. by Pd(0) catalysts such as tetrakis(triphenylphosphine)palladium(0) [$Pd(PPh_3)_4$], tris(dibenzylideneacetone)di-palladium(0) [$Pd_2(dba)_3$], or by Pd(II) catalysts such as dichlorobis(triphenylphosphine)-palladium(II) [$Pd(PPh_3)_2Cl_2$], palladium(II) acetate and triphenylphosphine or by [1,1'-bis(diphenylphosphino)ferrocene]palladium dichloride.

The reaction can preferably be carried out in a mixture of a solvent such as 1,2-dimethoxyethane, dioxane, DMF, DME, THF, or isopropanol with water and in the presence of a base such as potassium carbonate, sodium bicarbonate or potassium phosphate.

(review: D. G. Hall, Boronic Acids, 2005 WILEY-VCH Verlag GmbH & Co. KGaA, Weinheim, ISBN 3-527-30991-8 and references cited therein).

The reaction can be performed at temperatures ranging from room temperature (i.e. approx. 20° C.) to the boiling point of the respective solvent. Further on, the reaction can be performed at temperatures above the boiling point using pressure tubes and a microwave oven. The reaction is preferably completed after 1 to 36 hours of reaction time.

In the second step, a compound of formula (3) can be converted to a compound of formula (4). This reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', 2nd ed.: A. de Meijere, F. Diederich, Eds.: Wiley-VCH: Weinheim, Germany, 2004).

Preferred is the herein described use of lithium bis(trimethylsilyl)amide, tris(dibenzylideneacetone)dipalladium(0) and 2-(dicyclohexylphosphino)-2',4',6'-triisopropylbiphenyl in THF. The reactions are preferably run under an atmosphere of argon for 3-24 hours at 60° C. in an oil bath.

In the third step, a compound of formula (4) can be converted to a compound of formula (5), by means of cleaving the methyl ether present in compounds of formula (4).

Preferred is the herein described use of boron tribromide in DCM. The reactions are preferably run for 1-24 hours at 0° C. to room temperature.

In the fourth step, a compound of formula (5) can be coupled with a compound of formula (6), in which $R^1$, $R^2$ and L are as defined for the compound of general formula (I) and in which LG represents a leaving group such as a chlorine atom, a bromine atom or a iodine atom, $C_1$-$C_4$-alkyl-S(=O)$_2$O—, trifluoromethanesulfonyloxy-, benzenesulfonyloxy-, or para-toluenesulfonyloxy-, to give a compound of formula (7). Preferred is the herein described use of potassium carbonate and potassium iodide in DMF. The reactions are preferably run for 1-36 hours at 40 to 80° C.

Compounds of the formula (6) can be prepared as outlined in Scheme 1c, infra.

In the fifth step, a compound of formula (7) is converted to a macrocycle of formula (Ia). This cyclization reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', 2nd ed.: A. de Meijere, F. Diederich, Eds.: Wiley-VCH: Weinheim, Germany, 2004).

Preferred is the herein described use of chloro(2-dicyclohexylphosphino-2',4',6'-tri-iso-propyl-1,1'-biphenyl) [2-(2-aminoethyl)phenyl] palladium(II) methyl-tert-butylether adduct, 2-(dicyclohexylphosphino)-2',4',6'-triisopropylbiphenyl as catalyst and ligand, an alkali carbonate or an alkali phosphate, preferably potassium phosphate, as a base, in a mixture of a $C_1$-$C_3$-alkylbenzene and a carboxamide based solvent, preferably a mixture of toluene and NMP, as a solvent. The reactions are preferably run under an atmosphere of argon for 2-24 hours at 100-130° C. in a microwave oven or in an oil bath.

In the sixth step, the tert-butoxycarbonyl-group attached to the sulfoximine nitrogen can be cleaved under acidic conditions to give an unprotected sulfoximine of formula (Ib) (see for example: J. A. Bull, J. Org. Chem. 2015, 80, 6391).

Preferred is the herein described use of an acid, preferably trifluoroacetic acid in dichloromethane as a solvent.

Said N-unprotected sulfoximine of formula (Ib) ($R^5$=H) may be further converted into a N-functionalized derivative of formula (Ic). There are multiple methods for the preparation of N-functionalized sulfoximines by functionalization of the nitrogen of the sulfoximine group:

- Alkylation: see for example: a) U. Lücking et al, US 2007/0232632; b) C. R. Johnson, J. Org. Chem. 1993, 58, 1922; c) C. Bolm et al, Synthesis 2009, 10, 1601.
- Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.
- Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C. Bolm et al, J. Org. Chem. 2005, 70, 2346; e) U. Lücking et al, WO2007/71455.
- Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.
- Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.
- Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.
- Reaction with bromocyane: see for example: a) D. T. Sauer et al, Inorganic Chemistry 1972, 11, 238; b) C. Bolm et al, Org. Lett. 2007, 9, 2951; c) U. Lücking et al, WO 2011/29537.

Scheme 1c

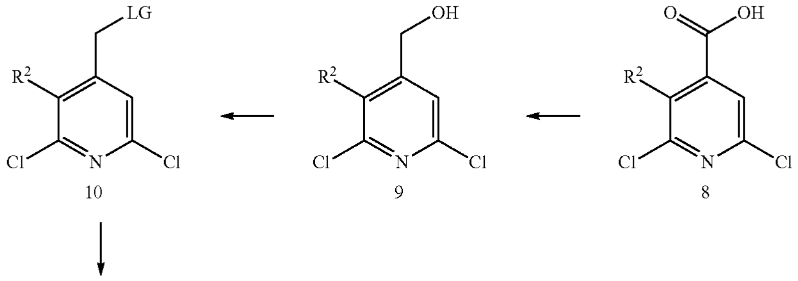

10

9

8

-continued

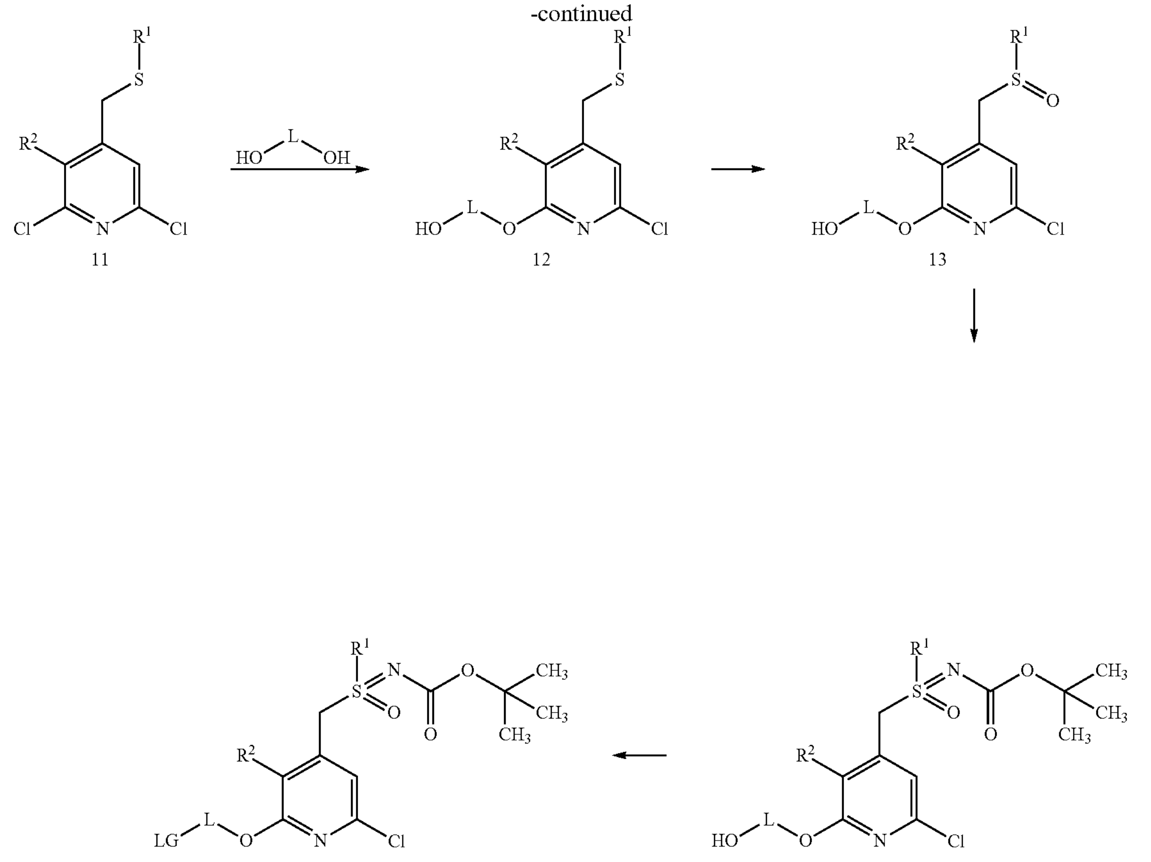

11 12 13 14 6

Intermediates of the formula (6), in which $R^1$, $R^2$ and L are as defined for the compound of general formula (I) according to the present invention and in which LG represents a leaving group such as a chlorine atom, a bromine atom or a iodine atom, $C_1$-$C_4$-alkyl-S(=O)$_2$O—, trifluoromethanesulfonyloxy-, benzenesulfonyloxy-, or para-toluenesulfonyloxy-, can be prepared according to Scheme 1c, starting e.g. from a 2,6-dichloroisonicotinic acid derivative of formula (8), in which $R^2$ is as defined for the compound of general formula (I), which can be reduced to the corresponding pyridinemethanol of formula (9), by means of reduction. Preferred is the herein described use of sulfanediyldimethane-borane (1:1 complex) in tetrahydrofuran.

Derivatives of isonicotinic acid of formula (8), and esters thereof, are well known to the person skilled in the art, and are often commercially available.

In a second step, said pyridinemethanol of formula (9) can be reacted to give a compound of formula (10), in which LG represents a leaving group such as a chlorine atom, a bromine atom or a iodine atom, $C_1$-$C_4$-alkyl-S(=O)$_2$O—, trifluoromethanesulfonyloxy-, benzenesulfonyloxy-, or para-toluenesulfonyloxy-. Such conversions are well known to the person skilled in the art; preferred is the herein described use of methanesulfonyl chloride in the presence of triethylamine as a base, in dichloromethane as a solvent, to give a compound of formula (10) in which LG represents methanesulfonyloxy-.

In a third step, a compound of formula (10) can be reacted with a thiol of the formula $R^1$—SH, in which $R^1$ is as defined for the compound of general formula (I), to give a thioether derivative of formula (11). Thiols of the formula $R^1$SH are well known to the person skilled in the art and are commercially available in considerable variety.

In a fourth step, a thioether derivative of formula (11) can be reacted with an anion formed in situ from a diol of the formula HO-L-OH, in which L is as defined for the compound of general formula (I), and an alkali metal, preferably sodium, or sodium hydride in tetrahydrofuran as a solvent, to give intermediate compounds of formula (12).

In a fifth step, oxidation of a thioether of formula (12) can be used to obtain the corresponding sulfoxide of formula (13). The oxidation can be performed analogously to known processes (see for example: (a) M. H. Ali et al, Synthesis 1997, 764; (b) M. C. Carreno, Chem. Rev. 1995, 95, 1717; (c) I. Patel et al, Org. Proc. Res. Dev. 2002, 6, 225; (d) N. Khiar et al, Chem. Rev. 2003, 103, 3651).

Preferred is the herein described use of periodic acid und iron(III) chloride.

In a sixth step, Rhodium-catalyzed imination of a sulfoxide of formula (13) can be used to prepare the N-Boc-protected sulfoximines of formula (14) (Bull et al, J. Org. Chem. 2015, 80, 6391). Preferred is the herein described use of sulfoxide (13), tert-butyl carbamate, magnesium oxide, rhodium(II) acetate dimer and iodobenzene diacetate in DCM at room temperature to 45° C.

In a seventh step, the alcohol can be reacted with methanesulfonyl chloride to form the methanesulfonate (6).

Preferred is the herein described use of trimethylamine as the base in DCM as the solvent at room temperature.

Scheme 1d

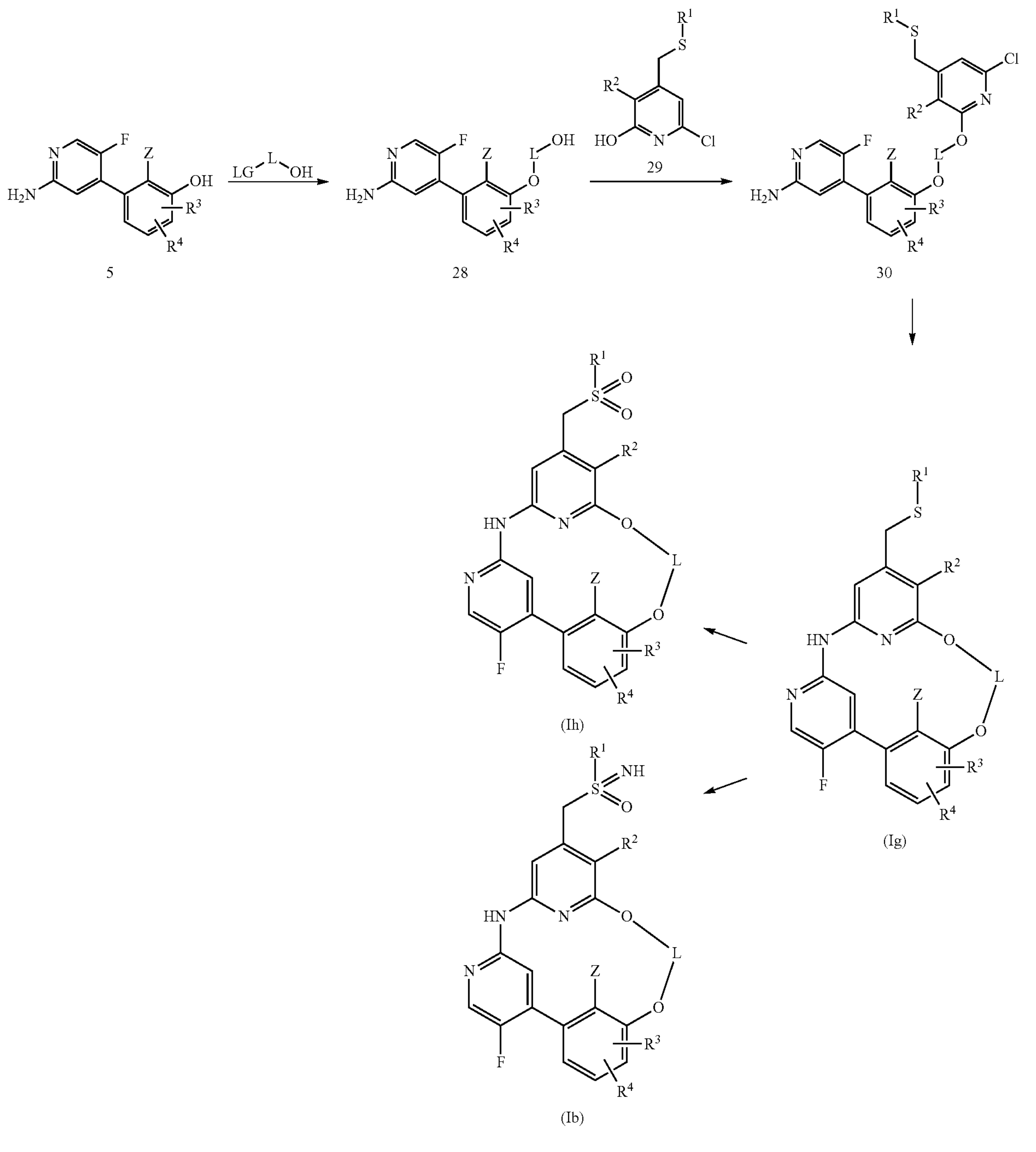

In alternative approach is outlined in Scheme 1d.

In the first step, a compound of formula (5) can be coupled with an alcohol LG-L-OH, in which L is as defined for the compound of general formula (I) and in which LG represents a leaving group such as a chlorine atom, a bromine atom or a iodine atom, $C_1$-$C_4$-alkyl-S(═O)$_2$O—, trifluoromethanesulfonyloxy-, benzenesulfonyloxy-, or para-toluenesulfonyloxy-, to give a compound of formula (28). Preferred is the herein described use a $CH_3$—S(═O)$_2$O— leaving group in combination with potassium carbonate and potassium iodide in DMF. The reactions are preferably run for 1-36 hours at 40 to 80° C.

In the second step, a compound of formula (28) can be coupled with a compound of formula (29) to give a compound of formula (30).

This reaction can be carried out by a Mitsunobu reaction (see for example: a) K. C. K. Swamy et al, Chem. Rev. 2009, 109, 2551).

In the third step, a compound of formula (30) can be converted to a macrocycle compound of the invention (Ig), which constitutes a subset of the general formula (I) according to the present invention, This cyclization reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of chloro(2-dicyclohexylphosphino-2',4',6'-tri-iso-propyl-1,1'-biphenyl) [2-(2-aminoethyl)phenyl] palladium(II) methyl-tert-butylether adduct, 2-(dicyclohexylphosphino)-2',4',6'-triisopropylbiphenyl as catalyst and ligand, an alkali carbonate or an alkali phosphate, preferably potassium phosphate, as a base, in a mixture of a $C_1$-$C_3$-alkylbenzene and a carboxamide based solvent, preferably a mixture of toluene and NMP, as a solvent. The reactions are preferably run under an atmosphere of argon for 2-24 hours at 100-130° C. in a microwave oven or in an oil bath.

In the last step, oxidation of a thioether of formula (Ig) can be used to obtain the corresponding sulfone of formula (Ih), which constitutes a subset of the general formula (I) according to the present invention. The oxidation can be performed analogously to known processes.

Preferred is the herein described use of 3-chloroperbenzoic acid in DCM.

Alternatively, In the last step, one-pot oxidation/imination reaction of a thioether of formula (Ig) can be used to obtain the corresponding NH sulfoximine of formula (Ib), which constitutes a subset of the general formula (I) according to the present invention.

Preferred is the herein described procedure based on A. Tota, M. Zenzola, S. J. Chawner, S. St. John-Campell, C. Carlucci, G. Romanazzi, L. Degennaro, J. A. Bull, R. Luisi; ChemComm 2017, 348

The syntheses of the pyrimidine derivatives of formulae (Id), (Ie) and (If), all of them also constituting subsets of the general formula (I) according to the present invention, are preferably carried out according to the general synthetic sequences as shown in Schemes 2a and 2b.

Schemes 2a and 2b, wherein $R^1$, $R^2$, $R^3$, $R^4$, $R^5$, Z and L are as defined for the compound of general formula (I) according to the present invention, outline the preparation of pyrimidine compounds of the general formula (Id), (Ie) and (If) from 2,4-dichloro-5-fluoropyrimidine (CAS #2927-71-1), (15). Said starting material (15) can be reacted with a boronic acid derivative of formula (2) to give a compound of formula (16). The boronic acid derivative (2) may be a boronic acid (R=—H) or an ester of the boronic acid, e.g. its isopropyl ester (R=—$CH(CH_3)_2$), preferably an ester derived from pinacol in which the boronic acid intermediate forms a 2-aryl-4,4,5,5-tetramethyl-1,3,2-dioxaborolane (R—R=—$C(CH_3)_2$—$C(CH_3)_2$—). Boronic acids and their esters are commercially available and well-known to the person skilled in the art; see e.g. D. G. Hall, Boronic Acids, 2005 WILEY-VCH Verlag GmbH & Co. KGaA, Weinheim, ISBN 3-527-30991-8 and references cited therein.

The coupling reaction is catalyzed by Pd catalysts, e.g. by Pd(0) catalysts such as tetrakis(triphenylphosphine)palladium(0) $[Pd(PPh_3)_4]$, tris(dibenzylideneacetone)di-palladium(0) $[Pd_2(dba)_3]$, or by Pd(II) catalysts such as dichlorobis(triphenylphosphine)-palladium(II) $[Pd(PPh_3)_2Cl_2]$, palladium(II) acetate and triphenylphosphine or by [1,1'-bis(diphenylphosphino)ferrocene]palladium dichloride $[Pd(dppf)Cl_2]$.

The reaction can preferably be carried out in a mixture of a solvent such as 1,2-dimethoxyethane, dioxane, DMF, DME, THF, or isopropanol with water and in the presence of a base such as aqueous potassium carbonate, aqueous sodium bicarbonate or potassium phosphate.

The reaction can be performed at temperatures ranging from room temperature (=20° C.) to the boiling point of the solvent. Further on, the reaction can be performed at temperatures above the boiling point using pressure tubes and a microwave oven. (review: D. G. Hall, Boronic Acids, 2005 WILEY-VCH Verlag GmbH & Co. KGaA, Weinheim, ISBN 3-527-30991-8 and references cited therein).

The reaction is preferably completed after 1 to 36 hours of reaction time.

In the second step, a compound of formula (16) can be coupled with a compound of formula (17) to give a compound of formula (18).

This reaction can be carried out by a Mitsunobu reaction (see for example: a) K. C. K. Swamy et al, Chem. Rev. 2009, 109, 2551).

Compounds of the formula (17) can be prepared as outlined in Scheme 2b, infra.

Said compounds of formula (18) (Scheme 2a), wherein $R^1$, $R^2$, $R^3$, $R^4$, L and Z are defined for the compound of general formula (I) according to the present invention, can be reduced to give an aniline of formula (19). The reduction can be prepared analogously to known processes (see for example: (a) Sammond et al; Bioorg. Med. Chem. Lett. 2005, 15, 3519; (b) R. C. Larock, Comprehensive Organic Transformations, VCH, New York, 1989, 411-415). Preferred is the herein described use of Platinum 1% and vanadium 2%, on activated carbon in methanol and THF at room temperature under a hydrogen atmosphere.

In the fourth step, a compound of formula (19) can be converted to a macrocycle compound of the invention (Id). This cyclization reaction can be carried out by a Palladium-catalyzed C—N cross-coupling reaction (for a review on C—N cross coupling reactions see for example: a) L. Jiang, S. L. Buchwald in 'Metal-Catalyzed Cross-Coupling Reactions', $2^{nd}$ ed.: A. de Meijere, F. Diederich, Eds.: Wiley-VCH: Weinheim, Germany, 2004).

Preferred is the herein described use of chloro(2-dicyclohexylphosphino-2',4',6'-tri-iso-propyl-1,1'-biphenyl) [2-(2-aminoethyl)phenyl] palladium(II) methyl-tert-butylether adduct, 2-(dicyclohexylphosphino)-2',4',6'-triisopropylbiphenyl as catalyst and ligand, an alkali carbonate or an alkali phosphate, preferably potassium phosphate, as a base, in a mixture of a $C_1$-$C_3$-alkylbenzene and a carboxamide based solvent, preferably a mixture of toluene and NMP, as a solvent. The reactions are preferably run under an atmosphere of argon for 2-24 hours at 100-130° C. in a microwave oven or in an oil bath.

In the fifth step, the tert-butoxycarbonyl-group attached to the sulfoximine nitrogen can be cleaved under acidic conditions to give an unprotected sulfoximine of formula (Ie) (see for example: J. A. Bull, J. Org. Chem. 2015, 80, 6391).

Preferred is the herein described use of an acid, preferably trifluoroacetic acid in dichloromethane as a solvent.

Said N-unprotected sulfoximine of formula (Ie) ($R^5$=H) may be further converted into a N-functionalized derivative of formula (If). There are multiple methods for the preparation of N-functionalized sulfoximines by functionalization of the nitrogen of the sulfoximine group:

- Alkylation: see for example: a) U. Lücking et al, US 2007/0232632; b) C. R. Johnson, J. Org. Chem. 1993, 58, 1922; c) C. Bolm et al, Synthesis 2009, 10, 1601.
- Acylation: see for example: a) C. Bolm et al, Chem. Europ. J. 2004, 10, 2942; b) C. Bolm et al, Synthesis 2002, 7, 879; c) C. Bolm et al, Chem. Europ. J. 2001, 7, 1118.
- Arylation: see for example: a) C. Bolm et al, Tet. Lett. 1998, 39, 5731; b) C. Bolm et al., J. Org. Chem. 2000, 65, 169; c) C. Bolm et al, Synthesis 2000, 7, 911; d) C.

Bolm et al, J. Org. Chem. 2005, 70, 2346; e) U. Lücking et al, WO2007/71455.

Reaction with isocyanates: see for example: a) V. J. Bauer et al, J. Org. Chem. 1966, 31, 3440; b) C. R. Johnson et al, J. Am. Chem. Soc. 1970, 92, 6594; c) S. Allenmark et al, Acta Chem. Scand. Ser. B 1983, 325; d) U. Lücking et al, US2007/0191393.

Reaction with sulfonylchlorides: see for example: a) D. J. Cram et al, J. Am. Chem. Soc. 1970, 92, 7369; b) C. R. Johnson et al, J. Org. Chem. 1978, 43, 4136; c) A. C. Barnes, J. Med. Chem. 1979, 22, 418; d) D. Craig et al, Tet. 1995, 51, 6071; e) U. Lücking et al, US2007/191393.

Reaction with chloroformiates: see for example: a) P. B. Kirby et al, DE2129678; b) D. J. Cram et al, J. Am. Chem. Soc. 1974, 96, 2183; c) P. Stoss et al, Chem. Ber. 1978, 111, 1453; d) U. Lücking et al, WO2005/37800.

Reaction with bromocyane: see for example: a) D. T. Sauer et al, Inorganic Chemistry 1972, 11, 238; b) C. Bolm et al, Org. Lett. 2007, 9, 2951; c) U. Lücking et al, WO 2011/29537.

Scheme 2a

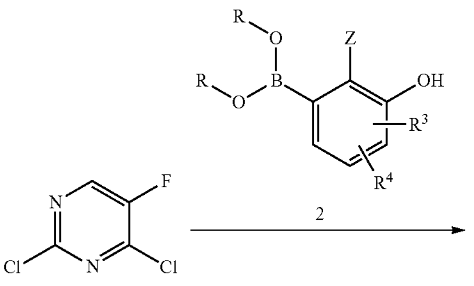

15

2

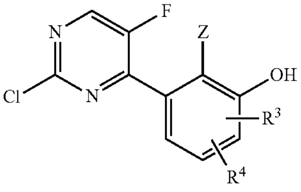

16

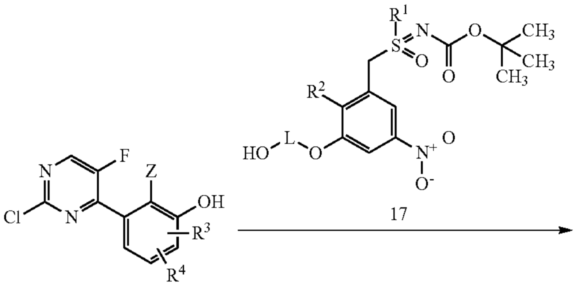

16

17

-continued

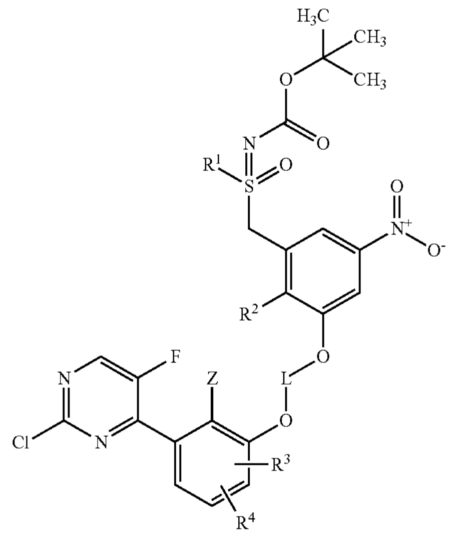

18

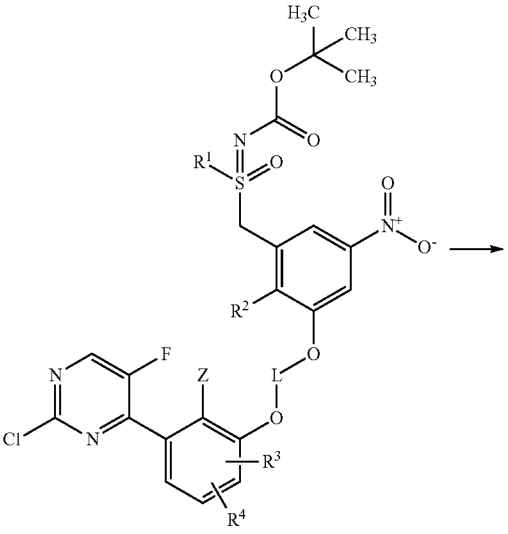

18

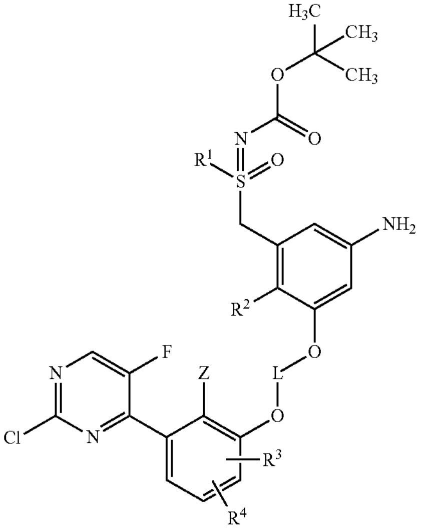

19

-continued

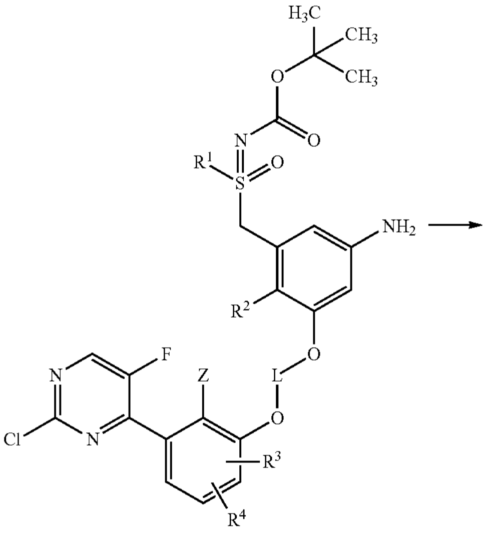

19

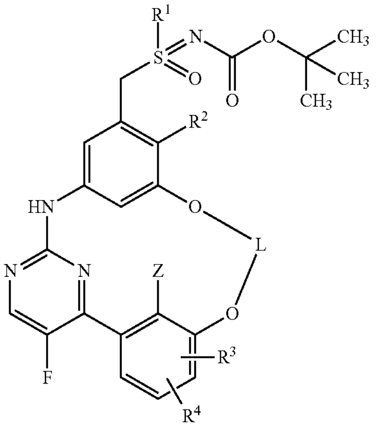

(Id)

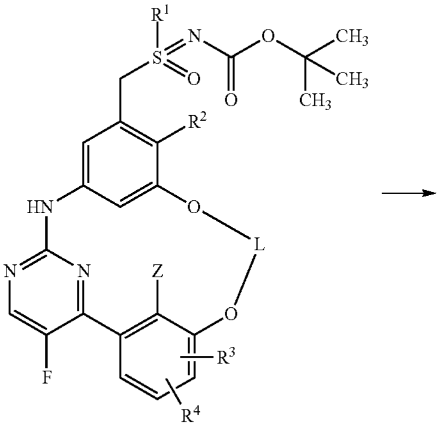

(Id)

-continued

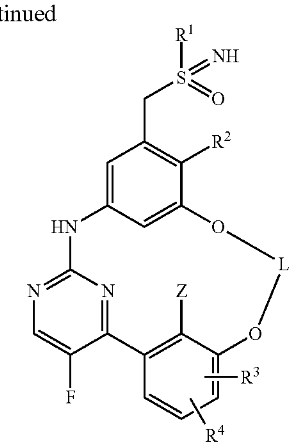

(Ie)

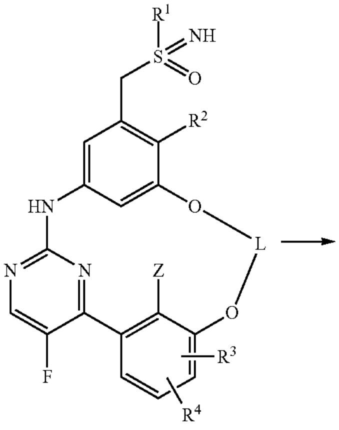

(Ie)

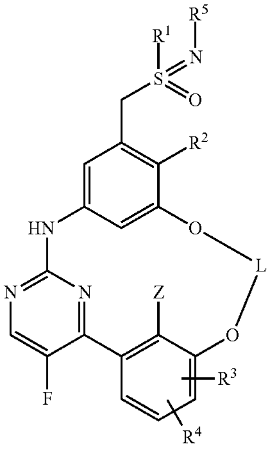

(If)

Compounds of the formula (17), in which $R^1$, $R^2$ and L are as defined for the compound of general formula (I) according to the present invention, can be prepared according to Scheme 2b, starting e.g. from a benzylic alcohol derivative of formula (20), in which $R^2$ is as defined for the compound of general formula (I), is reacted to give a compound of formula (21), in which LG represents a leaving group such as a chlorine atom, a bromine atom or an iodine atom, $C_1$-$C_4$-alkyl-S(=O)$_2$O—, trifluoromethanesulfonyloxy-, benzenesulfonyloxy-, or para-toluenesulfonyloxy-. Such conversions are well known to the person skilled in the art; preferred is the herein described use of thionyl chloride in N,N-dimethylformamide (DMF) as a solvent, to give a compound of formula (21) in which LG represents a chlorine atom.

Benzylic alcohol derivative of formula (20), or the corresponding carboxylic acids and their esters, are known to the person skilled in the art, and are commercially available in certain cases.

In a second step, a compound of formula (21) can be reacted with a thiol of the formula $R^1$—SH, in which $R^1$ is as defined for the compound of general formula (I), to give a thioether derivative of formula (22). Thiols of the formula $R^1SH$ are well known to the person skilled in the art and are commercially available in considerable variety.

In a third step, a thioether derivative of formula (22) can be reacted with a carboxylic ester of formula (23), in which L' represents a $C_2$-$C_7$-alkylene group featuring one carbon atom less as compared to the corresponding group L in formula (17), $R^E$ represents a $C_1$-$C_4$-alkyl group, and in which LG represents a leaving group such as a chlorine atom, a bromine atom or an iodine atom, $CH_3$—S(=O)$_2$ O—, trifluoromethanesulfonyloxy-, benzenesulfonyloxy-, or para-toluenesulfonyloxy-, in the presence of a base, such as an alkali carbonate, preferably potassium carbonate, in N,N-dimethylformamide (DMF) as a solvent, to give a compound of formula (24).

In a fourth step, oxidation of a thioether of formula (24) can be used to obtain the corresponding sulfoxide of formula (25) The oxidation can be performed analogously to known processes (see for example: (a) M. H. Ali et al, Synthesis 1997, 764; (b) M. C. Carreno, Chem. Rev. 1995, 95, 1717; (c) I. Patel et al, Org. Proc. Res. Dev. 2002, 6, 225; (d) N. Khiar et al, Chem. Rev. 2003, 103, 3651). Preferred is the herein described use of periodic acid und iron(III) chloride.

In a fifth step, a Rhodium-catalyzed imination of a sulfoxide of formula (25) can be used to prepare the N-Boc-protected sulfoximines of formula (26) (Bull et al, J. Org. Chem. 2015, 80, 6391). Preferred is the herein described use of sulfoxide, tert-butyl carbamate, magnesium oxide, rhodium(II) acetate dimer and iodobenzene diacetate in DCM at room temperature to 45° C.

In a sixth step, an ester of the formula (26) can be reduced using a reducing agent such as lithium aluminium hydride or di-iso-butylaluminiumhydride (DIBAL), in an ether, preferably tetrahydrofuran, as a solvent, to give compound of the formula (17) which can be further processed as shown in the Scheme 2a.

Scheme 2b

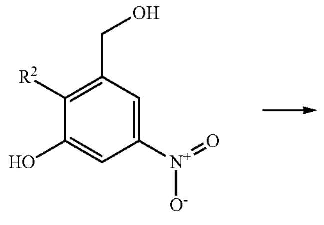

20

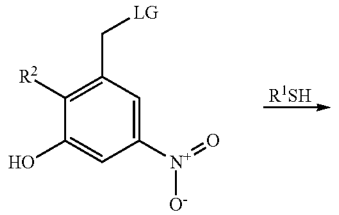

21

-continued

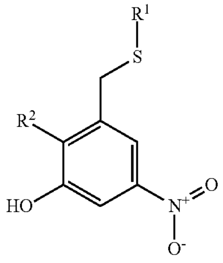

22

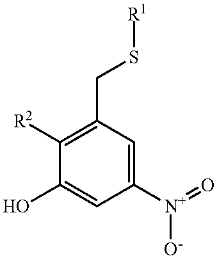

22

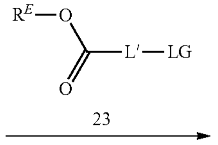

23

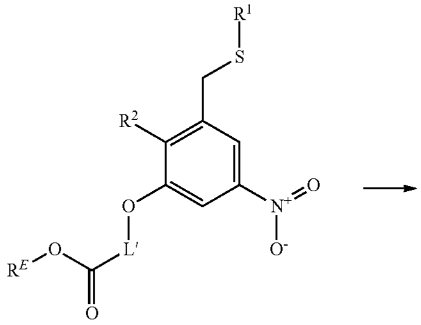

24

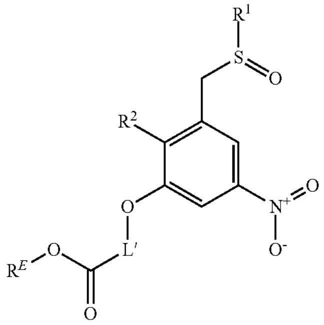

25

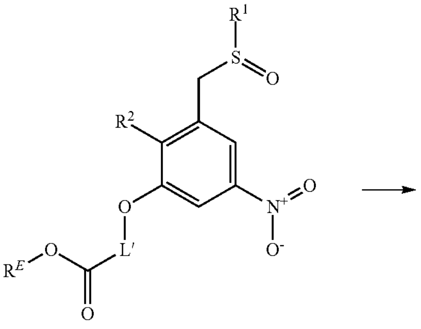

25

-continued

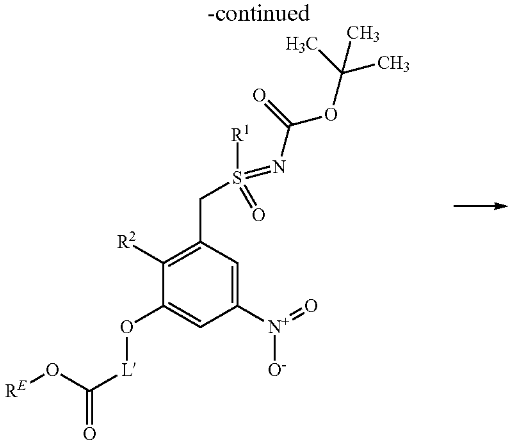

26

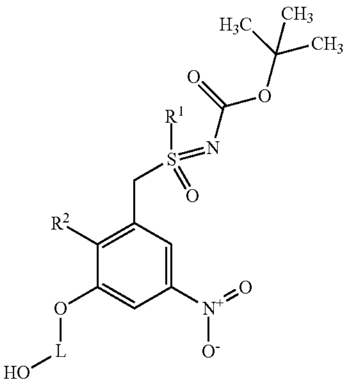

17

Abbreviations Used in the Description of the Chemistry and in the Examples that Follow are:

br. (broad, $^{1}H$ NMR signal); $CDCl_3$ (deuterated chloroform); cHex (cyclohexane); DCE (dichloroethane); d (doublet, $^{1}H$ NMR signal); DCM (dichloromethane); DIPEA (di-iso-propylethylamine); DMAP (4-N,N-dimethylaminopyridine), DME (1,2-dimethoxyethane), DMF (N,N-dimethylformamide); DMSO (dimethyl sulfoxide); ES (electrospray); EtOAc (ethyl acetate); EtOH (ethanol); h (hour(s)); $^{1}H$ NMR (proton nuclear magnetic resonance spectroscopy); HPLC (High Performance Liquid Chromatography), iPrOH (iso-propanol); m (multiplet, $^{1}H$ NMR signal); mCPBA (meta-chloroperoxybenzoic acid), MeCN (acetonitrile), MeOH (methanol); min (minute(s)); MS (mass spectrometry); MTBE (methyl tert-butyl ether); NMP (N-Methylpyrrolidin-2-one); NMR (nuclear magnetic resonance); $Pd(dppf)Cl_2$ ([1,1'-bis(diphenylphosphino)ferrocene]dichloro palladium(II) complex with dichloromethane); q (quartet, $^{1}H$ NMR signal); quin (quintet, $^{1}H$ NMR signal); rac (racemic); RT (room temperature); s (singlet, $^{1}H$ NMR signal); sat. aq. (saturated aqueous); $SiO_2$ (silica gel); t (triplet, $^{1}H$ NMR signal); TFA (trifluoroacetic acid); TFAA (trifluoroacetic anhydride), THF (tetrahydrofuran); UPLC (Ultra-High Performance Liquid Chromatography), UV (ultraviolet), wt-% (percent by weight).

$^{1}H$-NMR Spectra $^{1}H$-NMR signals are specified with their multiplicity/combined multiplicities as apparent from the spectrum; possible higher-order effects are not considered. Chemical shifts of the signals (δ) are specified as ppm (parts per million).

Chemical Naming:

Chemical names were generated using the ACD/Name software from ACD/Labs. In some cases generally accepted names of commercially available reagents were used in place of ACD/Name generated names.

Salt Stoichiometry:

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "xHCl", "$xCF_3COOH$", "$xNa^+$", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

Preparative HPLC Methods:

Autopurifier: Acidic Conditions

| | |
|---|---|
| System: | Waters Autopurificationsystem: Pump 2545, Sample Manager 2767, CFO, DAD 2996, ELSD 2424, SQD |
| Column: | XBrigde C18 5 μm 100 × 30 mm |
| Solvent: | A = $H_2O$ + 0.1 vol-% HCOOH (99%)<br>B = MeCN |
| Gradient: | 0.00-0.50 min 5% B, 25 mL/min<br>0.51-5.50 min 10-100% B, 70 mL/min<br>5.51-6.50 min 100% B, 70 mL/min |
| Temperature: | RT |
| Solution: | max. 250 mg/max. 2.5 mL DMSO or DMF |
| Injection: | 1 × 2.5 ml |
| Detection: | DAD scan range 210-400 nm<br>MS ESI+, ESI−, scan range 160-1000 m/z |

| | |
|---|---|
| System: | Waters Autopurificationsystem: Pump 2545, Sample Manager 2767, CFO, DAD 2996, ELSD 2424, SQD |
| Column: | XBrigde C18 5 μm 100 × 30 mm |
| Solvent: | A = $H_2O$ + 0.2% vol-% aqueous $NH_3$ (32%)<br>B = MeCN |
| Gradient: | 0.00-0.50 min 5% B, 25 mL/min<br>0.51-5.50 min 10-100% B, 70 mL/min<br>5.51-6.50 min 100% B, 70 mL/min |
| Temperature: | RT |
| Solution: | max. 250 mg/max. 2.5 mL DMSO or DMF |
| Injection: | 1 × 2.5 ml |
| Detection: | DAD scan range 210-400 nm<br>MS ESI+, ESI−, scan range 160-1000 m/z |

General Methods for LC-MS Analysis

Method a:

Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method b:

Instrument: Waters Acquity UPLCMS SingleQuad; Column: Acquity UPLC BEH C18 1.7 μm, 50×2.1 mm; eluent A: water+0.2 vol % aqueous ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

EXAMPLE 1

(rac)-tert-butyl [{[3,20-difluoro-13,18-dioxa-5,7,24-triazatetracyclo[17.3.1.1$^{2,6}$.1$^{8,12}$]pentacosa-1(23),2(25),3,5,8(24),9,11,19,21-nonaen-10-yl]methyl}(methyl)oxido-λ$^{6}$-sulfanylidene]carbamate

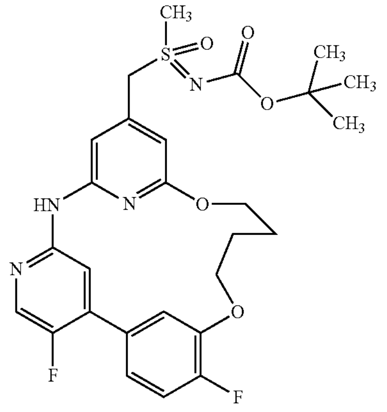 [SMILES: CC(C)(C)OC(=O)N=S(C)(=O)Cc1cc2nc(c1)OCCCCOc1cc(ccc1F)-c1cc(ncc1F)N2]

Preparation of Intermediate 1.1

2-chloro-5-fluoro-4-(4-fluoro-3-methoxyphenyl)pyridine

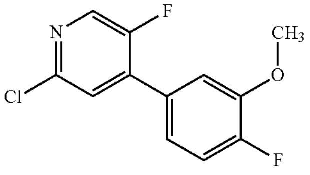 [SMILES: COc1cc(-c2cc(Cl)ncc2F)ccc1F]

A batch with 2-chloro-5-fluoro-4-iodopyridine [CAS-RN: 884494-49-9] (3000 mg; 11.65 mmol), (4-fluoro-3-methoxyphenyl)boronic acid [CAS-RN: 854778-31-7] (1981 mg; 11.65 mmol) and [1,1'-bis(diphenylphosphino)ferrocene]dichloropalladium(II) [CAS-RN: 72287-26-4] (952 mg; 1.17 mmol) in 1,2-dimethoxyethane (30.0 mL) and 2 M aqueous solution of potassium carbonate (23 mL) was degassed using argon. The batch was stirred under an atmosphere of argon for 4 hours at 100° C. After cooling, the batch was diluted with ethyl acetate and THF and washed with a saturated aqueous solution of sodium chloride. The organic layer was filtered using a Whatman filter and concentrated. The residue was purified by column chromatography (hexane to hexane/ethyl acetate 50%) to give the title compound (2600 mg; 10.2 mmol).

$^{1}$H-NMR (400 MHz, DMSO-$d_6$): δ [ppm]=3.92 (s, 3H), 7.28 (ddt, 1H), 7.39 (dd, 1H), 7.48 (dd, 1H), 7.86 (d, 1H), 8.55 (d, 1H).

Preparation of Intermediate 1.2

5-fluoro-4-(4-fluoro-3-methoxyphenyl)pyridin-2-amine

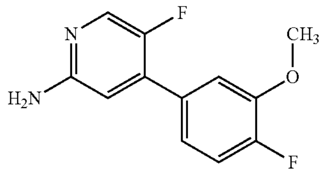 [SMILES: COc1cc(-c2cc(N)ncc2F)ccc1F]

A solution of lithium bis(trimethylsilyl)amide in THF (1M; 10.2 mL; 10.17 mmol; Aldrich Chemical Company Inc.) [CAS-RN: 4039-32-1] was added to a mixture of 2-chloro-5-fluoro-4-(4-fluoro-3-methoxyphenyl)pyridine (1.30 μg; 5.09 mmol; see Intermediate 1.1), tris(dibenzylideneacetone)dipalladium (0) (0.09 g; 0.10 mmol; Aldrich Chemical Company Inc.) [CAS-RN: 51364-51-3] and 2-(dicyclohexylphosphino)-2',4',6'-triisopropylbiphenyl (0.10 g; 0.20 mmol; Aldrich Chemical Company Inc.) [CAS-RN: 564483-18-7] in THF (10.4 mL) under an atmosphere of argon at room temperature. The mixture was stirred at 60° C. for 5 hours. The mixture was cooled to −20° C. and the pH was adjusted under cooling to 4-6 by the addition of aqueous hydrogen chloride solution (1N). The mixture was stirred at room temperature for 15 minutes before the pH was adjusted to 11 by the addition of aqueous sodium hydroxide solution (2N). The mixture was three times extracted with ethyl acetate. The combined organic layers were filtered using a Whatman filter and concentrated. The residue was purified by column chromatography on silica gel (hexane to hexane/ethyl acetate 80%) to give the title compound (0.99 g; 4.2 mmol).

1H-NMR (400 MHz, DMSO-d6): δ [ppm]=2.32-2.45 (m, 1H), 2.67 (s, 1H), 3.50 (s, 1H), 3.88 (s, 3H), 5.92 (s, 2H), 6.55 (d, 1H), 7.10 (ddd, 1H), 7.28-7.37 (m, 2H), 7.94 (d, 1H).

Preparation of Intermediate 1.3

5-(2-amino-5-fluoropyridin-4-yl)-2-fluorophenol

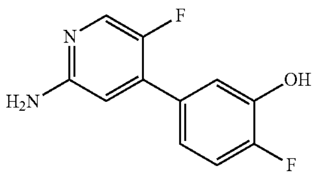 [SMILES: Nc1cc(-c2ccc(F)c(O)c2)c(F)cn1]

A solution of boron tribromide in DCM (1M; 11.7 mL; 11.7 mmol; Aldrich Chemical Company Inc.) [CAS-RN: 10294-33-4] was added dropwise to a stirred solution of 5-fluoro-4-(4-fluoro-3-methoxyphenyl)pyridin-2-amine (988 mg; 4.18 mmol) in DCM (19 mL) at 0° C. The mixture was slowly warmed to room temperature while stirring overnight. The mixture was cautiously diluted with a saturated, aqueous solution of sodium bicarbonate under stirring at 0° C. and was stirred at room temperature for 1 hour. A saturated solution of sodium chloride was added and the mixture was extracted with ethyl acetate. The combined organic layers were filtered using a Whatman filter and concentrated to give the title compound (1240 mg) that was used without further purification.

$^1$H-NMR (400 MHz, DMSO-$d_6$): δ [ppm]=5.92 (s, 2H), 6.48 (d, 1H), 6.96 (ddd, 1H), 7.13 (dt, 1H), 7.25 (dd, 1H), 7.92 (d, 1H), 10.19 (br s, 1H).

Preparation of Intermediate 1.4

(2,6-Dichloropyridin-4-yl)methanol

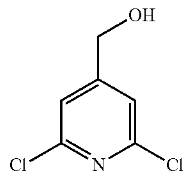

To a stirred solution 2,6-dichloroisonicotinic acid (10.0 g, 52.1 mmol) [CAS-RN: 5398-44-7] in THF (300 mL) at 0° C. was added a solution of sulfanediyldimethane-borane (1:1) [CAS-RN: 13292-87-0](16.0 g, 210.5 mmol) in THF. The mixture was allowed to react at room temperature overnight. Then MeOH (22 mL) was cautiously added to the stirred mixture while cooling with an ice bath. The reaction mixture was diluted with ethyl acetate (300 mL), washed with an aqueous sodium hydroxide solution (1N, 100 mL) and saturated aqueous sodium chloride solution. The organic layer was concentrated and the residue was purified by column chromatography on silica gel (hexane/ethyl acetate=7:1 to 3:1) to give the title compound (8.3 g; 46.6 mmol).

$^1$H-NMR (400 MHz, CDCl3, 300K): δ [ppm]=2.24 (br s, 1H), 4.77 (s, 2H), 7.25 (s, 2H), Preparation of Intermediate 1.5

(2,6-dichloropyridin-4-yl)methyl methanesulfonate

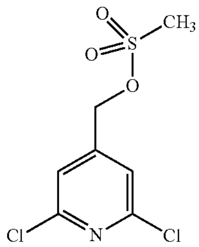

(2,6-Dichloropyridin-4-yl)methanol (1.0 g; 5.62 mmol) was dissolved in DCM (20 mL) and triethyl amine (1.0 g; 9.88 mmol) was added. The resulting mixture was cooled to 0° C. and methanesulfonyl chloride [CAS-RN: 124-63-0] (0.9 g, 7.9 mmol) was added. The mixture was stirred at room temperature for 1 hour. By adding an aqueous hydrogen chloride solution (1N), the pH value of the mixture was adjusted to 3, before it was extracted three times with ethyl acetate. The combined organic layers were concentrated to give the crude title compound (1.4 g) that was used without further purification.

Preparation of Intermediate 1.6

2,6-Dichloro-4-[(methylsulfanyl)methyl]pyridine

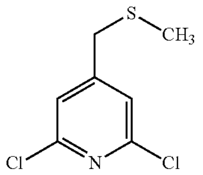

(2,6-Dichloropyridin-4-yl)methyl methanesulfonate (1.40 g) was dissolved in THF (20 mL) and a mixture of sodium thiomethoxide and sodium hydroxide (wt 1/1, 0.70 g, 5 mmol, supplied by Shanghai DEMO Medical Tech Co., Ltd) was added. The resulting mixture was stirred overnight at room temperature. The reaction mixture was diluted with water (10 mL) and extracted three times with ethyl acetate. The combined organic layers were concentrated and the residue was purified by column chromatography on silica gel (hexane/ethyl acetate=6:1 to 3:1) to give the title compound (0.54 g; 2.60 mmol).

$^1$H-NMR (400 MHz, DMSO-$d_6$): δ [ppm]=1.97 (s, 3H), 3.53-3.92 (s, 2H), 7.54 (s, 2H).

Preparation of Intermediate 1.7

4-({6-Chloro-4-[(methylsulfanyl)methyl]pyridin-2-yl}oxy)butan-1-ol)

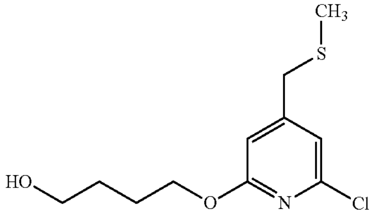 [SMILES: CSCc1cc(Cl)nc(OCCCCO)c1]

Sodium hydride (55-60%; 1.15 g) was added to a stirred solution of butane-1,4-diol (5.41 g; 60.1 mmol) in THF (165 mL) at 0° C. The ice bath was removed and the reaction mixture was stirred at room temperature for 30 min. 2,6-dichloro-4-[(methylsulfanyl)methyl]pyridine (5.0 g; 24.0 mmol) was added and the reaction mixture was stirred under reflux overnight. After cooling the batch was concentrated and ethyl acetate and water was added. The mixture was three times extracted with ethyl acetate. The combined organic layers were washed with an aqueous solution of sodium chloride, filtered using a Whatman filter and concentrated. The residue was purified by column chromatography on silica gel (hexane to hexane/ethyl acetate 60%) to give the title compound (4.3 g; 16.4 mmol).

$^1$H-NMR (400 MHz, DMSO-$d_6$): δ [ppm]=1.49-1.61 (m, 2H), 1.64-1.90 (m, 2H), 1.95-2.00 (m, 3H), 3.37-3.47 (m, 2H), 3.58-3.70 (m, 2H), 4.21 (t, 2H), 4.46 (t, 1H), 6.74 (s, 1H), 7.02 (d, 1H).

Preparation of Intermediate 1.8

(rac)-4-({6-chloro-4-[(methylsulfinyl)methyl]pyridin-2-yl}oxy)butan-1-ol

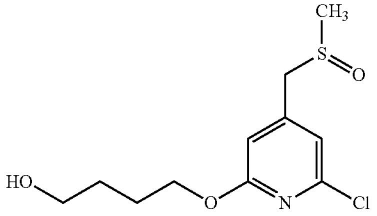 [SMILES: CS(=O)Cc1cc(Cl)nc(OCCCCO)c1]

Iron(III)chloride (37 mg; 0.22 mmol) was added to a mixture of 4-({6-chloro-4-[(methylsulfanyl)methyl]pyridin-2-yl}oxy)butan-1-ol (2000 mg; 7.64 mmol) in acetonitrile (18.5 mL) and the batch was stirred at room temperature for 10 minutes. The batch was cooled to 0° C. and periodic acid (1.86 g; 8.18 mmol) was added under stirring in one portion. After 5 hours the ice bath was removed and the mixture was stirred at room temperature. Additional periodic acid (0.52 g; 2.29 mmol) was added and the mixture was stirred for 2 hours at room temperature before it was added to a stirred solution of sodium thiosulfate pentahydrate [CAS-RN: 10102-17-7] (10.62 g; 42.79 mmol) in ice water (220 mL). The batch was stirred at room temperature for 1 hour and then extracted twice with ethyl acetate. The combined organic layers were washed with an aqueous solution of sodium chloride, filtered using a Whatman filter and concentrated. The residue was purified by column chromatography on silica gel (ethyl acetate to ethyl acetate/ethanol 30%) to give the title compound (1.30 g; 4.68 mmol).

$^1$H-NMR (400 MHz, DMSO-$d_6$): δ [ppm]=1.48-1.58 (m, 2H), 1.65-1.81 (m, 2H), 3.35-3.51 (m, 2H), 3.90-4.05 (m, 1H), 4.13-4.26 (m, 3H), 4.45 (t, 1H), 6.75 (d, 1H), 7.02 (d, 1H).

Preparation of Intermediate 1.9

(rac)-tert-butyl [{[2-chloro-6-(4-hydroxybutoxy)pyridin-4-yl]methyl}(methyl)oxido-$\lambda^6$-sulfanylidene]carbamate

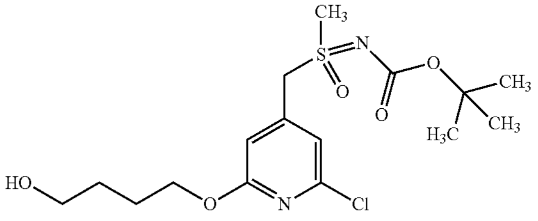 [SMILES: CC(C)(C)OC(=O)N=S(C)(=O)Cc1cc(Cl)nc(OCCCCO)c1]

To a suspension of (rac)-4-({6-chloro-4-[(methylsulfinyl)methyl]pyridin-2-yl}oxy)butan-1-ol (1.30 g, 4.68 mmol), tert-butyl carbamate (822 mg, 7.02 mmol), magnesium oxide (754 mg, 18.72 mmol) and rhodium(II) acetate dimer [CAS-RN: 15956-28-2] (103 mg, 0.23 mmol) in DCM (45 mL) was added iodobenzene diacetate [CAS-RN: 3240-34-4] (2.26 g, 7.02 mmol) at room temperature. The batch was stirred for 18 h at room temperature, filtered over celite and concentrated. The residue was purified by column chromatography on silica gel (ethyl acetate) to give the title compound (960 mg, 2.44 mmol).

1H-NMR (400 MHz, DMSO-d6): δ [ppm]=1.29-1.41 (m, 9H), 1.48-1.58 (m, 2H), 1.66-1.81 (m, 2H), 3.15-3.29 (m, 3H), 3.36-3.47 (m, 2H), 4.20-4.29 (m, 2H), 4.46 (t, 1H), 4.91 (d, 2H), 6.86 (s, 1H), 7.08 (d, 1H).

Preparation of Intermediate 1.10

(rac)-4-[(4-{[N-(tert-butoxycarbonyl)-S-methylsulfonimidoyl]methyl}-6-chloropyridin-2-yl)oxy]butyl Methanesulfonate

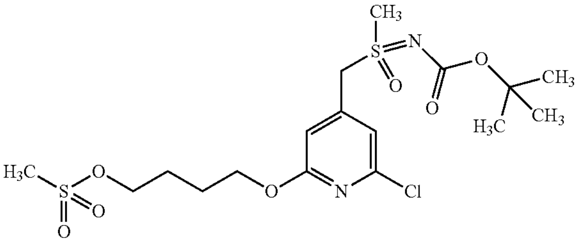 [SMILES: CC(C)(C)OC(=O)N=S(C)(=O)Cc1cc(Cl)nc(OCCCCOS(C)(=O)=O)c1]

Methanesulfonyl chloride [CAS-RN: 124-63-0] (133 mg; 1.16 mmol) was added dropwise to a stirred solution of (rac)-tert-butyl [{[2-chloro-6-(4-hydroxybutoxy)pyridin-4-yl]methyl}(methyl)oxido-$\lambda^6$-sulfanylidene]carbamate (380 mg; 0.97 mmol) and trimethylamine (196 mg; 1.93 mmol) in DCM (4.2 mL) at 0° C. The ice bath was removed after 30 minutes and the reaction mixture was stirred for 2 hours at room temperature. The reaction mixture was diluted with water and extracted twice with ethyl acetate. The combined organic layers were filtered using a Whatman filter and concentrated. The residue was purified by column chromatography on silica gel (hexane to hexane/ethyl acetate 70%) to give the title compound (450 mg, 0.96 mmol).

$^1$H-NMR (400 MHz, DMSO-$d_6$): δ [ppm]=1.39 (s, 9H), 1.75-1.86 (m, 4H), 3.18 (s, 6H), 4.22-4.31 (m, 4H), 4.91 (d, 2H), 6.88 (d, 1H), 7.10 (d, 1H).

Preparation of Intermediate 1.11

(rac)-tert-butyl {[(2-{4-[5-(2-amino-5-fluoropyridin-4-yl)-2-fluorophenoxy]butoxy}-6-chloropyridin-4-yl)methyl](methyl)oxido-$\lambda^6$-sulfanylidene}carbamate

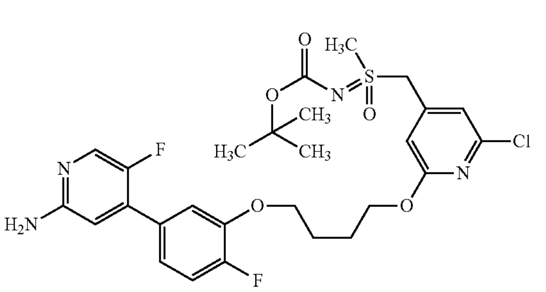 [SMILES: CC(C)(C)OC(=O)N=S(C)(=O)Cc1cc(Cl)nc(OCCCCOc2cc(-c3cc(N)ncc3F)ccc2F)c1]

A mixture of 5-(2-amino-5-fluoropyridin-4-yl)-2-fluorophenol (see Intermediate 1.3; 94 mg, 0.43 mmol), (rac)-4-[(4-{[N-(tert-butoxycarbonyl)-S-methylsulfonimidoyl]

methyl}-6-chloropyridin-2-yl)oxy]butyl methanesulfonate (200 mg; 0.43 mmol) potassium carbonate (70 mg; 0.51 mmol) and potassium iodide (7 mg; 0.04 mmol) in DMF (3.3 mL) was stirred at 40° C. overnight. After cooling the mixture was diluted with ethyl acetate and washed with water. The organic phase was concentrated and the residue was purified by preparative HPLC (see method Autopurifier: acidic conditions) to give the title compound (70 mg; 0.12 mmol).

EXAMPLE 1 PREPARATION OF END PRODUCT

To a solution of (rac)-tert-butyl {[(2-{4-[5-(2-amino-5-fluoropyridin-4-yl)-2-fluorophenoxy]butoxy}-6-chloropyridin-4-yl)methyl](methyl)oxido-λ$^6$-sulfanylidene}carbamate (70 mg, 0.12 mmol) in toluene (8.4 mL) and NMP (0.6 mL) was sequentially added potassium phosphate (124 mg, 0.59 mmol), 2-dicyclohexylphosphino-2',4',6'-triisopropylbiphenyl [CAS-RN: 564483-18-7] (5.6 mg, 0.01 mmol) and chloro(2-dicyclohexylphosphino-2',4',6'-tri-iso-propyl-1,1'-biphenyl) [2-(2-aminoethyl)phenyl]palladium(II) methyl-tert-butylether adduct [CAS-RN: 1028206-56-5] (9.7 mg, 0.01 mmol). The suspension was degassed and heated under an atmosphere of argon to 110° C. for 4 hours. After cooling, the reaction mixture was diluted with aqueous sodium chloride solution and extracted three times with ethyl acetate. The combined organic layers were filtered using a Whatman filter and concentrated. The residue was purified with preparative HPLC (see method Autopurifier: acidic conditions) to give the title compound (3 mg) still showing minor impurities.

$^1$H-NMR (400 MHz, DMSO-d$_6$): δ [ppm]=1.28-1.43 (m, 9H), 1.65-1.82 (m, 4H), 3.20 (s, 3H), 4.41-4.56 (m, 4H), 4.71-4.82 (m, 2H), 6.32 (d, 1H), 6.66 (s, 1H), 7.30-7.42 (m, 2H), 7.60 (d, 1H), 8.32 (d, 1H), 8.80 (d, 1H), 10.02 (s, 1H).

EXAMPLE 2

(rac)-3,20-difluoro-10-[(S-methylsulfonimidoyl) methyl]-13,18-dioxa-5,7,24-triazatetracyclo [17.3.1.1$^{2,6}$.1$^{8,12}$]pentacosa-1(23),2(25),3,5,8(24),9, 11,19,21-nonaene

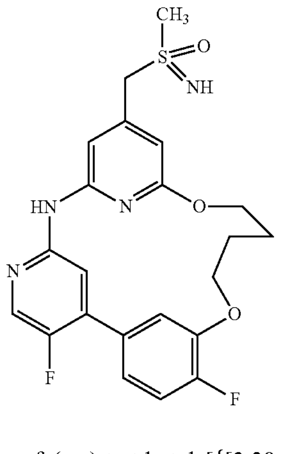

To a solution of (rac)-tert-butyl [{[3,20-difluoro-13,18-dioxa-5,7,24-triazatetracyclo[17.3.1.1$^{2,6}$.1$^{8,12}$]pentacosa-1 (23),2(25),3,5,8(24),9,11,19,21-nonaen-10-yl]methyl} (methyl)oxido-λ$^6$-sulfanylidene]carbamate (5 mg) in dichloromethane (0.2 mL) was added trifluoroacetic acid (22 μL) and the mixture was stirred for 2 h. The pH value of the reaction mixture was adjusted to pH>7 by the addition of saturated aqueous sodium bicarbonate solution. The mixture was extracted three times with dichloromethane. The combined organic layers were filtered using a Whatman filter and concentrated to give the title compound (3 mg, 6.5 μmol).

$^1$H-NMR (400 MHz, DMSO-d$_6$): δ [ppm]=1.62-1.85 (m, 4H), 2.92 (s, 3H), 4.03 (q, 1H), 4.30-4.56 (m, 7H), 6.36 (s, 1H), 6.66 (s, 1H), 7.32-7.41 (m, 2H), 7.62 (d, 1H), 8.33 (d, 1H), 8.83 (d, 1H), 9.97 (s, 1H).

EXAMPLE 3

(rac)-tert-butyl [{[3,20-difluoro-13,18-dioxa-5,7,25-triazatetracyclo[17.3.1.1$^{2,6}$.1$^{8,12}$]pentacosa-1(23),2 (25),3,5,8(24),9,11,19,21-nonaen-10-yl]methyl} (methyl)oxido-λ$^6$-sulfanylidene]carbamate

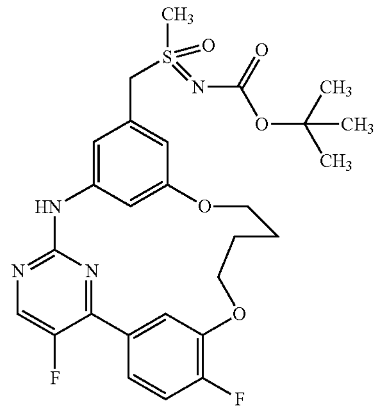 [SMILES: CC(C)(C)OC(=O)N=S(C)(=O)Cc1cc2cc(c1)OCCCCOc1cc(ccc1F)-c1nc(ncc1F)N2]

Preparation of Intermediate 3.1

5-(2-chloro-5-fluoropyrimidin-4-yl)-2-fluorophenol

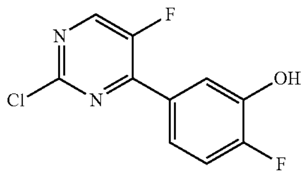 [SMILES: Oc1cc(-c2nc(Cl)ncc2F)ccc1F]

A batch with 2,4-dichloro-5-fluoropyrimidine [CAS-RN: 1293994-86-1] (1000 mg; 5.99 mmol), (4-fluoro-3-hydroxyphenyl)boronic acid [CAS-RN: 913835-74-2] (1027 mg; 6.59 mmol) and [1,1'-bis(diphenylphosphino)ferrocene]dichloropalladium(II) [CAS-RN: 72287-26-4] (489 mg; 0.60 mmol) in 1,2-dimethoxyethane (18 mL) and 2 M aqueous solution of potassium carbonate (9 mL) was degassed using argon. The batch was stirred under an atmosphere of argon for 3 hours at 90° C. After cooling, the batch was diluted with ethyl acetate and washed with an aqueous solution of sodium chloride. The organic layer was filtered using a Whatman filter and concentrated. The residue was purified by column chromatography (hexane to hexane/ethyl acetate 30%) to give the title compound (307 mg; 1.3 mmol).

$^1$H-NMR (400 MHz, DMSO-$d_6$): δ [ppm]=7.33-7.41 (m, 1H), 7.53 (dddt, 1H), 7.73 (dd, 1H), 8.93 (d, 1H), 10.42 (br s, 1H).

Preparation of Intermediate 3.2

3-(Chloromethyl)-5-nitrophenol

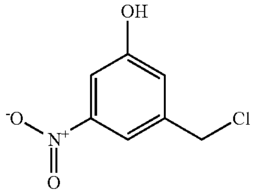

Thionyl chloride (84.0 g; 712 mmol) was added dropwise to a stirred solution of 3-(hydroxymethyl)-5-nitrophenol (60.0 g; 355 mmol) [CAS-RN: 180628-74-4] purchased from Struchem in DMF (1200 mL) at 0° C. The mixture was stirred at 10° C. for 3 hours. The mixture was concentrated, diluted with water and extracted three times with ethyl acetate. The combined organic layers were washed twice with water and concentrated to afford the crude title compound (60.0 g) that was used without further purification.

Preparation of Intermediate 3.3

3-[(Methylsulfanyl)methyl]-5-nitrophenol

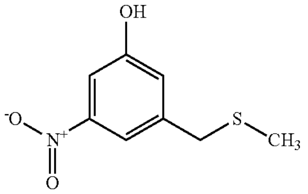

To a solution of crude 3-(chloromethyl)-5-nitrophenol (60.0 g) in acetone (600 mL) at room temperature was added an aqueous solution of sodium thiomethoxide (21%, 180 mL). The mixture was stirred at room temperature for 3 hours before additional aqueous solution of sodium thiomethoxide (21%, 180 mL) was added and the mixture was stirred at room temperature overnight. Finally, additional aqueous solution of sodium thiomethoxide (21%, 90 mL) was added and the mixture was stirred at room temperature for 6 hours. The batch was diluted with ethyl acetate and an aqueous solution of sodium chloride and extracted three times with ethyl acetate. The combined organic layers were concentrated and the residue was purified by column chromatography on silica gel (pentane/ethyl acetate 4:1) to afford the desired product (60.0 g, 302 mmol).

$^1$H NMR (300 MHz, $CDCl_3$, 300K) δ=7.71 (1H), 7.57 (1H), 7.15 (1H), 3.66 (2H), 1.99 (3H).

Preparation of Intermediate 3.4 ethyl 4-{3-[(methylsulfanyl)methyl]-5-nitrophenoxy}butanoate

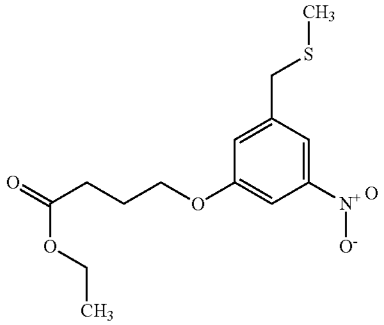

To a suspension of 3-[(methylsulfanyl)methyl]-5-nitrophenol (6.00 g) and potassium carbonate (4.99 g) in DMF (58 ml) at 0° C. was added dropwise ethyl 4-bromobutanoate [CAS-RN: 2969-81-5] (4.7 mL). The mixture was allowed to warm to room temperature and stirred for 24 h. The reaction was diluted with water (300 mL) and the mixture was extracted three times with ethyl acetate (200 mL each). The combined organic layers were washed with saturated aqueous sodium chloride, dried and concentrated to yield the title compound (11.69 g, 90% purity) that was contaminated by DMF and excess ethyl 4-bromobutanoate and which was used without further purification.

$^1$H NMR (400 MHz, DMSO-$d_6$, 295 K) δ/ppm=1.15-1.21 (m, 3H), 1.94-2.03 (m, 5H), 3.74-3.81 (m, 2H), 4.02-4.14 (m, 4H), 7.33-7.36 (m, 1H), 7.57-7.61 (m, 1H), 7.75-7.80 (m, 1H) (one methylene group is overlayed by residual DMSO).

Preparation of Intermediate 3.5

(rac)-ethyl 4-(3-{[S-methylsulfinyl]methyl}-5-nitrophenoxy)butanoate

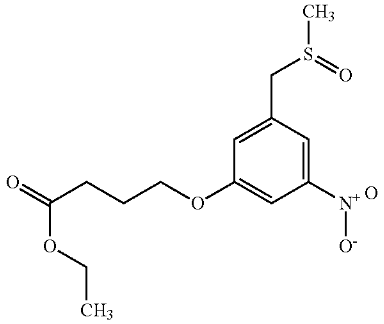

To a solution of crude ethyl 4-{3-[(methylsulfanyl)methyl]-5-nitrophenoxy}butanoate (11.7 g) in acetonitrile (410 mL) at 0° C. was added iron trichloride (605 mg) and the mixture was stirred for 15 min. Then, periodic acid (25.5 g) was added and the reaction was stirred for 1.5 h at 0° C. The reaction was stopped by the addition of saturated aqueous sodium thiosulfate solution, and the mixture was extracted three times with ethyl acetate (300 mL each). The combined organic layers were washed with saturated aqueous sodium chloride, dried and concentrated to yield the title compound (10.5 g, 99% purity) that was used without further purification.

$^1$H NMR (400 MHz, DMSO-$d_6$, 295 K) δ/ppm=1.15-1.21 (m, 3H), 1.97-2.06 (m, 2H), 4.04-4.15 (m, 5H), 4.24-4.31 (m, 1H), 7.28-7.36 (m, 1H), 7.65-7.69 (m, 1H), 7.76-7.82 (m, 1H).

Preparation of Intermediate 3.6

(rac)-ethyl 4-(3-{[N-(tert-butoxycarbonyl)-S-methylsulfonimidoyl]methyl}-5-nitrophenoxy)butanoate

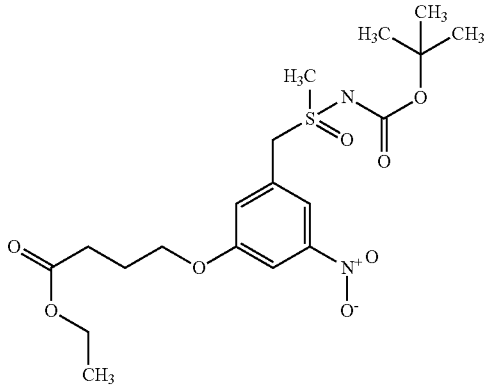

To a suspension of (rac)-ethyl 4-(3-{[S-methylsulfinyl]methyl}-5-nitrophenoxy)butanoate (10.5 g), tert-butyl carbamate (5.60 g), magnesium oxide (5.14 g), and rhodium (II)acetate dimer [CAS-RN: 15956-28-2] (352 mg) in dichloromethane (530 mL) was added iodobenzene diacetate [CAS-RN: 3240-34-4] (15.4 g), and the mixture was stirred for 4.5 h at 45° C. Additional portions of tert-butyl carbamate (1.87 g), rhodium(II)acetate dimer (117 mg) and iodobenzene diacetate (5.1 g) were added, and the mixture was stirred for further 12 h at 45° C. The mixture was allowed to cool to room temperature, filtered over a pad of Celite and concentrated. The crude product was purified by flash column chromatography (silica gel, hexanes/ethyl acetate) to yield the title compound (12.8 g, 97% purity).

$^1$H NMR (400 MHz, DMSO-$d_6$, 295 K) δ/ppm=1.15-1.24 (m, 3H), 1.39 (s, 9H), 1.98-2.06 (m, 2H), 2.44-2.44 (m, 1H), 3.09-3.19 (m, 3H), 4.04-4.16 (m, 4H), 4.95-5.10 (m, 2H), 7.41-7.47 (m, 1H), 7.73-7.80 (m, 1H), 7.88-7.94 (m, 1H)

Preparation of Intermediate 3.7

(rac)-tert-butyl {[3-(4-hydroxybutoxy)-5-nitrobenzyl](methyl)oxido-λ$^6$-sulfanylidene}carbamate

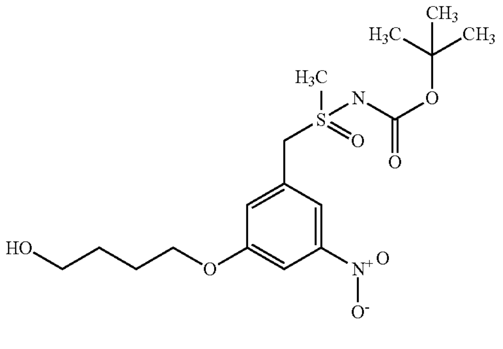

To a solution of (rac)-ethyl 4-(3-{[N-(tert-butoxycarbonyl)-S-methylsulfonimidoyl]methyl}-5-nitrophenoxy)butanoate (12.8 g) in THF (210 mL) at −20° C. was added dropwise diisobutylaluminum hydride (120 mL, 1.0 M in THF). The mixture was allowed to warm to room temperature and stirred for 2.5 h. The reaction was stopped by the addition of saturated aqueous sodium potassium tartrate solution. The mixture was vigorously stirred for 2 h and subsequently extracted three times with ethyl acetate (100 mL each). The combined organic layers were washed with saturated aqueous sodium chloride solution, dried and concentrated. The crude product was purified by flash column chromatography (silica gel, hexane/ethyl acetate 40%→ethyl acetate→ethyl acetate/methanol 20%) to yield the title compound (8.01 g, 97% purity).

$^1$H NMR (400 MHz, DMSO-$d_6$, 295 K) δ/ppm=1.39 (s, 9H), 1.51-1.65 (m, 2H), 1.73-1.83 (m, 2H), 3.14 (s, 3H), 3.43-3.51 (m, 2H), 4.09-4.16 (m, 2H), 4.46-4.51 (m, 1H), 4.93-5.07 (m, 2H), 7.37-7.50 (m, 1H), 7.73-7.79 (m, 1H), 7.86-7.92 (m, 1H).

Preparation of Intermediate 3.8

(rac)-tert-butyl [(3-{4-[5-(2-chloro-5-fluoropyrimidin-4-yl)-2-fluorophenoxy]butoxy}-5-nitrobenzyl)(methyl)oxido-λ$^6$-sulfanylidene]carbamate

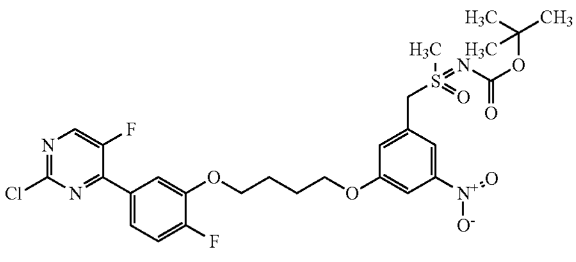 [SMILES: CC(C)(C)OC(=O)N=S(C)(=O)Cc1cc(OCCCCOc2cc(-c3nc(Cl)ncc3F)ccc2F)cc([N+](=O)[O-])c1]

Under argon, diisopropyl azodicarboxylate [CAS-RN: 2446-83-5] (0.45 mL; 2.27 mmol) was added dropwise to a stirred mixture of 5-(2-chloro-5-fluoropyrimidin-4-yl)-2-fluorophenol (see Intermediate 3.1; 300 mg; 1.24 mmol), (rac)-tert-butyl {[3-(4-hydroxybutoxy)-5-nitrobenzyl](methyl)oxido-λ$^6$-sulfanylidene}carbamate (452 mg; 1.12 mmol) and triphenylphosphine (613 mg; 2.34 mmol) in THF (29 mL) at 0° C. The ice bath was removed and the mixture was stirred at room temperature overnight. The mixture was concentrated and the residue was purified by column chromatography on silica gel (hexane to hexane/ethyl acetate 50%) to give the desired title compound (285 mg), still containing some impurities.

Preparation of Intermediate 3.9

(rac)-tert-butyl [(3-amino-5-{4-[5-(2-chloro-5-fluoropyrimidin-4-yl)-2-fluorophenoxy]butoxy}benzyl)(methyl)oxido-$\lambda^6$-sulfanylidene]carbamate

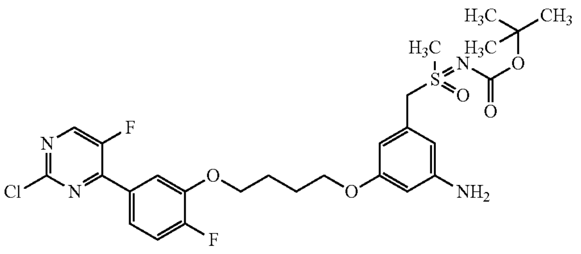 [SMILES: CC(C)(C)OC(=O)N=S(C)(=O)Cc1cc(N)cc(OCCCCOc2cc(-c3nc(Cl)ncc3F)ccc2F)c1]

Platinum 1% and vanadium 2%, on activated carbon (50-70% wetted powder, 44 mg) was added to a solution of (rac)-tert-butyl [(3-{4-[5-(2-chloro-5-fluoropyrimidin-4-yl)-2-fluorophenoxy]butoxy}-5-nitrobenzyl)(methyl)oxido-$\lambda^6$-sulfanylidene]carbamate (282 mg) in methanol (7 mL) and THF (2 mL) and the mixture was stirred for 3 h at room temperature at room temperature under a hydrogen atmosphere. Additional platinum 1% and vanadium 2%, on activated carbon (50-70% wetted powder, 44 mg) was added and the mixture was stirred for additional 3 h at room temperature under a hydrogen atmosphere. The mixture was filtered and the filtrate was concentrated to give the title compound that was used without further purification (231 mg).

EXAMPLE 3—PREPARATION OF THE END PRODUCT

To a solution of (rac)-tert-butyl [(3-amino-5-{4-[5-(2-chloro-5-fluoropyrimidin-4-yl)-2-fluorophenoxy]butoxy}benzyl)(methyl)oxido-$\lambda^6$-sulfanylidene]carbamate (229 mg) in toluene (29 mL) and NMP (1 mL) was sequentially added potassium phosphate (407 mg, 1.91 mmol), 2-dicyclohexylphosphino-2',4',6'-triisopropylbiphenyl [CAS-RN: 564483-18-7] (18 mg, 0.038 mmol) and chloro(2-dicyclohexylphosphino-2',4',6'-tri-iso-propyl-1,1'-biphenyl) [2-(2-aminoethyl)phenyl]palladium(II) methyl-tert-butylether adduct [CAS-RN: 1028206-56-5] (32 mg, 0.038 mmol). The suspension was degassed and heated under argon to 110° C. for 3 hours. After cooling, the reaction mixture was diluted with aqueous sodium chloride solution and extracted three times with ethyl acetate. The combined organic layers were filtered using a Whatman filter and concentrated. The residue was purified by column chromatography on silica gel (hexane/ethyl acetate 30% to ethyl acetate) to give the title compound (53 mg; 0.09 mmol).

$^1$H-NMR (400 MHz, DMSO-$d_6$): δ [ppm]=1.38 (s, 9H), 1.66-1.88 (m, 2H), 1.92-2.03 (m, 2H), 3.16 (s, 3H), 4.16 (t, 2H), 4.30 (t, 2H), 4.70-4.85 (m, 2H), 6.78 (s, 1H), 6.87 (s, 1H), 7.39 (dd, 1H), 7.62-7.71 (m, 1H), 8.01 (t, 1H), 8.18 (dd, 1H), 8.66 (d, 1H), 9.93 (s, 1H).

EXAMPLE 4

(rac)-3,20-difluoro-10-[(S-methylsulfonimidoyl)methyl]-13,18-dioxa-5,7,25-triazatetracyclo[17.3.1.1$^{2,6}$.1$^{8,12}$]pentacosa-1(23),2(25),3,5,8(24),9,11,19,21-nonaene

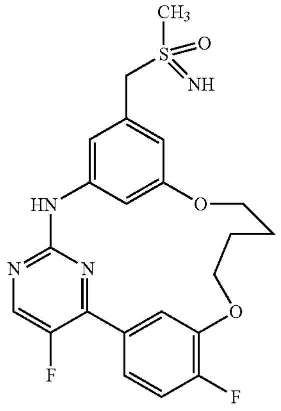

To a solution of (rac)-tert-butyl [{[3,20-difluoro-13,18-dioxa-5,7,25-triazatetracyclo[17.3.1.1$^{2,6}$.1$^{8,12}$]pentacosa-1(23),2(25),3,5,8(24),9,11,19,21-nonaen-10-yl]methyl}(methyl)oxido-$\lambda^6$-sulfanylidene]carbamate (see Example 3; 53 mg; 0.09 mmol) in dichloromethane (0.7 mL) was added trifluoroacetic acid (0.2 mL) and the mixture was stirred for 2 h. The pH value of the reaction mixture was adjusted to pH>7 by the addition of saturated aqueous sodium bicarbonate solution. The mixture was extracted three times with ethyl acetate/THF. The combined organic layers were filtered using a Whatman filter and concentrated. The residue was purified by column chromatography on silica gel (DCM to DCM/ethanol 20%) to give the title compound (20 mg, 0.04 mmol).

$^1$H-NMR (400 MHz, DMSO-$d_6$): δ [ppm]=1.70-1.87 (m, 2H), 1.87-2.04 (m, 2H), 2.84 (s, 3H), 3.63 (s, 1H), 4.12-4.21 (m, 2H), 4.25-4.34 (m, 4H), 6.79 (s, 1H), 6.84 (s, 1H), 7.39 (dd, 1H), 7.60-7.72 (m, 1H), 7.95 (t, 1H), 8.19 (dd, 1H), 8.65 (d, 1H), 9.87 (s, 1H).

EXAMPLE 5

(rac)-tert-butyl [{[3,21-difluoro-13,19-dioxa-5,7,26-triazatetracyclo[$18.3.1.1^{2,6}.1^{8,12}$]hexacosa-1(24),2(26),3,5,8(25),9,11,20,22-nonaen-10-yl]methyl}(methyl)oxido-$\lambda^6$-sulfanylidene]carbamate

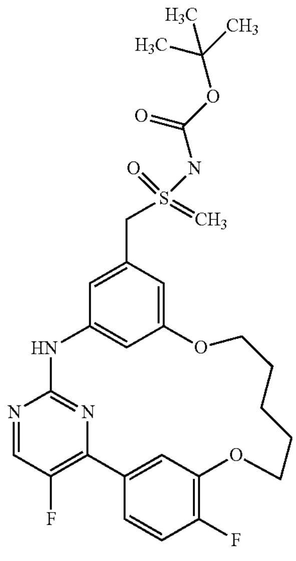 [SMILES: C=S(=O)(Cc1cc2cc(c1)OCCCCCOc1cc(ccc1F)-c1nc(ncc1F)N2)NC(=O)OC(C)(C)C]

Preparation of Intermediate 5.1 methyl 5-{3-[(methylsulfanyl)methyl]-5-nitrophenoxy}pentanoate

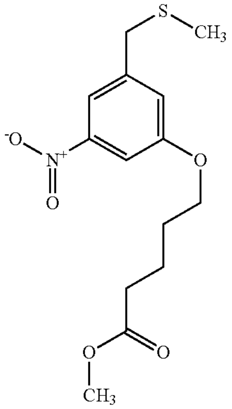

To a suspension of 3-[(methylsulfanyl)methyl]-5-nitrophenol (see Intermediate 3.3; 2.00 g; 10.0 mmol) and potassium carbonate (2.08 g; 15.1 mmol) in DMF (20 ml) at 0° C. was added methyl 5-bromopentanoate [CAS-RN: 5454-83-1] (1.7 mL; 12.0 mmol). The mixture was allowed to warm to room temperature and stirred overnight. The reaction was diluted with aqueous sodium chloride solution and was three times extracted with ethyl acetate. The combined organic layers were filtered using a Whatman filter and concentrated to give the title compound (2.90 g) which was used without further purification.

$^1$H-NMR (400 MHz, DMSO-$d_6$): δ [ppm]=1.56-1.84 (m, 4H), 1.96 (s, 3H), 2.40 (tr, 3H), 3.33 (s, 3H), 3.79 (s, 2H), 4.10 (t, 2H), 7.35 (s, 1H), 7.59 (t, 1H), 7.78 (s, 1H).

Preparation of Intermediate 5.2

5-{3-[(methylsulfanyl)methyl]-5-nitrophenoxy}pentan-1-ol

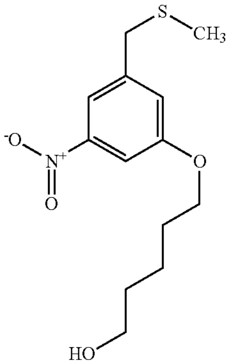

To a solution of methyl 5-{3-[(methylsulfanyl)methyl]-5-nitrophenoxy}pentanoate (2.90 g) in THF (45 mL) at −78° C. was added dropwise a solution of diisobutylaluminum hydride in THF (1.0 M; 32.9 mL, 32.9 mmol). The mixture was allowed to warm to 0° C. and stirred for 2 h at this temperature. Water was cautiously added and the pH was adjusted to pH 4 by the addition of an aqueous solution of hydrogen chloride (1N). The mixture was three times extracted with ethyl acetate. The combined organic layers were washed with saturated aqueous sodium chloride solution, filtered using a Whatman filter and concentrated. The residue was purified by flash column chromatography on silica gel (hexane to hexane/ethyl acetate 70%) to give the title compound (2.40 g, 8.4 mmol).

$^1$H-NMR (400 MHz, DMSO-$d_6$): δ [ppm]=1.35-1.52 (m, 4H), 1.69-1.80 (m, 2H), 1.96 (s, 3H), 3.32-3.43 (m, 2H), 3.76 (s, 3H), 3.97-4.11 (m, 2H), 4.39 (t, 1H), 7.35 (s, 1H), 7.58 (t, 1H), 7.77 (t, 1H).

Preparation of Intermediate 5.3

(rac)-5-{3-[(methylsulfinyl)methyl]-5-nitrophenoxy}pentan-1-ol

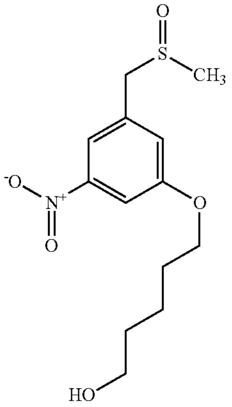

To a solution of 5-{3-[(methylsulfanyl)methyl]-5-nitrophenoxy}pentan-1-ol (2.30 g; 8.06 mmol) in acetonitrile (215 mL) at 0° C. was added iron trichloride (38 mg; 0.23 mmol) and the mixture was stirred for 15 min at room temperature. Periodic acid (1.97 g; 8.62 mmol) was added and the reaction was stirred for 4 h at 0° C. The ice bath was removed and the reaction was warmed to room temperature under stirring before it was added to a stirred solution of sodium thiosulfate pentahydrate (11.20 g; 45.14 mmol) in ice water (250 mL). The batch was saturated with solid sodium chloride and extracted twice with THF and extracted twice with ethyl acetate. The combined organic layers were filtered using a Whatman filter and concentrated. The residue was purified by flash column chromatography on silica gel (hexane to hexane/ethyl acetate 70%) to give the title compound (1.43 g, 4.75 mmol).

1H-NMR (400 MHz, DMSO-d6): Shift [ppm]=1.40-1.52 (m, 4H), 1.75 (quin, 2H), 3.38-3.44 (m, 2H), 4.03-4.12 (m, 3H), 4.28 (d, 1H), 4.39 (t, 1H), 7.35 (s, 1H), 7.68 (t, 1H), 7.79 (s, 1H).

Preparation of Intermediate 5.4

(rac)-tert-butyl [{3-[(5-hydroxypentyl)oxy]-5-nitrobenzyl}(methyl)oxido-$\lambda^6$-sulfanylidene]carbamate

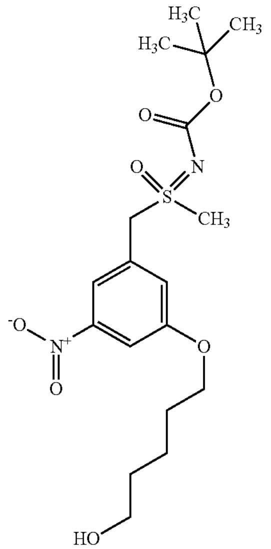

To a suspension of (rac)-5-{3-[(methylsulfinyl)methyl]-5-nitrophenoxy}pentan-1-ol (1430 mg; 4.75 mmol), tert-butyl carbamate (833 mg; 7.11 mmol), magnesium oxide (765 mg; 18.98 mmol), and rhodium(II)acetate dimer [CAS-RN: 15956-28-2] (105 mg; 0.24 mmol) in dichloromethane (46 mL) was added iodobenzene diacetate [CAS-RN: 3240-34-4] (2293 mg; 7.12 mmol), and the mixture was stirred at room temperature overnight. Additional portions of tert-butyl carbamate (416 mg; 3.56 mmol), magnesium oxide (382 mg; 9.49 mmol), rhodium(II)acetate dimer (52 mg; 0.12 mmol) and iodobenzene diacetate (1146 mg; 3.56 mmol) were added, and the mixture was stirred for further 12 h at room temperature. The mixture was filtered over a pad of Celite and concentrated. The residue was purified by flash column chromatography on silica gel, (hexane to hexane/ethyl acetate 30%) to give the title compound (920 mg; 2.20 mmol).

$^1$H-NMR (400 MHz, DMSO-$d_6$): δ [ppm]=1.32-1.55 (m, 13H), 1.70-1.83 (m, 2H), 3.14 (s, 3H), 3.35-3.44 (m, 2H), 4.06-4.13 (m, 2H), 4.39 (t, 1H), 4.95-5.05 (m, 2H), 7.44 (s, 1H), 7.72-7.77 (m, 1H), 7.90 (s, 1H).

Preparation of Intermediate 5.5

(rac)-tert-butyl {[3-({5-[5-(2-chloro-5-fluoropyrimidin-4-yl)-2-fluorophenoxy]pentyl}oxy)-5-nitrobenzyl](methyl)oxido-$\lambda^6$-sulfanylidene}carbamate

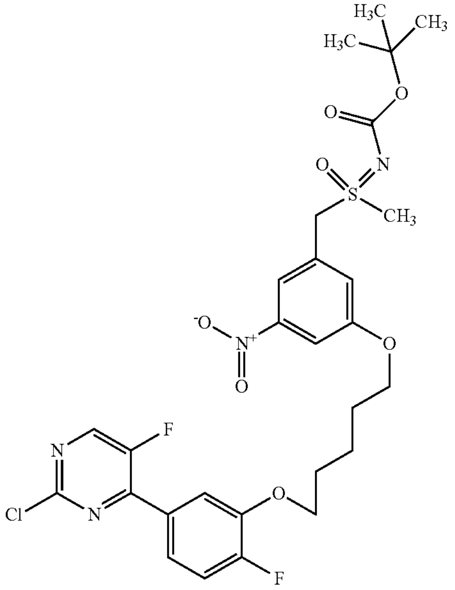

Under an atmosphere of argon, diisopropyl azodicarboxylate [CAS-RN: 2446-83-5] (0.88 mL; 4.46 mmol) was added dropwise to a stirred mixture of 5-(2-chloro-5-fluoropyrimidin-4-yl)-2-fluorophenol (see Intermediate 3.1; 589 mg; 2.43 mmol), (rac)-tert-butyl [{3-[(5-hydroxypentyl)oxy]-5-nitrobenzyl}(methyl)oxido-$\lambda^6$-sulfanylidene]carbamate (920 mg; 2.21 mmol) and triphenylphosphine (1205 mg; 4.60 mmol) in THF (10 mL) at 0° C. The ice bath was removed and the mixture was stirred at room temperature overnight. Additional portions of triphenylphosphine (1205 mg; 4.60 mmol) and diisopropyl azodicarboxylate (0.88 mL; 4.46 mmol) were added and the mixture was stirred for 5 h at room temperature. The mixture was concentrated and the residue was purified by column chromatography on silica gel (hexane to hexane/ethyl acetate 50%) to give the desired title compound (456 mg), still containing some impurities.

Preparation of Intermediate 5.6

(rac)-tert-butyl {[3-amino-5-({5-[5-(2-chloro-5-fluoropyrimidin-4-yl)-2-fluorophenoxy]pentyl}oxy)benzyl](methyl)oxido-λ$^6$-sulfanylidene}carbamate

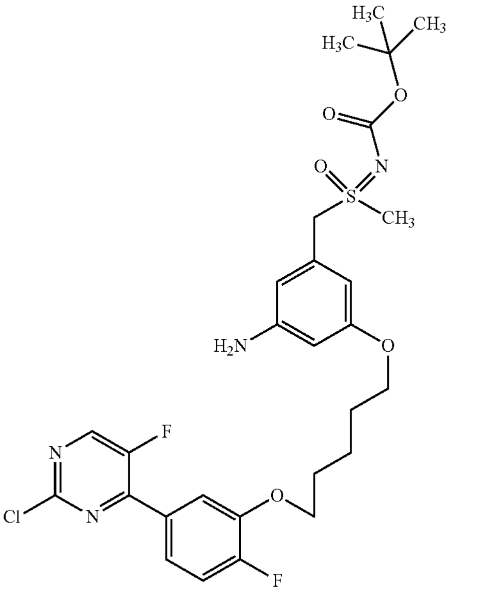 [SMILES: CC(C)(C)OC(=O)N=S(C)(=O)Cc1cc(N)cc(OCCCCCOc2cc(-c3nc(Cl)ncc3F)ccc2F)c1]

Platinum 1% and vanadium 2%, on activated carbon (50-70% wetted powder, 117 mg) was added to a solution of (rac)-tert-butyl {[3-({5-[5-(2-chloro-5-fluoropyrimidin-4-yl)-2-fluorophenoxy]pentyl}oxy)-5-nitrobenzyl](methyl) oxido-λ$^6$-sulfanylidene}carbamate (456 mg; 0.71 mmol) in methanol (115 mL) and the mixture was stirred for 2 h at room temperature under a hydrogen atmosphere. The mixture was filtered and the filtrate was concentrated to give the title compound that was used without further purification (385 mg).

EXAMPLE 5—PREPARATION OF THE END PRODUCT

To a solution of (rac)-tert-butyl {[3-amino-5-({5-[5-(2-chloro-5-fluoropyrimidin-4-yl)-2-fluorophenoxy] pentyl}oxy)benzyl](methyl)oxido-λ$^6$-sulfanylidene}carbamate (385 mg) in toluene (47 mL) and NMP (6 mL) was sequentially added potassium phosphate (668 mg, 3.15 mmol), 2-dicyclohexylphosphino-2',4',6'-tri-isopropylbiphenyl [CAS-RN: 564483-18-7] (30 mg, 0.063 mmol) and chloro(2-dicyclohexylphosphino-2',4',6'-tri-iso-propyl-1,1'-biphenyl) [2-(2-aminoethyl)phenyl]palladium (II) methyl-tert-butylether adduct [CAS-RN: 1028206-56-5] (52 mg, 0.063 mmol). The suspension was degassed and heated under argon to 110° C. for 5 hours. After cooling, the reaction mixture was diluted with aqueous sodium chloride solution and extracted twice with DCM and extracted twice with ethyl acetate. The combined organic layers were filtered using a Whatman filter and concentrated. The residue was purified with preparative HPLC see method: Autopurifier: acidic conditions) to give the title compound (60 mg; 0.10 mmol).

$^1$H-NMR (400 MHz, DMSO-d6): δ [ppm]=1.39 (s, 9H), 1.61-1.70 (m, 2H), 1.81-1.87 (m, 2H), 1.88-1.97 (m, 2H), 3.16 (s, 3H), 3.97 (t, 2H), 4.26-4.32 (m, 2H), 4.72-4.80 (m, 2H), 6.62 (s, 1H), 6.88 (s, 1H), 7.41 (dd, 1H), 7.59-7.75 (m, 1H), 8.16 (dd, 1H), 8.47 (t, 1H), 8.68 (d, 1H), 10.01 (s, 1H).

EXAMPLE 6

(rac)-3,21-difluoro-10-[(S-methylsulfonimidoyl) methyl]-13,19-dioxa-5,7,26-triazatetracyclo [18.3.1.1$^{2,6}$.1$^{8,12}$]hexacosa-1(24),2(26),3,5,8(25),9, 11,20,22-nonaene

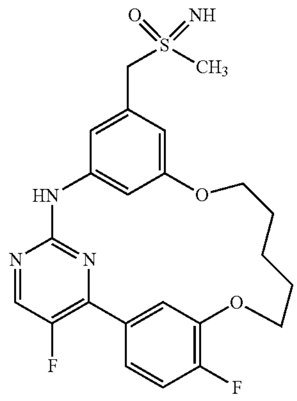 [SMILES: CS(=N)(=O)Cc1cc2cc(c1)OCCCCCOc1cc(ccc1F)-c1nc(ncc1F)N2]

To a solution of (rac)-tert-butyl [{[3,21-difluoro-13,19-dioxa-5,7,26-triazatetracyclo[18.3.1.1$^{2,6}$.1$^{8,12}$]hexacosa-1 (24),2(26),3,5,8(25),9,11,20,22-nonaen-10-yl]methyl} (methyl)oxido-λ$^6$-sulfanylidene]carbamate (58 mg; 0.10 mmol) in dichloromethane (0.90 mL) was added trifluoroacetic acid (0.25 mL) and the mixture was stirred for 2 h. The pH value of the reaction mixture was adjusted to pH>7 by the addition of saturated aqueous sodium bicarbonate solution. The mixture was extracted three times with ethyl acetate. The combined organic layers filtered using a Whatman filter and concentrated. The residue was purified by preparative HPLC (see method: Autopurifier: basic conditions) to give the title compound (5 mg, 0.01 mmol).

$^1$H-NMR (400 MHz, DMSO-d6): Shift [ppm]=1.60-1.70 (m, 2H), 1.80-1.99 (m, 4H), 2.85 (s, 3H), 3.62 (s, 1H), 3.97 (t, 2H), 4.23-4.34 (m, 4H), 6.63 (s, 1H), 6.84 (s, 1H), 7.41 (dd, 1H), 7.56-7.75 (m, 1H), 8.16 (dd, 1H), 8.42 (t, 1H), 8.67 (d, 1H), 9.95 (s, 1H).

EXAMPLE 7

(rac)-tert-butyl [methyl(oxido){[3,20,23-trifluoro-13,18-dioxa-5,7,25-triazatetracyclo[17.3.1.1$^{2,6}$.1$^{8,12}$] pentacosa-1(23),2(25),3,5,8(24),9,11,19,21-nonaen-10-yl]methyl}-1λ$^6$-sulfanylidene]carbamate

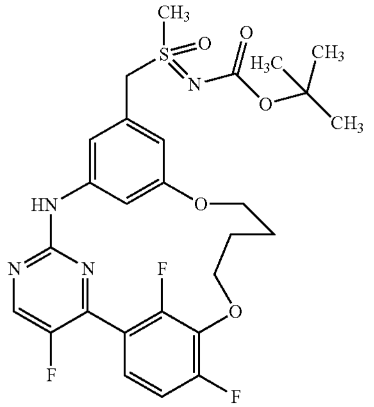 [SMILES: CC(C)(C)OC(=O)N=S(C)(=O)Cc1cc2cc(c1)OCCCCOc1c(F)ccc(c1F)-c1nc(ncc1F)N2]

Preparation of Intermediate 7.1

2-chloro-4-(2,4-difluoro-3-methoxyphenyl)-5-fluoropyrimidine

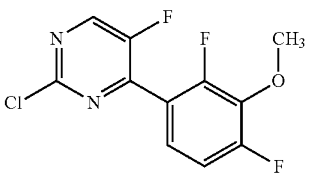 [SMILES: COc1c(F)ccc(-c2nc(Cl)ncc2F)c1F]

A batch with 2,4-dichloro-5-fluoropyrimidine [CAS-RN: 2927-71-1] (3978 mg; 23.82 mmol), (2,4-difluoro-3-methoxyphenyl)boronic acid [CAS-RN: 406482-18-6) (4925 mg; 26.21 mmol) and [1,1'-bis(diphenylphosphino) ferrocene]dichloropalladium(II) [CAS-RN: 72287-26-4] (1945 mg; 2.38 mmol) in 1,2-dimethoxyethane (70 mL) and 2 M aqueous solution of potassium carbonate (36 mL) was degassed using argon. The batch was stirred under an atmosphere of argon for 3 hours at 100° C. After cooling, the batch was diluted with ethyl acetate and washed with a saturated aqueous solution of sodium chloride. The organic layer was filtered using a Whatman filter and concentrated. The residue was purified by column chromatography (hexane to hexane/ethyl acetate 33%) to give the title compound (4030 mg; 14.7 mmol).

1H-NMR (400 MHz, DMSO-d6): δ [ppm]=3.99 (s, 3H), 7.39-7.43 (m, 1H), 7.45 (d, 1H), 9.06 (d, 1H).

Preparation of Intermediate 7.2

3-(2-chloro-5-fluoropyrimidin-4-yl)-2,6-difluorophenol

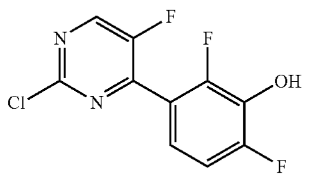 [SMILES: Oc1c(F)ccc(-c2nc(Cl)ncc2F)c1F]

A solution of boron tribromide [CAS-RN: 10294-33-4] in DCM (1M; 74.9 mL; 74.9 mmol) was added dropwise to a stirred solution of 2-chloro-4-(2,4-difluoro-3-methoxyphenyl)-5-fluoropyrimidine (3700 mg; 13.5 mmol) in DCM (325 mL) at 0° C. The mixture was slowly warmed to room temperature while stirring overnight. The mixture was cautiously diluted with a saturated, aqueous solution of sodium bicarbonate under stirring at 0° C. and then solid sodium bicarbonate was added. The mixture was stirred at room temperature for 1 hour before being filtered using a Whatman filter. The filtrate was concentrated to give the crude product (2160 mg) that was used without further purification.

$^1$H-NMR (400 MHz, DMSO-d6): δ [ppm]=7.15 (ddd, 1H), 7.25-7.31 (m, 1H), 9.03 (d, 1H), 10.73 (br s, 1H).

Preparation of Intermediate 7.3

(rac)-tert-butyl [(3-{4-[3-(2-chloro-5-fluoropyrimidin-4-yl)-2,6-difluorophenoxy]butoxy}-5-nitrobenzyl)(methyl)oxido-λ$^6$-sulfanylidene]carbamate

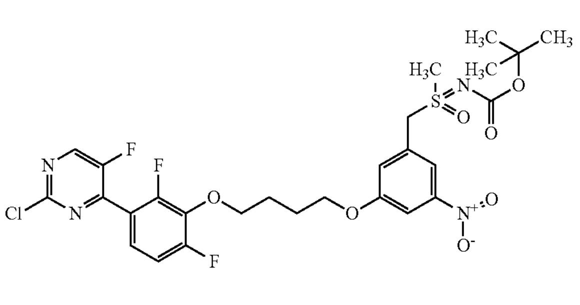 [SMILES: CC(C)(C)OC(=O)N=S(C)(=O)Cc1cc(OCCCCOc2c(F)ccc(-c3nc(Cl)ncc3F)c2F)cc([N+](=O)[O-])c1]

Under an atmosphere of argon, diisopropyl azodicarboxylate [CAS-RN: 2446-83-5] (0.21 mL; 1.06 mmol) was added dropwise to a stirred mixture of crude 3-(2-chloro-5-fluoropyrimidin-4-yl)-2,6-difluorophenol (150 mg), (rac)-tert-butyl {[3-(4-hydroxybutoxy)-5-nitrobenzyl](methyl)oxido-λ$^6$-sulfanylidene}carbamate (see Intermediate 3.7; 211 mg; 0.52 mmol) and triphenylphosphine (285 mg; 1.09 mmol) in THF (2.5 mL) at 0° C. The ice bath was removed and the mixture was stirred at room temperature for 3 days. The mixture was concentrated and the residue was purified by column chromatography on silica gel (hexane to hexane/ethyl acetate 50%) to give the desired title compound (309 mg), still containing some impurities.

Preparation of Intermediate 7.4

(rac)-tert-butyl [(3-amino-5-{4-[3-(2-chloro-5-fluoropyrimidin-4-yl)-2,6-difluorophenoxy]butoxy}benzyl)(methyl)oxido-λ$^6$-sulfanylidene]carbamate

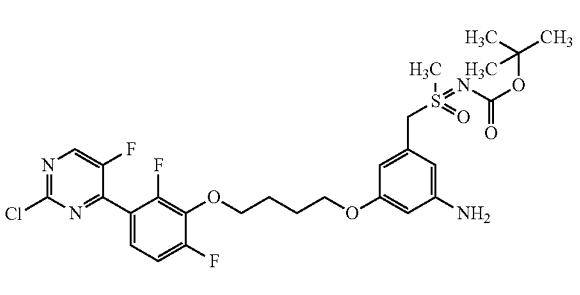 [SMILES: CC(C)(C)OC(=O)N=S(C)(=O)Cc1cc(N)cc(OCCCCOc2c(F)ccc(-c3nc(Cl)ncc3F)c2F)c1]

Platinum 1% and vanadium 2%, on activated carbon (50-70% wetted powder, 46 mg) was added to a solution of (rac)-tert-butyl [(3-{4-[3-(2-chloro-5-fluoropyrimidin-4-yl)-2,6-difluorophenoxy]butoxy}-5-nitrobenzyl)(methyl)oxido-λ$^6$-sulfanylidene]carbamate (307 mg) in methanol (7 mL) and THF (2 mL) and the mixture was stirred for 3 h at room temperature under a hydrogen atmosphere. The mixture was filtered and the filtrate was concentrated to give the title compound that was used without further purification (310 mg).

EXAMPLE 7—PREPARATION OF THE END PRODUCT

To a solution of (rac)-tert-butyl [(3-amino-5-{4-[3-(2-chloro-5-fluoropyrimidin-4-yl)-2,6-difluorophenoxy] butoxy}benzyl)(methyl)oxido-λ$^6$-sulfanylidene]carbamate (100 mg) in toluene (12 mL) and NMP (1.5 mL) was sequentially added potassium phosphate (172 mg, 0.81 mmol), 2-dicyclohexylphosphino-2',4',6'-triisopropylbiphenyl [CAS-RN: 564483-18-7] (8 mg, 0.016 mmol) and chloro (2-dicyclohexylphosphino-2',4',6'-tri-iso-propyl-1,1'-biphenyl) [2-(2-aminoethyl)phenyl]palladium(II) methyl-tert-butylether adduct [CAS-RN: 1028206-56-5] (13 mg, 0.016 mmol). The suspension was degassed and heated under an atmosphere of argon to 110° C. for 3 hours. After cooling, the reaction mixture was diluted with aqueous sodium chloride solution and extracted three times with ethyl acetate. The combined organic layers were filtered using a Whatman filter and concentrated. The residue was purified with preparative HPLC (see method: Autopurifier: acidic conditions) to give the title compound (3 mg; 0.01 mmol).

1H-NMR (400 MHz, DMSO-d6): Shift [ppm]=1.38 (s, 9H), 1.63-1.79 (m, 2H), 1.80-1.95 (m, 2H), 3.13 (s, 3H), 3.90-4.01 (m, 2H), 4.37 (br t, 2H), 4.64-4.78 (m, 2H), 6.57 (s, 1H), 6.84 (s, 1H), 7.32 (t, 1H), 7.47 (q, 1H), 8.36 (s, 1H), 8.77 (d, 1H), 10.06 (s, 1H).

EXAMPLE 8

(rac)-3,20,23-trifluoro-10-[(S-methylsulfonimidoyl) methyl]-13,18-dioxa-5,7,25-triazatetracyclo [17.3.1.1$^{2,6}$.1$^{8,12}$]pentacosa-1(23),2(25),3,5,8(24),9, 11,19,21-nonaene

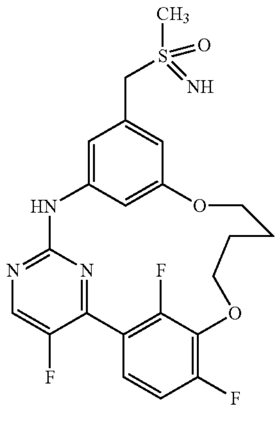 [SMILES: CS(=N)(=O)Cc1cc2cc(c1)OCCCCOc1c(F)ccc(c1F)-c1nc(ncc1F)N2]

To a solution of (rac)-tert-butyl [methyl(oxido){[3,20,23-trifluoro-13,18-dioxa-5,7,25-triazatetracyclo[17.3.1.1$^{2,6}$.1$^{8,12}$]pentacosa-1(23),2(25),3,5,8(24),9,11,19,21-nonaen-10-yl]methyl}-λ$^6$-sulfanylidene]carbamate (3.0 mg; 0.005 mmol) in dichloromethane (0.5 mL) was added trifluoroacetic acid (0.012 mL) and the mixture was stirred for 2 h. The pH value of the reaction mixture was adjusted to pH>7 by the addition of saturated aqueous sodium bicarbonate solution. The mixture was extracted with three times with ethyl acetate. The combined organic layers were filtered using a Whatman filter and concentrated to give the title compound (2.6 mg, 0.005 mmol).

$^1$H-NMR (400 MHz, DMSO-d6): Shift [ppm]=1.62-1.78 (m, 2H), 1.80-1.99 (m, 2H), 2.99 (s, 3H), 3.87-4.05 (m, 2H), 4.33-4.49 (m, 4H), 6.59 (s, 1H), 6.83 (s, 1H), 7.32 (t, 1H), 7.41-7.65 (m, 1H), 8.35 (t, 1H), 8.77 (d, 1H), 10.05 (s, 1H).

EXAMPLE 9

(rac)-tert-butyl [{[3,19-difluoro-13,17-dioxa-5,7,24-triazatetracyclo[16.3.1.1$^{2,6}$.1$^{8,12}$]tetracosa-1(22),2 (24),3,5,8(23),9,11,18,20-nonaen-10-yl]methyl} (methyl)oxido-λ$^6$-sulfanylidene]carbamate

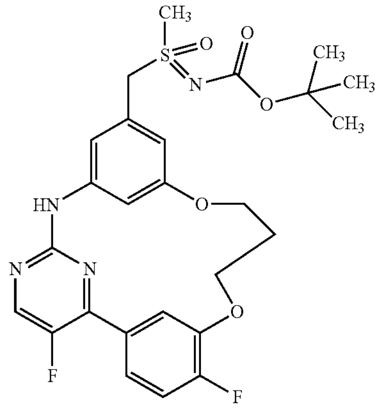 [SMILES: CC(C)(C)OC(=O)N=S(C)(=O)Cc1cc2cc(c1)OCCCOc1cc(ccc1F)-c1nc(ncc1F)N2]

Preparation of Intermediate 9.1

3-{3-[(Methylsulfanyl)methyl]-5-nitrophenoxy}propan-1-ol

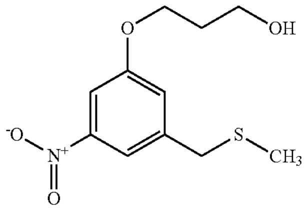

3-Bromopropan-1-ol (1.13 g; 8.1 mmol) was added dropwise to a stirred mixture of 3-[(methylsulfanyl)methyl]-5-nitrophenol (see Intermediate 3.3; 1.5 g; 7.5 mmol) and potassium carbonate (1.25 g; 9.0 mmol) in DMF (15 mL) at 0° C. The ice bath was removed and the reaction mixture was stirred overnight at room temperature. The reaction mixture was diluted with an aqueous solution of sodium chloride and extracted three times with ethyl acetate. The combined organic layers were filtered using a Whatman filter and concentrated. The residue was purified by column chromatography on silica gel (hexane to hexane/ethyl acetate 60%) to give the title compound (1.6 g; 6.2 mmol).

$^1$H NMR (400 MHz, DMSO, 300K) δ=1.85-1.97 (m, 5H), 3.56 (q, 2H), 3.80 (s, 2H), 4.15 (t, 2H), 4.60 (t, 1H), 7.36 (s, 1H), 7.58 (t, 1H), 7.78 (s, 1H).

Preparation of Intermediate 9.2

(rac)-3-{3-[(methylsulfinyl)methyl]-5-nitrophenoxy}propan-1-ol

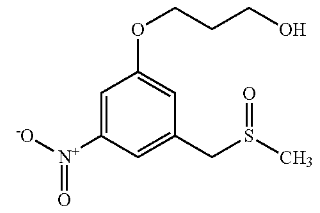

(rac)-3-{3-[(methylsulfinyl)methyl]-5-nitrophenoxy}propan-1-ol (1.30 g; 4.8 mmol) was prepared from 3-{3-[(methylsulfanyl)methyl]-5-nitrophenoxy}propan-1-ol (1.30 g; 5.1 mmol) under similar conditions as described in the preparation protocol for Intermediate 5.3.

$^1$H NMR (400 MHz, DMSO, 300K) δ=1.89 (quin, 2H), 3.36-3.59 (m, 2H), 4.00-4.10 (m, 1H), 4.12-4.19 (m, 2H), 4.28 (d, 1H), 4.61 (t, 1H), 7.35 (dd, 1H), 7.69 (t, 1H), 7.79 (s, 1H).

Preparation of Intermediate 9.3

(rac)-tert-butyl {[3-(3-hydroxypropoxy)-5-nitrobenzyl](methyl)oxido-$\lambda^6$-sulfanylidene}carbamate

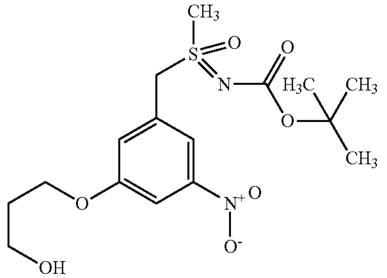

(rac)-tert-butyl {[3-(3-hydroxypropoxy)-5-nitrobenzyl](methyl)oxido-$\lambda^6$-sulfanylidene}carbamate (1.10 g; 2.8 mmol) was prepared from (rac)-3-{3-[(methylsulfinyl)methyl]-5-nitrophenoxy}propan-1-ol (1.30 g; 4.8 mmol) under similar conditions as described in the preparation protocol for Intermediate 5.4.

$^1$H NMR (400 MHz, DMSO, 300K) δ=1.39 (s, 9H), 1.89 (quin, 2H), 3.14 (s, 3H), 3.54-3.59 (m, 2H), 4.17 (t, 2H), 4.61 (t, 1H), 4.96-5.05 (m, 2H), 7.45 (dd, 1H), 7.76 (t, 1H), 7.90 (t, 1H).

Preparation of Intermediate 9.4

(rac)-tert-butyl [(3-{3-[5-(2-chloro-5-fluoropyrimidin-4-yl)-2-fluorophenoxy]propoxy}-5-nitrobenzyl)(methyl)oxido-$\lambda^6$-sulfanylidene]carbamate

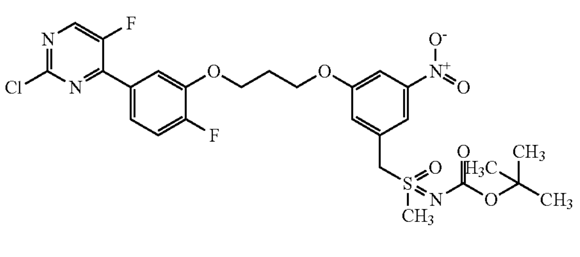 [SMILES: CC(C)(C)OC(=O)N=S(C)(=O)Cc1cc(OCCCOc2cc(-c3nc(Cl)ncc3F)ccc2F)cc([N+](=O)[O-])c1]

(rac)-tert-butyl [(3-{3-[5-(2-chloro-5-fluoropyrimidin-4-yl)-2-fluorophenoxy]propoxy}-5-nitrobenzyl)(methyl)oxido-$\lambda^6$-sulfanylidene]carbamate (293 mg; 0.48 mmol) was prepared from 5-(2-chloro-5-fluoropyrimidin-4-yl)-2-fluorophenol (206 mg; 0.85 mmol) and (rac)-tert-butyl {[3-(3-hydroxypropoxy)-5-nitrobenzyl](methyl)oxido-26-sulfanylidene}carbamate (300 mg; 0.77 mmol) under similar conditions as described in the preparation protocol for Intermediate 5.5.

$^1$H NMR (400 MHz, DMSO, 300K) δ=1.36 (s, 9H), 2.26-2.32 (m, 2H), 3.14 (s, 3H), 4.28-4.36 (m, 4H), 4.95-5.05 (m, 2H), 7.44-7.50 (m, 2H), 7.61-7.68 (m, 1H), 7.76-7.81 (m, 2H), 7.91 (t, 1H), 8.98 (d, 1H).

Preparation of Intermediate 9.5

(rac)-tert-butyl [(3-amino-5-{3-[5-(2-chloro-5-fluoropyrimidin-4-yl)-2-fluorophenoxy]propoxy}benzyl)(methyl)oxido-$\lambda^6$-sulfanylidene]carbamate

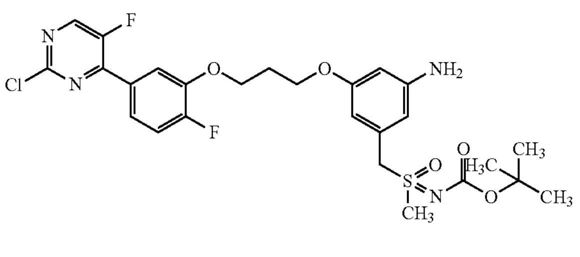 [SMILES: CC(C)(C)OC(=O)N=S(C)(=O)Cc1cc(N)cc(OCCCOc2cc(-c3nc(Cl)ncc3F)ccc2F)c1]

(rac)-tert-butyl [(3-amino-5-{3-[5-(2-chloro-5-fluoropyrimidin-4-yl)-2-fluorophenoxy]propoxy}benzyl)(methyl)oxido-$\lambda^6$-sulfanylidene]carbamate (148 mg) was prepared as a crude product from (rac)-tert-butyl [(3-{3-[5-(2-chloro-5-fluoropyrimidin-4-yl)-2-fluorophenoxy]propoxy}-5-nitrobenzyl)(methyl)oxido-λ6-sulfanylidene]carbamate (293 mg; 0.48 mmol) under similar conditions as described in the preparation protocol for Intermediate 5.6.

EXAMPLE 9—PREPARATION OF THE END PRODUCT (rac)-tert-butyl [{[3,19-difluoro-13,17-dioxa-5,7,24-triazatetracyclo[16.3.1.$1^{2,6}$.$1^{8,12}$]tetracosa-1(22),2(24),3,5,8(23),9,11,18,20-nonaen-10-yl]methyl}(methyl)oxido-$\lambda^6$-sulfanylidene]carbamate (31 mg; 0.06 mmol) was prepared from crude (rac)-tert-butyl [(3-amino-5-{3-[5-(2-chloro-5-fluoropyrimidin-4-yl)-2-fluorophenoxy]propoxy}benzyl)

(methyl)oxido-λ$^6$-sulfanylidene]carbamate (148 mg; 0.25 mmol) under similar conditions as described in the preparation protocol for Example 5. The product was purified by preparative HPLC (see method: Autopurifier: basic conditions).

$^1$H-NMR (400 MHz, DMSO-d6)=1.37 (s, 9H), 2.14-2.31 (m, 2H), 3.13 (s, 3H), 4.32 (br t, 2H), 4.47 (br t, 2H), 4.74 (s, 2H), 6.70 (s, 1H), 6.84 (s, 1H), 7.36 (dd, 1H), 7.46-7.58 (m, 1H), 8.09-8.16 (m, 2H), 8.67 (d, 1H), 9.91 (s, 1H).

EXAMPLE 10

(rac)-3,19-difluoro-10-[(S-methylsulfonimidoyl)methyl]-13,17-dioxa-5,7,24-triazatetracyclo[16.3.1.1$^{2,6}$.1$^{8,12}$]tetracosa-1(22),2(24),3,5,8(23),9,11,18,20-nonaene

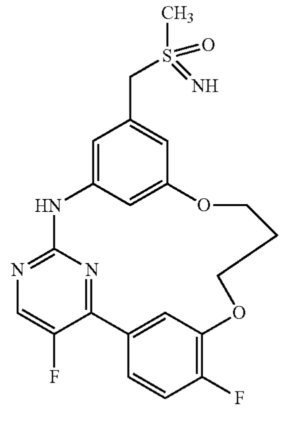 [SMILES: CS(=N)(=O)Cc1cc2cc(c1)OCCCOc1cc(ccc1F)-c1nc(ncc1F)N2]

(rac)-3,19-difluoro-10-[(S-methylsulfonimidoyl)methyl]-13,17-dioxa-5,7,24-triazatetracyclo[16.3.1.1$^{2,6}$.1$^{8,12}$]tetracosa-1(22),2(24),3,5,8(23),9,11,18,20-nonaene (9 mg; 0.02 mmol) was prepared from (rac)-tert-butyl [{[3,19-difluoro-13,17-dioxa-5,7,24-triazatetracyclo[16.3.1.1$^{2,6}$.1$^{8,12}$]tetracosa-1(22),2(24),3,5,8(23),9,11,18,20-nonaen-10-yl]methyl}(methyl)oxido-λ$^6$-sulfanylidene]carbamate (28 mg; 0.05 mmol) under similar conditions as described in the preparation protocol for Example 6.

$^1$H-NMR (400 MHz, DMSO-d6)=2.16-2.31 (m, 2H), 2.81 (s, 3H), 4.15-4.34 (m, 4H), 4.43-4.62 (m, 2H), 6.71 (s, 1H), 6.82 (s, 1H), 7.32-7.41 (m, 1H), 7.47-7.62 (m, 1H), 8.05-8.15 (m, 2H), 8.66 (d, 1H), 9.85 (s, 1H).

EXAMPLE 11

(rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene

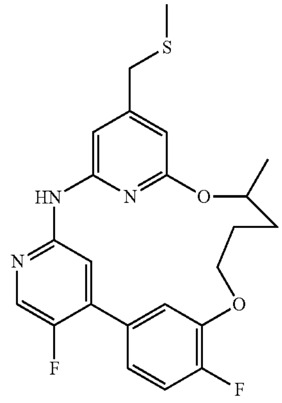 [SMILES: CSCc1cc2nc(c1)OC(C)CCCOc1cc(ccc1F)-c1cc(ncc1F)N2]

Preparation of Intermediate 11.1

5-[5-(2-amino-5-fluoropyridin-4-yl)-2-fluorophenoxy]pentan-2-one

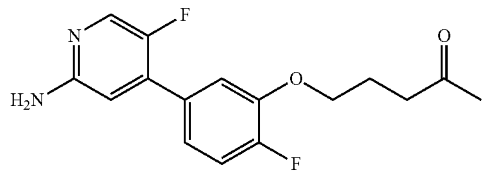 [SMILES: CC(=O)CCCOc1cc(-c2cc(N)ncc2F)ccc1F]

A mixture of 5-(2-amino-5-fluoropyridin-4-yl)-2-fluorophenol (Intermediate 1.3; 1.00 g; 4.50 mmol), 5-chloropentan-2-one (1.63 g; 13.5 mmol), potassium carbonate (1.86 g; 13.5 mmol) and potassium iodide (0.07 g; 0.45 mmol) in DMF (20 mL) was stirred for 4 h at 80° C. Additional chloropentan-2-one (0.81 g; 6.75 mmol) and potassium carbonate (0.62 g; 4.50 mmol) was added and the mixture was stirred at 80° C. overnight. After cooling the mixture was diluted with water and the mixture was three times extracted with ethyl acetate. The combined organic layers were filtered using a Whatman filter and concentrated. The residue was purified by column chromatography on silica gel (DCM to DCM/EtOH 20%) to give the title compound (1.20 g; 3.91 mmol).

$^1$H-NMR (400 MHz, DMSO-d$_6$): δ [ppm]=1.77-1.99 (m, 2H), 2.11 (s, 3H), 2.61 (t, 2H), 4.07 (t, 2H), 5.92 (s, 2H), 6.53 (d, 1H), 7.10 (ddd, 1H), 7.28 (d, 1H), 7.33 (t, 1H), 7.94 (d, 1H).

Preparation of Intermediate 11.2

(rac)-5-[5-(2-amino-5-fluoropyridin-4-yl)-2-fluorophenoxy]pentan-2-ol

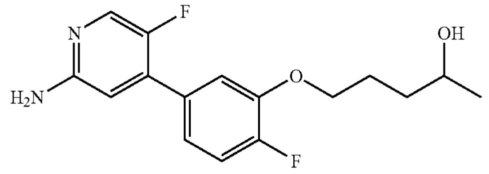 [SMILES: CC(O)CCCOc1cc(-c2cc(N)ncc2F)ccc1F]

Sodium borohydride (0.30 g; 7.84 mmol) was added portionwise to a stirred solution of 5-[5-(2-amino-5-fluoropyridin-4-yl)-2-fluorophenoxy]pentan-2-one (1.20 g; 3.91 mmol) in methanol (18 mL) at 0° C. After the addition the ice bath was removed and the mixture was stirred at room temperature for 1 h. The mixture was concentrated using a rotovab. The residue was taken up with ethyl acetate and was washed two times with a saturated aqueous solution of sodium bicarbonate. The organic phase was filtered using a Whatman filter and concentrated. The residue was purified by column chromatography on silica gel (hexane to hexane/ethylacetate 100%) to give the title compound (0.70 g; 2.27 mmol).

$^1$H-NMR (400 MHz, DMSO-d$_6$): δ [ppm]=1.07 (d, 3H), 1.40-1.53 (m, 2H), 1.62-1.89 (m, 2H), 3.60-3.69 (m, 1H), 4.09 (t, 2H), 4.45 (d, 1H), 5.92 (s, 2H), 6.54 (d, 1H), 7.09 (ddt, 1H), 7.28 (d, 1H), 7.30-7.36 (m, 1H), 7.94 (d, 1H).

Preparation of Intermediate 11.3

6-chloro-4-[(methylsulfanyl)methyl]pyridin-2-ol

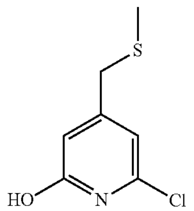

Potassium hydroxide (2.0 g; 36.0 mmol) was added to a solution of 2,6-dichloro-4-[(methylsulfanyl)methyl]pyridine (Intermediate 1.6; 5.0 g; 24.0 mmol) in tert-butanol (150 mL) and the mixture was stirred at 100° C. overnight. After cooling the mixture was diluted with a saturated aqueous solution of sodium chloride and extracted three times with ethyl acetate. The combined organic layers were filtered using a Whatman filter and concentrated. The residue was taken up in ethyl acetate and washed with aqueous hydrogen chloride solution. The organic layer was filtered using a Whatman filter and concentrated. The residue was stirred in hexane for 1 h before it was filtered and dried in vacuo to give the title compound (2.3 g; 12.1 mmol).

$^1$H-NMR (400 MHz, DMSO-$d_6$): δ [ppm]=1.96 (s, 3H), 3.62 (s, 2H), 6.54 (s, 1H), 6.88 (s, 1H), 11.48 (br s, 1H).

Preparation of Intermediate 11.4

(rac)-4-(3-{[4-({6-chloro-4-[(methylsulfanyl)methyl]pyridin-2-yl}oxy)pentyl]oxy}-4-fluorophenyl)-5-fluoropyridin-2-amine

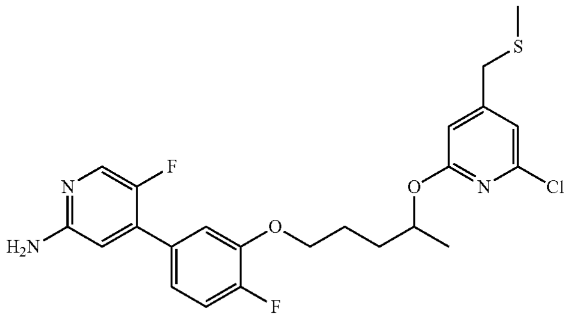 [SMILES: CSCc1cc(Cl)nc(OC(C)CCCOc2cc(-c3cc(N)ncc3F)ccc2F)c1]

Under argon, diisopropyl azodicarboxylate [CAS-RN: 2446-83-5] (0.98 mL; 5.00 mmol) was added dropwise to a stirred mixture of (rac) 5-[5-(2-amino-5-fluoropyridin-4-yl)-2-fluorophenoxy]pentan-2-ol (Intermediate 11.2; 1.40 g; 4.54 mmol), 6-chloro-4-[(methylsulfanyl)methyl]pyridin-2-ol (Intermediate 11.3; 861 mg; 4.54 mmol) and triphenylphosphine (1.31 g; 5.00 mmol) in DCM (28 mL) and the mixture was stirred at room temperature overnight. The mixture was concentrated and the residue was purified by column chromatography on silica gel (hexane to hexane/ethyl acetate 80%) to give the desired title compound (1.50 g; 3.13 mmol).

$^1$H-NMR (400 MHz, DMSO-$d_6$): δ [ppm]=1.29 (d, 3H), 1.73-1.90 (m, 4H), 1.95 (s, 3H), 3.62 (s, 2H), 4.09-4.16 (m, 2H), 5.09-5.17 (m, 1H), 5.92 (s, 2H), 6.53 (d, 1H), 6.68 (s, 1H), 6.99 (d, 1H), 7.09 (ddd, 1H), 7.25-7.35 (m, 2H), 7.93 (d, 1H).

EXAMPLE 11: PREPARATION OF END PRODUCT

To a solution of (rac)-4-(3-{[4-({6-chloro-4-[(methylsulfanyl)methyl]pyridin-2-yl}oxy)pentyl]oxy}-4-fluorophenyl)-5-fluoropyridin-2-amine (1.50 g, 3.13 mmol) in toluene (225 mL) and NMP (15 mL) was sequentially added potassium phosphate (3.32 g, 15.63 mmol), 2-dicyclohexylphosphino-2',4',6'-triisopropylbiphenyl [CAS-RN: 564483-18-7] (149 mg, 0.31 mmol) and chloro(2-dicyclohexylphosphino-2',4',6'-tri-iso-propyl-1,1'-biphenyl)[2-(2-aminoethyl)phenyl] palladium(II) methyl-tert-butylether adduct [CAS-RN: 1028206-56-5] (258 mg, 0.31 mmol). The suspension was degassed and stirred under an atmosphere of argon at 110° C. overnight. After cooling, the reaction mixture was diluted with an aqueous, saturated sodium chloride solution and extracted three times with ethyl acetate. The combined organic layers were filtered using a Whatman filter and concentrated. The residue was purified by column chromatography on silica gel (hexane to hexane/ethyl acetate 40%) to give the desired title compound (1.30 g; 2.93 mmol).

$^1$H-NMR (400 MHz, DMSO-$d_6$): δ [ppm]=1.11 (d, 3H), 1.37-1.60 (m, 2H), 1.81-2.04 (m, 5H), 3.50-3.62 (m, 2H), 4.36-4.48 (m, 2H), 5.19-5.27 (m, 1H), 6.20 (s, 1H), 6.60 (s, 1H), 7.37 (d, 2H), 7.58 (d, 1H), 8.30 (d, 1H), 8.68 (d, 1H), 9.83 (s, 1H).

EXAMPLE 12 AND 13

Enantiomers of 3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene

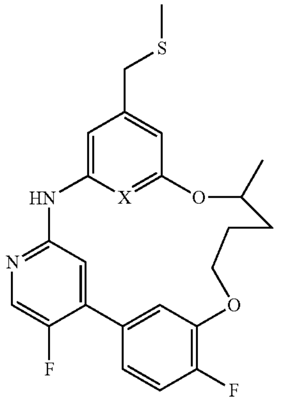

(rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene (1.30 g; Example 11) was separated into the single enantiomers by preparative chiral HPLC.

| | |
|---|---|
| System: | Labomatic HD5000, Labocord-5000; Gilson GX-241, Labcol Vario 4000 |
| Column: | YMC Amylose SA, 5 µm 250 × 30 mm |
| Solvent: | Hexane/EtOH 1:1 |
| Flow: | 40 mL/min |
| Temperature: | 25° C. |
| Solution: | 1.30 g in 6 ml DCM/MeOH 1:1 |
| Injection: | 6 × 1 mL |
| Detection: | UV 280 nm |

| | Retention time in min | purity in % | yield |
|---|---|---|---|
| Example 12 Enantiomer 1 | 5.9-8.1 | 98.1% | 150 mg |
| Example 13 Enantiomer 2 | 10.1-12.4 | 94.2% | 126 mg |

EXAMPLES 14 AND 15

Diastereoisomers 1 and 2 of 3,20-difluoro-14-methyl-10-[(S-methylsulfonimidoyl)methyl]-13,18-dioxa-5,7,24-triazatetracyclo[$17.3.1.1^{2,6}.1^{8,12}$]pentacosa-1(23),2(25),3,5,8(24),9,11,19,21-nonaene

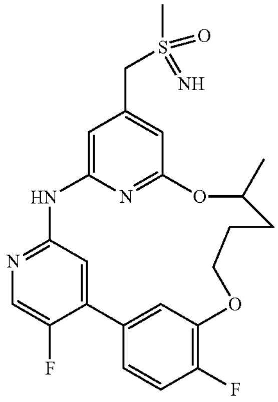 [SMILES: CC1CCCOc2cc(ccc2F)-c2cc(ncc2F)Nc2cc(CS(C)(=N)=O)cc(n2)O1]

Ammonium carbamate (38 mg; 0.49 mmol) and (diacetoxyiodo)benzene (221 mg; 0.69 mmol) were added to a solution of 3,20-difluoro-14-methyl-10-[(methylsulfanyl)methyl]-13,18-dioxa-5,7,24-triazatetracyclo[$17.3.1.1^{2,6}.1^{8,12}$]pentacosa-1(23),2(25),3,5,8(24),9,11,19,21-nonaene (Enantiomer 1, example 12; 145 mg; 0.33 mmol) in methanol (2.2 mL). The mixture was stirred in an open flask for 2 hours at room temperature before it was concentrated. The residue was purified with preparative HPLC (see method: Autopurifier: acidic conditions) to give the mixture of two diastereoisomers (32 mg; 0.06 mmol). The mixture of two diastereoisomers was then separated into the single diastereoisomers by preparative chiral HPLC.

| | |
|---|---|
| System: | Labomatic HD5000, Labocord-5000; Gilson GX-241, Labcol Vario 4000 |
| Column: | YMC Amylose SA, 5 µm 250 × 30 mm |
| Solvent: | tert-Butyl methyl ether/MeOH 1:1 |
| Flow: | 40 mL/min |
| Temperature: | 25° C. |
| Solution: | 20 mg in 1 mL DCM/MeOH 1:1 |
| Injection: | 1 × 1 mL |
| Detection: | UV 280 nm |

-continued

| | Retention time in min | purity in % | yield |
|---|---|---|---|
| Example 14 Diasteroisomer 1 | 5.4-6.1 | 99.2% | 4.5 mg |
| Example 15 Diasteroisomer 2 | 6.9-8.1 | 99.5% | 3.6 mg |

EXAMPLE 14

1H-NMR (400 MHz, DMSO-d6): Shift [ppm]=1.09-1.17 (m, 3H), 1.43 (br dd, 1H), 1.57 (td, 1H), 1.82-2.04 (m, 2H), 2.86 (s, 3H), 3.72-3.79 (m, 1H), 4.24-4.48 (m, 4H), 5.21-5.29 (m, 1H), 6.33 (s, 1H), 6.67 (s, 1H), 7.34-7.40 (m, 2H), 7.59 (d, 1H), 8.31 (d, 1H), 8.67 (d, 1H), 9.92 (s, 1H).

EXAMPLE 15

1H-NMR (400 MHz, DMSO-d6): Shift [ppm]=1.08-1.17 (m, 3H), 1.35-1.48 (m, 1H), 1.48-1.66 (m, 1H), 1.86 (ddt, 1H), 1.94-2.03 (m, 1H), 2.87 (s, 3H), 3.71-3.79 (m, 1H), 4.25-4.34 (m, 2H), 4.36-4.49 (m, 2H), 5.21-5.29 (m, 1H), 6.32 (s, 1H), 6.67 (s, 1H), 7.34-7.40 (m, 2H), 7.59 (br d, 1H), 8.31 (d, 1H), 8.67 (d, 1H), 9.91 (s, 1H).

EXAMPLES 16 AND 17

Diastereoisomers 3 and 4 of 3,20-difluoro-14-methyl-10-[(S-methylsulfonimidoyl)methyl]-13,18-dioxa-5,7,24-triazatetracyclo[$17.3.1.1^{2,6}.1^{8,12}$]pentacosa-1(23),2(25),3,5,8(24),9,11,19,21-nonaene

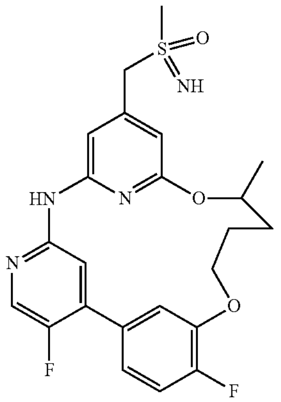 [SMILES: CC1CCCOc2cc(ccc2F)-c2cc(ncc2F)Nc2cc(CS(C)(=N)=O)cc(n2)O1]

Ammonium carbamate (32 mg; 0.41 mmol) and (diacetoxyiodo)benzene (186 mg; 0.58 mmol) were added to a solution of 3,20-difluoro-14-methyl-10-[(methylsulfanyl)methyl]-13,18-dioxa-5,7,24-triazatetracyclo[$17.3.1.1^{2,6}.1^{8,12}$]pentacosa-1(23),2(25),3,5,8(24),9,11,19,21-nonaene (Enantiomer 2, example 12; 122 mg; 0.28 mmol) in methanol (1.9 mL). The mixture was stirred in an open flask for 2 hours at room temperature before it was concentrated. The residue was purified with preparative HPLC (see method: Autopurifier: acidic conditions) to give the mixture of two diastereoisomers (32 mg; 0.06 mmol). The mixture of two diastereoisomers was separated into the single diastereoisomers by preparative chiral HPLC.

| | |
|---|---|
| System: | Labomatic HD5000, Labocord-5000; Gilson GX-241, Labcol Vario 4000 |
| Column: | YMC Amylose SA, 5 μm 250 × 30 mm |
| Solvent: | tert-Butyl methyl ether/MeOH 1:1 |
| Flow: | 40 mL/min |
| Temperature: | 25° C. |
| Solution: | 20 mg in 1 mL DCM/MeOH 1:1 |
| Injection: | 1 × 1 mL |
| Detection: | UV 280 nm |

| | Retention time in min | purity in % | yield |
|---|---|---|---|
| Example 16 Diasteroisomer 3 | 14.1-16.2 | 99.7% | 9.0 mg |
| Example 17 Diasteroisomer 4 | 16.9-18.9 | 97.0% | 8.3 mg |

EXAMPLE 16

1H-NMR (400 MHz, DMSO-d6): Shift [ppm]=1.09-1.17 (m, 3H), 1.43 (br s, 1H), 1.57 (br d, 1H), 1.87 (br d, 1H), 1.94-2.03 (m, 1H), 2.87 (s, 3H), 3.75 (s, 1H), 4.29 (d, 2H), 4.38-4.48 (m, 2H), 5.25 (br d, 1H), 6.32 (s, 1H), 6.67 (s, 1H), 7.38 (d, 2H), 7.60 (d, 1H), 8.32 (d, 1H), 8.67 (d, 1H), 9.92 (s, 1H).

EXAMPLE 17

1H-NMR (400 MHz, DMSO-d6): Shift [ppm]=1.06-1.18 (m, 3H), 1.44 (br d, 1H), 1.57 (br d, 1H), 1.82-1.93 (m, 1H), 1.99 (br s, 1H), 2.86 (s, 3H), 3.75 (s, 1H), 4.24-4.35 (m, 2H), 4.38-4.48 (m, 2H), 5.21-5.31 (m, 1H), 6.33 (s, 1H), 6.67 (s, 1H), 7.38 (d, 2H), 7.60 (d, 1H), 8.32 (d, 1H), 8.68 (d, 1H), 9.92 (s, 1H).

EXAMPLE 18

(rac)-3,21-difluoro-14-methyl-10-[(methylsulfanyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene

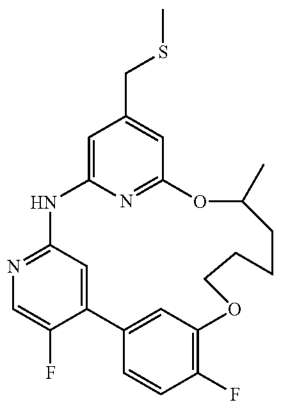 [SMILES: CSCc1cc2nc(c1)OC(C)CCCCOc1cc(ccc1F)-c1cc(ncc1F)N2]

Preparation of Intermediate 18.1

(rac)-5-hydroxyhexyl Methanesulfonate

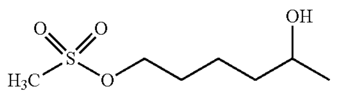

Methanesulfonyl chloride (2.6 mL; 33.8 mmol) was added dropwise to a stirred solution of hexane-1,5-diol (5.1 mL; 42.3 mmol) and triethylamine (5.9 mL; 42.3 mmol) in DCM (182 mL) at 0° C. The mixture was stirred at 0° C. for 30 min before the ice bath was removed and the mixture was stirred for 3 hours at room temperature. The mixture was diluted with an aqueous solution of sodium chloride and extracted two times with DCM. The combined organic layers were filtered using a Whatman filter and concentrated. The residue was taken up in ethyl acetate and the solution was washed with water and two times with aqueous sodium chloride solution. The organic layer was filtered using a Whatman filter and concentrated to give the crude product (5.6 g), that was used without further purification.

Preparation of Intermediate 18.2: 6365-2

6-[5-(2-amino-5-fluoropyridin-4-yl)-2-fluorophenoxy]hexan-2-ol

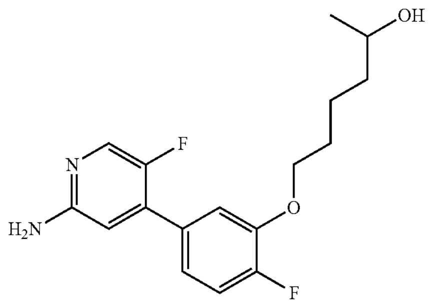 [SMILES: CC(O)CCCCOc1cc(-c2cc(N)ncc2F)ccc1F]

(rac)-5-Hydroxyhexyl methanesulfonate (697 mg; 3.56 mmol) was slowly added to a mixture of 5-(2-amino-5-fluoropyridin-4-yl)-2-fluorophenol (Intermediate 1.3; 790 mg; 3.56 mmol), potassium carbonate (589 mg; 4.27 mmol) and potassium iodide (59 mg; 0.36 mmol) in DMF (28 mL) at 0° C. The mixture was stirred at 60° C. overnight. After cooling, the mixture was diluted with ethyl acetate and washed with aqueous sodium chloride solution. The organic layer was filtered using a Whatman filter and concentrated. The residue was purified by column chromatography on silica gel (hexane/ethyl acetate 50% to ethyl acetate 100%) to give the desired title compound (688 mg, 2.13 mmol).

1H-NMR (400 MHz, DMSO-d6): Shift [ppm]=1.00-1.06 (m, 3H), 1.26-1.54 (m, 4H), 1.68-1.79 (m, 2H), 3.53-3.63 (m, 1H), 4.00-4.11 (m, 2H), 4.36 (d, 1H), 5.92 (s, 2H), 6.54 (d, 1H), 7.09 (ddt, 1H), 7.26-7.35 (m, 2H), 7.92-7.96 (m, 1H).

Preparation of Intermediate 18.3

(rac)-4-(3-{[5-({6-chloro-4-[(methylsulfanyl)methyl] pyridin-2-yl}oxy)hexyl]oxy}-4-fluorophenyl)-5-fluoropyridin-2-amine

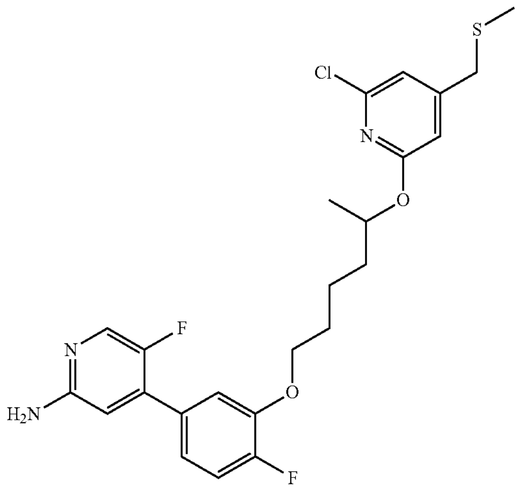 [SMILES: CSCc1cc(Cl)nc(OC(C)CCCCOc2cc(-c3cc(N)ncc3F)ccc2F)c1]

(rac)-4-(3-{[5-({6-chloro-4-[(methylsulfanyl)methyl] pyridin-2-yl}oxy)hexyl]oxy}-4-fluorophenyl)-5-fluoropyridin-2-amine (530 mg; 1.07 mmol) was prepared from 6-[5-(2-amino-5-fluoropyridin-4-yl)-2-fluorophenoxy]hexan-2-ol (685 mg; 2.13 mmol) and 6-chloro-4-[(methylsulfanyl) methyl]pyridin-2-ol (Intermediate 11.3; 403 mg; 2.13 mmol) under similar conditions as described in the preparation protocol for Intermediate 11.4.

1H-NMR (400 MHz, DMSO-d6): Shift [ppm]=1.15-1.29 (m, 3H), 1.41-1.81 (m, 6H), 1.95 (s, 3H), 3.63 (s, 2H), 4.00-4.14 (m, 2H), 5.08 (sxt, 1H), 5.91 (s, 2H), 6.53 (d, 1H), 6.68 (d, 1H), 6.98 (d, 1H), 7.08 (ddt, 1H), 7.25-7.34 (m, 2H), 7.93 (d, 1H).

EXAMPLE 18: PREPARATION OF END PRODUCT (rac)-3,21-difluoro-14-methyl-10-[(methylsulfanyl) methyl]-13,19-dioxa-5,7,25-triazatetracyclo[18.3.1.1$^{2,6}$.1$^{8,12}$]hexacosa-1(24),2(26),3,5,8(25),9,11,20,22-nonaene (215 mg; 0.47 mmol) was prepared from (rac)-4-(3-{[5-({6-chloro-4-[(methylsulfanyl)methyl]pyridin-2-yl}oxy)hexyl] oxy}-4-fluorophenyl)-5-fluoropyridin-2-amine (528 mg; 1.07 mmol) under similar conditions as described in the preparation protocol for Example 11.

1H-NMR (400 MHz, DMSO-d6): Shift [ppm]=1.11 (d, 3H), 1.39-1.54 (m, 1H), 1.57-1.82 (m, 4H), 1.90-2.00 (m, 4H), 3.52-3.60 (m, 2H), 4.36 (brt, 2H), 5.11-5.19 (m, 1H), 6.19 (s, 1H), 6.55 (s, 1H), 7.24-7.45 (m, 3H), 8.25 (d, 1H), 8.31 (d, 1H), 9.77 (s, 1H).

EXAMPLE 19 AND 20

Enantiomers of 3,21-difluoro-14-methyl-10-[(methylsulfanyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene

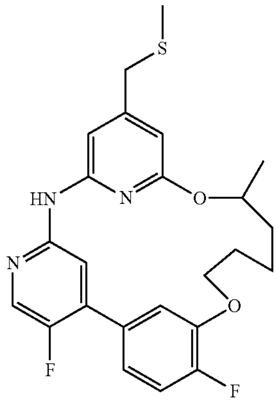 [SMILES: CSCc1cc2nc(c1)OC(C)CCCCOc1cc(ccc1F)-c1cc(ncc1F)N2]

(rac)-3,21-difluoro-14-methyl-10-[(methylsulfanyl) methyl]-13,19-dioxa-5,7,25-triazatetracyclo[18.3.1.1$^{2,6}$.1$^{8,12}$]hexacosa-1(24),2(26),3,5,8(25),9,11,20,22-nonaene (1.32 g) was separated into the single enantiomers by preparative chiral HPLC.

| | |
|---|---|
| System: | Sepiatec: Prep SFC100 |
| Column: | Chiralpak IG, 5 μm 250 × 30 mm |
| Solvent: | $CO_2$/EtOH; 40% EtOH |
| Flow: | 100 mL/min |
| Temperature: | 40° C. |
| Solution: | 1.32 g in 17.5 ml DCM/MeOH/DMSO 1:1:1.5 |
| Injection: | 20 × 0.9 mL |
| Detection: | UV 254 nm |

| | Retention time in min | purity in % | yield |
|---|---|---|---|
| Example 19 Enantiomer 1 | 6.5-8.5 | 97.1% | 560 mg |
| Example 20 Enantiomer 2 | 9.8-12.8 | 98.8% | 385 mg |

EXAMPLE 21

Mixture of two diastereoisomers 1 and 2 of 3,21-difluoro-14-methyl-10-[(S-methylsulfonimidoyl) methyl]-13,19-dioxa-5,7,25-triazatetracyclo [18.3.1.1$^{2,6}$.1$^{8,12}$]hexacosa-1(24),2(26),3,5,8(25),9,11,20,22-nonaene

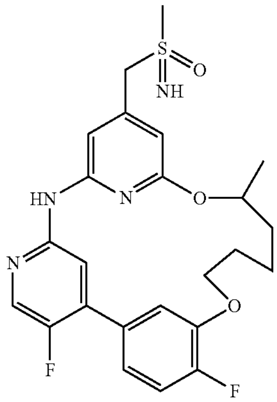 [SMILES: CC1CCCCOc2cc(ccc2F)-c2cc(ncc2F)Nc2cc(CS(C)(=N)=O)cc(n2)O1]

The mixture of diastereoisomers 1 and 2 of 3,21-difluoro-14-methyl-10-[(S-methylsulfonimidoyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene (12 mg; 0.02 mmol) was prepared from enantiomer 1 of 3,21-difluoro-14-methyl-10-[(methylsulfanyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene (Example 19; 505 mg; 1.10 mmol) under similar conditions as described in the preparation protocol for Examples 14 and 15.

1H-NMR (400 MHz, DMSO-d6): Shift [ppm]=1.09-1.16 (m, 3H), 1.36-1.55 (m, 1H), 1.58-1.82 (m, 4H), 1.86-2.06 (m, 1H), 2.86 (d, 3H), 3.71-3.88 (m, 1H), 4.20-4.40 (m, 4H), 4.99-5.31 (m, 1H), 6.12-6.45 (m, 1H), 6.50-6.71 (m, 1H), 7.18-7.49 (m, 3H), 8.14-8.28 (m, 1H), 8.28-8.44 (m, 1H), 9.76-9.99 (m, 1H).

EXAMPLE 22

Mixture of two diastereoisomers 3 and 4 of 3,21-difluoro-14-methyl-10-[(S-methylsulfonimidoyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene

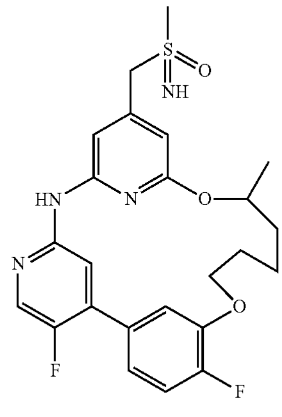 [SMILES: CC1CCCCOc2cc(ccc2F)-c2cc(ncc2F)Nc2cc(CS(C)(=N)=O)cc(n2)O1]

The mixture of diastereoisomers 3 and 4 of 3,21-difluoro-14-methyl-10-[(S-methylsulfonimidoyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene (27 mg; 0.06 mmol) was prepared from enantiomer 2 of 3,21-difluoro-14-methyl-10-[(methylsulfanyl)methyl]-13,19-dioxa-5,7,25-triazatetracyclo[18.3.1.$1^{2,6}$.$1^{8,12}$]hexacosa-1(24),2(26),3,5,8(25),9,11,20,22-nonaene (Example 20; 330 mg; 0.72 mmol) under similar conditions as described in the preparation protocol for Examples 14 and 15.

1H-NMR (400 MHz, DMSO-d6): Shift [ppm]=1.10-1.14 (m, 3H), 1.49 (br d, 1H), 1.59-1.82 (m, 4H), 1.89-2.00 (m, 1H), 2.87 (d, 3H), 3.76 (s, 1H), 4.23-4.39 (m, 4H), 5.12-5.20 (m, 1H), 6.32 (dd, 1H), 6.61 (d, 1H), 7.28 (br s, 1H), 7.33-7.45 (m, 2H), 8.24 (dd, 1H), 8.32 (d, 1H), 9.84 (d, 1H).

EXAMPLE 23

(rac)-3,22-difluoro-14-methyl-10-[(methylsulfanyl)methyl]-13,20-dioxa-5,7,26-triazatetracyclo[19.3.1.$1^{2,6}$.$1^{8,12}$]heptacosa-1(25),2(27),3,5,8(26),9,11,21,23-nonaene

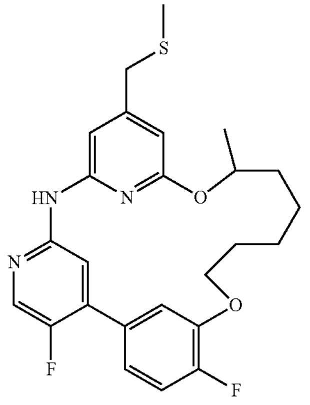 [SMILES: CSCc1cc2nc(c1)OC(C)CCCCCOc1cc(ccc1F)-c1cc(ncc1F)N2]

Preparation of Intermediate 23.1

(rac)-6-hydroxyheptyl Methanesulfonate

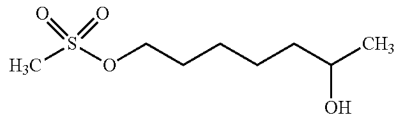

Crude (rac)-6-hydroxyheptyl methanesulfonate (4.0 g) was prepared from heptane-1,6-diol (3.5 g; 26.5 mmol) under similar conditions as described in the preparation protocol for Intermediate 18.1.

Preparation of Intermediate 23.2

(rac)-7-[5-(2-amino-5-fluoropyridin-4-yl)-2-fluorophenoxy]heptan-2-ol

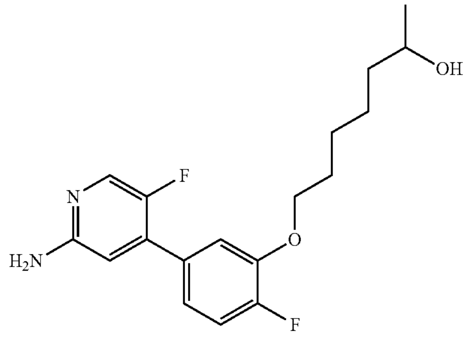 [SMILES: CC(O)CCCCCOc1cc(-c2cc(N)ncc2F)ccc1F]

(rac)-7-[5-(2-amino-5-fluoropyridin-4-yl)-2-fluorophenoxy]heptan-2-ol (528 mg; 1.57 mmol) was prepared from crude (rac)-6-hydroxyheptyl methanesulfonate (748 mg)

and 5-(2-amino-5-fluoropyridin-4-yl)-2-fluorophenol (Intermediate 1.3; 790 mg; 3.56 mmol) under similar conditions as described in the preparation protocol for Intermediate 18.2.

1H-NMR (400 MHz, DMSO-d6): Shift [ppm]=1.03 (d, 3H), 1.23-1.45 (m, 6H), 1.69-1.79 (m, 2H), 3.57 (dt, 1H), 4.09 (t, 2H), 4.32 (d, 1H), 5.92 (s, 2H), 6.54 (d, 1H), 7.06-7.12 (m, 1H), 7.26-7.36 (m, 2H), 7.92-7.96 (m, 1H).

Preparation of Intermediate 23.3

(rac)-4-(3-{[6-({6-chloro-4-[(methylsulfanyl)methyl]pyridin-2-yl}oxy)heptyl]oxy}-4-fluorophenyl)-5-fluoropyridin-2-amine

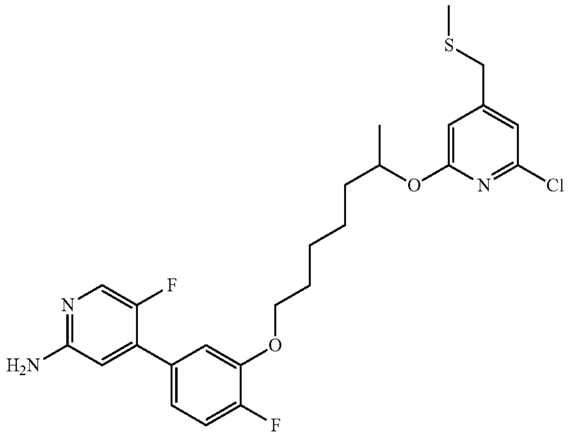 [SMILES: CSCc1cc(Cl)nc(OC(C)CCCCCOc2cc(-c3cc(N)ncc3F)ccc2F)c1]

(rac)-4-(3-{[6-({6-chloro-4-[(methylsulfanyl)methyl]pyridin-2-yl}oxy)heptyl]oxy}-4-fluorophenyl)-5-fluoropyridin-2-amine (573 mg; 1.13 mmol) was prepared from (rac)-7-[5-(2-amino-5-fluoropyridin-4-yl)-2-fluorophenoxy]heptan-2-ol (476 mg; 1.42 mmol)) and 6-chloro-4-[(methylsulfanyl)methyl]pyridin-2-ol (Intermediate 11.3; 268 mg; 1.42 mmol) under similar conditions as described in the preparation protocol for Intermediate 18.3.

EXAMPLE 23: PREPARATION OF END PRODUCT (rac)-3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene (224 mg; 0.48 mmol) was prepared from (rac)-4-(3-{[6-({6-chloro-4-[(methylsulfanyl)methyl]pyridin-2-yl}oxy)heptyl]oxy}-4-fluorophenyl)-5-fluoropyridin-2-amine (571 mg; 1.12 mmol) under similar conditions as described in the preparation protocol for Example 18.

1H-NMR (400 MHz, DMSO-d6): Shift [ppm]=1.05 (d, 3H), 1.29-1.55 (m, 5H), 1.62-1.75 (m, 3H), 1.99-2.02 (m, 3H), 3.53-3.60 (m, 2H), 4.28 (dt, 1H), 4.36-4.45 (m, 1H), 4.82-4.90 (m, 1H), 6.16-6.19 (m, 1H), 6.57 (s, 1H), 7.25-7.39 (m, 2H), 7.50 (dd, 1H), 8.29 (d, 1H), 8.53 (d, 1H), 9.81 (s, 1H).

EXAMPLE 24 AND 25

Enantiomers of 3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene

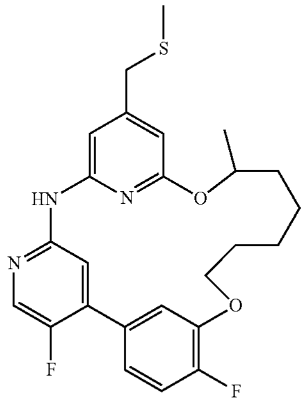 [SMILES: CSCc1cc2nc(c1)OC(C)CCCCCOc1cc(ccc1F)-c1cc(ncc1F)N2]

(rac)-3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene (150 mg) was separated into the single enantiomers by preparative chiral HPLC.

| | |
|---|---|
| System: | Sepiatec: Prep SFC100 |
| Column: | Chiralpak IA, 5 μm 250 × 30 mm |
| Solvent: | $CO_2$/EtOH; 35% EtOH |
| Flow: | 100 mL/min |
| Temperature: | 40° C. |
| Solution: | 150 mg in 2 mL DMSO |
| Injection: | 5 × 0.4 mL |
| Detection: | UV 254 nm |

| | Retention time in min | purity in % | yield |
|---|---|---|---|
| Example 24 Enantiomer 1 | 5.5-7.0 | 99.7% | 65 mg |
| Example 25 Enantiomer 2 | 7.4-10.0 | 97.6% | 75 mg |

EXAMPLE 26

Mixture of two diastereoisomers 1 and 2 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene

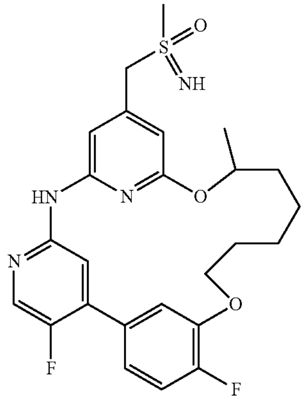 [SMILES: CC1CCCCCOc2cc(ccc2F)-c2cc(ncc2F)Nc2cc(CS(C)(=N)=O)cc(n2)O1]

The mixture of diastereoisomers 1 and 2 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene (14 mg; 0.03 mmol) was prepared from Enantiomer 1 of 3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene (Example 24; 60 mg; 0.13 mmol) under similar conditions as described in the preparation protocol for Examples 14 and 15.

1H-NMR (400 MHz, DMSO-d6): Shift [ppm]=1.02-1.10 (m, 3H), 1.30-1.60 (m, 5H), 1.61-1.78 (m, 3H), 2.88 (s, 3H), 3.76 (s, 1H), 4.25-4.33 (m, 3H), 4.40 (s, 1H), 4.79-4.95 (m, 1H), 6.30 (s, 1H), 6.64 (s, 1H), 7.29 (br s, 1H), 7.34-7.40 (m, 1H), 7.50 (d, 1H), 8.30 (d, 1H), 8.53 (dd, 1H), 9.89 (d, 1H).

EXAMPLE 27

Mixture of two diastereoisomers 3 and 4 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene

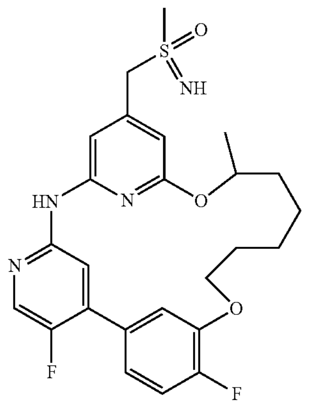 [SMILES: CC1CCCCCOc2cc(ccc2F)-c2cc(ncc2F)Nc2cc(CS(C)(=N)=O)cc(n2)O1]

The mixture of diastereoisomers 3 and 4 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene (6 mg; 0.01 mmol) was prepared from Enantiomer 2 of 3,22-difluoro-14-methyl-10-[(methylsulfanyl)methyl]-13,20-dioxa-5,7,26-triazatetracyclo [19.3.1.1$^{2,6}$.1$^{8,12}$]heptacosa-1(25),2(27),3,5,8(26),9,11,21,23-nonaene (Example 25; 70 mg; 0.15 mmol) under similar conditions as described in the preparation protocol for Examples 14 and 15.

1H-NMR (400 MHz, DMSO-d6): Shift [ppm]=1.04-1.14 (m, 3H), 1.30-1.56 (m, 5H), 1.58-1.79 (m, 3H), 2.88 (s, 3H), 3.76 (s, 1H), 4.24-4.44 (m, 4H), 4.86 (br s, 1H), 6.30 (s, 1H), 6.64 (s, 1H), 7.25-7.43 (m, 2H), 7.50 (dd, 1H), 8.24-8.32 (m, 1H), 8.53 (dd, 1H), 9.83-9.91 (m, 1H).

EXAMPLE 28

Mixture of enantiomers of 3,20-difluoro-14-methyl-10-[(methylsulfonyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene

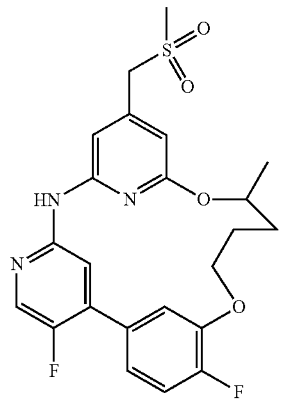 [SMILES: CC1CCCOc2cc(ccc2F)-c2cc(ncc2F)Nc2cc(CS(C)(=O)=O)cc(n2)O1]

3-Chloroperbenzoic acid (23 mg; 0.14 mmol) was added to a solution of (rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene (30 mg; 0.07 mmol) in DCM (0.7 mL) at 0° C. The ice bath was removed and the mixture was stirred at room temperature for 1 hour. The mixture was diluted with an aqueous solution of sodium bicarbonate and extracted two times with DCM. The combined organic layers were filtered using a Whatman filter and concentrated. The residue was purified with preparative HPLC (see method: Autopurifier: acidic conditions) to give the title compound (7 mg; 0.01 mmol).

1H-NMR (400 MHz, DMSO-d6): Shift [ppm]=1.11 (d, 3H), 1.40 (br dd, 1H), 1.53-1.62 (m, 1H), 1.81-1.94 (m, 1H), 1.97-2.01 (m, 1H), 2.94-3.00 (m, 3H), 4.30-4.46 (m, 4H), 5.19-5.27 (m, 1H), 6.28 (s, 1H), 6.65 (s, 1H), 7.33-7.40 (m, 2H), 7.56 (br d, 1H), 8.30 (d, 1H), 8.65 (d, 1H), 9.90 (s, 1H).

EXAMPLES 29 AND 30

Enantiomer 1 and 2 of 3,21-difluoro-14-methyl-10-[(methylsulfonyl)methyl]-13,19-dioxa-5,7,25-triaza-tetracyclo[18.3.1.1$^{2,6}$.1$^{8,12}$]hexacosa-1(24),2(26),3,5,8(25),9,11,20,22-nonaene

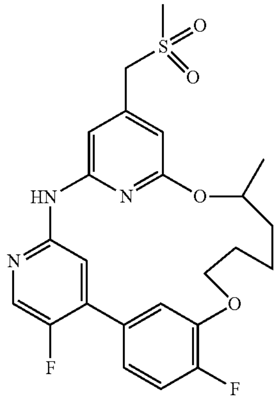 [SMILES: CC1CCCCOc2cc(ccc2F)-c2cc(ncc2F)Nc2cc(CS(C)(=O)=O)cc(n2)O1]

3-Chloroperbenzoic acid (75 mg; 0.43 mmol) was added to a solution of (rac)-3,21-difluoro-14-methyl-10-[(methylsulfanyl)methyl]-13,19-dioxa-5,7,25-triazatetracyclo [18.3.1.1$^{2,6}$.1$^{8,12}$]hexacosa-1(24),2(26),3,5,8(25),9,11,20,22-nonaene (Example 18; 100 mg; 0.22 mmol) in DCM (2.1 mL) at 0° C. The ice bath was removed and the mixture was stirred at room temperature for 1 hour. The mixture was diluted with an aqueous solution of sodium bicarbonate and extracted two times with DCM. The combined organic layers were filtered using a Whatman filter and concentrated. The residue was purified with preparative HPLC (see method: Autopurifier: acidic conditions) to give the racemate (32 mg; 0.07 mmol).

1H-NMR (400 MHz, DMSO-d6): Shift [ppm]=1.12 (d, 3H), 1.49 (br d, 1H), 1.58-1.83 (m, 4H), 1.87-2.01 (m, 1H), 2.99 (s, 3H), 4.32-4.47 (m, 4H), 5.12-5.21 (m, 1H), 6.28 (s, 1H), 6.62 (s, 1H), 7.27 (br dd, 1H), 7.36 (t, 1H), 7.43 (d, 1H), 8.24 (d, 1H), 8.33 (d, 1H), 9.90 (s, 1H).

The racemate was separated into the single enantiomers by preparative chiral HPLC.

| | |
|---|---|
| System: | Sepiatec: Prep SFC100 |
| Column: | Chiralpak IA, 5 μm 250 × 30 mm |
| Solvent: | $CO_2$/EtOH + 0.2 vol % aqueous ammonia (32%); 50% EtOH |
| Flow: | 100 mL/min |
| Temperature: | 40° C. |
| Solution: | 150 mg in 2 mL DMSO |
| Injection: | 5 × 0.4 mL |
| Detection: | UV 220 nm |

| | Retention time in min | purity in % | yield |
|---|---|---|---|
| Example 29 Enantiomer 1 | 7.1-9.1 | 99.7% | 5 mg |
| Example 30 Enantiomer 2 | 10.1-13.1 | 97.9% | 5 mg |

EXAMPLE 31 AND 32

Enantiomer 1 and 2 of 3,22-difluoro-14-methyl-10-[(methylsulfonyl)methyl]-13,20-dioxa-5,7,26-triaza-tetracyclo[19.3.1.1$^{2,6}$.1$^{8,12}$]hexacosa-1 (25),2(27),3,5,8(26),9,11,21,23-nonaene

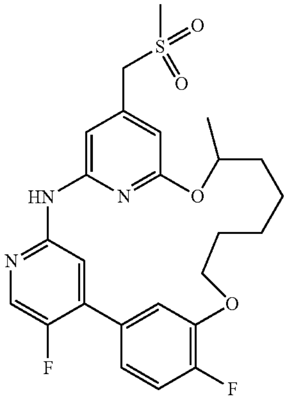 [SMILES: CC1CCCCCOc2cc(ccc2F)-c2cc(ncc2F)Nc2cc(CS(C)(=O)=O)cc(n2)O1]

3-Chloroperbenzoic acid (71 mg; 0.31 mmol) was added to a solution of (rac)-3,22-difluoro-14-methyl-10-[(methylsulfanyl)methyl]-13,20-dioxa-5,7,26-triazatetracyclo [19.3.1.1$^{2,6}$.1$^{8,12}$]heptacosa-1(25),2(27),3,5,8(26),9,11,21,23-nonaene (Example 23; 68 mg; 0.14 mmol) in DCM (3.5 mL) at 0° C. The ice bath was removed and the mixture was stirred at room temperature for 3 hours. The mixture was diluted with an aqueous solution of sodium bicarbonate and extracted two times with DCM. The combined organic layers were filtered using a Whatman filter and concentrated. The residue was purified with preparative HPLC (see method: Autopurifier: acidic conditions) to give the racemate (35 mg; 0.07 mmol).

1H-NMR (400 MHz, DMSO-d6): Shift [ppm]=1.06 (d, 3H), 1.32-1.56 (m, 5H), 1.64-1.74 (m, 3H), 3.00 (s, 3H), 4.27 (dt, 1H), 4.39-4.46 (m, 3H), 4.83-4.91 (m, 1H), 6.26 (d, 1H), 6.64 (d, 1H), 7.26-7.31 (m, 1H), 7.34-7.39 (m, 1H), 7.51 (dd, 1H), 8.31 (d, 1H), 8.52 (d, 1H), 9.95 (s, 1H).

The racemate was separated into the single enantiomers by preparative chiral HPLC.

| | |
|---|---|
| System: | Labomatic HD5000, Labocord-5000; Gilson GX-241, Labcol Vario 4000 |
| Column: | YMC Amylose SA, 5 μm 250 × 30 mm |
| Solvent: | Hexane/EtOH 60:40 |
| Flow: | 40 mL/min |
| Temperature: | 25° C. |
| Solution: | 31 mg in 1 mL DCM/MeOH 1:1 |
| Injection: | 1 × 1 mL |
| Detection: | UV 254 nm |

| | Retention time in min | purity in % | yield |
|---|---|---|---|
| Example 31 Enantiomer 1 | 14.2-16.0 | 98.1% | 15 mg |
| Example 32 Enantiomer 2 | 20.0-22.0 | 96.6% | 15 mg |

The following Table 1 provides an overview on the compounds described in the example section:

TABLE 1

| Example No. | Structure | Name of compound |
|---|---|---|
| 1 | 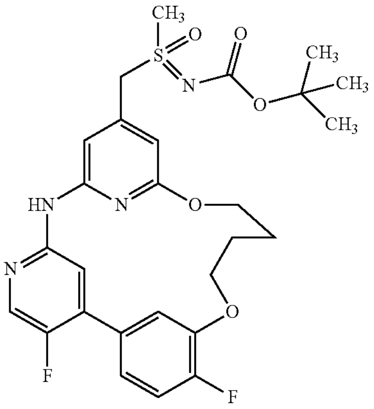 [SMILES: CC(C)(C)OC(=O)N=S(C)(=O)Cc1cc2nc(c1)OCCCCOc1cc(ccc1F)-c1cc(ncc1F)N2] | - (rac)-tert-butyl [{[3,20-difluoro-13,18-dioxa-5,7,24-triazatetracyclo[17.3.1.$1^{2,6}$.$1^{8,12}$[pentacosa-1(23),2(25),3,5,8(24),9,11,19,21-nonaen-10-yl]methyl{(methyl)oxido-$\lambda^6$-sulfanylidene]carbamate |
| 2 | 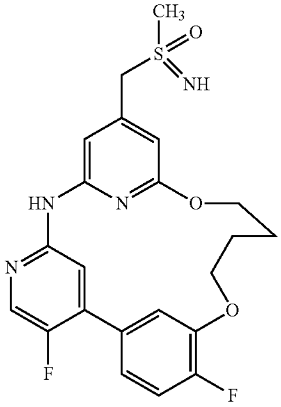 [SMILES: CS(=N)(=O)Cc1cc2nc(c1)OCCCCOc1cc(ccc1F)-c1cc(ncc1F)N2] | - (rac)-3,20-difluoro-10-[(S-methylsulfonimidoyl)methyl]-13,18-dioxa-5,7,24-triazatetracyclo[17.3.1.$1^{2,6}$.$1^{8,12}$]pentacosa-1(23),2(25),3,5,8(24),9,11,19,21-nonaene |
| 3 | 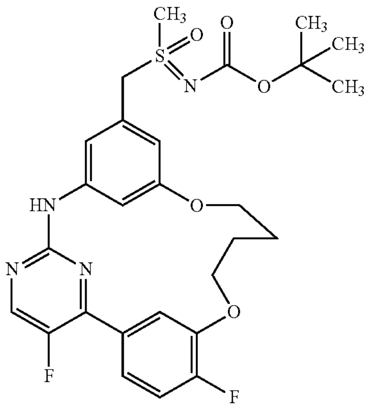 [SMILES: CC(C)(C)OC(=O)N=S(C)(=O)Cc1cc2cc(c1)OCCCCOc1cc(ccc1F)-c1nc(ncc1F)N2] | - (rac)-tert-butyl [{[3,20-difluoro-13,18-dioxa-5,7,25-triazatetracyclo[17.3.1.$1^{2,6}$.$1^{8,12}$]pentacosa-1(23),2(25),3,5,8(24),9,11,19,21-nonaen-10-yl]methyl}(methyl)oxido-$\lambda^6$-sulfanylidene]carbamate |

TABLE 1-continued

| Example No. | Structure | Name of compound |
|---|---|---|
| 4 | 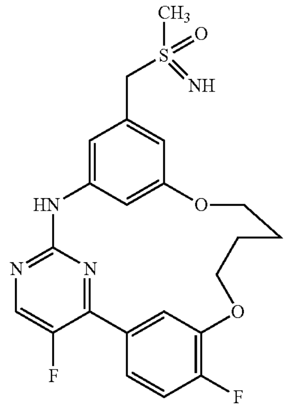 [SMILES: CS(=N)(=O)Cc1cc2cc(c1)OCCCCOc1cc(ccc1F)-c1nc(ncc1F)N2] | - (rac)-3,20-difluoro-10-[(S-methylsulfonimidoyl)methyl]-13,18-dioxa-5,7,25-triazatetracyclo[17.3.1.1$^{2,6}$.1$^{8,12}$]pentacosa-1(23),2(25),3,5,8(24),9,11,19,21-nonaene |
| 5 | 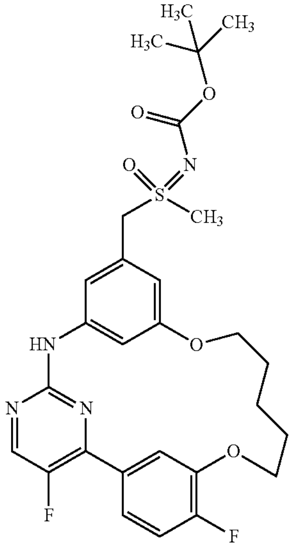 [SMILES: CC(C)(C)OC(=O)N=S(C)(=O)Cc1cc2cc(c1)OCCCCCOc1cc(ccc1F)-c1nc(ncc1F)N2] | - (rac)-tert-butyl [{[3,21-difluoro-13,19-dioxa-5,7,26-triazatetracyclo[18.3.1.1$^{2,6}$.1$^{8,12}$]hexacosa-1(24),2(26),3,5,8(25),9,11,20,22-nonaen-10-yl]methyl}(methyl)oxido-λ$^6$-sulfanylidene]carbamate |
| 6 | 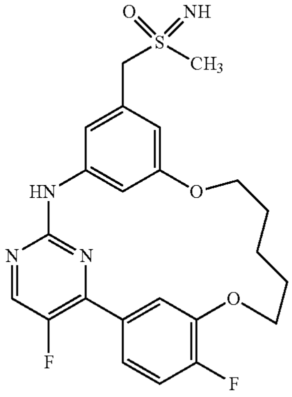 [SMILES: CS(=N)(=O)Cc1cc2cc(c1)OCCCCCOc1cc(ccc1F)-c1nc(ncc1F)N2] | - (rac)-3,21-difluoro-10-[(S-methylsulfonimidoyl)methyl]-13,19-dioxa-5,7,26-triazatetracyclo[18.3.1.1$^{2,6}$.1$^{8,12}$]hexacosa-1(24),2(26),3,5,8(25),9,11,20,22-nonaene |

TABLE 1-continued

| Example No. | Structure | Name of compound |
|---|---|---|
| 7 | 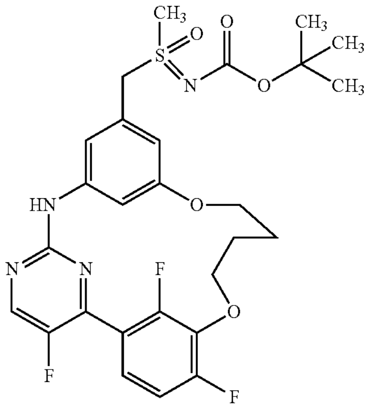 [SMILES: CC(C)(C)OC(=O)N=S(C)(=O)Cc1cc2cc(c1)OCCCCOc1c(F)ccc(c1F)-c1nc(ncc1F)N2] | - (rac)-tert-butyl [methyl(oxido){[3,20,23-trifluoro-13,18-dioxa-5,7,25-triazatetracyclo[17.3.1.1$^{2,6}$.1$^{8,12}$]pentacosa-1(23),2(25),3,5,8(24),9,11,19,21-nonaen-10-yl]methyl}-1 λ$^6$-sulfanylidene]carbamate |
| 8 | 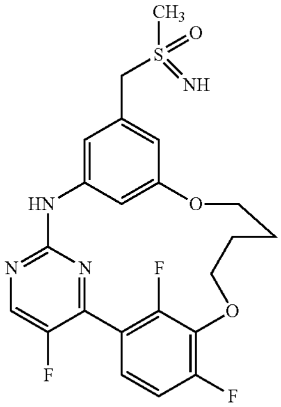 [SMILES: CS(=N)(=O)Cc1cc2cc(c1)OCCCCOc1c(F)ccc(c1F)-c1nc(ncc1F)N2] | - (rac)-3,20,23-trifluoro-10-[(S-methylsulfonimidoyl)methyl]-13,18-dioxa-5,7,25-triazatetracyclo[17.3.1.1$^{2,6}$.1$^{8,12}$]pentacosa-1(23),2(25),3,5,8(24),9,11,19,21-nonaene |
| 9 | 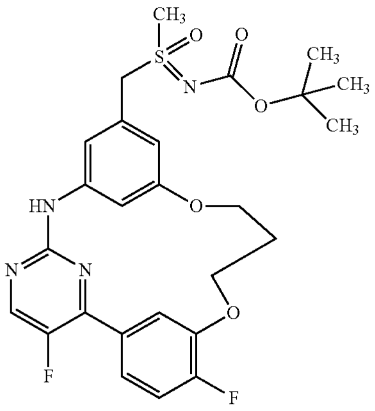 [SMILES: CC(C)(C)OC(=O)N=S(C)(=O)Cc1cc2cc(c1)OCCCOc1cc(ccc1F)-c1nc(ncc1F)N2] | - (rac)-tert-butyl [{[3,19-difluoro-13,17-dioxa-5,7,24-triazatetracyclo[16.3.1.1$^{2,6}$.1$^{8,12}$]tetracosa-1(22),2(24),3,5,8(23),9,11,18,20-nonaen-10-yl]methyl}(methyl)oxido-λ$^6$-sulfanylidene]carbamate |

TABLE 1-continued
| Example No. | Structure | Name of compound |
|---|---|---|
| 10 | 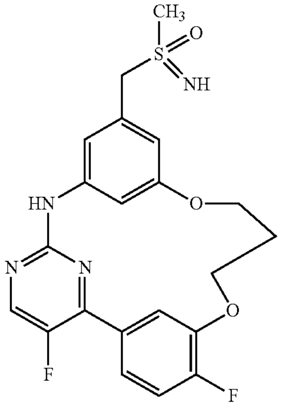 [SMILES: CS(=N)(=O)Cc1cc2cc(c1)OCCCOc1cc(ccc1F)-c1nc(ncc1F)N2] | - (rac)-3,19-difluoro-10-[(S-methylsulfonimidoyl)methyl]-13,17-dioxa-5,7,24-triazatetracyclo[16.3.1.1$^{2,6}$.1$^{8,12}$]tetracosa-1(22),2(24),3,5,8(23),9,11,18,20-nonaene |
| 11 | 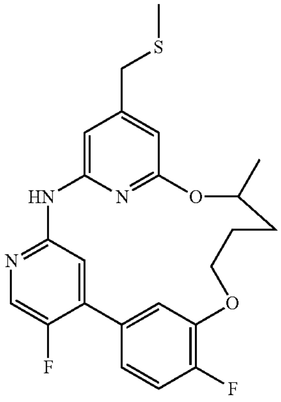 [SMILES: CSCc1cc2nc(c1)OC(C)CCCOc1cc(ccc1F)-c1cc(ncc1F)N2] | - (rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene |
| 12 | 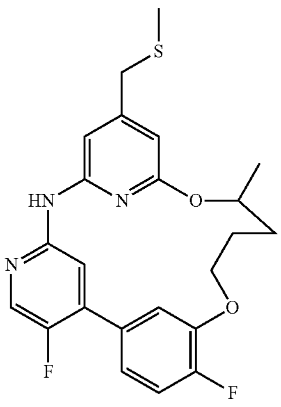 [SMILES: CSCc1cc2nc(c1)OC(C)CCCOc1cc(ccc1F)-c1cc(ncc1F)N2] | - Enantiomer 1 of (rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene |

TABLE 1-continued

| Example No. | Structure | Name of compound |
|---|---|---|
| 13 | 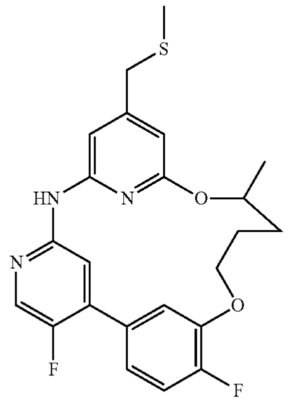 [SMILES: CSCc1cc2nc(c1)OC(C)CCCOc1cc(ccc1F)-c1cc(ncc1F)N2] | - Enantiomer 2 of (rac)-3,20-difluoro-14-methyl-10-[(methylsulfanyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene |
| 14 | 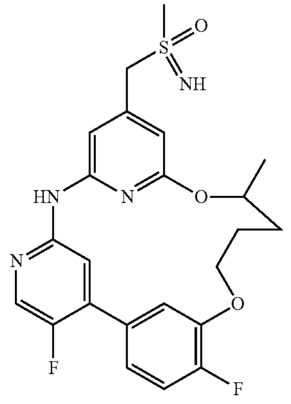 [SMILES: CC1CCCOc2cc(ccc2F)-c2cc(ncc2F)Nc2cc(CS(C)(=N)=O)cc(n2)O1] | Diastereoisomer 1 of 3,20-difluoro-14-methyl-10-[(S-methylsulfonimidoyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene - |
| 15 | 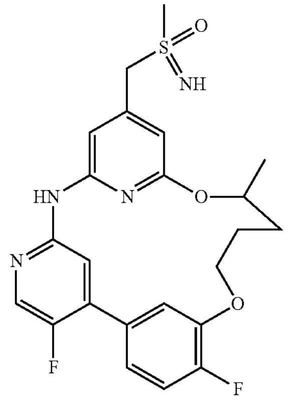 [SMILES: CC1CCCOc2cc(ccc2F)-c2cc(ncc2F)Nc2cc(CS(C)(=N)=O)cc(n2)O1] | Diastereoisomer 2 of 3,20-difluoro-14-methyl-10-[(S-methylsulfonimidoyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene - |
| 16 | 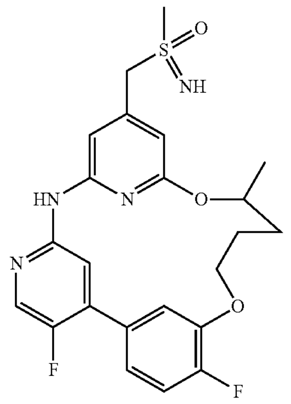 [SMILES: CC1CCCOc2cc(ccc2F)-c2cc(ncc2F)Nc2cc(CS(C)(=N)=O)cc(n2)O1] | Diastereoisomer 3 of 3,20-difluoro-14-methyl-10-[(S-methylsulfonimidoyl)methyl}-13,18-dioxa-5,7,24-triazatetracyclo[17.3.1.1$^{2,6}$.1$^{8,12}$]pentacosa-1(23),2(25),3,5,8(24),9,11,19,21-nonaene - |

TABLE 1-continued

| Example No. | Structure | Name of compound |
|---|---|---|
| 17 | 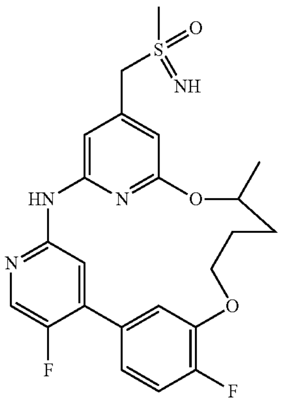 [SMILES: CC1CCCOc2cc(ccc2F)-c2cc(ncc2F)Nc2cc(CS(C)(=N)=O)cc(n2)O1] | Diastereoisomer 4 of 3,20-difluoro-14-methyl-10-[(S-methylsulfonimidoyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene - |
| 18 | 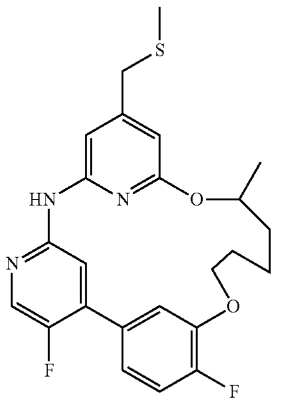 [SMILES: CSCc1cc2nc(c1)OC(C)CCCCOc1cc(ccc1F)-c1cc(ncc1F)N2] | (rac)-3,21-difluoro-14-methyl-10-[(methylsulfanyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |
| 19 | 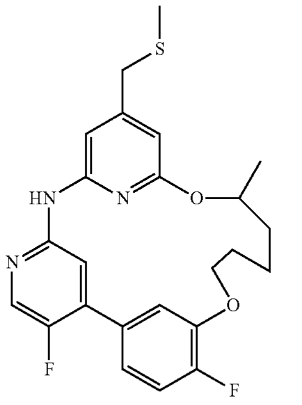 [SMILES: CSCc1cc2nc(c1)OC(C)CCCCOc1cc(ccc1F)-c1cc(ncc1F)N2] | Enantiomer 1 of 3,21-difluoro-14-methyl-10-[(methylsulfanyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |

TABLE 1-continued

| Example No. | Structure | Name of compound |
|---|---|---|
| 20 | 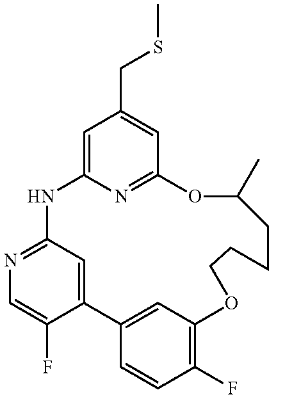 [SMILES: CSCc1cc2nc(c1)OC(C)CCCCOc1cc(ccc1F)-c1cc(ncc1F)N2] | Enantiomer 2 of 3,21-difluoro-14-methyl-10-[(methylsulfanyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |
| 21 | 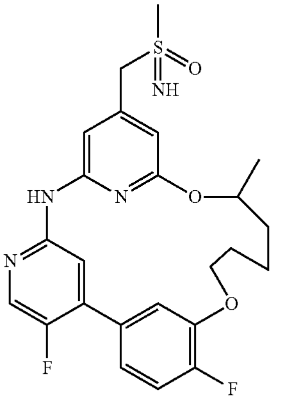 [SMILES: CC1CCCCOc2cc(ccc2F)-c2cc(ncc2F)Nc2cc(CS(C)(=N)=O)cc(n2)O1] | Mixture of diastereoisomers 1 and 2 of 3,21-difluoro-14-methyl-10-[(S-methylsulfonimidoyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |
| 22 | 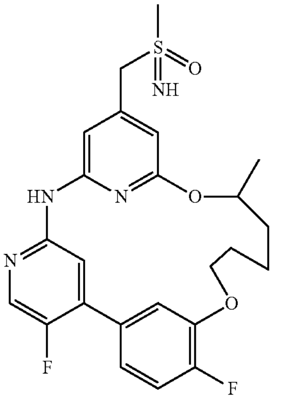 [SMILES: CC1CCCCOc2cc(ccc2F)-c2cc(ncc2F)Nc2cc(CS(C)(=N)=O)cc(n2)O1] | Mixture of diastereoisomers 3 and 4 of 3,21-difluoro-14-methyl-10-[(S-methylsulfonimidoyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |
| 23 | 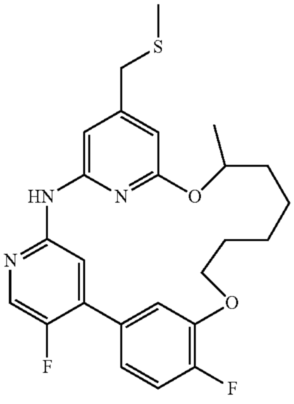 [SMILES: CSCc1cc2nc(c1)OC(C)CCCCCOc1cc(ccc1F)-c1cc(ncc1F)N2] | (rac)-3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene |

TABLE 1-continued

| Example No. | Structure | Name of compound |
|---|---|---|
| 24 | 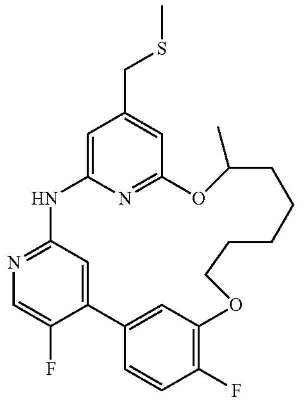 [SMILES: CSCc1cc2nc(c1)OC(C)CCCCCOc1cc(ccc1F)-c1cc(ncc1F)N2] | Enantiomer 1 of 3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene |
| 25 | 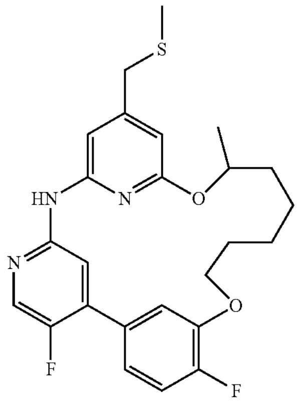 [SMILES: CSCc1cc2nc(c1)OC(C)CCCCCOc1cc(ccc1F)-c1cc(ncc1F)N2] | Enantiomer 2 of 3,22-difluoro-14-methyl-10-[(methylsulfanyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene |
| 26 | 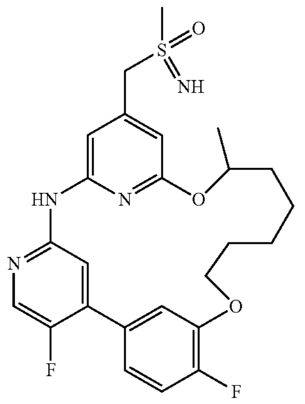 [SMILES: CC1CCCCCOc2cc(ccc2F)-c2cc(ncc2F)Nc2cc(CS(C)(=N)=O)cc(n2)O1] | Mixture of diastereoisomers 1 and 2 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene |

TABLE 1-continued

| Example No. | Structure | Name of compound |
| --- | --- | --- |
| 27 | 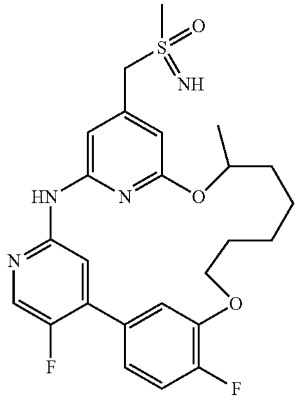 [SMILES: CC1CCCCCOc2cc(ccc2F)-c2cc(ncc2F)Nc2cc(CS(C)(=N)=O)cc(n2)O1] | Mixture of diastereoisomers 3 and 4 of 3,22-difluoro-14-methyl-10-[(S-methylsulfonimidoyl)methyl]-13,20-dioxa-5,7,26-triazatetracyclo[19.3.1.1$^{2,6}$.1$^{8,12}$]heptacosa-1(25),2(27),3,5,8(26),9,11,21,23-nonaene |
| 28 | 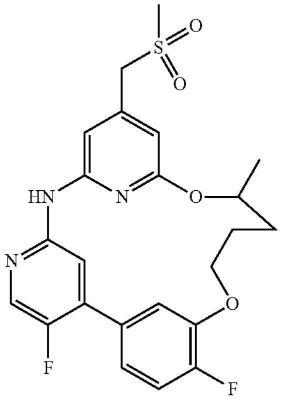 [SMILES: CC1CCCOc2cc(ccc2F)-c2cc(ncc2F)Nc2cc(CS(C)(=O)=O)cc(n2)O1] | Mixture of enantiomers of 3,20-difluoro-14-methyl-10-[(methylsulfonyl)methyl]-13,18-dioxa-5,7,24-triazatetracyclo[17.3.1.1$^{2,6}$.1$^{8,12}$]pentacosa-1(23),2(25),3,5,8(24),9,11,19,21-nonaene |
| 29 | 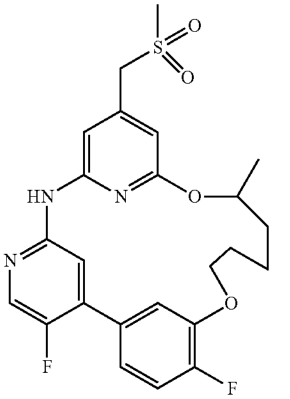 [SMILES: CC1CCCCOc2cc(ccc2F)-c2cc(ncc2F)Nc2cc(CS(C)(=O)=O)cc(n2)O1] | Enantiomer 1 of 3,21-difluoro-14-methyl-10-[(methylsulfonyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |
| 30 | 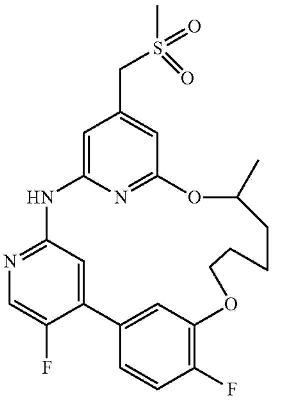 [SMILES: CC1CCCCOc2cc(ccc2F)-c2cc(ncc2F)Nc2cc(CS(C)(=O)=O)cc(n2)O1] | Enantiomer 2 of 3,21-difluoro-14-methyl-10-[(methylsulfonyl)methyl]-13,19-dioxa-5,7,25-triazatetracyclo[18.3.1.1$^{2,6}$.1$^{8,12}$]hexacosa-1(24),2(26),3,5,8(25),9,11,20,22-nonaene |

TABLE 1-continued

| Example No. | Structure | Name of compound |
| --- | --- | --- |
| 31 | 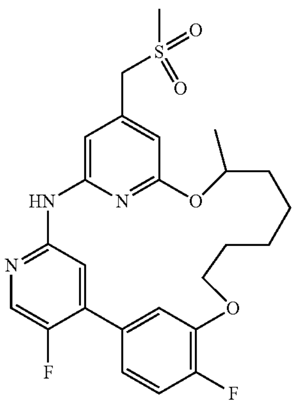 [SMILES: CC1CCCCCOc2cc(ccc2F)-c2cc(ncc2F)Nc2cc(CS(C)(=O)=O)cc(n2)O1] | Enantiomer 1 of 3,22-difluoro-14-methyl-10-[(methylsulfonyl)methyl]-13,20-dioxa-5,7,26-triazatetracyclo[$19.3.1.1^{2,6}.1^{8,12}$]hexacosa-1(25),2(27),3,5,8(26),9,11,21,23-nonaene |
| 32 | 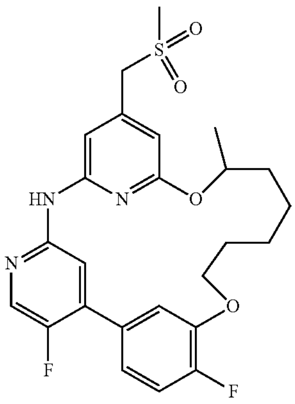 [SMILES: CC1CCCCCOc2cc(ccc2F)-c2cc(ncc2F)Nc2cc(CS(C)(=O)=O)cc(n2)O1] | Enantiomer 2 of 3,22-difluoro-14-methyl-10-[(methylsulfonyl)methyl]-13,20-dioxa-5,7,26-triazatetracyclo[$19.3.1.1^{2,6}.1^{8,12}$]hexacosa-1(25),2(27),3,5,8(26),9,11,21,23-nonaene |

Results:

Table 2: Inhibition for CDK9 and CDK2 of Compounds According to the Present Invention The $IC_{50}$ (inhibitory concentration at 50% of maximal effect) values are indicated in nM, "n.t." means that the compounds have not been tested in the respective assay.

①: Example Number

②: high ATP CDK9: CDK9/CycT1 kinase assay as described under Method 1b. of Materials and Methods ③: high ATP CDK2: CDK2/CycE kinase assay as described under Method 2b. of Materials and Methods ④: Selectivity high ATP CDK9 over high ATP CDK2: $IC_{50}$ (high ATP CDK2)/$IC_{50}$ (high ATP CDK9) according to Methods 1b. and 2b. of Materials and Methods Noteworthily, in the CDK9 assays, as described supra in the Methods 1a. and 1b. of Materials and Methods, resolution power is limited by the enzyme concentrations, the lower limit for $IC_{50}$s is about 1-2 nM in the CDK9 high ATP assay and 2-4 nM in the CDK low ATP assays. For compounds exhibiting $IC_{50}$s in this range the true affinity to CDK9 and thus the selectivity for CDK9 over CDK2 might be even higher, i.e. for these compounds the selectivity factors calculated in columns 4 and 7 of Table 2, infra, are minimal values, they could be also higher.

TABLE 2

| ① | Structure | ② | ③ | ④ |
| --- | --- | --- | --- | --- |
| 2 | 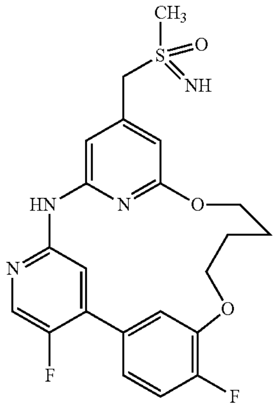 [SMILES: CS(=N)(=O)Cc1cc2nc(c1)OCCCCOc1cc(ccc1F)-c1cc(ncc1F)N2] | 7 | 737 | 105 |

TABLE 2-continued
| ① | Structure | ② | ③ | ④ |
|---|---|---|---|---|
| 3 | 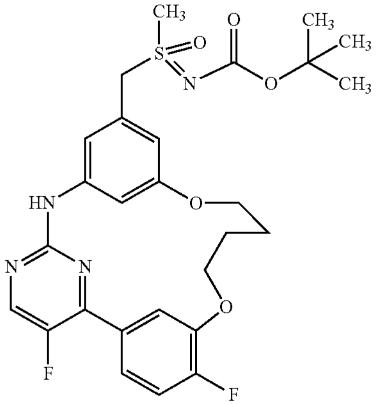 [SMILES: CC(C)(C)OC(=O)N=S(C)(=O)Cc1cc2cc(c1)OCCCCOc1cc(ccc1F)-c1nc(ncc1F)N2] | 5 | >20000 | >4000 |
| 4 | 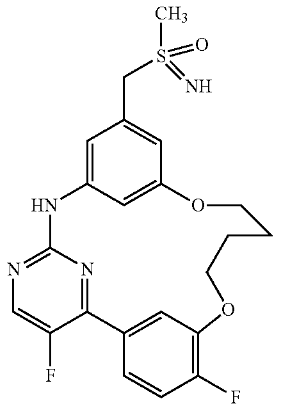 [SMILES: CS(=N)(=O)Cc1cc2cc(c1)OCCCCOc1cc(ccc1F)-c1nc(ncc1F)N2] | 3 | 1540 | 513 |
| 5 | 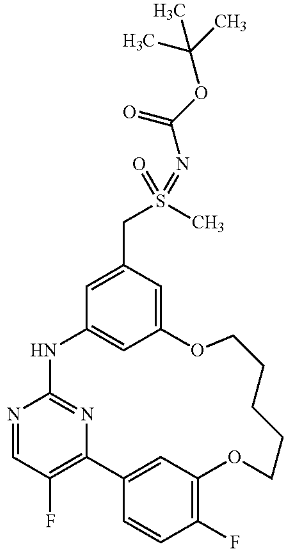 [SMILES: CC(C)(C)OC(=O)N=S(C)(=O)Cc1cc2cc(c1)OCCCCCOc1cc(ccc1F)-c1nc(ncc1F)N2] | 24 | >20000 | >833 |
| 6 | 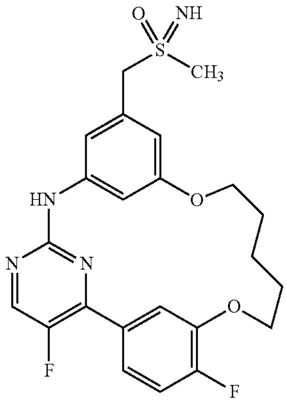 [SMILES: CS(=N)(=O)Cc1cc2cc(c1)OCCCCCOc1cc(ccc1F)-c1nc(ncc1F)N2] | 5 | 16200 | 3240 |
| 8 | 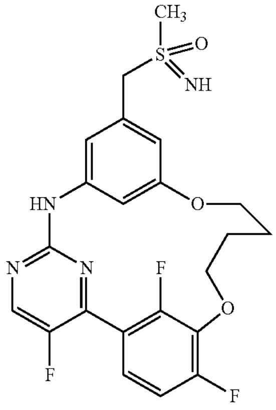 [SMILES: CS(=N)(=O)Cc1cc2cc(c1)OCCCCOc1c(F)ccc(c1F)-c1nc(ncc1F)N2] | 17 | 6520 | 385 |
| 10 | 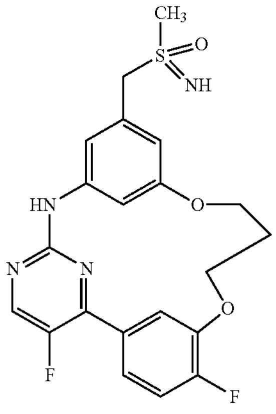 [SMILES: CS(=N)(=O)Cc1cc2cc(c1)OCCCOc1cc(ccc1F)-c1nc(ncc1F)N2] | 25 | 4750 | 190 |

TABLE 2-continued
| ① | Structure | ② | ③ | ④ |
|---|---|---|---|---|
| 11 | 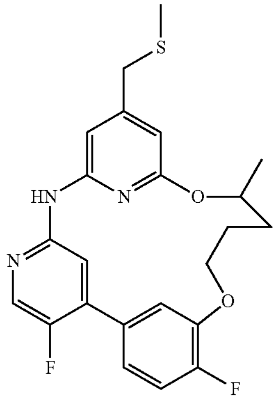 [SMILES: CSCc1cc2nc(c1)OC(C)CCCOc1cc(ccc1F)-c1cc(ncc1F)N2] | 7 | 4670 | 667 |
| 12 | 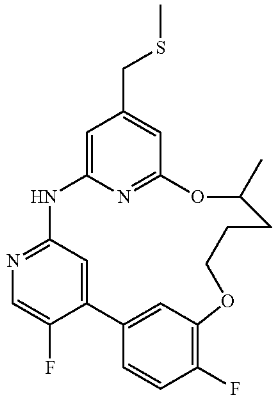 [SMILES: CSCc1cc2nc(c1)OC(C)CCCOc1cc(ccc1F)-c1cc(ncc1F)N2] | 4 | 6450 | 1613 |
| 13 | 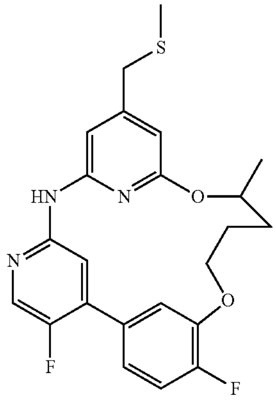 [SMILES: CSCc1cc2nc(c1)OC(C)CCCOc1cc(ccc1F)-c1cc(ncc1F)N2] | 4 | 711 | 178 |
| 14 | 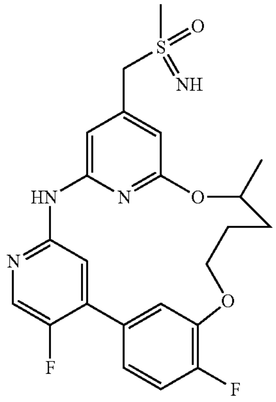 [SMILES: CC1CCCOc2cc(ccc2F)-c2cc(ncc2F)Nc2cc(CS(C)(=N)=O)cc(n2)O1] | 3 | 1510 | 503 |
TABLE 2-continued
| ① | Structure | ② | ③ | ④ |
|---|---|---|---|---|
| 15 | 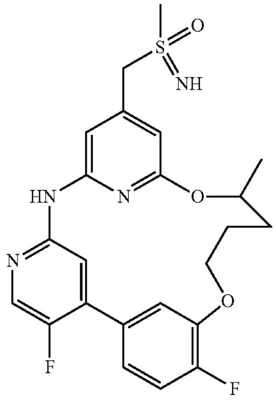 [SMILES: CC1CCCOc2cc(ccc2F)-c2cc(ncc2F)Nc2cc(CS(C)(=N)=O)cc(n2)O1] | 3 | 1620 | 540 |
| 16 | 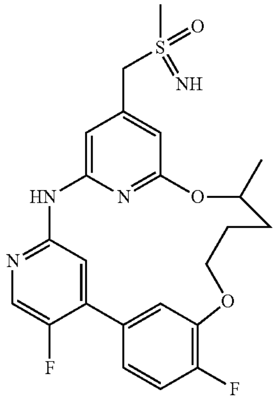 [SMILES: CC1CCCOc2cc(ccc2F)-c2cc(ncc2F)Nc2cc(CS(C)(=N)=O)cc(n2)O1] | 2 | 144 | 72 |
| 17 | 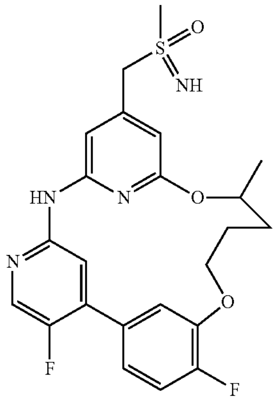 [SMILES: CC1CCCOc2cc(ccc2F)-c2cc(ncc2F)Nc2cc(CS(C)(=N)=O)cc(n2)O1] | 1 | 132 | 132 |

TABLE 2-continued
| ① | Structure | ② | ③ | ④ |
|---|---|---|---|---|
| 18 | 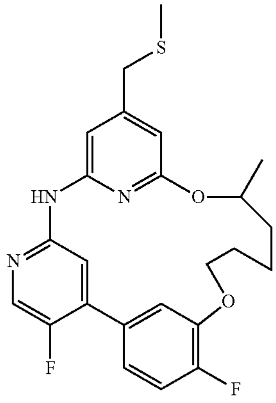 [SMILES: CSCc1cc2nc(c1)OC(C)CCCCOc1cc(ccc1F)-c1cc(ncc1F)N2] | 32 | >20000 | >625 |
| 19 | 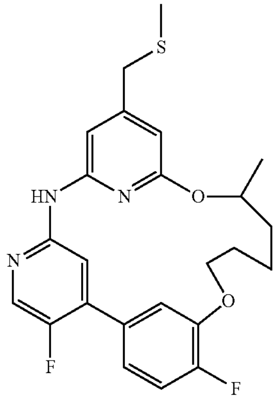 [SMILES: CSCc1cc2nc(c1)OC(C)CCCCOc1cc(ccc1F)-c1cc(ncc1F)N2] | 138 | >20000 | >145 |
| 20 | 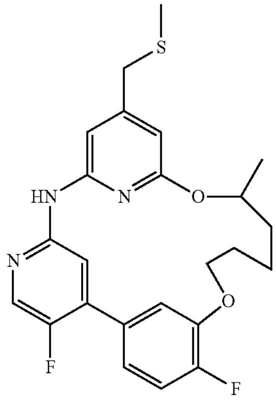 [SMILES: CSCc1cc2nc(c1)OC(C)CCCCOc1cc(ccc1F)-c1cc(ncc1F)N2] | 23 | 12600 | 548 |
| 21 | 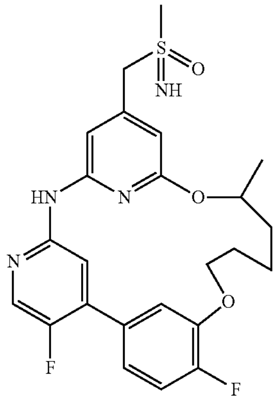 [SMILES: CC1CCCCOc2cc(ccc2F)-c2cc(ncc2F)Nc2cc(CS(C)(=N)=O)cc(n2)O1] | 2 | 2450 | 1225 |
| 22 | 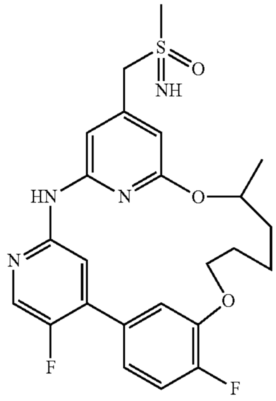 [SMILES: CC1CCCCOc2cc(ccc2F)-c2cc(ncc2F)Nc2cc(CS(C)(=N)=O)cc(n2)O1] | 2 | 501 | 251 |
| 23 | 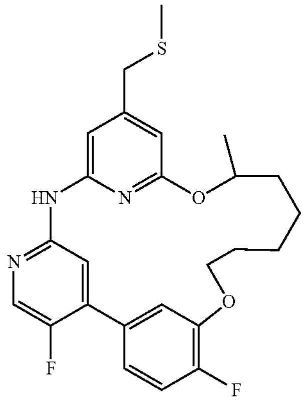 [SMILES: CSCc1cc2nc(c1)OC(C)CCCCCOc1cc(ccc1F)-c1cc(ncc1F)N2] | 67 | >20000 | >298 |
| 24 | 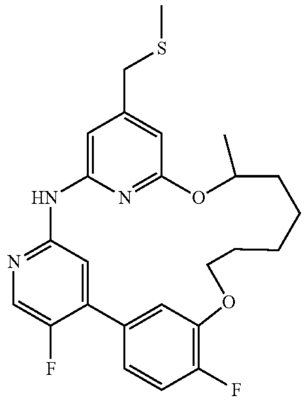 [SMILES: CSCc1cc2nc(c1)OC(C)CCCCCOc1cc(ccc1F)-c1cc(ncc1F)N2] | 68 | >20000 | >294 |

TABLE 2-continued
| ① | Structure | ② | ③ | ④ |
|---|---|---|---|---|
| 25 | 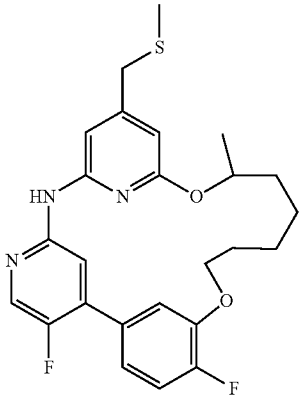 [SMILES: CSCc1cc2nc(c1)OC(C)CCCCCOc1cc(ccc1F)-c1cc(ncc1F)N2] | 93 | >20000 | >215 |
| 26 | 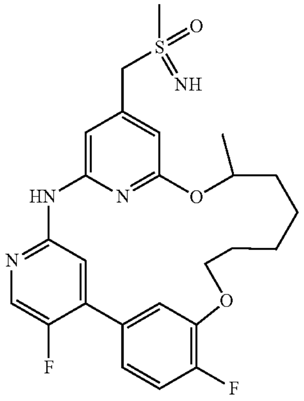 [SMILES: CC1CCCCCOc2cc(ccc2F)-c2cc(ncc2F)Nc2cc(CS(C)(=N)=O)cc(n2)O1] | 4 | 13000 | 3250 |
| 27 | 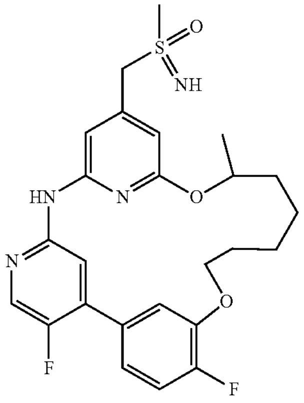 [SMILES: CC1CCCCCOc2cc(ccc2F)-c2cc(ncc2F)Nc2cc(CS(C)(=N)=O)cc(n2)O1] | 5 | 2720 | 544 |
| 28 | 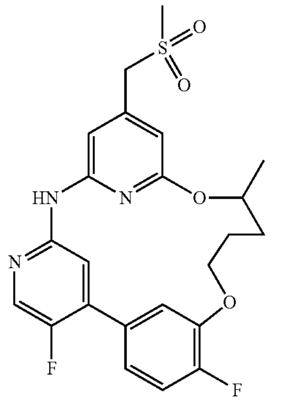 [SMILES: CC1CCCOc2cc(ccc2F)-c2cc(ncc2F)Nc2cc(CS(C)(=O)=O)cc(n2)O1] | 2 | 360 | 189 |
| 29 | 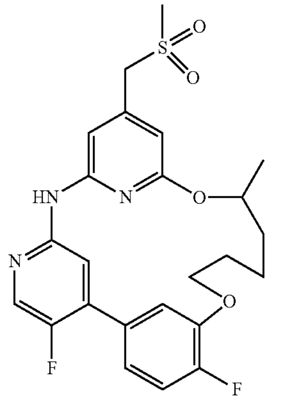 [SMILES: CC1CCCCOc2cc(ccc2F)-c2cc(ncc2F)Nc2cc(CS(C)(=O)=O)cc(n2)O1] | 4 | 691 | 173 |
| 30 | 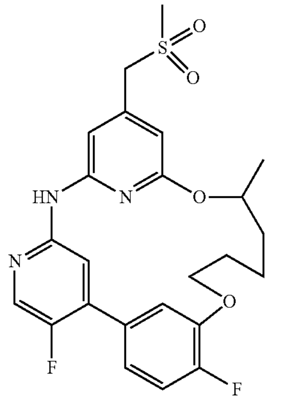 [SMILES: CC1CCCCOc2cc(ccc2F)-c2cc(ncc2F)Nc2cc(CS(C)(=O)=O)cc(n2)O1] | 3 | 3590 | 1196 |
| 31 | 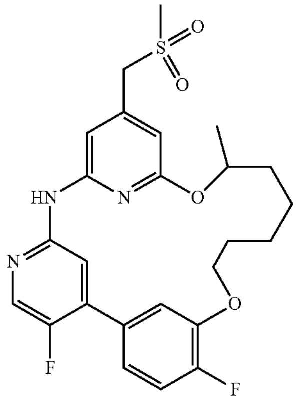 [SMILES: CC1CCCCCOc2cc(ccc2F)-c2cc(ncc2F)Nc2cc(CS(C)(=O)=O)cc(n2)O1] | 16 | >20000 | 1250 |

TABLE 2-continued

| ① | Structure | ② | ③ | ④ |
|---|---|---|---|---|
| 32 | 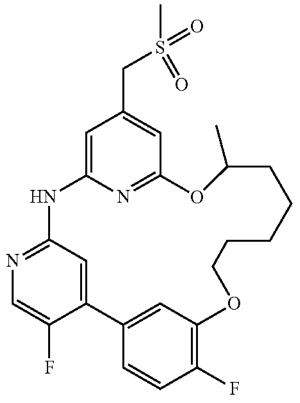 [SMILES: CC1CCCCCOc2cc(ccc2F)-c2cc(ncc2F)Nc2cc(CS(C)(=O)=O)cc(n2)O1] | 18 | 4980 | 277 |

Tables 3a and 3b:

Inhibition of proliferation of HeLa, HeLa-MaTu-ADR, NCI-H460, DU145, Caco-2, B16F10, A2780 and MOLM-13 cells by compounds according to the present invention, determined as described under Method 3. of Materials and Methods. All $IC_{50}$ (inhibitory concentration at 50% of maximal effect) values are indicated in nM, "n.t." means that the compounds have not been tested in the respective assay.

①: Example Number
②: Inhibition of HeLa cell proliferation
③: Inhibition of HeLa-MaTu-ADR cell proliferation
④: Inhibition of NCI-H460 cell proliferation
⑤: Inhibition of DU145 cell proliferation
⑥: Inhibition of Caco-2 cell proliferation
⑦: Inhibition of B16F10 cell proliferation
⑧: Inhibition of A2780 cell proliferation
⑨: Inhibition of MOLM-13 cell proliferation TABLE 3a

| Indications represented by cell lines | | |
|---|---|---|
| Cell line | Source | Indication |
| HeLa | ATCC | Human cervical tumour |
| HeLa-MaTu-ADR | EPO-GmbH Berlin | Multidrug-resistant human cervical carcinoma |
| NCI-H460 | ATCC | Human non-small cell lung carcinoma |
| DU 145 | ATCC | Hormone-independent human prostate carcinoma |
| Caco-2 | ATCC | Human colorectal carcinoma |
| B16F10 | ATCC | Mouse melanoma |
| A2780 | ECACC | Human ovarian carcinoma |
| MOLM-13 | DSMZ | Human acute myeloid leukemia |

TABLE 3b

| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 2 | 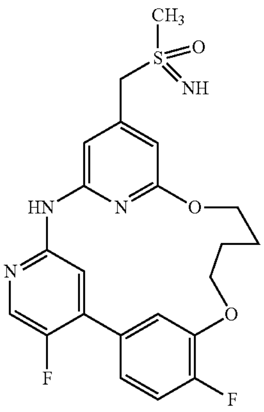 [SMILES: CS(=N)(=O)Cc1cc2nc(c1)OCCCCOc1cc(ccc1F)-c1cc(ncc1F)N2] | 90 | 78 | 157 | 85 | 96 | 110 | 9 | 27 |
| 3 | 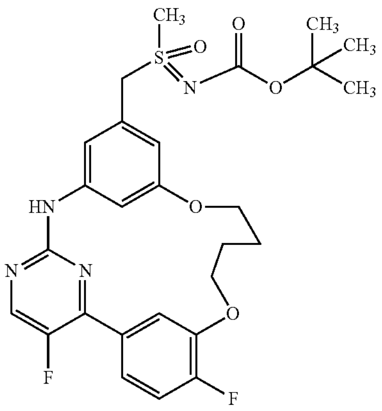 [SMILES: CC(C)(C)OC(=O)N=S(C)(=O)Cc1cc2cc(c1)OCCCCOc1cc(ccc1F)-c1nc(ncc1F)N2] | 244 | 218 | 267 | 206 | 163 | 270 | 56 | 108 |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 4 | 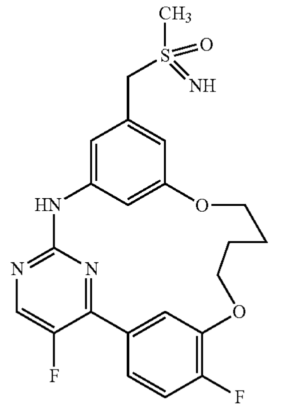 [SMILES: CS(=N)(=O)Cc1cc2cc(c1)OCCCCOc1cc(ccc1F)-c1nc(ncc1F)N2] | 150 | 140 | 331 | 138 | 177 | 176 | 41 | 20 |
| 5 | 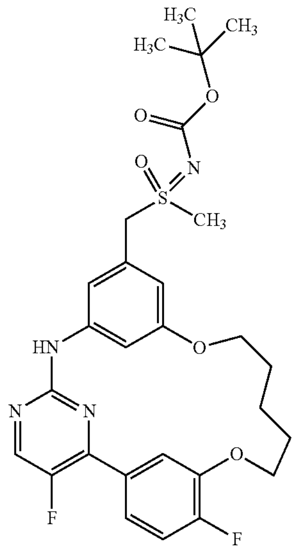 [SMILES: CC(C)(C)OC(=O)N=S(C)(=O)Cc1cc2cc(c1)OCCCCCOc1cc(ccc1F)-c1nc(ncc1F)N2] | 964 | 1000 | 479 | 585 | 658 | 993 | >100 | 228 |
| 6 | 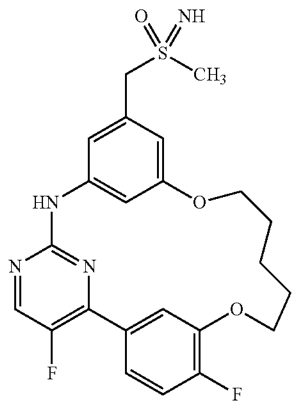 [SMILES: CS(=N)(=O)Cc1cc2cc(c1)OCCCCCOc1cc(ccc1F)-c1nc(ncc1F)N2] | 199 | 169 | 277 | 121 | 144 | 171 | 39 | 140 |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 8 | 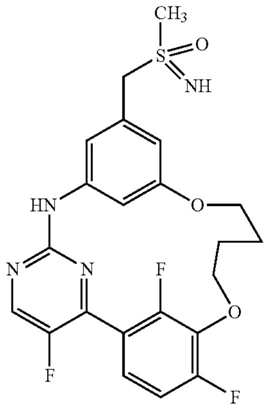 [SMILES: CS(=N)(=O)Cc1cc2cc(c1)OCCCCOc1c(F)ccc(c1F)-c1nc(ncc1F)N2] | 177 | 179 | 217 | 196 | 181 | 224 | 68 | 45 |
| 10 | 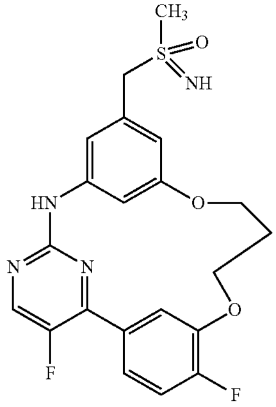 [SMILES: CS(=N)(=O)Cc1cc2cc(c1)OCCCOc1cc(ccc1F)-c1nc(ncc1F)N2] | 128 | 155 | 238 | 180 | 159 | 209 | 48 | 33 |
| 11 | 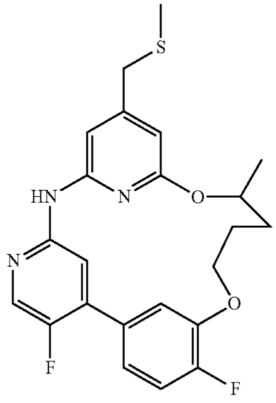 [SMILES: CSCc1cc2nc(c1)OC(C)CCCOc1cc(ccc1F)-c1cc(ncc1F)N2] | n.t. | n.t. | n.t. | n.t. | n.t. | n.t. | 346 | n.t. |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 14 | 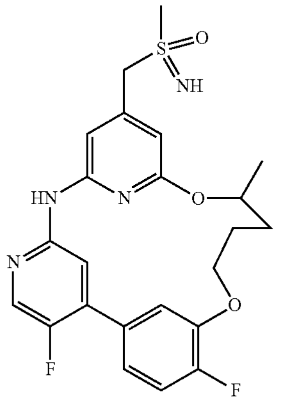 [SMILES: CC1CCCOc2cc(ccc2F)-c2cc(ncc2F)Nc2cc(CS(C)(=N)=O)cc(n2)O1] | n.t. | n.t. | n.t. | n.t. | n.t. | n.t. | 23 | n.t. |
| 15 | 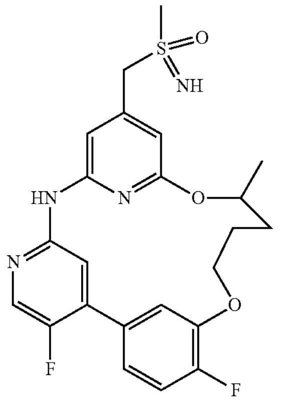 [SMILES: CC1CCCOc2cc(ccc2F)-c2cc(ncc2F)Nc2cc(CS(C)(=N)=O)cc(n2)O1] | n.t. | n.t. | n.t. | n.t. | n.t. | n.t. | 16 | n.t. |
| 16 | 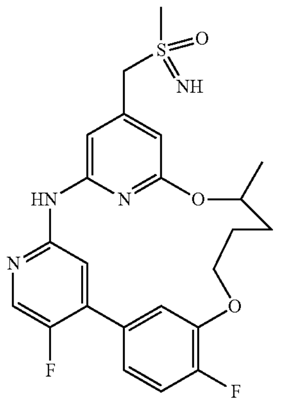 [SMILES: CC1CCCOc2cc(ccc2F)-c2cc(ncc2F)Nc2cc(CS(C)(=N)=O)cc(n2)O1] | n.t. | n.t. | n.t. | n.t. | n.t. | n.t. | 6 | n.t. |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 17 | 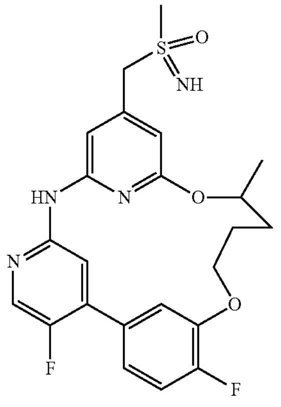 [SMILES: CC1CCCOc2cc(ccc2F)-c2cc(ncc2F)Nc2cc(CS(C)(=N)=O)cc(n2)O1] | n.t. | n.t. | n.t. | n.t. | n.t. | n.t. | 6 | n.t. |
| 21 | 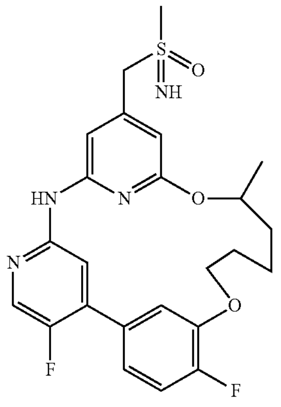 [SMILES: CC1CCCCOc2cc(ccc2F)-c2cc(ncc2F)Nc2cc(CS(C)(=N)=O)cc(n2)O1] | n.t. | n.t. | n.t. | n.t. | n.t. | n.t. | 27 | n.t. |
| 22 | 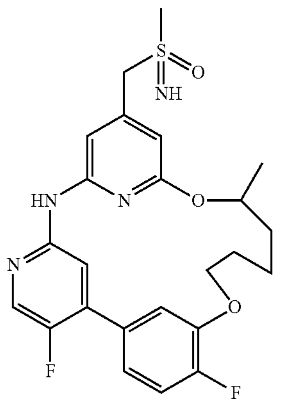 [SMILES: CC1CCCCOc2cc(ccc2F)-c2cc(ncc2F)Nc2cc(CS(C)(=N)=O)cc(n2)O1] | n.t. | n.t. | n.t. | n.t. | n.t. | n.t. | 0.7 | n.t. |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 26 | 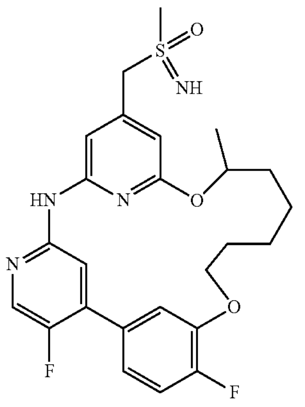 [SMILES: CC1CCCCCOc2cc(ccc2F)-c2cc(ncc2F)Nc2cc(CS(C)(=N)=O)cc(n2)O1] | n.t. | n.t. | n.t. | n.t. | n.t. | n.t. | 53 | n.t. |
| 27 | 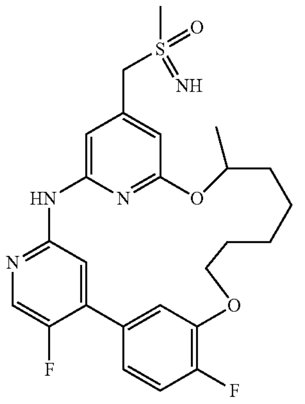 [SMILES: CC1CCCCCOc2cc(ccc2F)-c2cc(ncc2F)Nc2cc(CS(C)(=N)=O)cc(n2)O1] | n.t. | n.t. | n.t. | n.t. | n.t. | n.t. | 102 | n.t. |
| 28 | 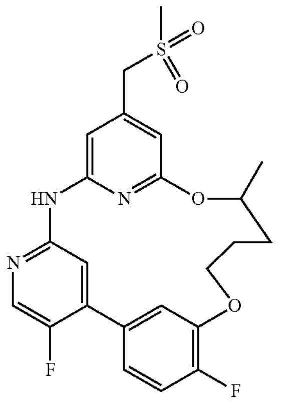 [SMILES: CC1CCCOc2cc(ccc2F)-c2cc(ncc2F)Nc2cc(CS(C)(=O)=O)cc(n2)O1] | n.t. | n.t. | n.t. | n.t. | n.t. | n.t. | 16. | n.t. |

TABLE 3b-continued
| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 29 | 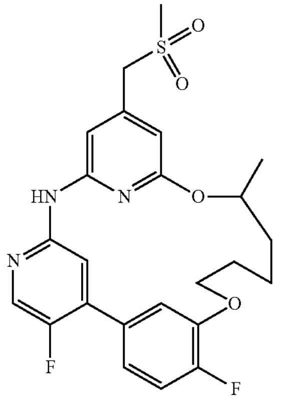 [SMILES: CC1CCCCOc2cc(ccc2F)-c2cc(ncc2F)Nc2cc(CS(C)(=O)=O)cc(n2)O1] | n.t. | n.t. | n.t. | n.t. | n.t. | n.t. | 25 | n.t. |
| 30 | 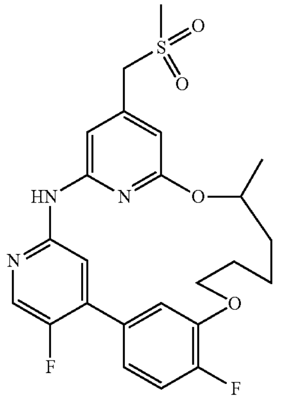 [SMILES: CC1CCCCOc2cc(ccc2F)-c2cc(ncc2F)Nc2cc(CS(C)(=O)=O)cc(n2)O1] | n.t | n.t. | n.t. | n.t. | n.t. | n.t. | 55 | n.t. |
| 31 | 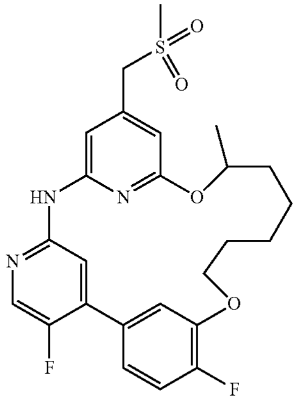 [SMILES: CC1CCCCCOc2cc(ccc2F)-c2cc(ncc2F)Nc2cc(CS(C)(=O)=O)cc(n2)O1] | n.t. | n.t. | n.t. | n.t. | n.t. | n.t. | 121 | n.t. |

TABLE 3b-continued

| Inhibition of proliferation | | | | | | | | | |
|---|---|---|---|---|---|---|---|---|---|
| ① | Structure | ② | ③ | ④ | ⑤ | ⑥ | ⑦ | ⑧ | ⑨ |
| 32 | 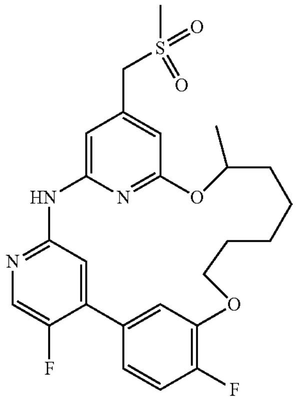 [SMILES: CC1CCCCCOc2cc(ccc2F)-c2cc(ncc2F)Nc2cc(CS(C)(=O)=O)cc(n2)O1] | n.t. | n.t. | n.t. | n.t. | n.t. | n.t. | 146 | n.t. |

Table 4:

Equilibrium dissociation constants $K_D$ [M], dissociation rate constants $k_{off}$ [1/s], and target residence times [min] as determined by Method 8.

Dissociation rate constants below of what is resolvable with the respective assay are reported using the "<"-symbol (e.g. <8.0 E-5 $s^{-1}$).

Values labeled with "*" represent arithmetic means of more than one value.

⓪: Example Number

②: Equilibrium dissociation constant $K_D$ [M]

③: Dissociation rate constant $k_{off}$[1/s]

④: Target residence time [min]

TABLE 4

| ① | Structure | ② | ③ | ④ |
|---|---|---|---|---|
| 2 | 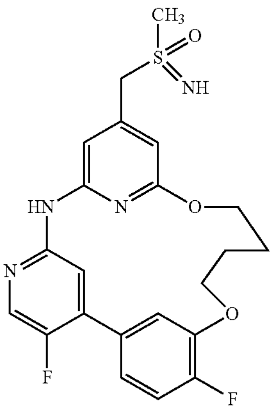 [SMILES: CS(=N)(=O)Cc1cc2nc(c1)OCCCCOc1cc(ccc1F)-c1cc(ncc1F)N2] | 1.2E−9* | 2.2E−4* | 75* |

TABLE 4-continued

| ① | Structure | ② | ③ | ④ |
|---|---|---|---|---|
| 4 | 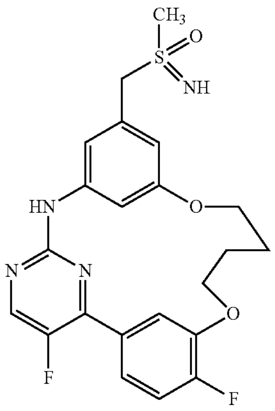 [SMILES: CS(=N)(=O)Cc1cc2cc(c1)OCCCCOc1cc(ccc1F)-c1nc(ncc1F)N2] | 1.2E−9* | 6.7E−4* | 25* |
| 16 | 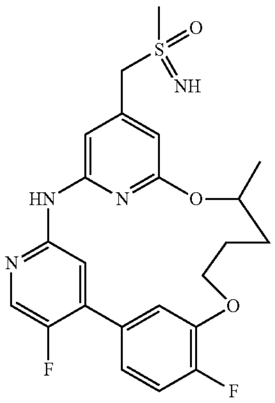 [SMILES: CC1CCCOc2cc(ccc2F)-c2cc(ncc2F)Nc2cc(CS(C)(=N)=O)cc(n2)O1] | 2.8E−10<br>6.6E−11<br>2.4E−11<br>2.9E−11 | <8.0E−5<br><8.0E−5<br>1.3E−4<br><8.0E−5 | >208<br>>208<br>131<br>>208 |

TABLE 4-continued

| ① | Structure | ② | ③ | ④ |
|---|---|---|---|---|
| 17 | 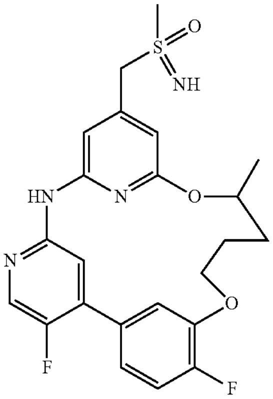 [SMILES: CC1CCCOc2cc(ccc2F)-c2cc(ncc2F)Nc2cc(CS(C)(=N)=O)cc(n2)O1] | 7.7E−11* | <8.0E−5* | >208* |
| 21 | 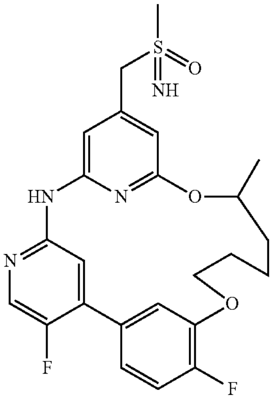 [SMILES: CC1CCCCOc2cc(ccc2F)-c2cc(ncc2F)Nc2cc(CS(C)(=N)=O)cc(n2)O1] | 1.0E−9* | 1.6E−3* | 10* |
| 22 | 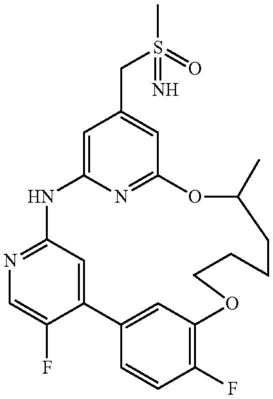 [SMILES: CC1CCCCOc2cc(ccc2F)-c2cc(ncc2F)Nc2cc(CS(C)(=N)=O)cc(n2)O1] | 1.9E−10* | 3.9E−4* | 43* |
| 28 | 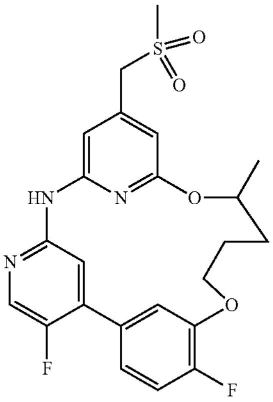 [SMILES: CC1CCCOc2cc(ccc2F)-c2cc(ncc2F)Nc2cc(CS(C)(=O)=O)cc(n2)O1] | 9.2E−11<br>9.1E−11<br>1.2E−10<br>1.5E−13 | 3.5E−4<br><8,0E−5<br>3.1E−4<br><8.0E−5 | 48<br>>208<br>54<br>>208 |

It is expected that that the prolonged residence time of macrocyclic CDK9 inhibitors according to the invention will result in a sustained inhibitory effect on CDK9 signaling, ultimately contributing to sustained target engagement and anti-tumor efficacy.

The invention claimed is:

1. A compound of general formula (I)

(I)

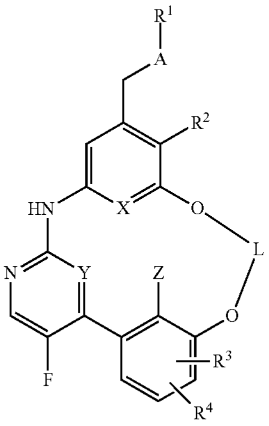

wherein

A represents a bivalent moiety selected from the group consisting of —S—, —S(═O)—, —S(═O)$_2$—, —S(═O)(═NR$^5$)—, and —S(═NR$^6$)(═NR$^7$)—;

Z represents a hydrogen atom or a fluorine atom;

L represents a $C_3$-$C_8$-alkylene moiety, wherein said moiety is optionally substituted with (i) one substituent selected from hydroxy, —NR$^8$R$^9$, $C_2$-$C_3$-alkenyl-, $C_2$-$C_3$-alkynyl-, $C_3$-$C_4$-cycloalkyl-, hydroxy-$C_1$-$C_3$-alkyl, and —(CH$_2$)NR$^8$R$^9$, and/or (ii) one or two or three or four substituents, identically or differently, selected from halogen and $C_1$-$C_3$-alkyl-, or wherein one carbon atom of said $C_3$-$C_8$-alkylene moiety forms a three- or four-membered ring together with a bivalent moiety to which it is attached, wherein said bivalent moiety is selected from —CH$_2$CH$_2$—, —CH$_2$CH$_2$CH$_2$—, and —CH$_2$OCH$_2$—;

X, Y represent CH or N with the proviso that one of X and Y represents CH and one of X and Y represents N;

R$^1$ represents a group selected from $C_1$-$C_6$-alkyl-, $C_3$-$C_6$-alkenyl-, $C_3$-$C_7$-cycloalkyl-, and heterocyclyl-, wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —NH$_2$, alkylamino-, dialkylamino-, acetylamino-, N-methyl-N-acetylamino-, cyclic amine, —OP(═O)(OH)$_2$, —C(═O)OH, and —C(═O)NH$_2$;

R$^2$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

R$^3$ and R$^4$ represent, independently from each other, a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^5$ represents a group selected from a hydrogen atom, cyano, —C(=O)$R^{10}$, —C(=O)O$R^{10}$, —S(=$O_2$) $R^{10}$, —C(=O)N$R^8R^9$, $C_1$-$C_6$-alkyl-, $C_3$-$C_7$-cycloalkyl-, and heterocyclyl-, wherein said $C_1$-$C_6$-alkyl-, $C_3$-$C_7$-cycloalkyl- and heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amine, halo-$C_1$-$C_3$-alkyl-, and $C_1$-$C_3$-fluoroalkoxy-;

$R^6$ and $R^7$ represent, independently from each other, a group selected from a hydrogen atom, cyano, —C(=O)$R^{10}$, —C(=O)O$R^{10}$, —S(=O)$_2R^{10}$, —C(=O)N$R^8R^9$, $C_1$-$C_6$-alkyl-, $C_3$-$C_7$-cycloalkyl-, and heterocyclyl-, wherein said $C_1$-$C_6$-alkyl-, $C_3$-$C_7$-cycloalkyl- or heterocyclyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, acetylamino-, N-methyl-N-acetylamino-, cyclic amine, halo-$C_1$-$C_3$-alkyl-, and $C_1$-$C_3$-fluoroalkoxy-;

$R^8$ and $R^9$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- and heteroaryl-group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amine, halo-$C_1$-$C_3$-alkyl-, and $C_1$-$C_3$-fluoroalkoxy-, or $R^8$ and $R^9$, together with the nitrogen atom they are attached to, form a cyclic amine;

$R^{10}$ represents a group selected from $C_1$-$C_6$-alkyl-, halo-$C_1$-$C_3$-alkyl-, $C_3$-$C_7$-cycloalkyl-, heterocyclyl-, phenyl-, benzyl- and heteroaryl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, acetylamino-, N-methyl-N-acetylamino-, cyclic amine, halo-$C_1$-$C_3$-alkyl-, and $C_1$-$C_3$-fluoroalkoxy-, or an enantiomer, diastereomer, salt, solvate or salt of solvate thereof.

2. The compound of general formula (I) according to claim 1, wherein A represents a bivalent moiety selected from the group consisting of —S—, —S(=O)—, —S(=O)$_2$ —, —S(=O)(=N$R^5$)—, and —S(=N$R^6$)(=N$R^7$)—;

Z represents a hydrogen atom or a fluorine atom;

L represents a $C_3$-$C_5$-alkylene moiety, wherein said moiety is optionally substituted with i) one substituent selected from hydroxy, $C_3$-$C_4$-cycloalkyl-, hydroxy-$C_1$-$C_3$-alkyl-, and —($CH_2$)N$R^8R^9$, and/or ii) one or two or three substituents, identically or differently, selected from halogen and $C_1$-$C_3$-alkyl-;

X, Y represent CH or N with the proviso that one of X and Y represents CH and one of X and Y represents N;

$R^1$ represents a group selected from $C_1$-$C_6$-alkyl- and $C_3$-$C_5$-cycloalkyl-, wherein said group is optionally substituted with one or two or three substituents, identically or differently, selected from the group consisting of hydroxy, cyano, halogen, $C_1$-$C_3$-alkyl-, fluoro-$C_1$-$C_2$-alkyl-, $C_1$-$C_3$-alkoxy-, $C_1$-$C_2$-fluoroalkoxy-, —$NH_2$, alkylamino-, dialkylamino-, cyclic amine, —OP(=O)(OH)$_2$, —C(=O)OH, and —C(=O)$NH_2$;

$R^2$ represents a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, and $C_1$-$C_2$-fluoroalkoxy-;

$R^3$ and $R^4$ represent, independently from each other, a group selected from a hydrogen atom, a fluorine atom, a chlorine atom, cyano, $C_1$-$C_2$-alkyl-, $C_1$-$C_2$-alkoxy-, fluoro-$C_1$-$C_2$-alkyl-, and $C_1$-$C_2$-fluoroalkoxy-;

$R^5$ represents a group selected from a hydrogen atom, cyano, —C(=O)$R^{10}$, —C(=O)O$R^{10}$, —S(=O)$_2R^{10}$, —C(=O)N$R^8R^9$, $C_1$-$C_6$-alkyl-, and $C_3$-$C_5$-cycloalkyl-, wherein said $C_1$-$C_6$-alkyl- and $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amine, fluoro-$C_1$-$C_2$-alkyl-, and $C_1$-$C_2$-fluoroalkoxy-;

$R^6$ and $R^7$ represent, independently from each other, a group selected from a hydrogen atom, cyano, —C(=O)$R^{10}$, —C(=O)O$R^{10}$, —S(=O)$_2R^{10}$, —C(=O)N$R^8R^9$, $C_1$-$C_6$-alkyl-, and $C_3$-$C_5$-cycloalkyl-, wherein said $C_1$-$C_6$-alkyl- and $C_3$-$C_5$-cycloalkyl-group is optionally substituted with one, two or three substituents, identically or differently, selected from the group consisting of halogen, hydroxy, cyano, $C_1$-$C_3$-alkyl-, $C_1$-$C_3$-alkoxy-, —$NH_2$, alkylamino-, dialkylamino-, cyclic amine, fluoro-$C_1$-$C_2$-alkyl-, and $C_1$-$C_2$-fluoroalkoxy-;

$R^8$ and $R^9$ represent, independently from each other, a group selected from a hydrogen atom, $C_1$-$C_6$-alkyl-, $C_3$-$C_5$-cycloalkyl-, phenyl- and benzyl-, wherein said $C_1$-$C_6$-alkyl-, $C_3$-$C_5$-cycloalkyl-, phenyl- and benzyl-group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amine, fluoro-$C_1$-$C_2$-alkyl-, and $C_1$-$C_2$-fluoroalkoxy-, or $R^8$ and $R^9$, together with the nitrogen atom they are attached to, form a cyclic amine;

$R^{10}$ represents a group selected from $C_1$-$C_6$-alkyl-, fluoro-$C_1$-$C_3$-alkyl-, $C_3$-$C_5$-cycloalkyl-, phenyl-, and benzyl-, wherein said group is optionally substituted with one, two or three substituents, identically or differently, selected from the group consisting of halogen, hydroxy, $C_1$-$C_3$-alkyl-, $C_1$-$C_3$-alkoxy-, —$NH_2$, alkylamino-, dialkylamino-, cyclic amine, fluoro-$C_1$-$C_2$-alkyl-, and $C_1$-$C_2$-fluoroalkoxy-, or an enantiomer, diastereomer, salt, solvate or salt of solvate thereof.

3. The compound of general formula (I) according to claim 1, wherein A represents a bivalent moiety selected from the group consisting of —S—, —S(=O)—, —S(=O)$_2$ —, —S(=O)(=N$R^5$)—, and —S(=N$R^6$)(=N$R^7$)—;

Z represents a hydrogen atom or a fluorine atom;

L represents a $C_3$-$C_5$-alkylene moiety, wherein said moiety is optionally substituted with
(i) one substituent selected from $C_3$-$C_4$-cycloalkyl- and hydroxymethyl, and/or
(ii) one or two or three $C_1$-$C_2$-alkyl-group substituents, identically or differently;

X, Y represent CH or N with the proviso that one of X and Y represents CH and one of X and Y represents N;

$R^1$ represents a group selected from $C_1$-$C_4$-alkyl- and $C_3$-$C_5$-cycloalkyl-,
wherein said group is optionally substituted with one or two or three substituents, identically or differently, selected from the group consisting of hydroxy, cyano, halogen, $C_1$-$C_2$-alkyl-, $C_1$-$C_2$-alkoxy-, —$NH_2$, and —C(═O)OH;

$R^2$ represents a group selected from a hydrogen atom, a fluorine atom, a chlorine atom, cyano, methyl-, methoxy-, trifluoromethyl-, and trifluoromethoxy-;

$R^3$ represents a group selected from a hydrogen atom, a fluorine atom, a chlorine atom, cyano, methyl-, methoxy-, trifluoromethyl-, and trifluoromethoxy-;

$R^4$ represents a hydrogen atom or a fluorine atom;

$R^5$ represents a group selected from a hydrogen atom, cyano, —C(═O)$R^{10}$, —C(═O)O$R^{10}$, —S(═O)$_2R^{10}$, —C(═O)N$R^8R^9$, and $C_1$-$C_4$-alkyl-, wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, and cyclic amine;

$R^6$ and $R^7$ represent, independently from each other, a group selected from a hydrogen atom, cyano, —C(═O)$R^{10}$, —C(═O)O$R^{10}$, —S(═O)$_2R^{10}$, —C(═O)N$R^8R^9$, and $C_1$-$C_4$-alkyl-,
wherein said $C_1$-$C_4$-alkyl-group is optionally substituted with one substituent selected from the group consisting of a fluorine atom, hydroxy, cyano, $C_1$-$C_3$-alkoxy-, —$NH_2$, alkylamino-, dialkylamino-, and cyclic amine;

$R^8$ and $R^9$ represent, independently from each other, a group selected from a hydrogen atom, $C_1$-$C_4$-alkyl- and $C_3$-$C_5$-cycloalkyl-;
wherein said $C_1$-$C_4$-alkyl- and $C_3$-$C_5$-cycloalkyl-group is optionally substituted with one or two substituents, identically or differently, selected from the group consisting of hydroxy, $C_1$-$C_2$-alkyl-, $C_1$-$C_2$-alkoxy-, —$NH_2$, alkylamino-, dialkylamino-, and cyclic amine, or $R^8$ and $R^9$, together with the nitrogen atom they are attached to, form a cyclic amine;

$R^{10}$ represents a group selected from $C_1$-$C_6$-alkyl-, fluoro-$C_1$-$C_3$-alkyl-, $C_3$-$C_5$-cycloalkyl- and benzyl-,
wherein said group is optionally substituted with one substituent selected from the group consisting of halogen, hydroxy, $C_1$-$C_2$-alkyl-, $C_1$-$C_2$-alkoxy-, and —$NH_2$, or an enantiomer, diastereomer, salt, solvate or salt of solvate thereof.

4. The compound of general formula (I) according to claim 1, wherein

A represents a bivalent moiety selected from the group consisting of —S—, —S(═O)—, —S(═O)$_2$—, —S(═O)(═N$R^5$)—, and —S(═N$R^6$)(═N$R^7$)—;

Z represents a hydrogen atom or a fluorine atom;

L represents a $C_3$-$C_5$-alkylene moiety;

X, Y represent CH or N with the proviso that one of X and Y represents CH and one of X and Y represents N;

$R^1$ represents a $C_1$-$C_4$-alkyl-group,
wherein said group is optionally substituted with one or two substituents, identically or differently, selected from the group consisting of hydroxy, $C_1$-$C_2$-alkoxy-, —$NH_2$, and —C(═O)OH;

$R^2$ represents a hydrogen atom or a fluorine atom;

$R^3$ represents a group selected from a hydrogen atom, a fluorine atom and a methoxy-group;

$R^4$ represents a hydrogen atom;

$R^5$ represents a group selected from a hydrogen atom, cyano, —C(═O)$R^{10}$, —C(═O)O$R^{10}$, —C(═O)N$R^8R^9$, and $C_1$-$C_4$-alkyl-,
wherein said $C_1$-$C_4$-alkyl-group is optionally substituted with one substituent selected from the group consisting of hydroxy, cyano, $C_1$-$C_3$-alkoxy-, —$NH_2$, alkylamino-, and dialkylamino-;

$R^6$ and $R^7$ represent, independently from each other, a group selected from a hydrogen atom, cyano, and $C_1$-$C_4$-alkyl-,
wherein said $C_1$-$C_4$-alkyl-group is optionally substituted with one hydroxy group;

$R^8$ and $R^9$ represent, independently from each other, a group selected from a hydrogen atom, $C_1$-$C_4$-alkyl- and $C_3$-$C_5$-cycloalkyl-, or $R^8$ and $R^9$, together with the nitrogen atom they are attached to, form a cyclic amine;

$R^{10}$ represents a group selected from $C_1$-$C_6$-alkyl-, fluoro-$C_1$-$C_3$-alkyl-, $C_3$-$C_5$-cycloalkyl- and benzyl-,
wherein said group is optionally substituted with one substituent selected from the group consisting of halogen, hydroxy, $C_1$-$C_2$-alkyl-, $C_1$-$C_2$-alkoxy-, and —$NH_2$, or an enantiomer, diastereomer, salt, solvate or salt of solvate thereof.

5. The compound of general formula (I) according to claim 1, wherein L represents a $C_3$-$C_5$-alkylene moiety, or an enantiomer, diastereomer, salt, solvate or salt of solvate thereof.

6. The compound of general formula (I) according to claim 1, wherein A represents a bivalent moiety selected from the group consisting of —S(═O)$_2$—, —S(═O)(═N$R^5$)—, and —S(═N$R^6$)(═N$R^7$)—;

Z represents a hydrogen atom or a fluorine atom;

L represents a $C_3$-$C_5$-alkylene moiety,

X, Y represent CH or N with the proviso that one of X and Y represents CH and one of X and Y represents N;

$R^1$ represents a methyl-group;

$R^2$ represents a hydrogen atom;

$R^3$ represents a group selected from a hydrogen atom or a fluorine atom;

$R^4$ represents a hydrogen atom;

$R^5$ represents a group selected from a hydrogen atom, cyano, —C(═O)$R^{10}$, —C(═O)O$R^{10}$, and $C_1$-$C_4$-alkyl-,
wherein said $C_1$-$C_4$-alkyl-group is optionally substituted with one substituent selected from the group consisting of hydroxy, cyano, $C_1$-$C_3$-alkoxy-, —$NH_2$, alkylamino-, and dialkylamino-;

$R^6$ and $R^7$ represent, independently from each other, a group selected from a hydrogen atom, cyano, and $C_1$-$C_4$-alkyl-,
wherein said $C_1$-$C_4$-alkyl-group is optionally substituted with one hydroxy group;

$R^8$ and $R^9$ represent, independently from each other, a group selected from a hydrogen atom, $C_1$-$C_2$-alkyl;

$R^{10}$ represents a $C_1$-$C_4$-alkyl group, or an enantiomer, diastereomer, salt, solvate or salt of solvate thereof.

7. The compound of general formula (I) according to claim 1, wherein A represents a bivalent moiety selected from the group consisting of —S—, —S(═O)—, —S(═O)$_2$ —, and —S(═O)(═NR$^5$)—;

Z represents a hydrogen atom or a fluorine atom;

L represents a $C_3$-$C_5$-alkylene moiety;

X, Y represent CH or N with the proviso that one of X and Y represents CH and one of X and Y represents N;

$R^1$ represents a $C_1$-$C_3$-alkyl-group;

$R^2$ represents a hydrogen atom or a fluorine atom;

$R^3$ represents a group selected from a hydrogen atom, a fluorine atom and a methoxy-group;

$R^4$ represents a hydrogen atom;

$R^5$ represents a group selected from a hydrogen atom, cyano, —C(═O)$R^{10}$, —C(═O)O$R^{10}$, and $C_1$-$C_3$-alkyl-;

$R^6$ and $R^7$ represent, independently from each other, a group selected from a hydrogen atom, cyano, —C(═O)$R^{10}$, —C(═O)O$R^{10}$, and $C_1$-$C_3$-alkyl-;

$R^{10}$ represents a group selected from $C_1$-$C_4$-alkyl-, trifluoromethyl-, and benzyl-, or an enantiomer, diastereomer, salt, solvate or salt of solvate thereof.

8. The compound of general formula (I) according to claim 1, wherein

A represents a bivalent moiety selected from the group consisting of —S—, —S(═O)—, —S(═O)$_2$—, —S(═O)(═NR$^5$)—, and —S(═NR$^6$)(═NR$^7$)—;

Z represents a group selected from a hydrogen atom and a fluorine atom;

L represents a $C_4$-$C_5$-alkylene moiety;

X, Y represent CH or N with the proviso that one of X and Y represents CH and one of X and Y represents N;

$R^1$ represents a methyl-group;

$R^2$ represents a hydrogen atom;

$R^3$ represents a hydrogen atom or a fluorine atom;

$R^4$ represents a hydrogen atom;

$R^5$ represents a group selected from a hydrogen atom and —C(═O)O$R^{10}$;

$R^6$ and $R^7$ represent, independently from each other, a group selected from a hydrogen atom and —C(═O)O$R^{10}$;

$R^{10}$ represents a group selected from tert-butyl- and benzyl-, or an enantiomer, diastereomer, salt, solvate or salt of solvate thereof.

9. The compound of general formula (I) according to claim 1, wherein represents a group selected from a hydrogen atom and a fluorine atom, $R^3$ represents a fluorine atom, and $R^4$ represents a hydrogen atom, or an enantiomer, diastereomer, salt, solvate or salt of solvate thereof.

10. The compound of general formula (I) according to claim 1, wherein

A represents a bivalent moiety —S(═O)(═NR$^5$)—;

Z represents a group selected from a hydrogen atom and a fluorine atom,

L represents a $C_3$-$C_5$-alkylene moiety;

X, Y represent CH or N with the proviso that one of X and Y represents CH and one of X and Y represents N;

$R^1$ represents a methyl-group;

$R^2$ represents a hydrogen atom;

$R^3$ represents a fluorine atom;

$R^4$ represents a hydrogen atom;

$R^5$ represents a hydrogen atom or a —C(═O)O$R^{10}$ group;

$R^{10}$ represents a tert butyl-group;

or an enantiomer, diastereomer, salt, solvate or salt of solvate thereof.

11. The compound according to claim 1, which is selected from the group consisting of:

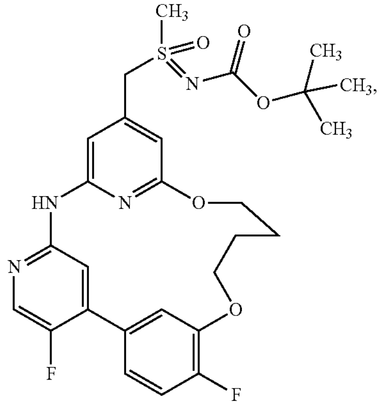

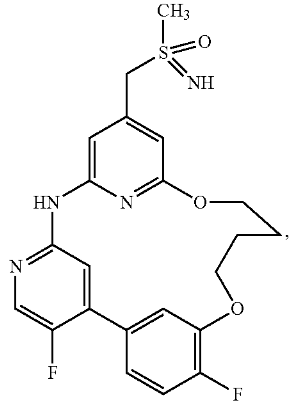

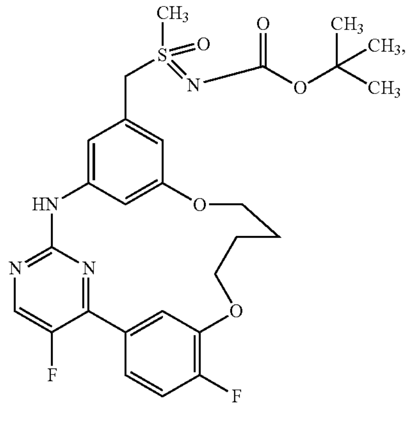

-continued
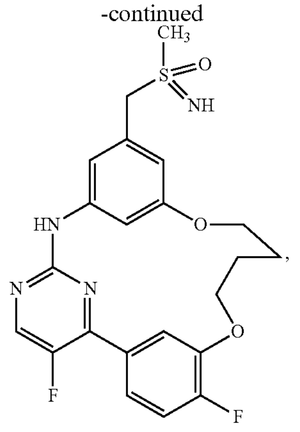
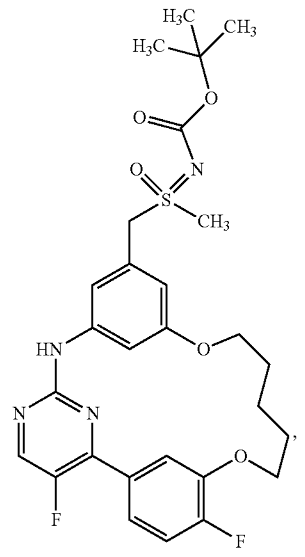
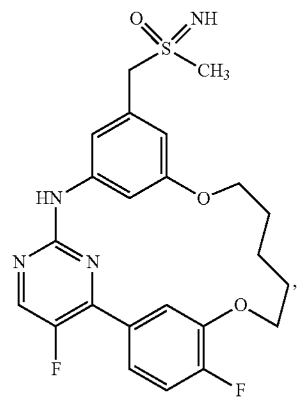
-continued
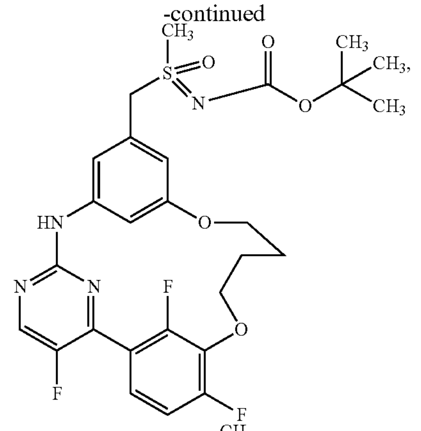
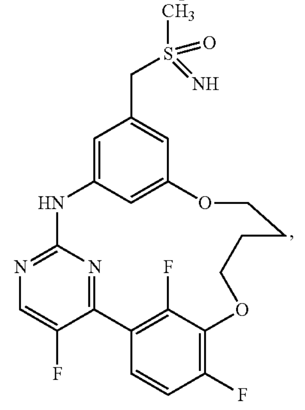
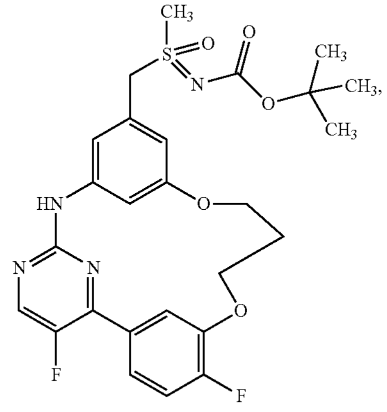
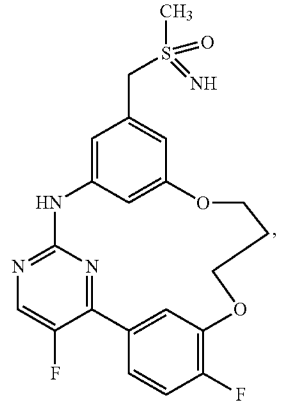

-continued
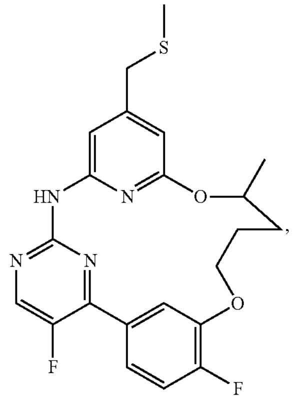
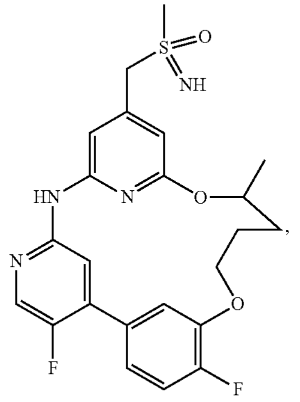
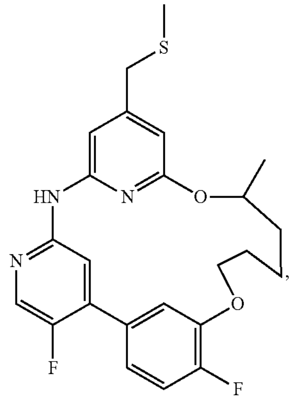
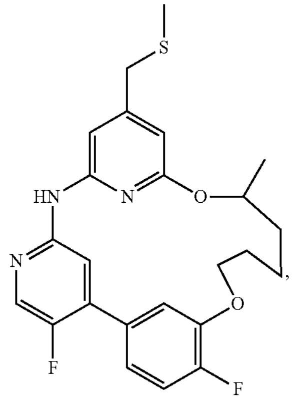
-continued
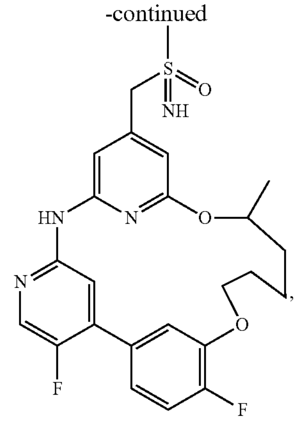
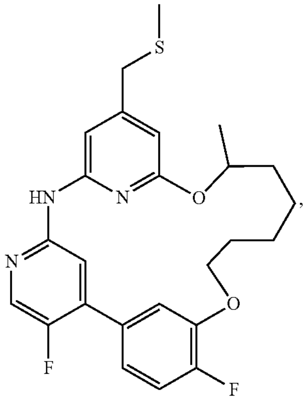
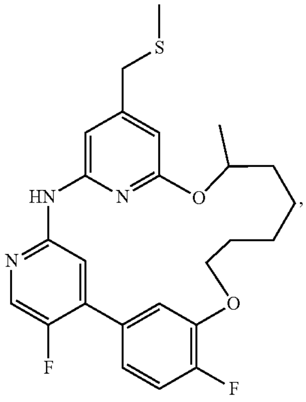
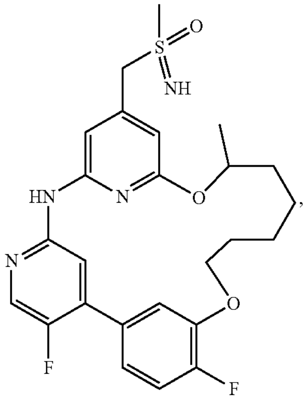

-continued

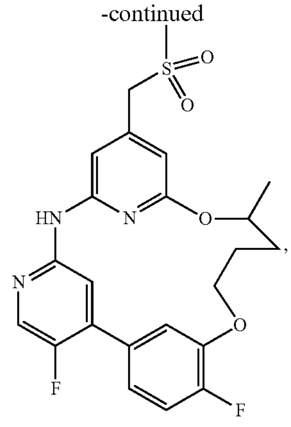

,

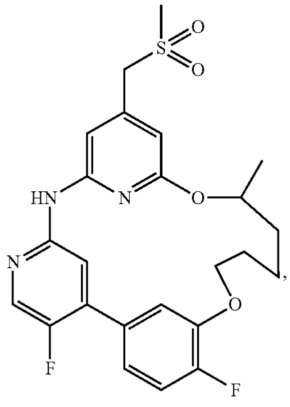

, and

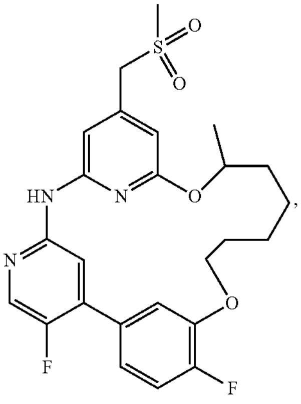 [SMILES: CC1CCCCCOc2cc(ccc2F)-c2cc(ncc2F)Nc2cc(CS(C)(=O)=O)cc(n2)O1]

, or an enantiomer, diastereomer, salt, solvate or salt of solvate thereof.

12. A pharmaceutical combination comprising a compound according to claim 1 in combination with at least one or more further active ingredients.

13. A pharmaceutical composition comprising a compound according to claim 1 in combination with an inert, nontoxic, pharmaceutically suitable adjuvant.

14. A process for the preparation of a compound of formula (Ia), comprising reacting a compound of the formula (7)

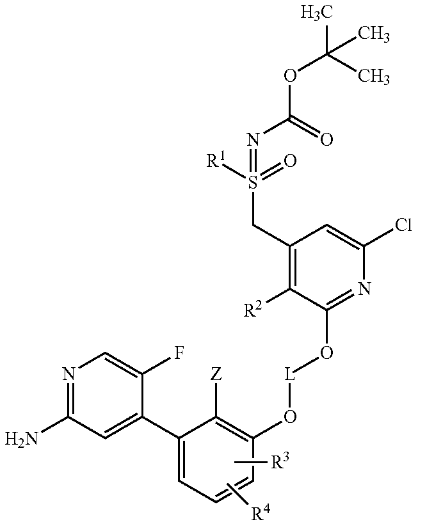

7 wherein:

Z represents a hydrogen atom or a fluorine atom;

L represents a $C_3$-$C_8$-alkylene moiety, wherein said moiety is optionally substituted with (i) one substituent selected from hydroxy, —$NR^8R^9$, $C_2$-$C_3$-alkenyl-, $C_2$-$C_3$-alkynyl-, $C_3$-$C_4$-cycloalkyl-, hydroxy-$C_1$-$C_3$-alkyl, and —$(CH_2)NR^8R^9$, and/or (ii) one or two or three or four substituents, identically or differently, selected from halogen and $C_1$-$C_3$-alkyl-, or wherein one carbon atom of said $C_3$-$C_8$-alkylene moiety forms a three- or four-membered ring together with a bivalent moiety to which it is attached, wherein said bivalent moiety is selected from —$CH_2CH_2$—, —$CH_2CH_2CH_2$—, and —$CH_2OCH_2$—;

$R^1$ represents a group selected from $C_1$-$C_6$-alkyl-, $C_3$-$C_6$-alkenyl-, $C_3$-$C_7$-cycloalkyl-, and heterocyclyl-, wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amine, —OP(═O)$(OH)_2$, —C(═O)OH, and —C(═O)$NH_2$;

$R^2$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^3$ and $R^4$ represent, independently from each other, a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^8$ and $R^9$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- and heteroaryl-group is optionally substituted with one, two or three substituents, identically or differently, selected from the group consisting of halogen, hydroxy, $C_1$-$C_3$-alkyl-, $C_1$-$C_3$-alkoxy-, alkylamino-, dialkylamino-, acetylamino-, N-methyl-N-acetylamino-, cyclic amine, halo-$C_1$-$C_3$-alkyl-, and $C_1$-$C_3$-fluoroalkoxy-, or $R^8$ and $R^9$, together with the nitrogen atom they are attached to, form a cyclic amine; in a C—N cross-coupling reaction to give compounds of the formula Ia

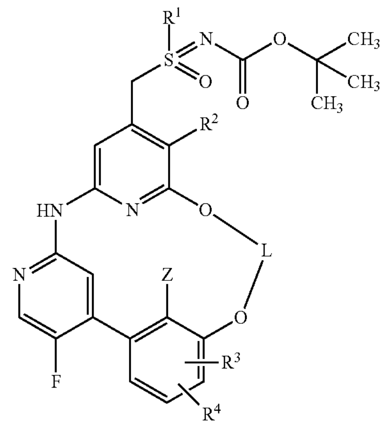

and in which process the resulting compound is optionally, if appropriate, converted with the corresponding (i) solvents and/or (ii) bases or acids to the solvates, salts and/or solvates of the salts thereof.

15. A process for the preparation of a compound of formula (Id), comprising reacting a compound of the formula (19)

19

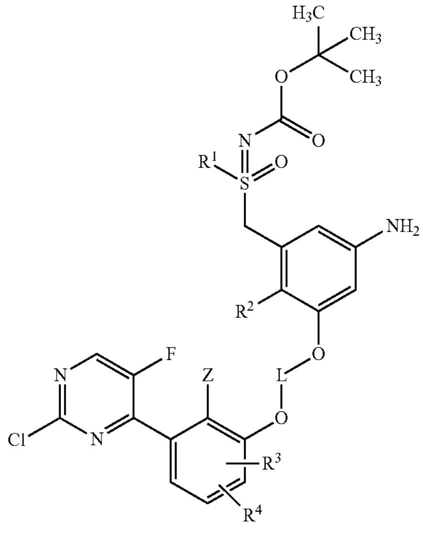

wherein:

Z represents a hydrogen atom or a fluorine atom;

L represents a $C_3$-$C_8$-alkylene moiety, wherein said moiety is optionally substituted with (i) one substituent selected from hydroxy, —$NR^8R^9$, $C_2$-$C_3$-alkenyl-, $C_2$-$C_3$-alkynyl-, $C_3$-$C_4$-cycloalkyl-, hydroxy-$C_1$-$C_3$-alkyl, and —$(CH_2)NR^8R^9$, and/or (ii) one or two or three or four substituents, identically or differently, selected from halogen and $C_1$-$C_3$-alkyl-, or wherein one carbon atom of said $C_3$-$C_8$-alkylene moiety forms a three- or four-membered ring together with a bivalent moiety to which it is attached, wherein said bivalent moiety is selected from —$CH_2CH_2$—, —$CH_2CH_2CH_2$—, and —$CH_2OCH_2$—;

$R^1$ represents a group selected from $C_1$-$C_6$-alkyl-, $C_3$-$C_6$-alkenyl-, $C_3$-$C_7$-cycloalkyl-, and heterocyclyl-, wherein said group is optionally substituted with one or two or three substituents, identically or differently, selected from the group consisting of hydroxy, cyano, halogen, $C_1$-$C_6$-alkyl-, halo-$C_1$-$C_3$-alkyl-, $C_1$-$C_6$-alkoxy-, $C_1$-$C_3$-fluoroalkoxy-, —$NH_2$, alkylamino-, dialkylamino-, acetylamino-, N-methyl-N-acetylamino-, cyclic amine, —$OP(=O)(OH)_2$, —$C(=O)OH$, and —$C(=O)NH_2$;

$R^2$ represents a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^3$ and $R^4$ represent, independently from each other, a group selected from a hydrogen atom, a fluorine atom, a chlorine atom, a bromine atom, cyano, $C_1$-$C_3$-alkyl-, $C_1$-$C_3$-alkoxy-, halo-$C_1$-$C_3$-alkyl-, and $C_1$-$C_3$-fluoroalkoxy-;

$R^8$ and $R^9$ represent, independently from each other, a group selected from a hydrogen atom, $C_1$-$C_6$-alkyl-, $C_3$-$C_7$-cycloalkyl-, heterocyclyl-, phenyl-, benzyl- and heteroaryl-, wherein said $C_1$-$C_6$-alkyl-, $C_3$-$C_7$-cycloalkyl-, heterocyclyl-, phenyl-, benzyl- and heteroaryl-group is optionally substituted with one, two or three substituents, identically or differently, selected from the group consisting of halogen, hydroxy, $C_1$-$C_3$-alkyl-, $C_1$-$C_3$-alkoxy-, alkylamino-, dialkylamino-, acetylamino-, N-methyl-N-acetylamino-, cyclic amine, halo-$C_1$-$C_3$-alkyl-, and $C_1$-$C_3$-fluoroalkoxy-, or $R^8$ and $R^9$, together with the nitrogen atom they are attached to, form a cyclic amine;

in a C—N cross-coupling reaction to give compounds of the formula (Id),

Id

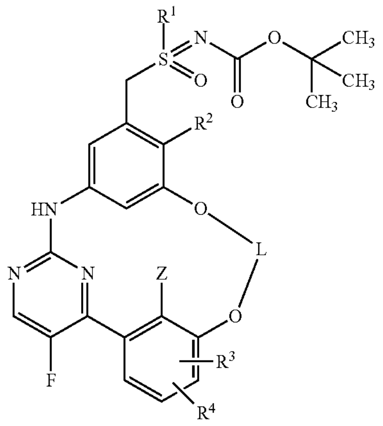

and in which process the resulting compound is optionally, if appropriate, converted with the corresponding (i) solvents and/or (ii) bases or acids to the solvates, salts and/or solvates of the salts thereof.

16. A method for the treatment of a hyper-proliferative disorder selected from the group consisting of cervical cancer, non-small cell lung cancer, prostate cancer, colorectal cancer, melanoma, ovarian cancer, acute myeloid leukemia, breast cancer, osteosarcoma, and lymphoma, comprising administering a therapeutically effective amount of the compound of general formula (I) according to claim 1 to a patient in need thereof.

17. The method of claim 16, wherein the prostate cancer is hormone-independent human prostate cancer.

18. The method of claim 16, wherein the cervical cancer is multidrug-resistant human cervical cancer.

19. A method for the treatment of a hyper-proliferative disorder selected from the group consisting of cervical cancer, non-small cell lung cancer, prostate cancer, colorectal cancer, melanoma, ovarian cancer, acute myeloid leukemia, breast cancer, osteosarcoma, and lymphoma, comprising administering a therapeutically effective amount of the pharmaceutical combination according to claim 12 to a patient in need thereof.

20. The method of claim 19, wherein the prostate cancer is hormone-independent human prostate cancer and the cervical cancer is multidrug-resistant human cervical cancer.

21. A method for the treatment of a hyper-proliferative disorder selected from the group consisting of cervical cancer, non-small cell lung cancer, prostate cancer, colorectal cancer, melanoma, ovarian cancer, acute myeloid leukemia, breast cancer, osteosarcoma, and lymphoma, comprising administering a therapeutically effective amount of the pharmaceutical composition according to claim 13 to patient in need thereof.

22. The method of claim 21, wherein the prostate cancer is hormone-independent human prostate cancer and the cervical cancer is multidrug-resistant human cervical cancer.

* * * * *

UNITED STATES PATENT AND TRADEMARK OFFICE

CERTIFICATE OF CORRECTION

PATENT NO. : 11,254,690 B2
APPLICATION NO. : 16/498662
DATED : February 22, 2022
INVENTOR(S) : Lucking et al.

It is certified that error appears in the above-identified patent and that said Letters Patent is hereby corrected as shown below:

In the Claims

Column 181, Lines 1-15, In Claim 11, replace 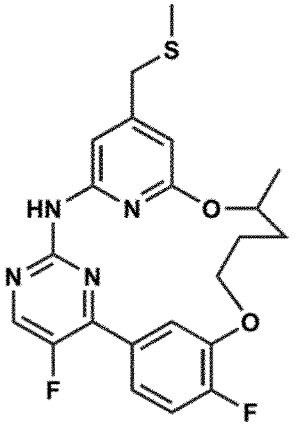 with 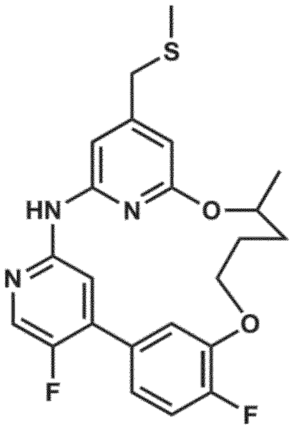

Signed and Sealed this
Twelfth Day of April, 2022

Drew Hirshfeld
*Performing the Functions and Duties of the*
*Under Secretary of Commerce for Intellectual Property and*
*Director of the United States Patent and Trademark Office*